United States Patent
Yang

(10) Patent No.: US 11,289,662 B2
(45) Date of Patent: Mar. 29, 2022

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventor: Jeong-Eun Yang, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 402 days.

(21) Appl. No.: 16/479,616

(22) PCT Filed: Jan. 31, 2018

(86) PCT No.: PCT/KR2018/001324
§ 371 (c)(1),
(2) Date: Jul. 22, 2019

(87) PCT Pub. No.: WO2018/143663
PCT Pub. Date: Aug. 9, 2018

(65) Prior Publication Data
US 2021/0367161 A1 Nov. 25, 2021

(30) Foreign Application Priority Data
Feb. 1, 2017 (KR) .................. 10-2017-0014450

(51) Int. Cl.
*H01L 51/00* (2006.01)
*C07D 471/14* (2006.01)
*C09K 11/06* (2006.01)
*H01L 51/50* (2006.01)

(52) U.S. Cl.
CPC ........ *H01L 51/0072* (2013.01); *C07D 471/14* (2013.01); *C09K 11/06* (2013.01); *H01L 51/0067* (2013.01); *C09K 2211/1007* (2013.01); *C09K 2211/1018* (2013.01); *H01L 51/5012* (2013.01)

(58) Field of Classification Search
CPC ............ H01L 51/0072; H01L 51/0067; C07D 471/14; C09K 11/06
USPC ......................................................... 544/212
See application file for complete search history.

(56) References Cited

U.S. PATENT DOCUMENTS

2015/0243896 A1    8/2015   Shi et al.

FOREIGN PATENT DOCUMENTS

| KR | 2014-0065357 A | 5/2014 |
|----|----------------|--------|
| WO | 2006/088028 A1 | 8/2006 |
| WO | 2015/126161 A2 | 8/2015 |

OTHER PUBLICATIONS

Keshtov, M.L. et al, "New Conjugated Electroluminescent Triphenylamine-Containing Polymers with Side-Chain Pyridin-2-ylimidazo[1,5-a]pyridine Groups for Polymer Light-Emitting Diodes", Doklady Chemistry, 2013, vol. 450, pp. 165-172 Compound 3, scheme 1, p. 166; Figs. 1-3, pp. 168-170.

*Primary Examiner* — Joseph R Kosack
*Assistant Examiner* — Sagar Patel
(74) *Attorney, Agent, or Firm* — G. Creston Campbell

(57) ABSTRACT

The present disclosure relates to an organic electroluminescent compound and an organic electroluminescent device comprising the same. By comprising the organic electroluminescent compound of the present disclosure, an organic electroluminescent device having low driving voltage and/or high luminous efficiency can be provided. At the same time or selectively, an organic electroluminescent device having excellent lifespan characteristic and/or formable of a thin film of excellent quality can be provided.

9 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

The most important factor in determining luminous efficiency in an organic electroluminescent device is light-emitting materials. Until now, fluorescent materials have been widely used as a light-emitting material. However, in view of electroluminescent mechanisms, since phosphorescent light-emitting materials theoretically enhance luminous efficiency by four (4) times compared to fluorescent light-emitting materials, development of phosphorescent light-emitting materials are widely being researched. To date, iridium(III) complexes have been widely known as phosphorescent light-emitting materials, including bis(2-(2'-benzothienyl)-pyridinato-N,C3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red, green, and blue materials, respectively.

At present, 4,4'-N,N'-dicarbazol-biphenyl (CBP) is the most widely known phosphorescent host material. Recently, Pioneer (Japan) et al. developed a high performance organic electroluminescent device using bathocuproine (BCP) and aluminum(III)bis(2-methyl-8-quinolinate)(4-phenylphenolate) (BAlq) etc., which were used as hole blocking layer materials, as host materials.

Although these materials provide good light-emitting characteristics, they have the following disadvantages: (1) Due to their low glass transition temperature and poor thermal stability, their degradation may occur during a high-temperature deposition process in a vacuum, and the lifespan of the device decreases. (2) The power efficiency of an organic electroluminescent device is given by [(π/voltage)×current efficiency], and the power efficiency is inversely proportional to the voltage. Although an organic electroluminescent device comprising phosphorescent host materials provides higher current efficiency (cd/A) than one comprising fluorescent materials, a significantly high driving voltage is necessary. Thus, there is no merit in terms of power efficiency (lm/W). (3) Further, when these materials are used in an organic electroluminescent device, the operational lifespan of an organic electroluminescent device is short and luminous efficiency is still required to be improved.

Meanwhile, Korean Patent Appln. Laying-Open No. KR 2014-0065357 A discloses a compound having a core structure wherein a benzimidazole is fused to a fused ring of a biphenyl and a 6-membered ring as a light-emitting material of an organic electroluminescent device. However, said reference does not specifically disclose a compound having a core structure wherein an imidazole substituted with two aryls is fused to a fused ring of a biphenyl and a 6-membered ring. Further, it is not sufficiently satisfactory in terms of lifespan characteristics of the device and the quality of a thin film.

DISCLOSURE OF THE INVENTION

Problems to be Solved

The objective of the present disclosure is to provide an organic electroluminescent compound which can efficiently produce an organic electroluminescent device having low driving voltage and/or high luminous efficiency. At the same time or selectively, the objective of the present disclosure is to provide an organic electroluminescent device having excellent lifespan characteristic and/or an organic electroluminescent compound which can form a thin film of excellent quality.

Solution to Problems

The present inventors found that the organic electroluminescent compound disclosed in the above reference has a low HOMO (highest occupied molecular orbital) energy level, which limits efficient hole transport from the auxiliary layer to the light-emitting layer, and the HOMO energy level difference of the auxiliary layer and the dopant is smaller than the HOMO energy level difference of the auxiliary layer and the light-emitting layer, which limits the lifespan of the device. In addition, the present inventors found that the organic electroluminescent compound of the above reference has an almost perfectly planar structure, crystallinity and aggregation increase when forming a thin film, and the quality of the thin film decreases.

As a result of intensive studies to solve the technical problem above and to develop a compound having excellent driving voltage or luminous efficiency, the present inventors found that the above objective can be achieved by an organic electroluminescent compound represented by the following formula 1:

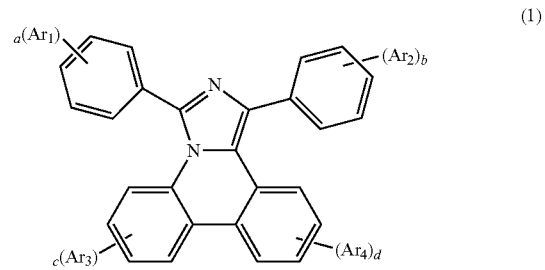

(1)

wherein

Ar$_1$ and Ar$_2$ each independently represent hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered) heterocycloalkyl, or a substituted or unsubstituted (C3-C30) cycloalkyl;

Ar$_3$ and Ar$_4$ each independently represent hydrogen, deuterium, a halogen, a cyano, —NR$_{11}$R$_{12}$, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; and at least one of two Ar₃'s and two Ar₄'s are linked to each other to form a fused ring of

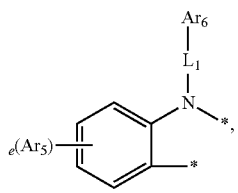

in which * represents a bonding site of Ar₃ or Ar₄;

R₁₁ and R₁₂ each independently represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, a substituted or unsubstituted (3- to 7-membered) heterocycloalkyl, or a substituted or unsubstituted (C3-C30)cycloalkyl;

L₁ represents a single bond, or a substituted or unsubstituted (C6-C30)arylene;

Ar₅ represents hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl;

Ar₆ represents a substituted or unsubstituted (C6-C30) aryl, or a substituted or unsubstituted (5- to 30-membered) heteroaryl;

the heteroaryl contains at least one heteroatom selected from B, N, O, S, Si, and P;

a and b each independently represent an integer of 1 to 5, and c to e each independently represent an integer of 1 to 4;

where a to e is an integer of 2 or more, each Ar₁, each Ar₂, each Ar₃, each Ar₄, and each Ar₅ may be the same or different.

Effects of the Invention

By using the organic electroluminescent compound according to the present disclosure, an organic electroluminescent device having low driving voltage, high luminous efficiency, and/or improved lifespan characteristic can be produced. At the same time or selectively, the organic electroluminescent compound of the present disclosure has a slightly distorted molecular structure than a planar structure and can limit recrystallization and aggregation quenching by effectively controlling the molecular interaction, and thus increases the quality of a thin film.

EMBODIMENTS OF THE INVENTION

Hereinafter, the present disclosure will be described in detail. However, the following description is intended to explain the disclosure, and it is not meant in any way to restrict the scope of the disclosure.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. The compound of formula 1 may be comprised in a light-emitting layer, but is not limited thereto. When comprised in the light-emitting layer, the compound of formula 1 can be comprised as a host. In addition, the compound of formula 1 may be comprised in an electron buffer layer. When comprised in the electron buffer layer, the compound of formula 1 can be comprised as an electron buffer material. In addition, the compound of formula 1 may be comprised in an electron transport layer. When comprised in the electron transport layer, the compound of formula 1 can be comprised as an electron transport material.

Hereinafter, the compound represented by formula 1 will be described in detail.

The compound of formula 1 may be represented by any one of the following formulas 2 and 3:

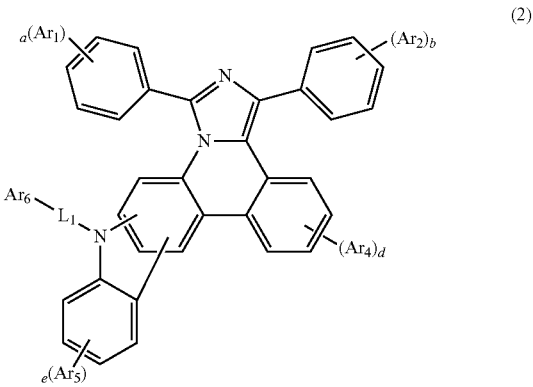

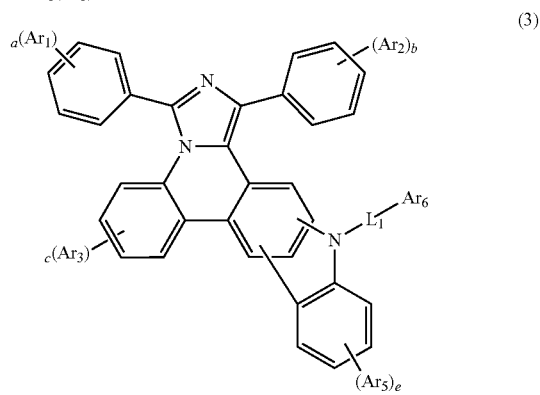

wherein

Ar₁ to Ar₆, L₁, and a to e are as defined in formula 1.

In formula 1 above, Ar₁ and Ar₂ each independently represent hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl, preferably each independently represent hydrogen, a substituted or unsubstituted (C6-C20)aryl, or a substituted or unsubstituted (5- to 20-membered)heteroaryl, and more preferably each independently represent hydrogen, an unsubstituted (C6-C20) aryl, or a (5- to 20-membered)heteroaryl substituted with a (C6-C12)aryl(s). Specifically, $Ar_1$ and $Ar_2$ may each independently represent hydrogen, a phenyl, or a diphenyltriazine.

$Ar_3$ and $Ar_4$ each independently represent hydrogen, deuterium, a halogen, a cyano, $-NR_{11}R_{12}$, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; and at least one of two $Ar_3$'s and two $Ar_4$'s are linked to each other to form a fused ring of

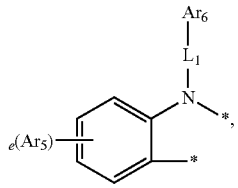

in which * represents a bonding site of $Ar_3$ or $Ar_4$, preferably each independently represent hydrogen, a halogen, $-NR_{11}R_{12}$, a substituted or unsubstituted (C6-C20)aryl, or a substituted or unsubstituted (5- to 20-membered)heteroaryl; and at least one of two $Ar_3$'s and two $Ar_4$'s are linked to each other to form said fused ring, and more preferably each independently represent hydrogen, a (C6-C20)aryl unsubstituted or substituted with a nitro(s), or a (5- to 20-membered)heteroaryl unsubstituted or substituted with a (C6-C12)aryl(s); and at least one of two $Ar_3$'s and two $Ar_4$'s are linked to each other to form said fused ring. Specifically, $Ar_3$ and $Ar_4$ may each independently represent hydrogen, a phenyl, or a diphenyltriazine. Herein, $R_{11}$ and $R_{12}$ each independently represent hydrogen, deuterium, a halogen, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl, and preferably each independently represent hydrogen, a substituted or unsubstituted (C6-C20)aryl, or a substituted or unsubstituted (5- to 20-membered)heteroaryl.

According to one embodiment of the present disclosure, one of two $Ar_3$'s and two $Ar_4$'s are linked to each other to form a fused ring of

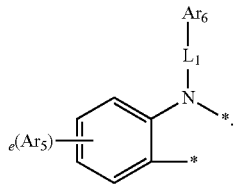

$L_1$ represents a single bond, or a substituted or unsubstituted (C6-C30)arylene, and preferably represents a single bond.

$Ar_5$ represents hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl, preferably represents hydrogen, or a substituted or unsubstituted (C6-C20)aryl, and more preferably represents hydrogen, or an unsubstituted (C6-C20)aryl. Specifically, $Ar_5$ may represent hydrogen or a phenyl.

$Ar_6$ represents a substituted or unsubstituted (C6-C30) aryl, or a substituted or unsubstituted (5- to 30-membered) heteroaryl, preferably represents a substituted or unsubstituted (C6-C20)aryl, or a substituted or unsubstituted (5- to 20-membered)heteroaryl, and more preferably represents an unsubstituted (C6-C20)aryl, or a (5- to 20-membered)heteroaryl unsubstituted or substituted with a (C6-C12)aryl(s). Specifically, $Ar_6$ may represent a phenyl, a pyridinyl, a diphenyltriazine, a phenylquinazolinyl, or a phenylquinoxalinyl.

According to one embodiment of the present disclosure, in formula 1 above, $A_1$ and $Ar_2$ each independently represent hydrogen, a substituted or unsubstituted (C6-C20)aryl, or a substituted or unsubstituted (5- to 20-membered)heteroaryl; $Ar_3$ and $Ar_4$ each independently represent hydrogen, a halogen, $-NR_{11}R_{12}$, a substituted or unsubstituted (C6-C20) aryl, or a substituted or unsubstituted (5- to 20-membered) heteroaryl, and at least one of two $Ar_3$'s and two $Ar_4$'s are linked to each other to form a fused ring of

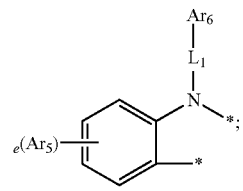

$L_1$ represents a single bond; $R_{11}$ and $R_{12}$ each independently represent hydrogen, a substituted or unsubstituted (C6-C20) aryl, or a substituted or unsubstituted (5- to 20-membered) heteroaryl; $Ar_5$ represents hydrogen, or a substituted or unsubstituted (C6-C20)aryl; and $Ar_6$ represents a substituted or unsubstituted (C6-C20)aryl, or a substituted or unsubstituted (5- to 20-membered)heteroaryl.

According to another embodiment of the present disclosure, in formula 1 above, $Ar_1$ and $Ar_2$ each independently represent hydrogen, an unsubstituted (C6-C20)aryl, or a (5- to 20-membered)heteroaryl substituted with a (C6-C12)-aryl(s); $Ar_3$ and $Ar_4$ each independently represent hydrogen, a (C6-C20)aryl unsubstituted or substituted with a nitro(s), or a (5- to 20-membered)heteroaryl unsubstituted or substituted with a (C6-C12)aryl(s); and at least one of two $Ar_3$'s and two $Ar_4$'s are linked to each other to form a fused ring of

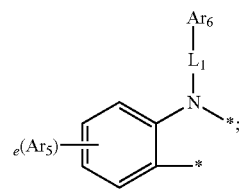

$L_1$ represents a single bond; $Ar_5$ represents hydrogen, or an unsubstituted (C6-C20)aryl; and $Ar_6$ represents an unsubstituted (C6-C20)aryl, or a (5- to 20-membered)heteroaryl unsubstituted or substituted with a (C6-C12)aryl(s).

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is meant to be a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is meant to be a cycloalkyl having at least one heteroatom selected from the group consisting of B, N, O, S, Si, and P, preferably selected from the group consisting of O, S, and N, and 3 to 7 ring backbone atoms, preferably 5 to 7 ring backbone atoms, and includes tetrahydrofuran, pyrrolidine, thiolan, tetrahydropyran, etc. "(C6-C30)aryl(ene)" is meant to be a monocyclic or fused ring radical derived from an aromatic hydrocarbon having 6 to 30 ring backbone carbon atoms and may be partially saturated, in which the number of ring backbone carbon atoms is preferably 6 to 25, more preferably 6 to 18, may include a spiro structure, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(3- to 30-membered)heteroaryl" is meant to be an aryl group having at least one, preferably 1 to 4 heteroatoms selected from the group consisting of B, N, O, S, Si, and P, and 3 to 30 ring backbone atoms; is a monocyclic ring, or a fused ring condensed with at least one benzene ring; may be partially saturated; may be one formed by linking at least one heteroaryl or aryl group to a heteroaryl group via a single bond(s); may include a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. "Halogen" includes F, Cl, Br, and I.

Herein, "substituted" in the expression "substituted or unsubstituted" means that a hydrogen atom in a certain functional group is replaced with another atom or functional group, i.e., a substituent. The substituents of the substituted (C1-C30)alkyl, the substituted (C6-C30)aryl(ene), the substituted (5- to 30-membered)heteroaryl, the substituted (3- to 7-membered)heterocycloalkyl, and the substituted (C3-C30)cycloalkyl in $Ar_1$ to $Ar_6$, and $L_1$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl(s); a (C6-C30)aryl unsubstituted or substituted with a (5- to 30-membered) heteroaryl(s); a tri(C1-C30)alkylsilyl, a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl, and preferably each independently are a nitro, a (C6-C12)aryl, or a (5- to 20-membered) heteroaryl unsubstituted or substituted with a (C6-C12)aryl(s).

The compound represented by formula 1 includes the following compounds, but is not limited thereto:

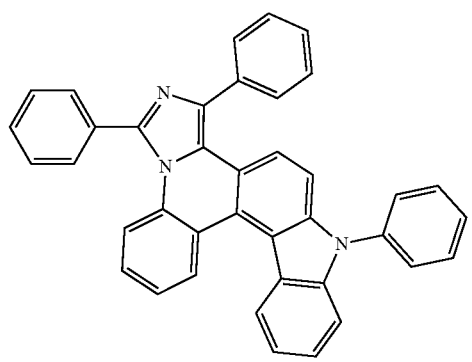

C-1

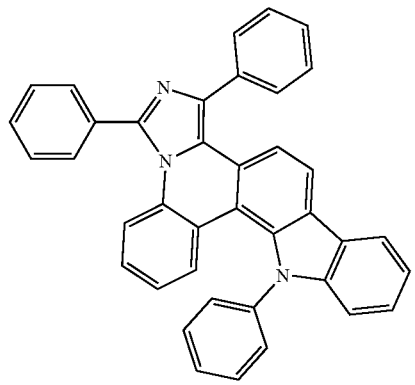

C-2

C-3
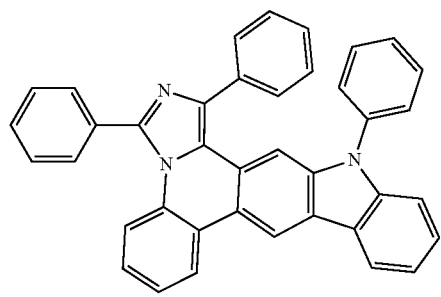
C-4
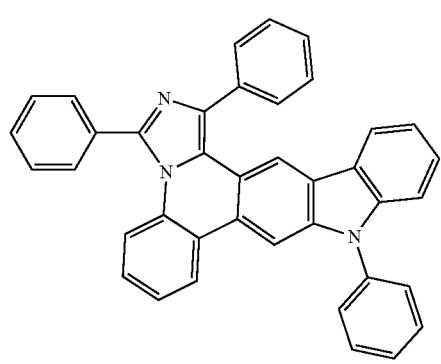
C-5
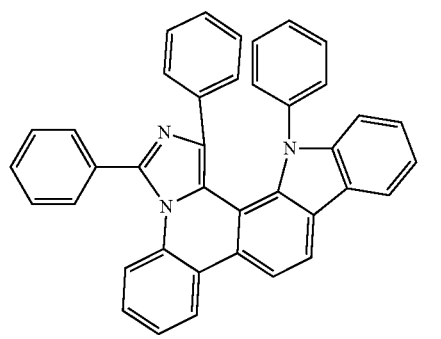
C-6
C-7
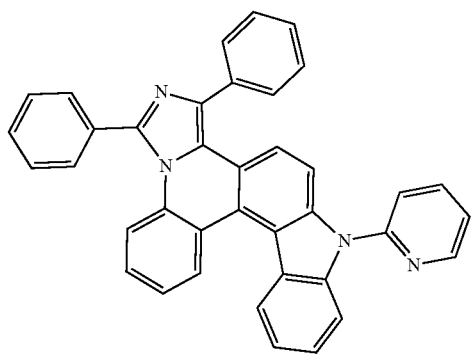
C-8
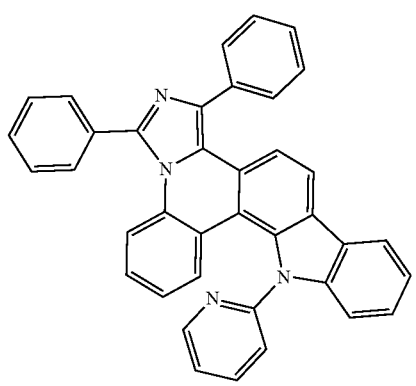
C-9
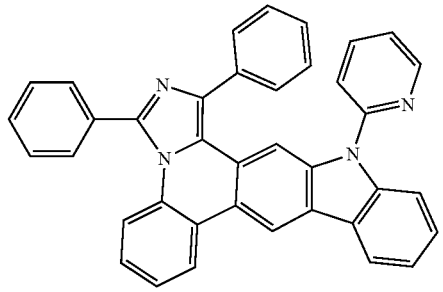
C-10
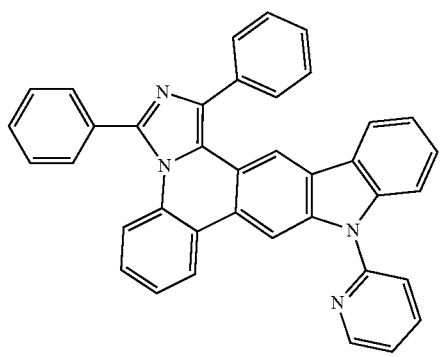

C-11
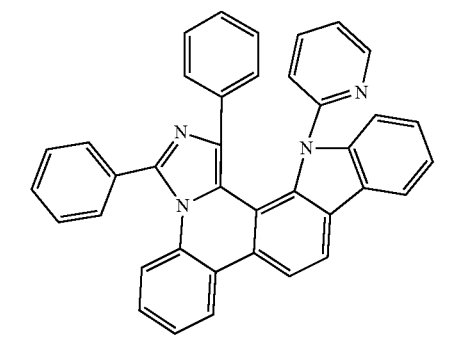
C-12
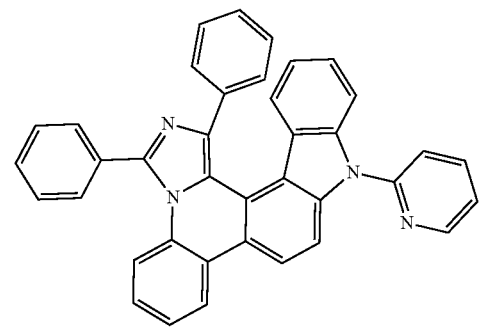
C-13
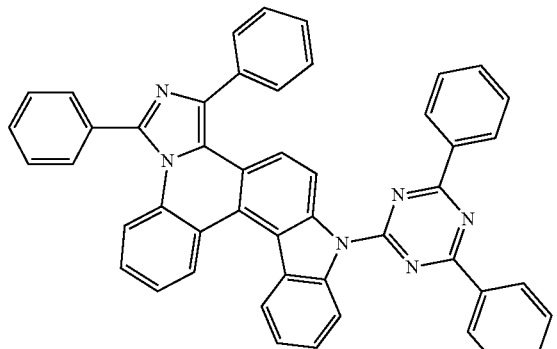
C-14
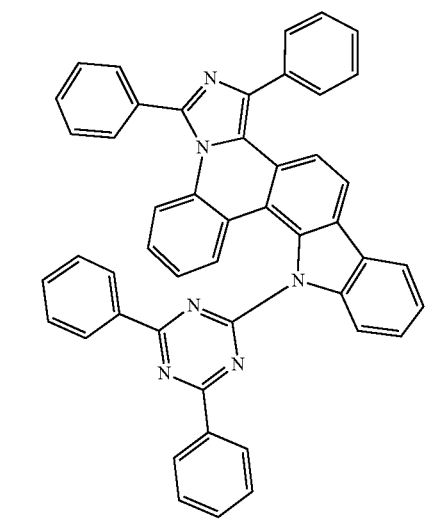
C-15
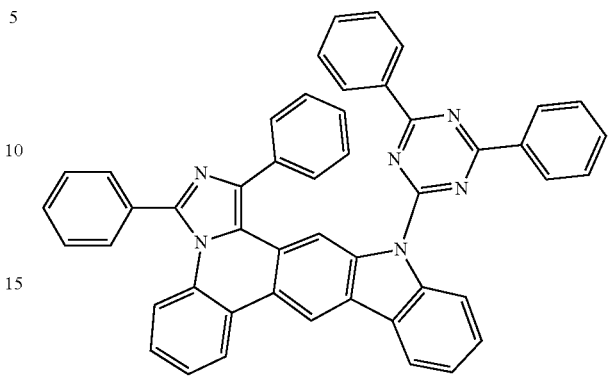
C-16
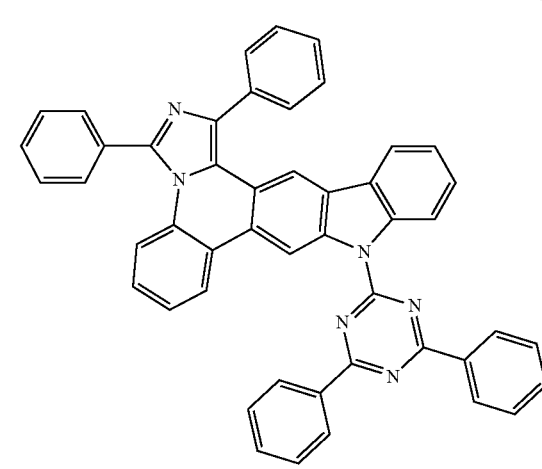
C-17
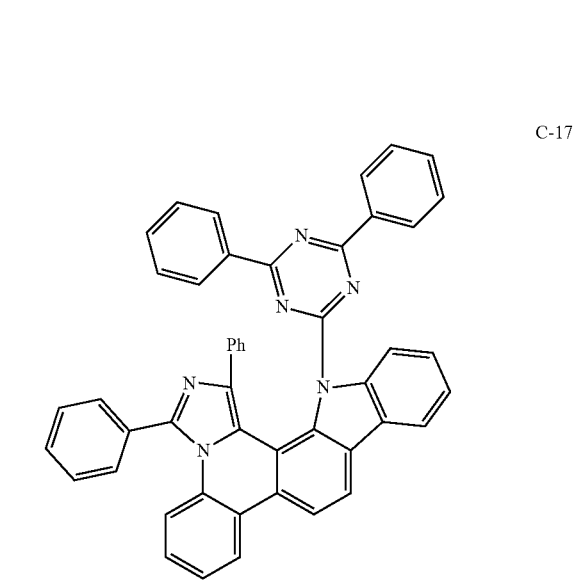

-continued
C-18
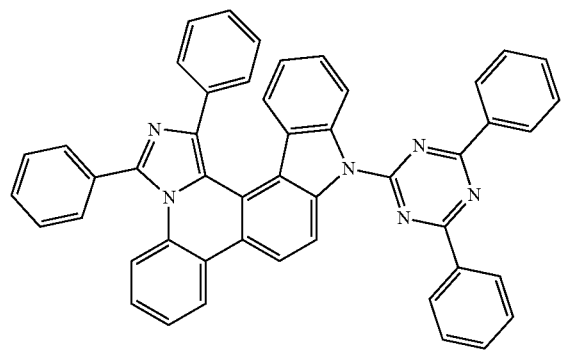
C-19
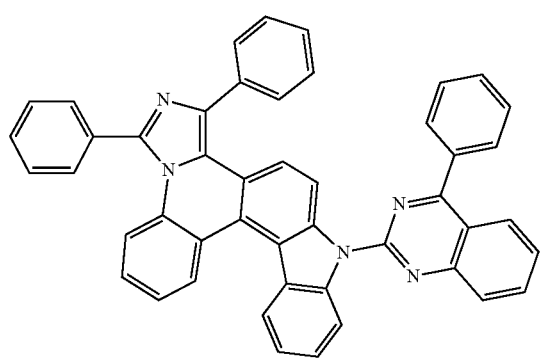
C-20
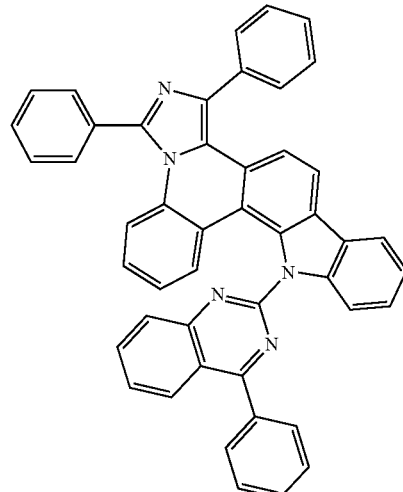
C-21
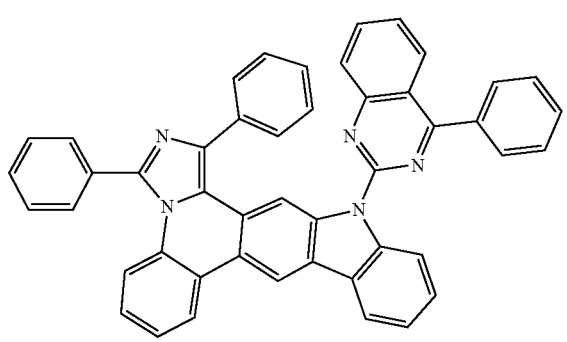
C-22
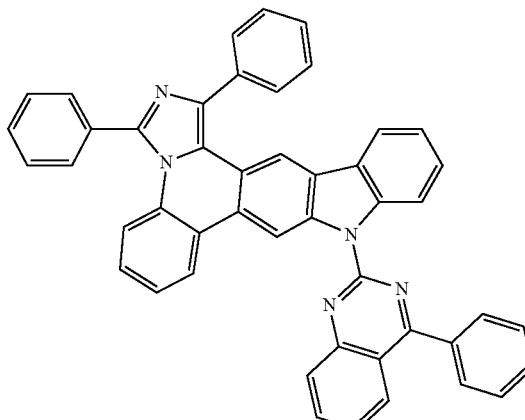
C-23
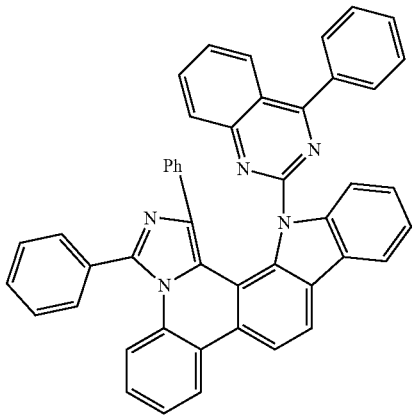
C-24
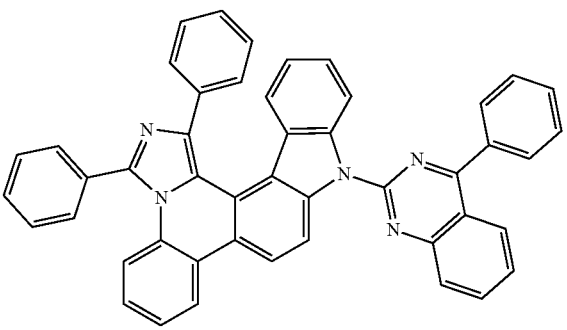
C-25
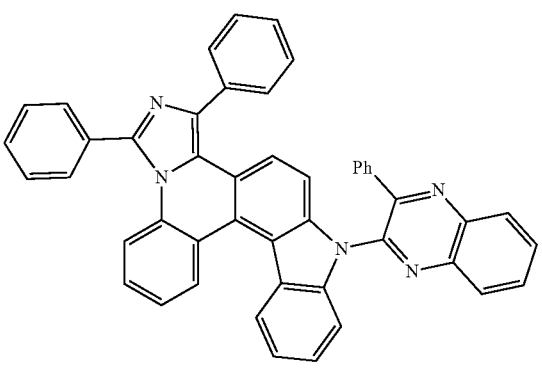

C-26
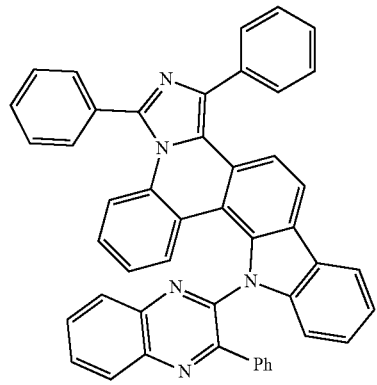
C-27
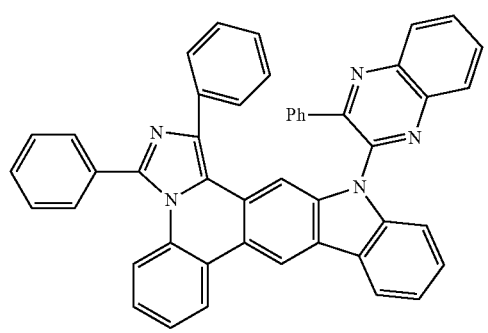
C-28
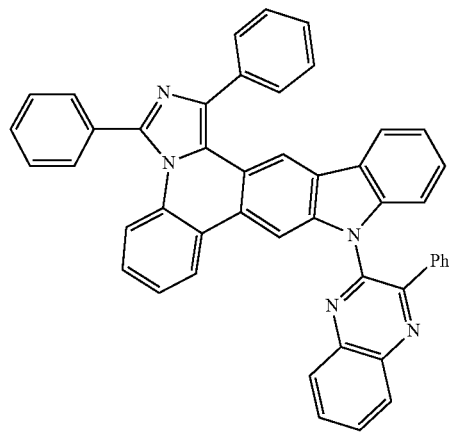
C-29
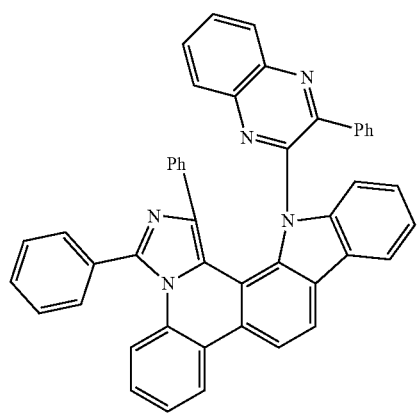
C-30
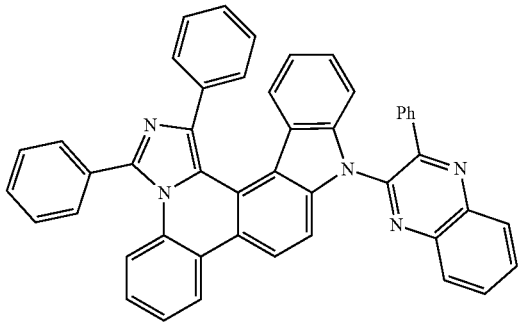
C-31
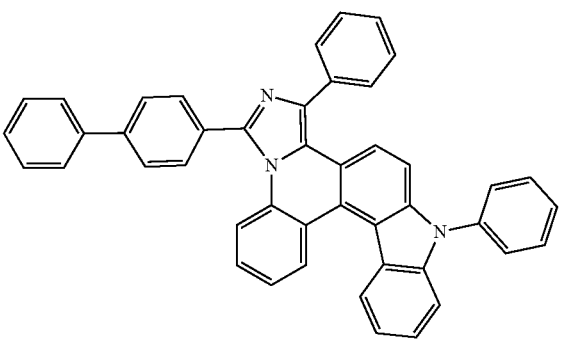
C-32
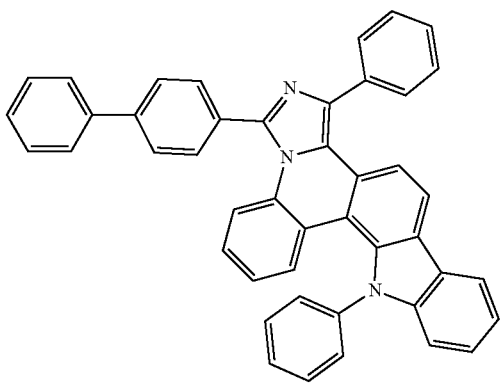
C-33
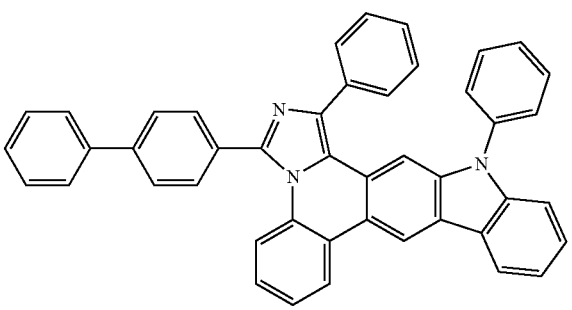

-continued
C-34
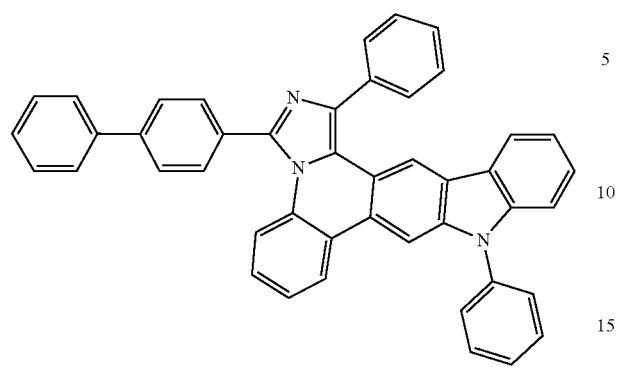
C-35
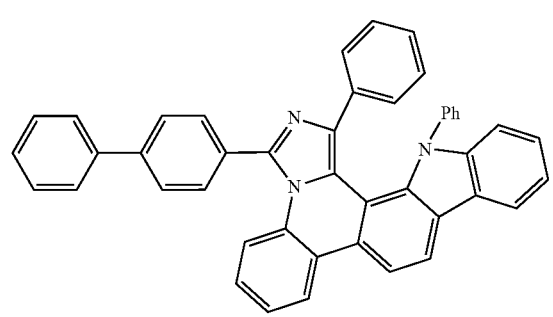
C-36
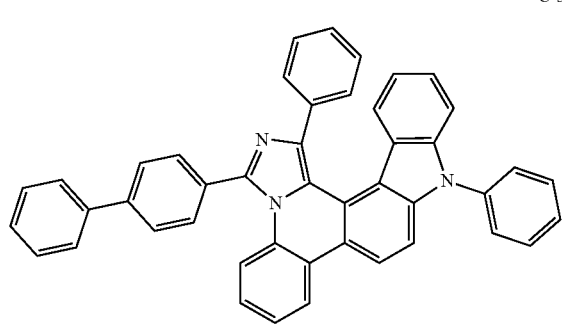
C-37
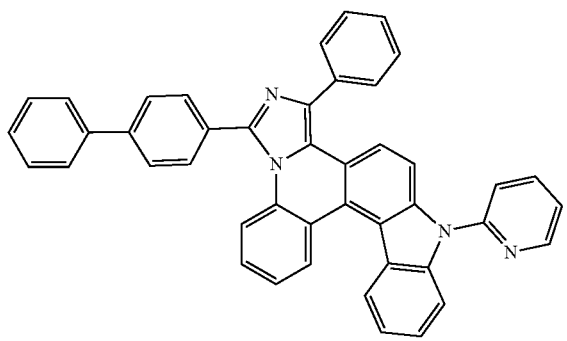
-continued
C-38
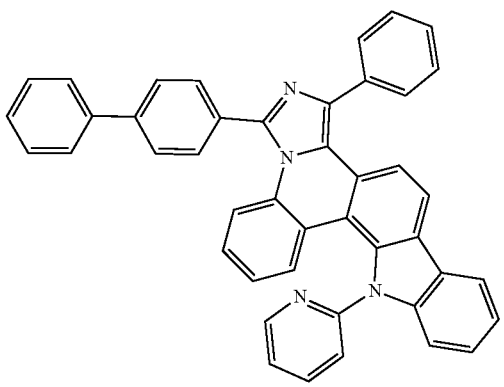
C-39
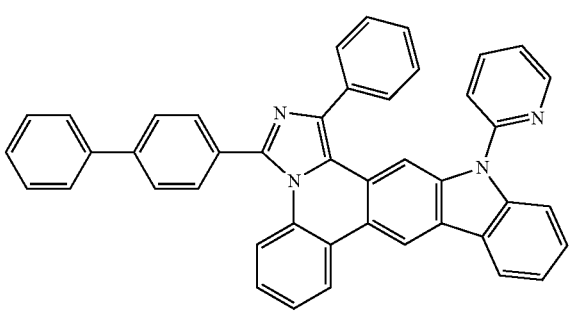
C-40
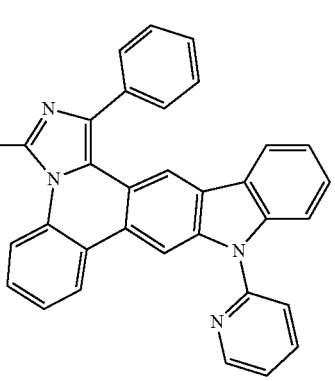
C-41
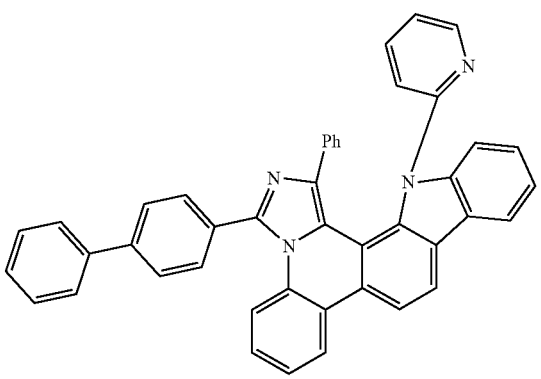

C-42
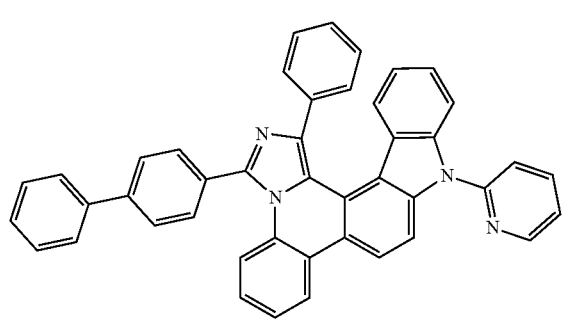
C-43
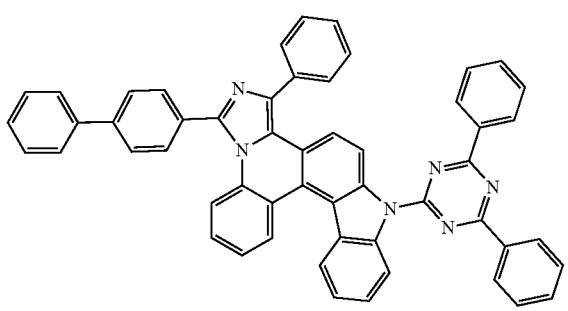
C-44
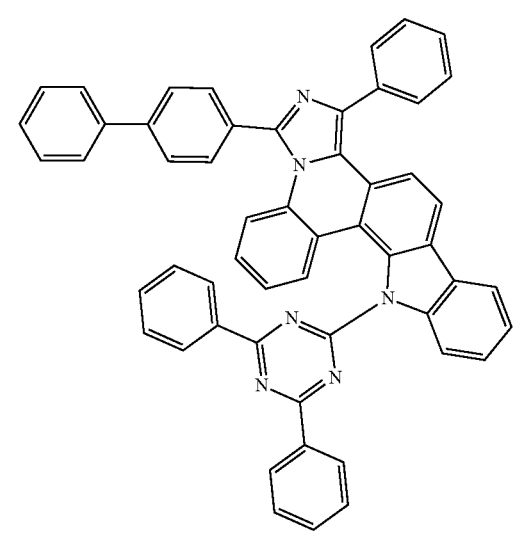
C-45
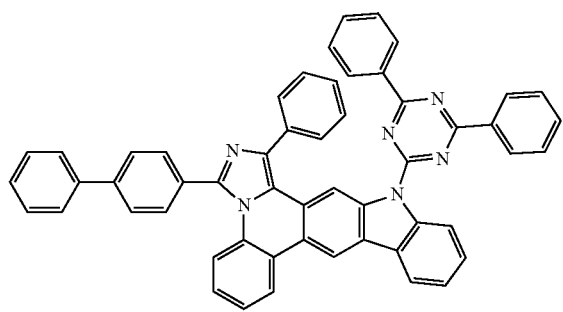
C-46
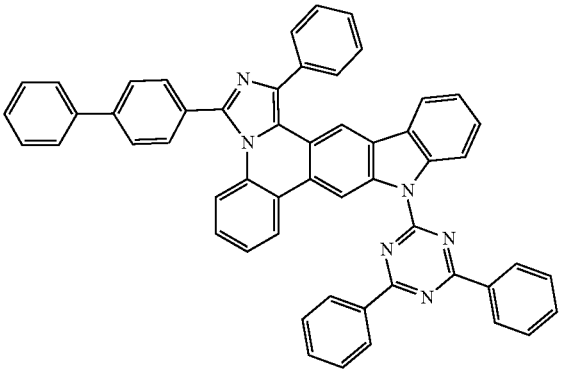
C-47
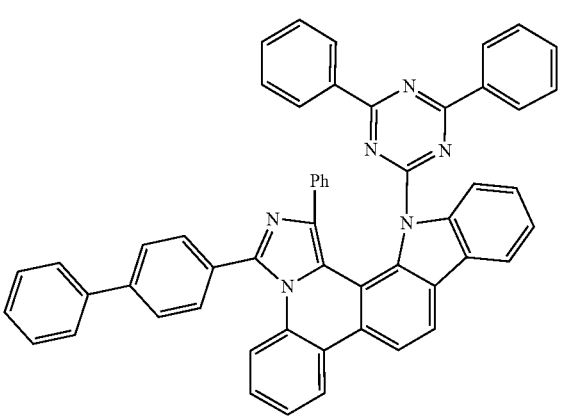
C-48
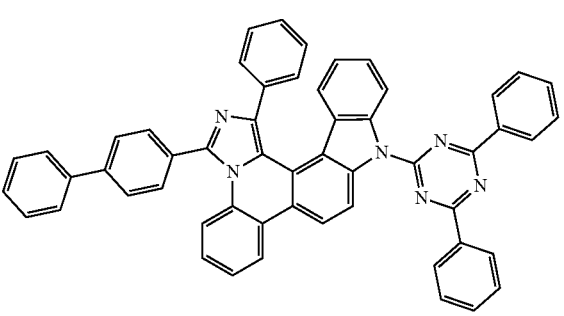
C-49
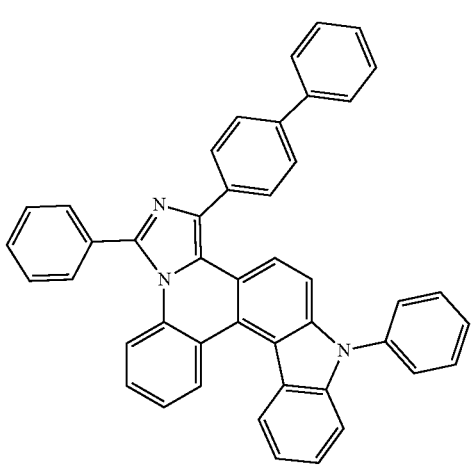

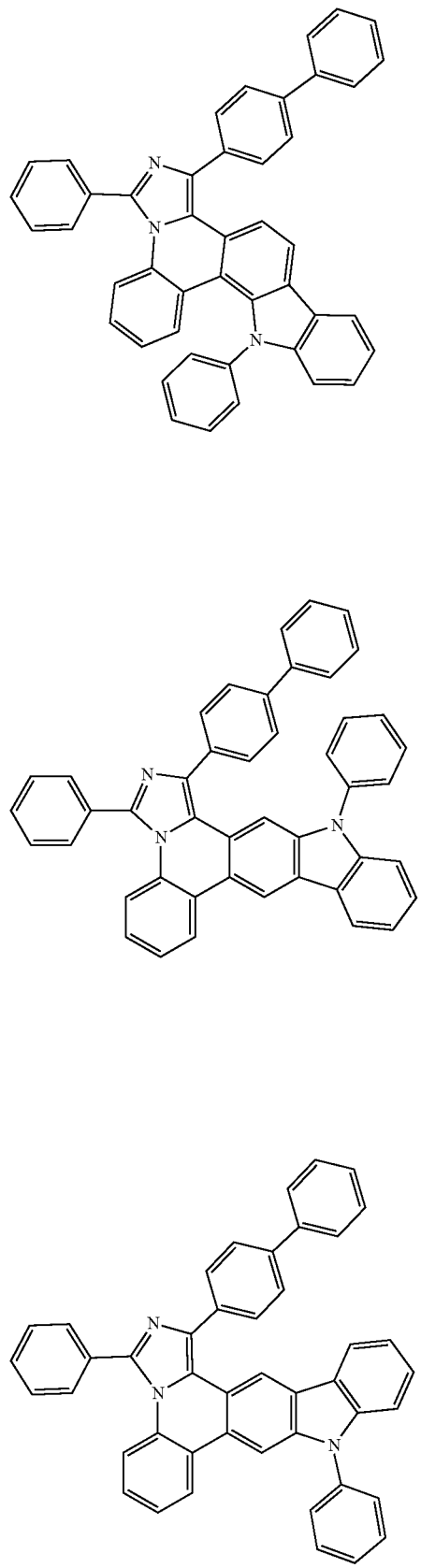
C-50
C-51
C-52
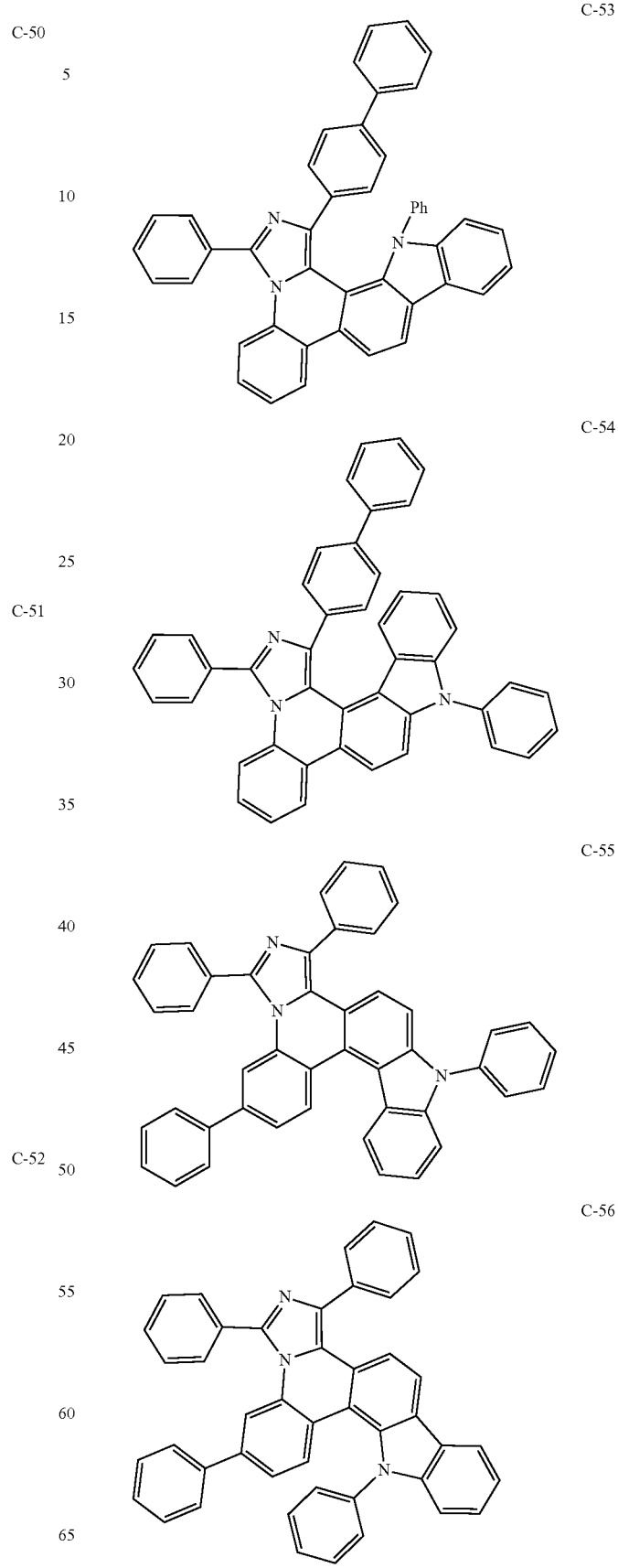
C-53
C-54
C-55
C-56

-continued
C-57
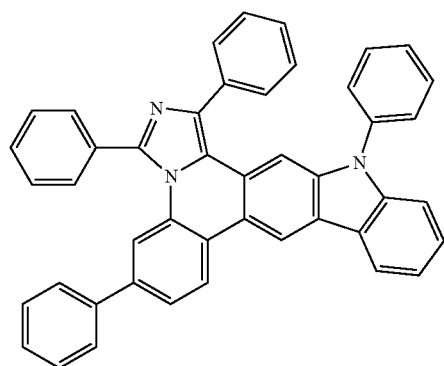
C-58
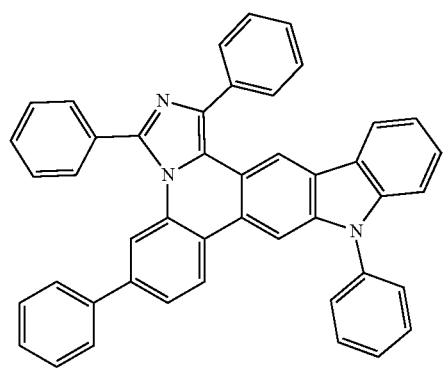
C-59
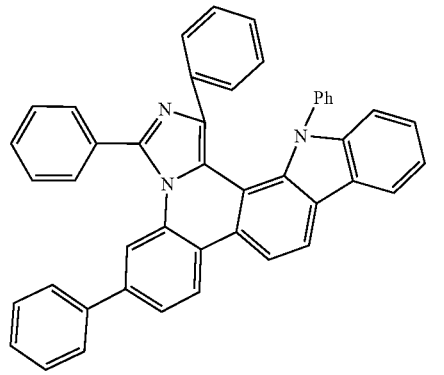
C-60
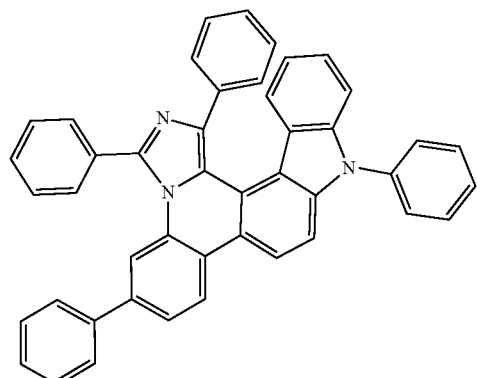
-continued
C-61
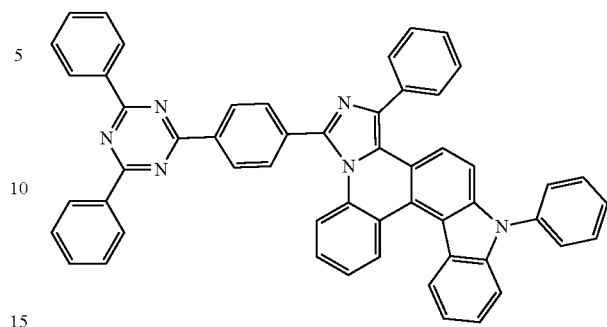
C-62
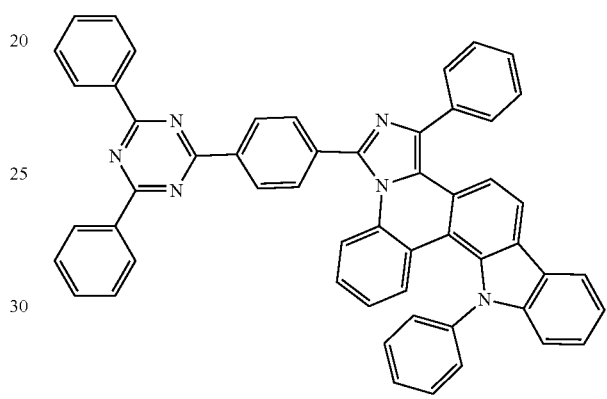
C-63
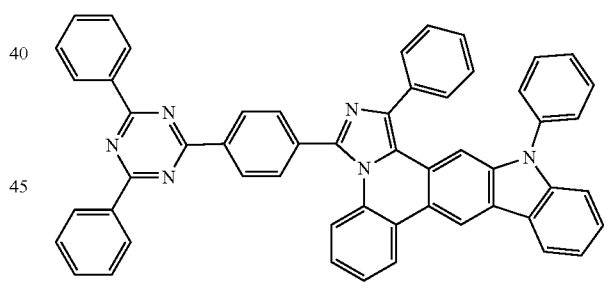
C-64
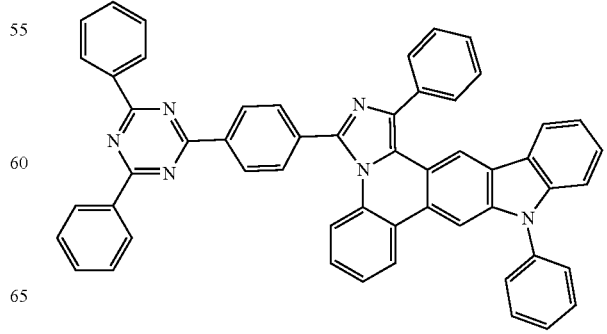

C-65
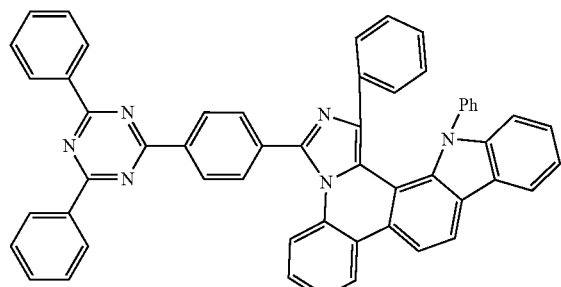
C-66
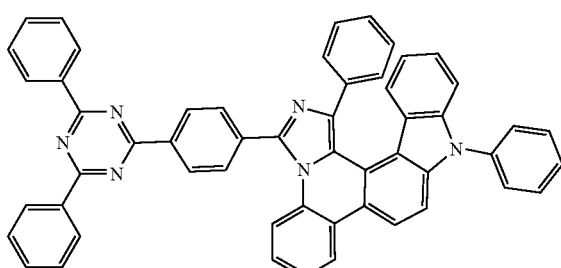
C-67
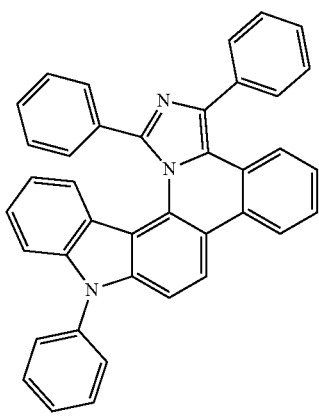
C-68
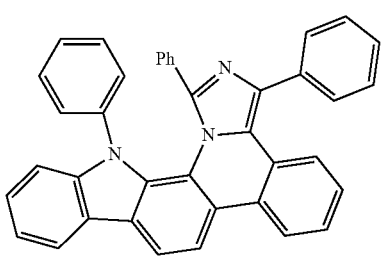
C-69
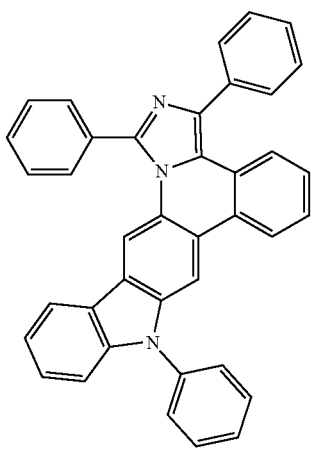
C-70
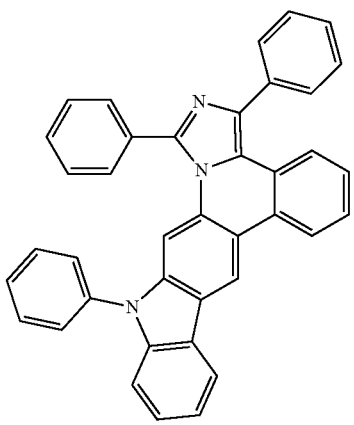
C-71
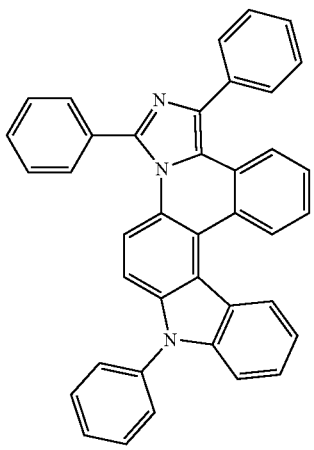

C-72
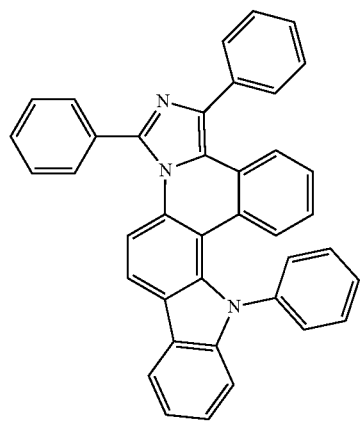
C-73
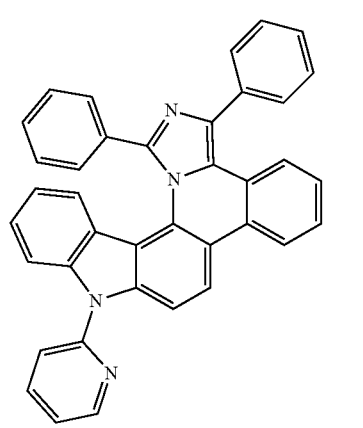
C-74
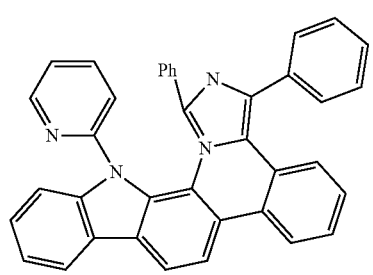
C-75
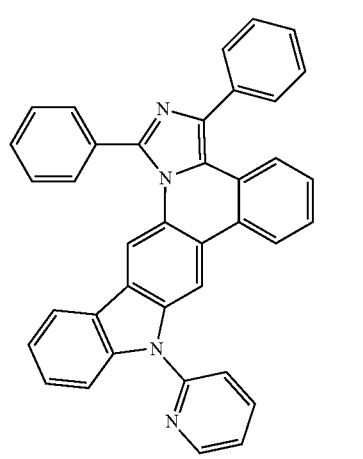
C-76
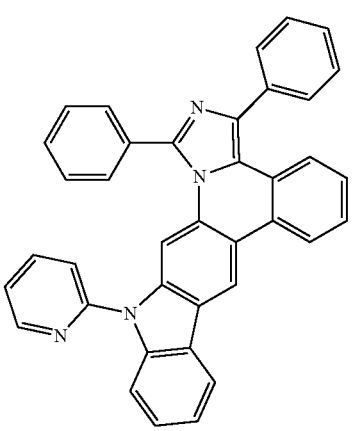
C-77
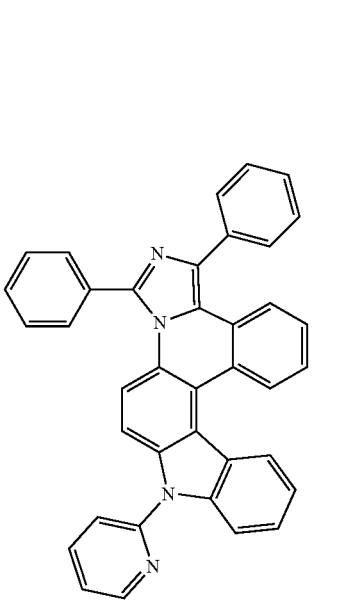
C-78
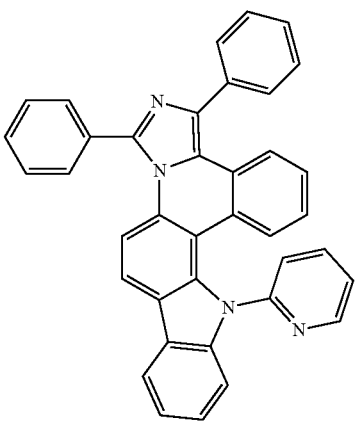

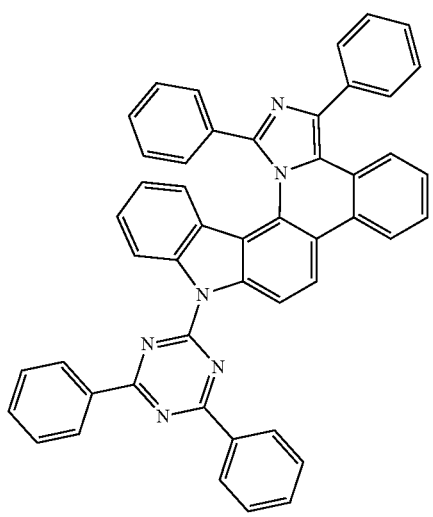
C-79
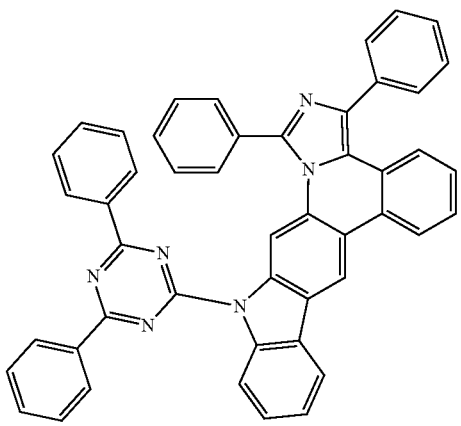
C-82
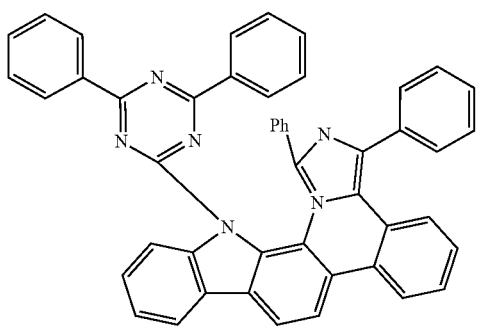
C-80
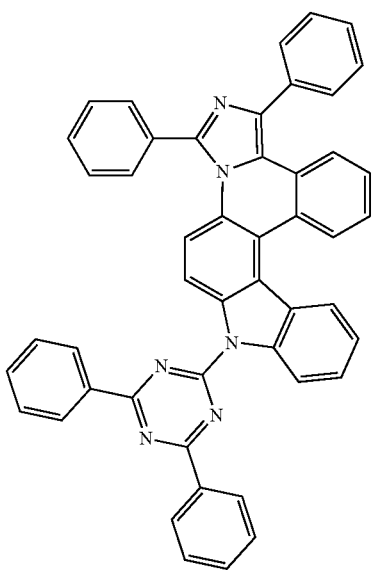
C-83
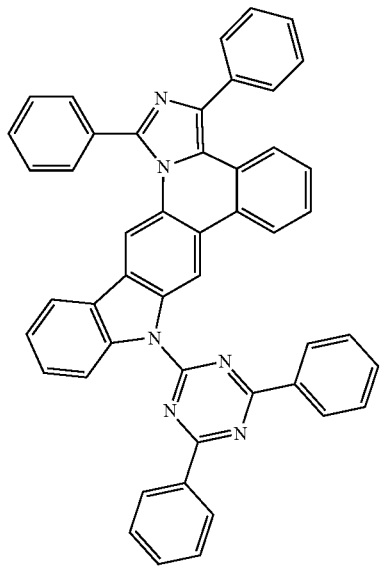
C-81
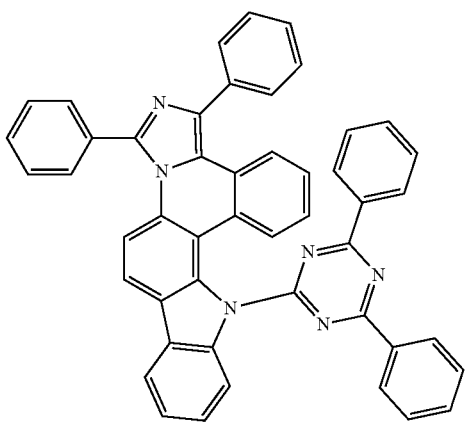
C-84

C-85
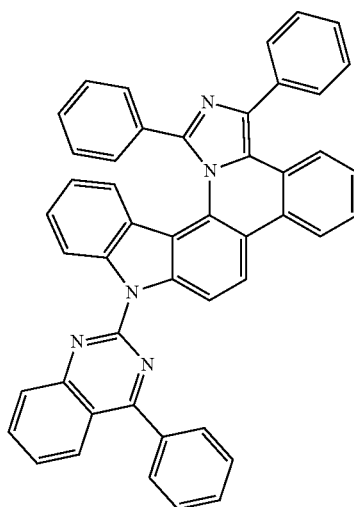
C-86
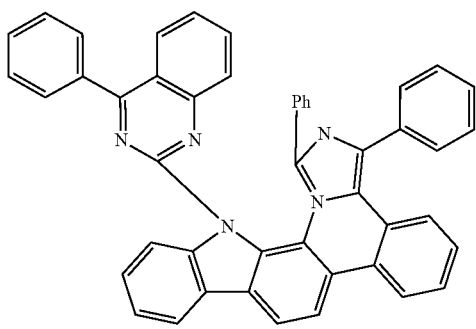
C-87
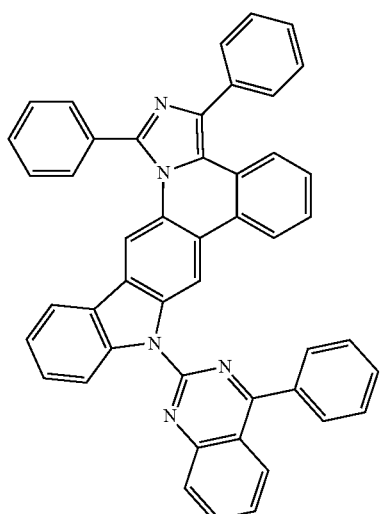
C-88
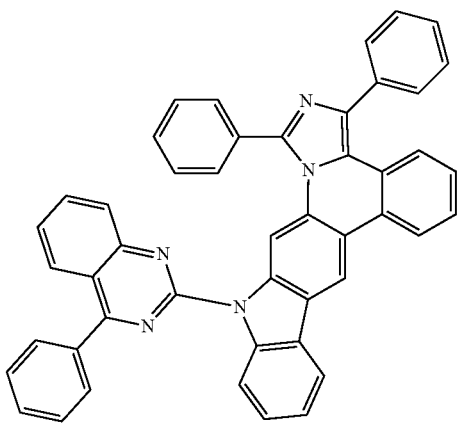
C-89
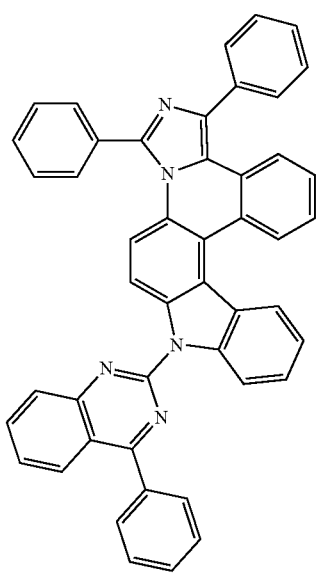
C-90
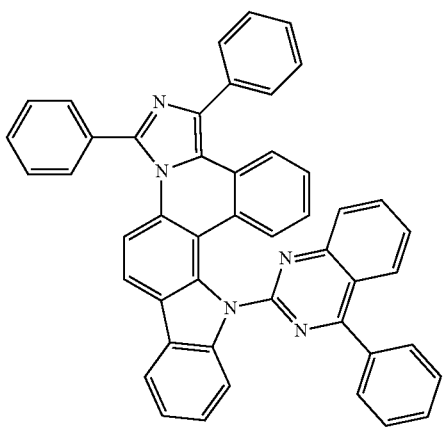

C-91
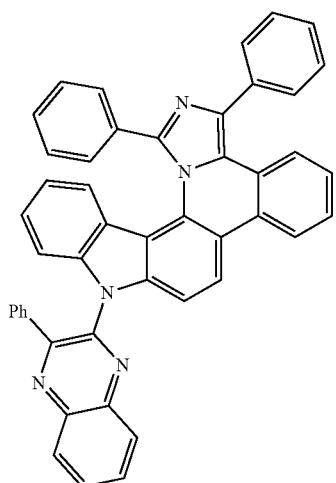
C-92
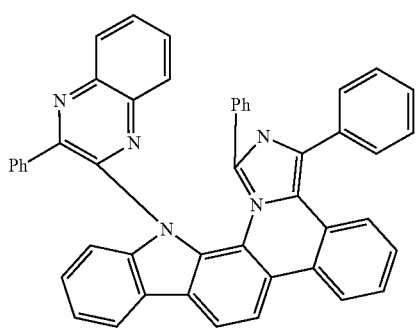
C-93
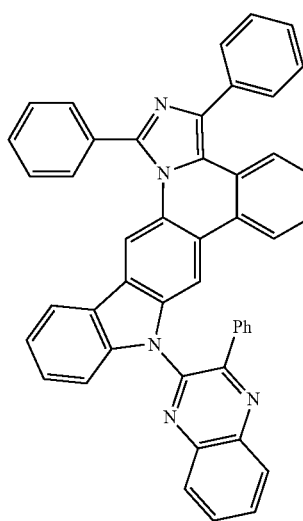
C-94
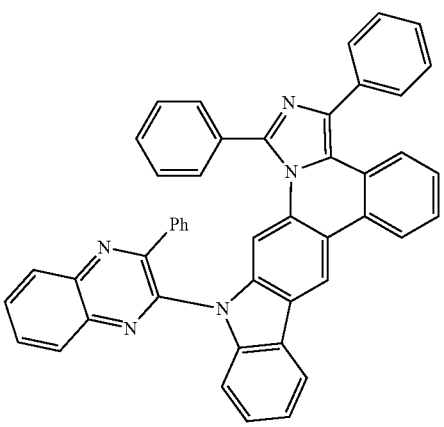
C-95
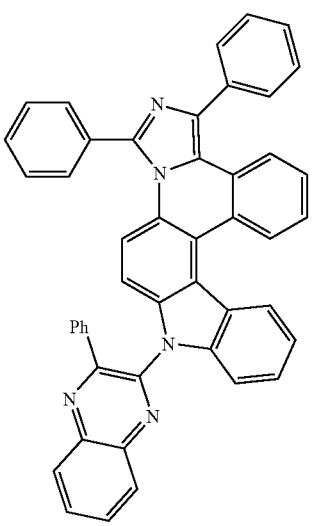
C-96
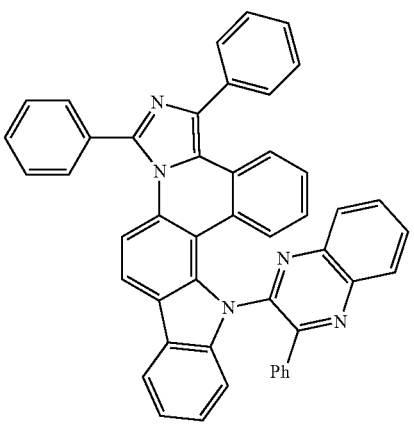

-continued
C-97
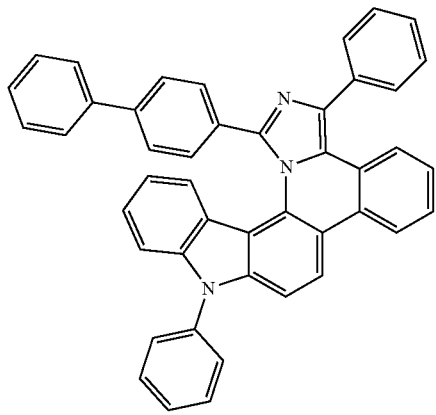
C-98
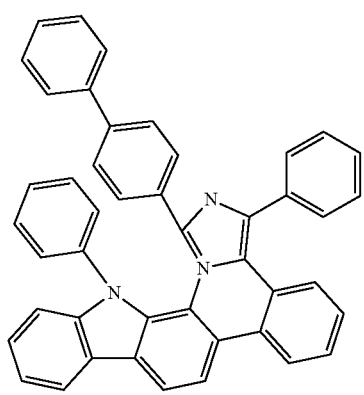
C-99
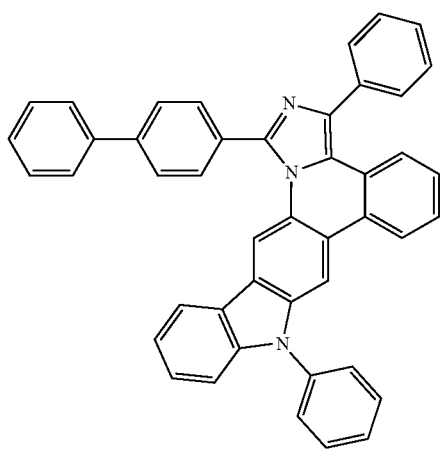
-continued
C-100
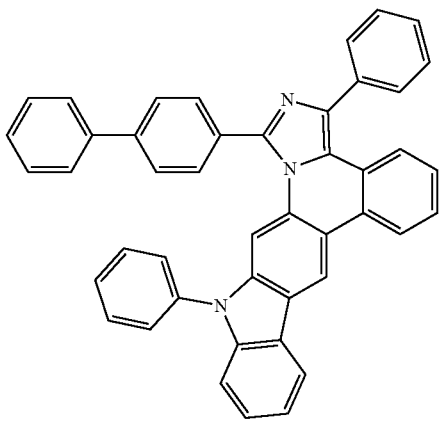
C-101
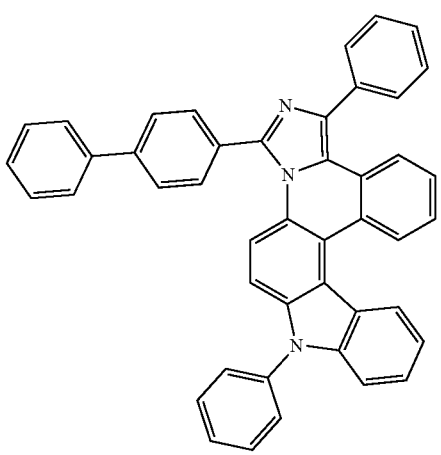
C-102
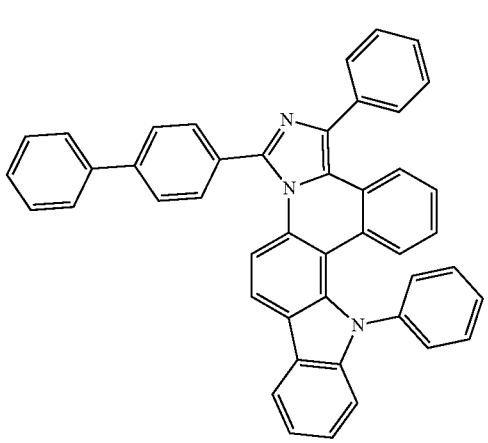

C-103
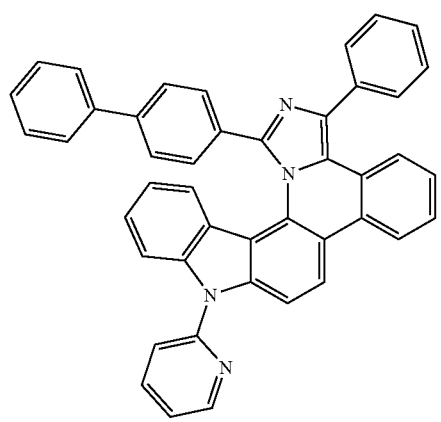
C-104
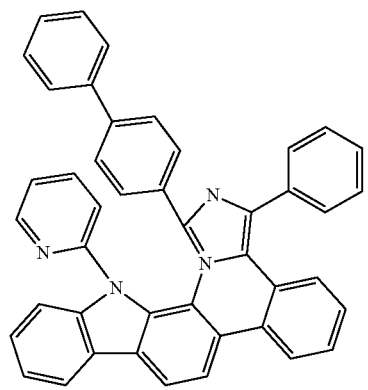
C-105
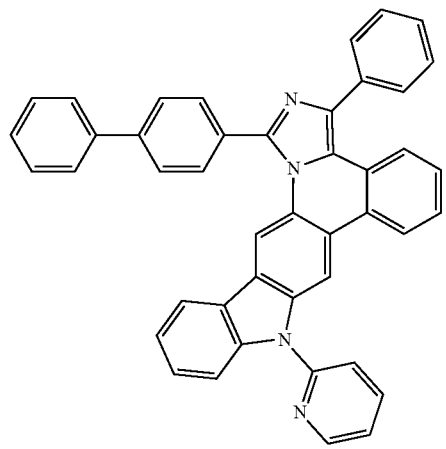
C-106
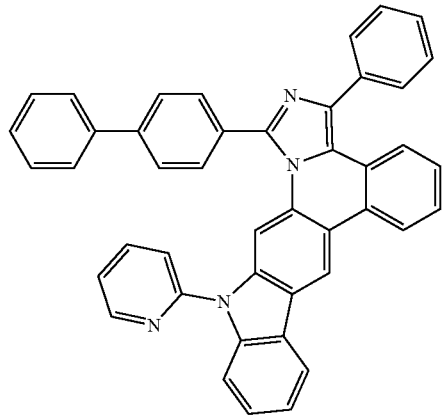
C-107
C-108
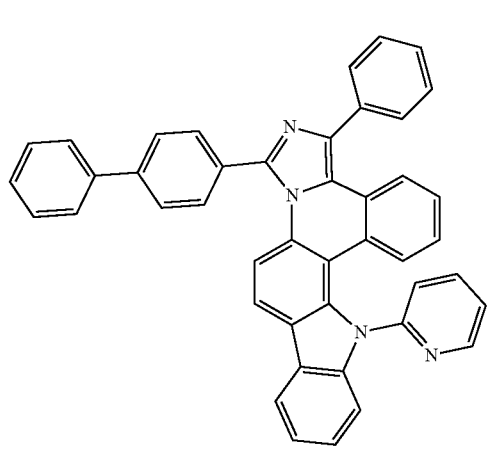

-continued
C-109
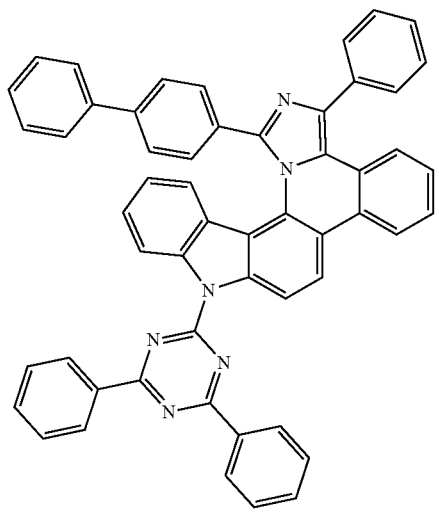
C-110
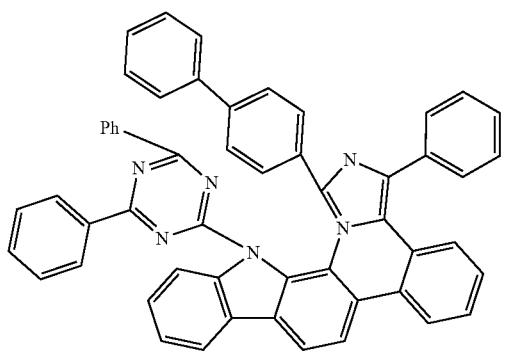
C-111
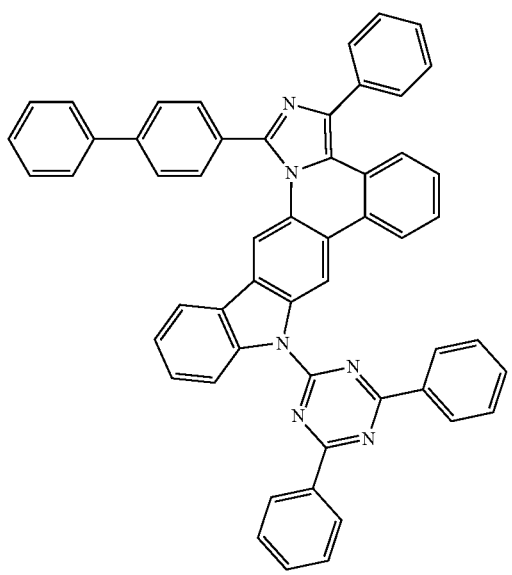
-continued
C-112
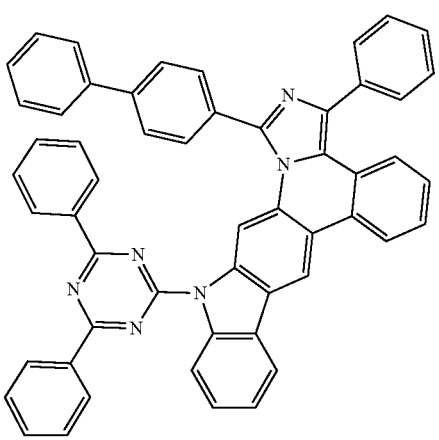
C-113
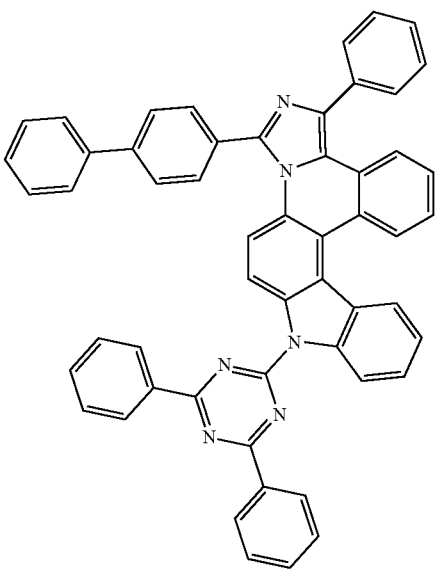
C-114
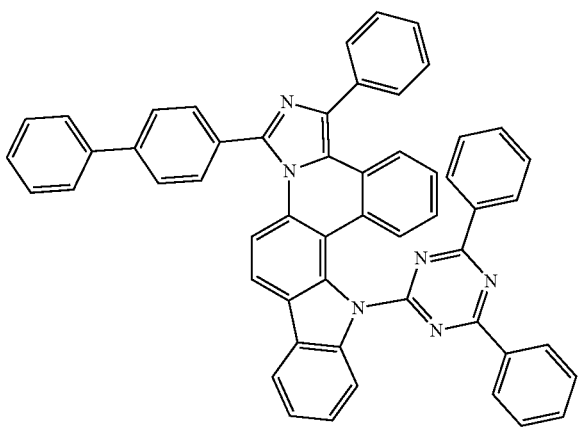

C-115
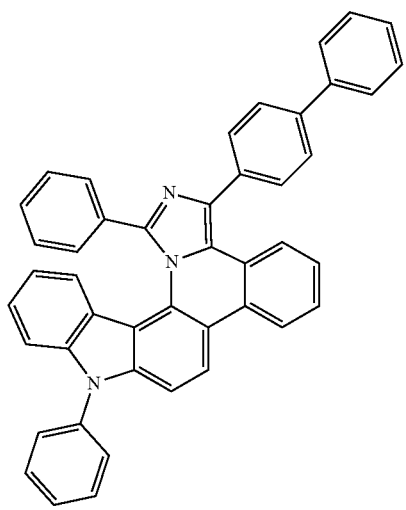
C-116
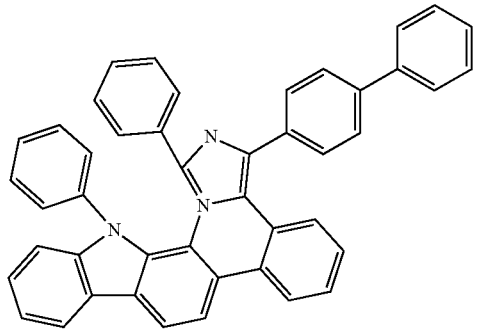
C-117
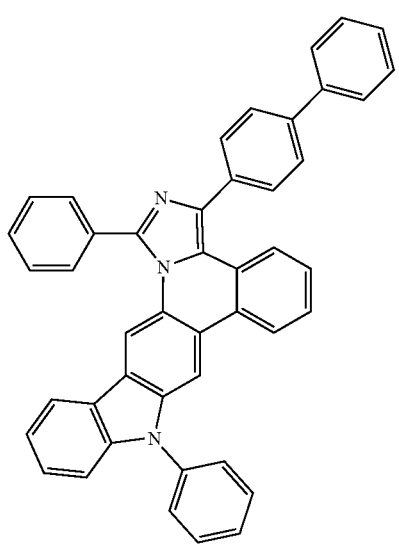
C-118
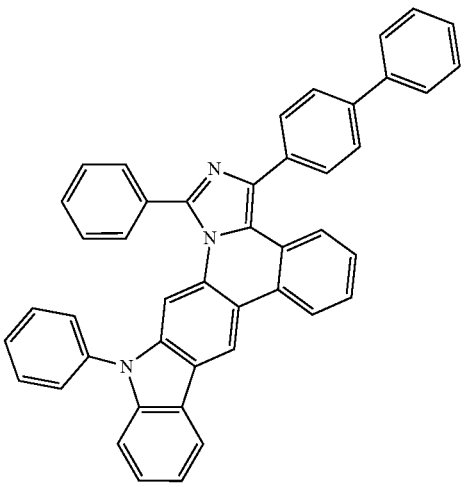
C-119
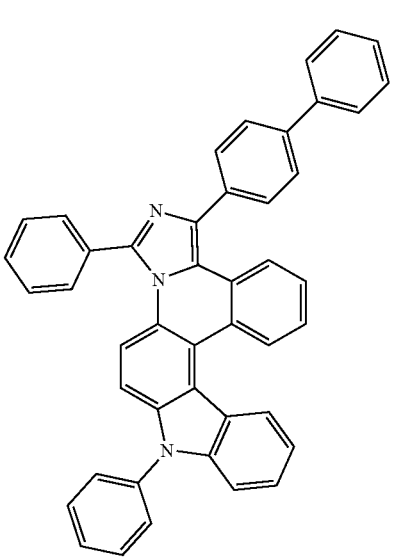
C-120
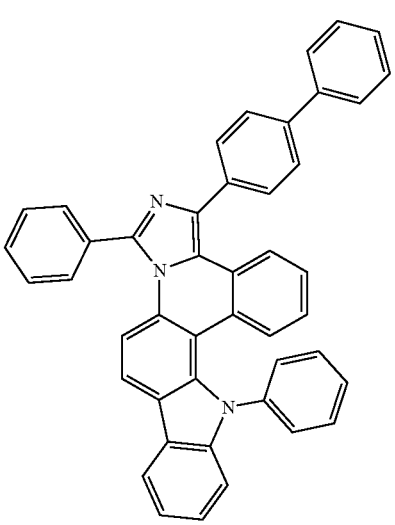

C-121
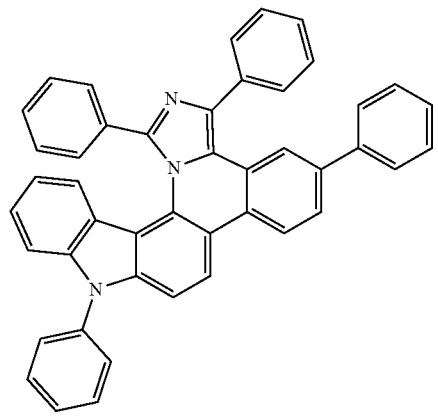
C-122
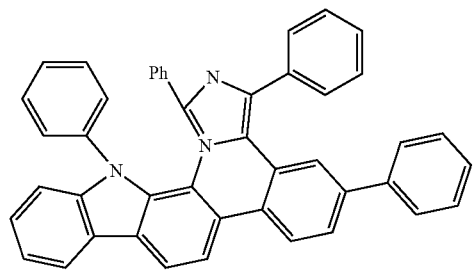
C-123
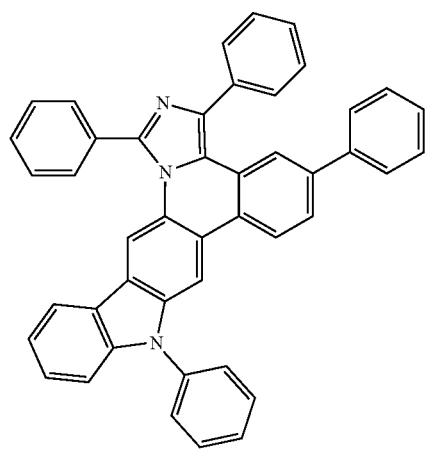
C-124
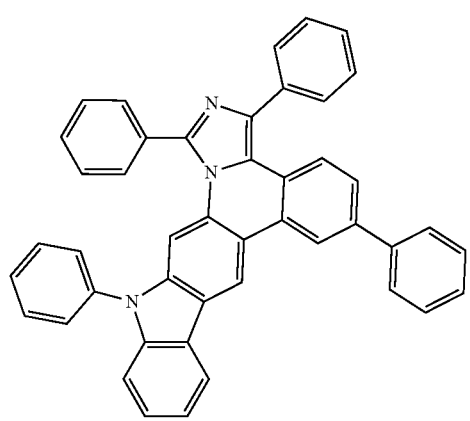
C-125
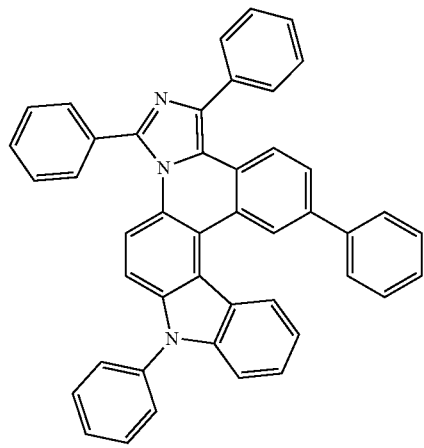
C-126
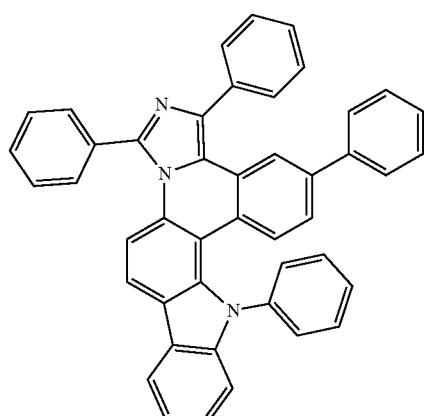
C-127
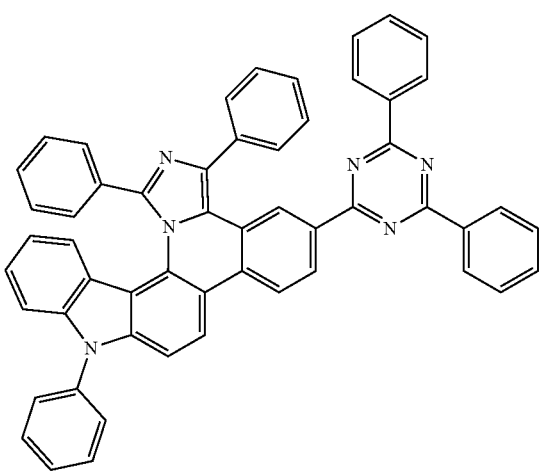

C-128
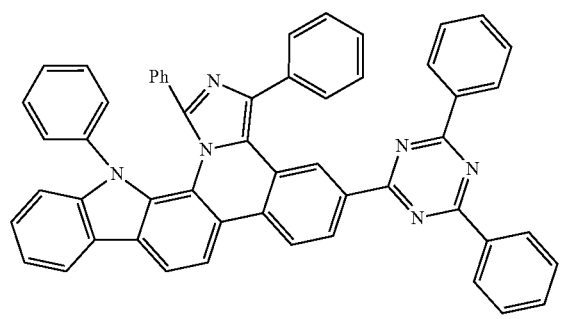
C-129
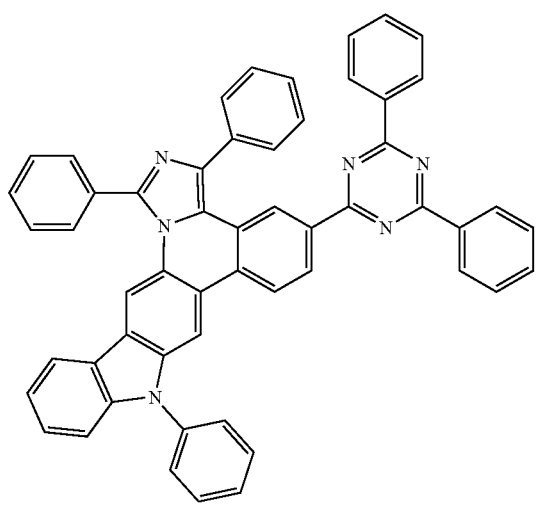
C-130
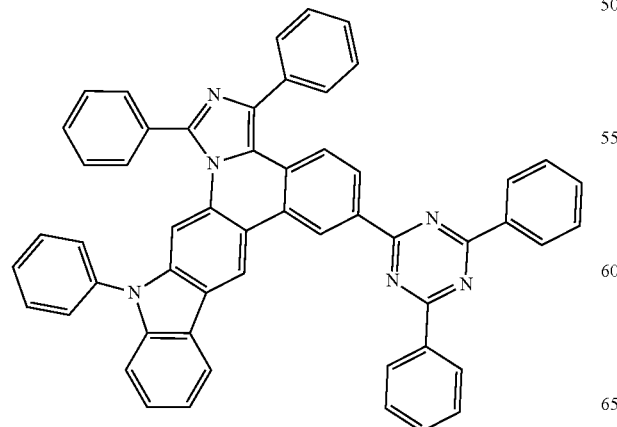
C-131
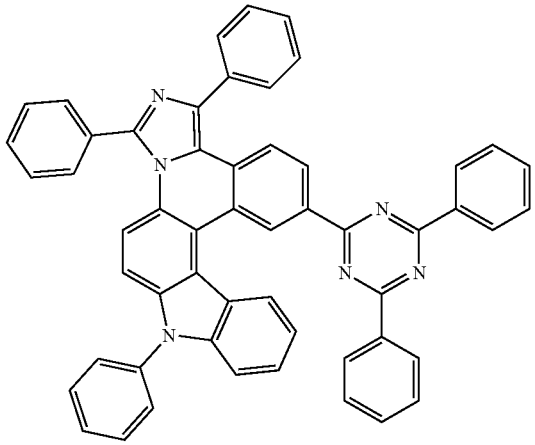
C-132
C-133
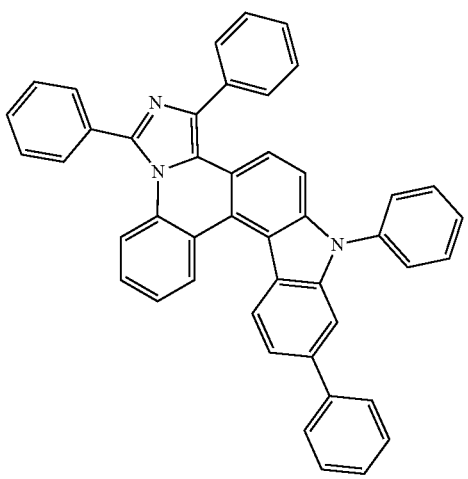

C-134
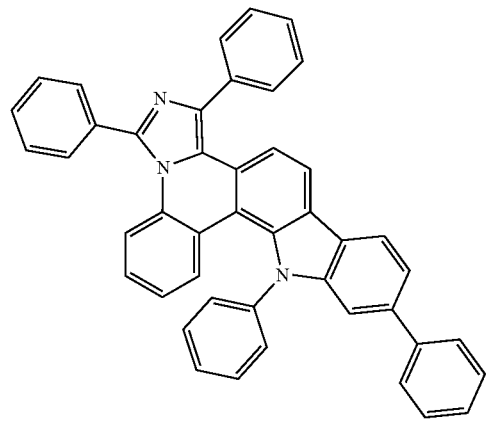
C-135
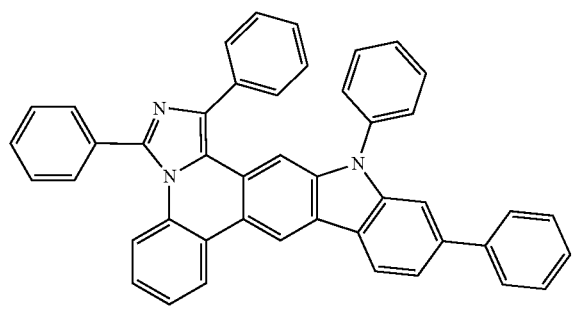
C-136
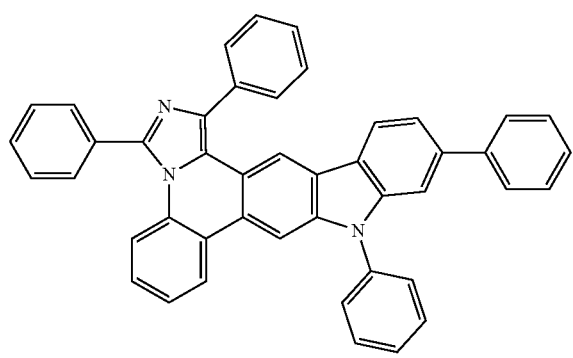
C-137
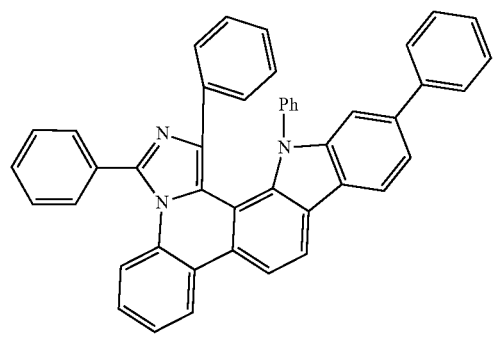
C-138
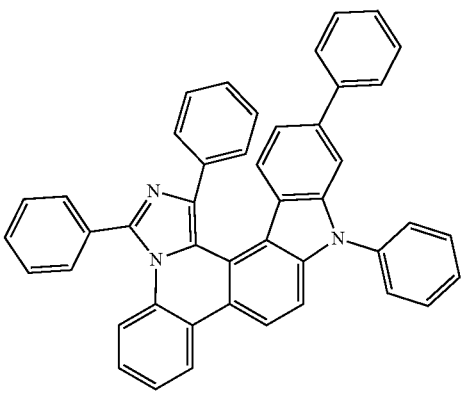
C-139
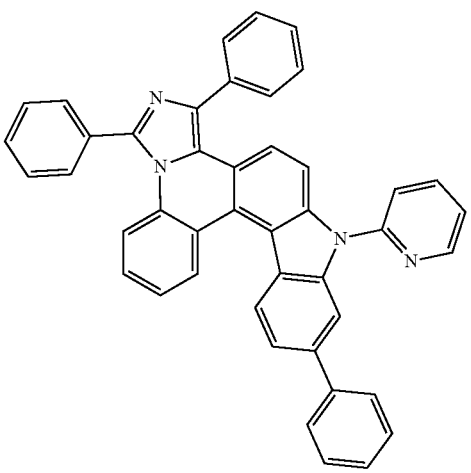
C-140
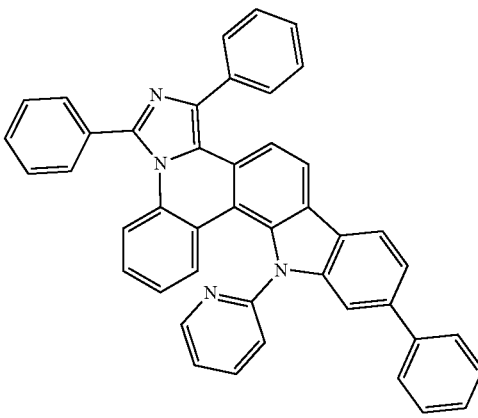
C-141
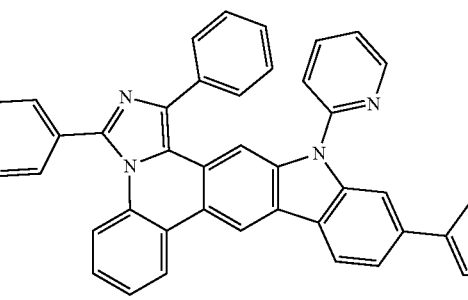

C-142
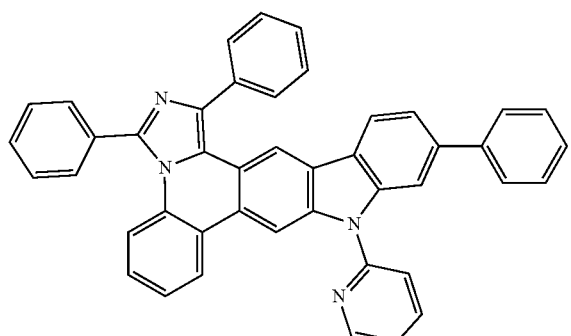
C-143
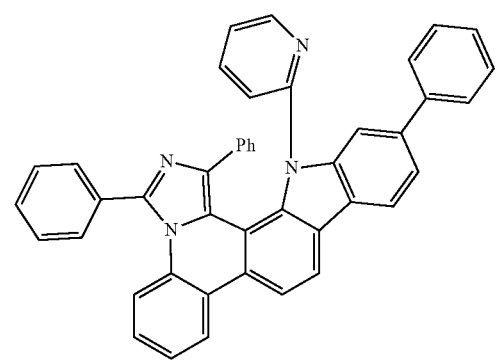
C-144
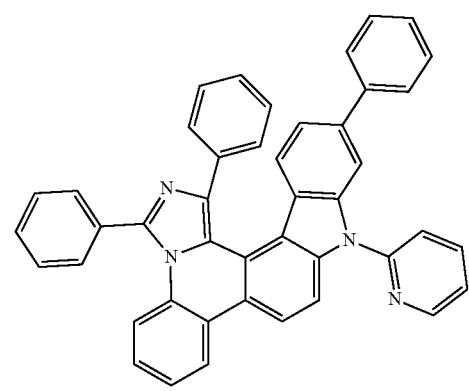
C-145
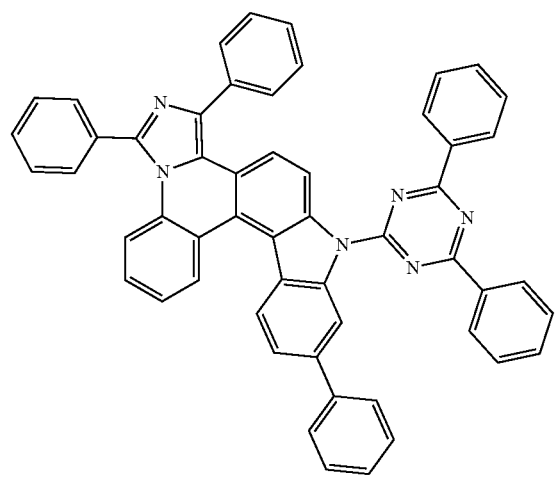
C-146
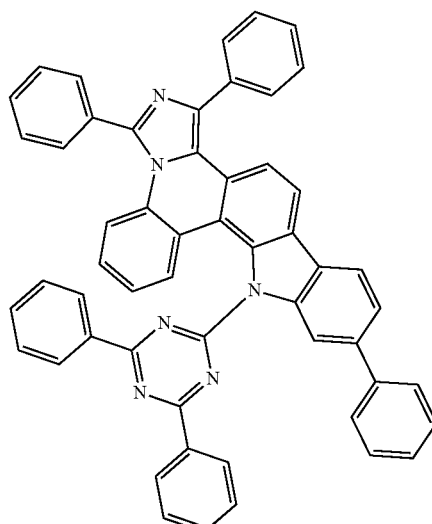
C-147
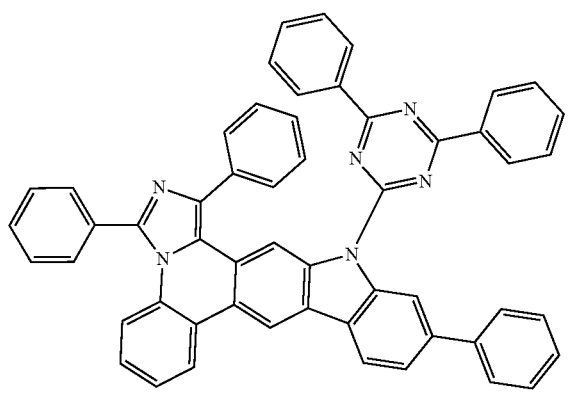
C-148
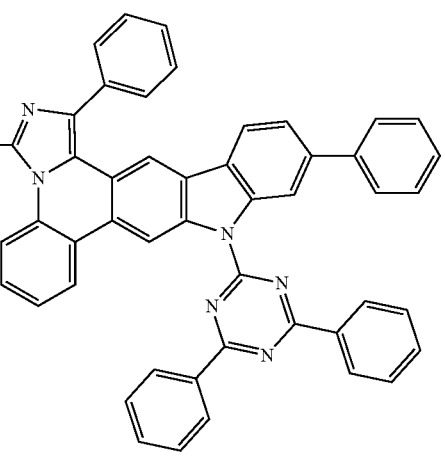

-continued
C-149
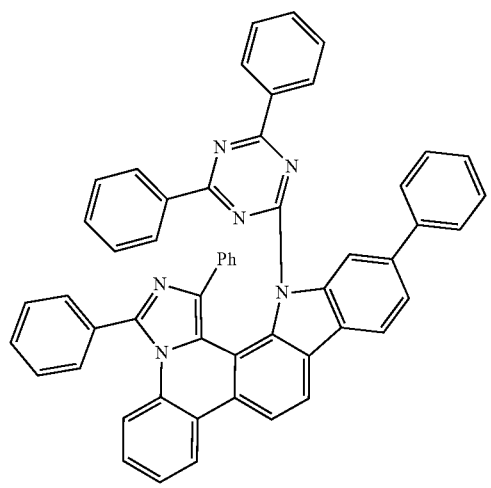
C-150
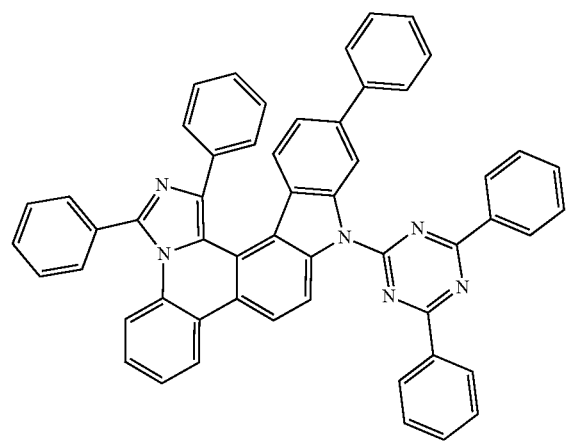
C-151
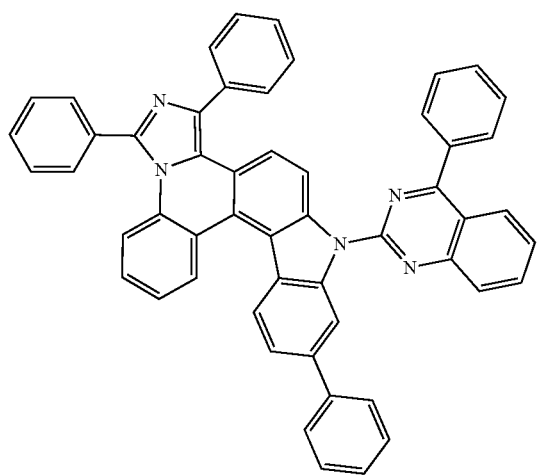
-continued
C-152
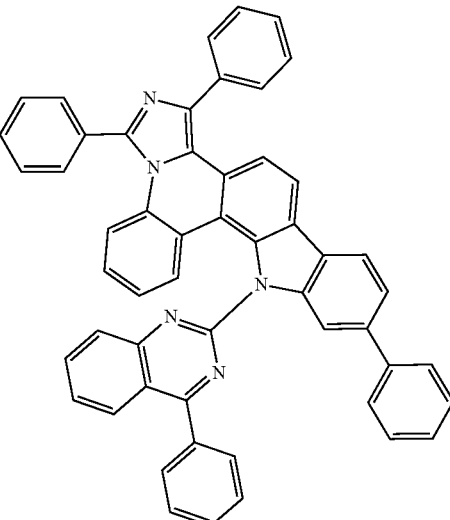
C-153
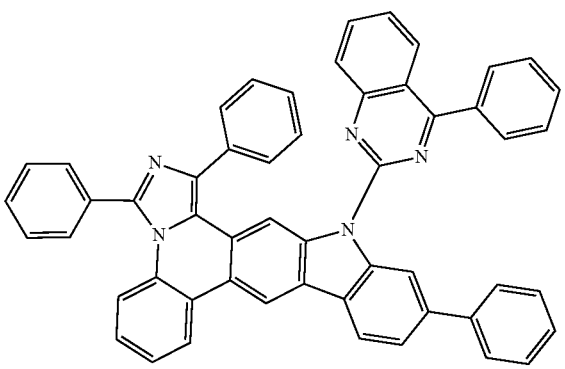
C-154
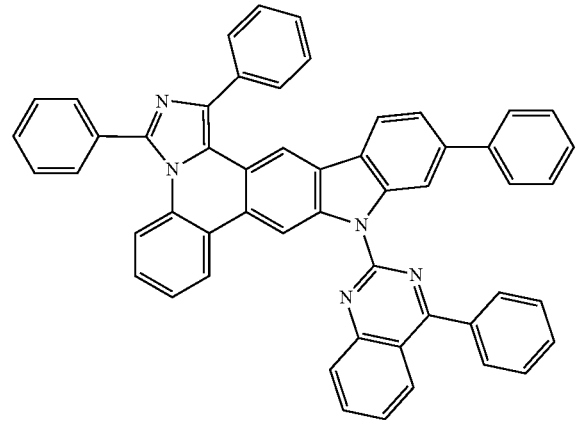

C-155
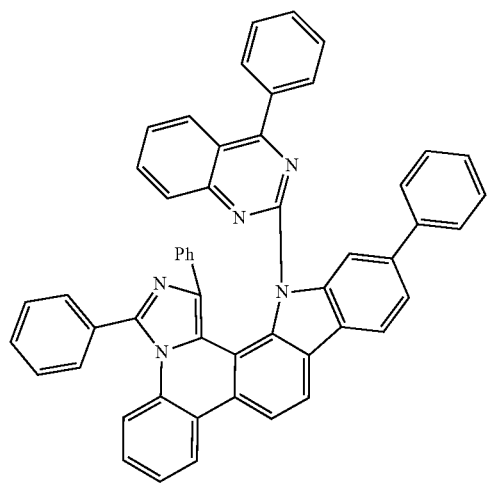
C-158
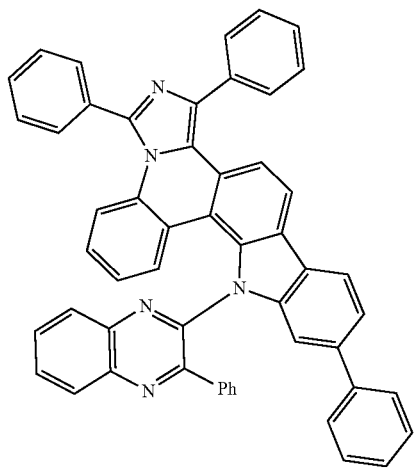
C-156
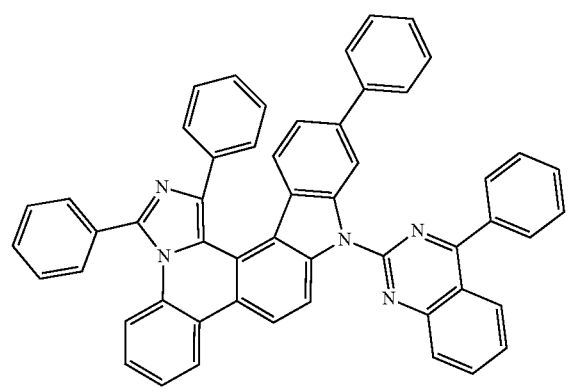
C-159
C-157
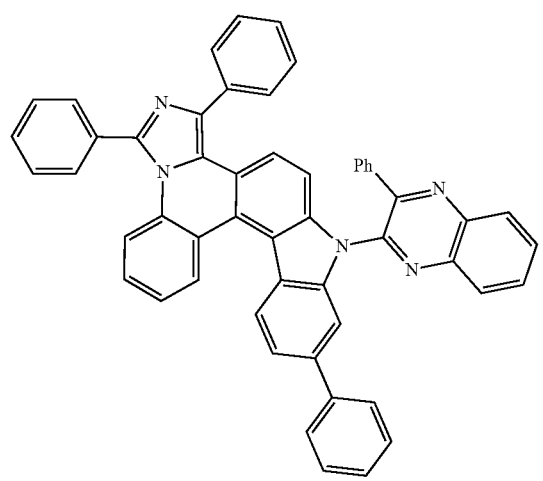
C-160
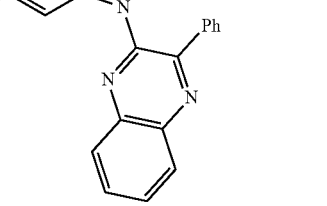

C-161
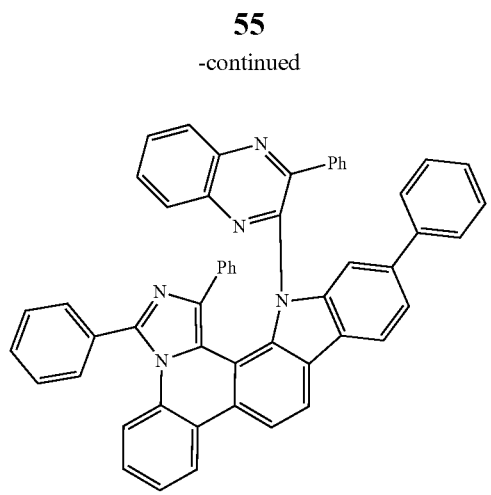
C-162
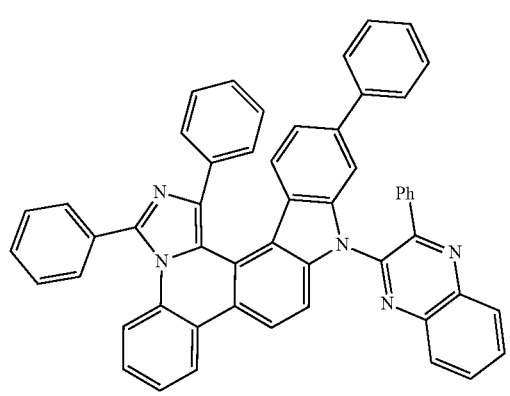
The compound of formula 1 according to the present disclosure can be prepared by a synthetic method known to a person skilled in the art. For example, it can be prepared according to the following reaction scheme.
[Reaction Scheme 1]
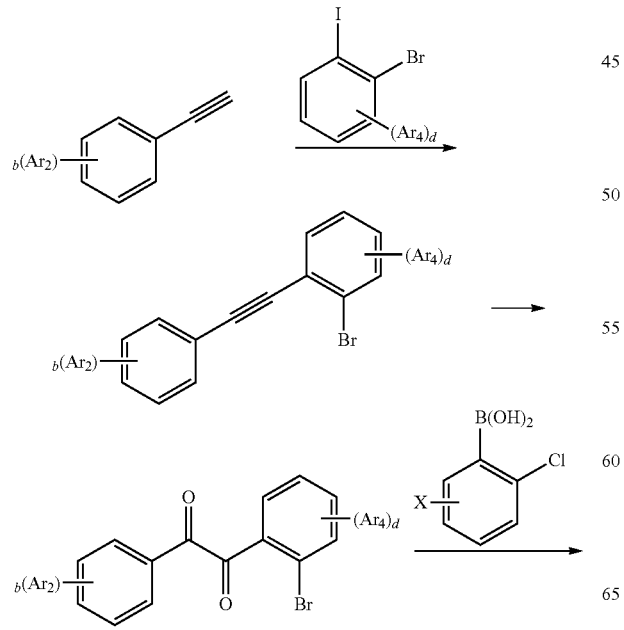
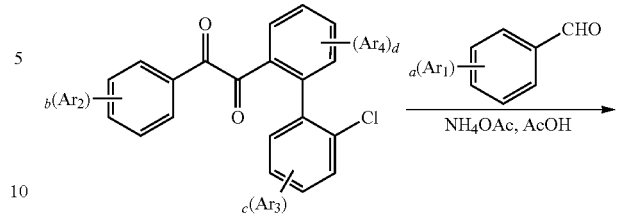
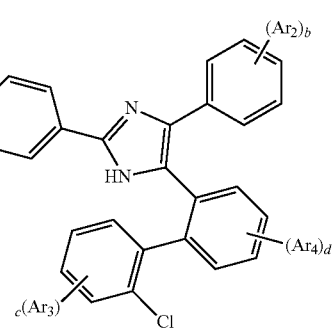
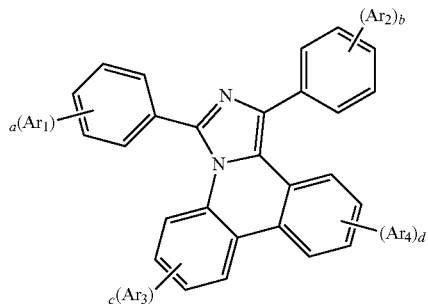
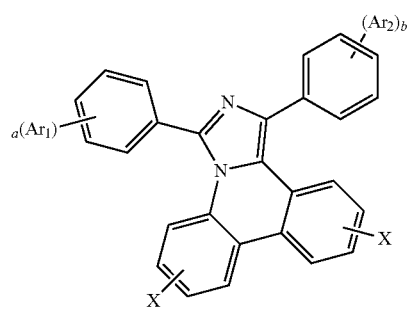

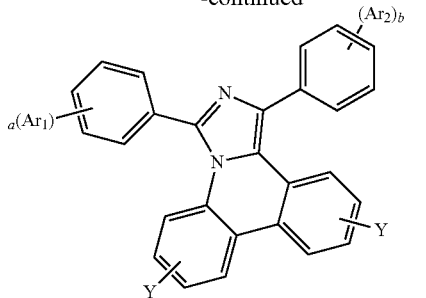

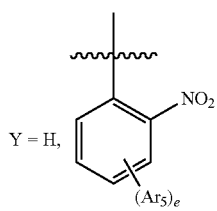

Y = H,

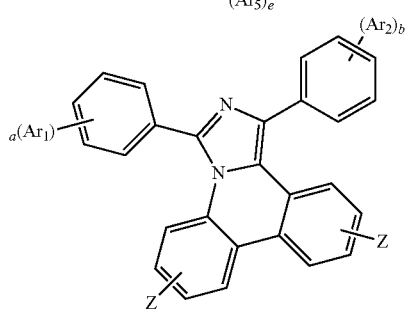

Z = H, 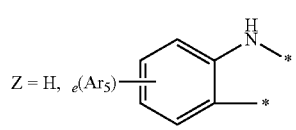

wherein Ar$_1$ to Ar$_6$, L$_1$, and a to e are as defined in formula 1, and X represents hydrogen or boronic acid ester.

The present disclosure provides an organic electroluminescent material comprising the organic electroluminescent compound of formula 1, and an organic electroluminescent device comprising the material.

The above material can be comprised of the organic electroluminescent compound according to the present disclosure alone, or can further include conventional materials generally used in organic electroluminescent materials.

The organic electroluminescent compound of formula 1 of the present disclosure may be comprised in one or more layers of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer; and preferably in one or more layers of the light-emitting layer, the electron buffer layer, and the electron transport layer. Where used in the light-emitting layer, the organic electroluminescent compound of formula 1 of the present disclosure can be comprised as a host material. In addition, where used in the electron buffer layer, the organic electroluminescent compound of formula 1 of the present disclosure can be comprised as an electron buffer material. In addition, where used in the electron transport layer, the organic electroluminescent compound of formula 1 of the present disclosure can be comprised as an electron transport material. Preferably, the light-emitting layer can further comprise one or more dopants. If necessary, the organic electroluminescent compound of the present disclosure can be used as a co-host material. That is, the light-emitting layer can additionally comprise a compound other than the organic electroluminescent compound of formula 1 of the present disclosure (first host material) as a second host material. Herein, the weight ratio of the first host material to the second host material is in the range of 1:99 to 99:1.

The second host material can be any of the known hosts. The host selected from the group consisting of the compounds of formulas 11 to 16 below may be preferable.

$$H-(Cz-L_4)_h-M \tag{11}$$

$$H-(Cz)_i-L_4-M \tag{12}$$

(13)

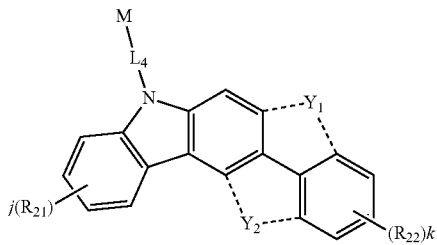

(14)

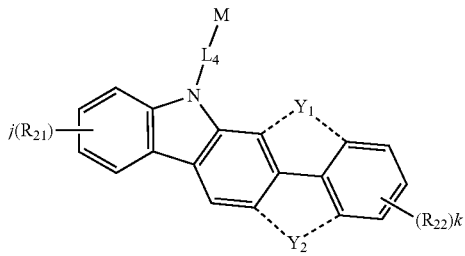

(15)

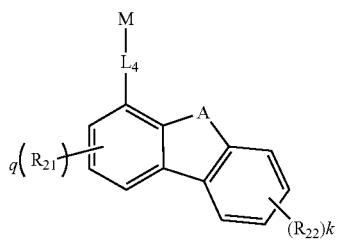

wherein

Cz represents the following structure:

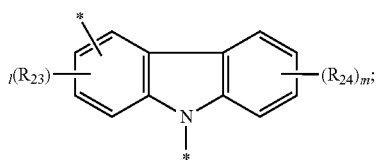

A represents —O— or —S—; and $R_{21}$ to $R_{24}$, each independently, represent hydrogen, deuterium, a halogen, a substituted or unsubstituted (C1-C30)alkyl, a substituted or unsubstituted (C6-C30)aryl, a substituted or unsubstituted (5- to 30-membered)heteroaryl, or —$SiR_{25}R_{26}R_{27}$; in which $R_{25}$ to $R_{27}$, each independently, represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted (5- to 30-membered)heteroarylene; M represents a substituted or unsubstituted (C6-C30)aryl, or a substituted or unsubstituted (5- to 30-membered)heteroaryl; $Y_1$ and $Y_2$, each independently, represent —O—, —S—, —N($R_{31}$)— or —C($R_{32}$)($R_{33}$)—, with the proviso that $Y_1$ and $Y_2$ are not present simultaneously; $R_{31}$ to $R_{33}$, each independently, represent a substituted or unsubstituted (C1-C30)alkyl, a substituted or unsubstituted (C6-C30)aryl, or a substituted or unsubstituted (5- to 30-membered)heteroaryl; $R_{32}$ and $R_{33}$ may be the same or different; h and i, each independently, represent an integer of 1 to 3; j, k, l, and m, each independently, represent an integer of 1 to 4; q represents an integer of 1 to 3; if h, i, j, k, l, m, or q represents an integer of 2 or more, each (Cz-$L_4$), each (Cz), each $R_{21}$, each $R_{22}$, each $R_{23}$, or each $R_{24}$ may be the same or different.

(16)

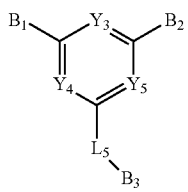

wherein $Y_3$ to $Y_5$, each independently, represent $CR_{34}$ or N;

$R_{34}$ represents hydrogen, a substituted or unsubstituted (C1-C30)alkyl, a substituted or unsubstituted (C6-C30)aryl, or a substituted or unsubstituted (5- to 30-membered)heteroaryl;

$B_1$ and $B_2$, each independently, represent hydrogen, a substituted or unsubstituted (C6-C30)aryl, or a substituted or unsubstituted (5- to 30-membered)heteroaryl;

$B_3$ represents a substituted or unsubstituted (C6-C30)aryl, or a substituted or unsubstituted (5- to 30-membered)heteroaryl; and $L_5$ represents a single bond, a substituted or unsubstituted (C6-C30)arylene, or a substituted or unsubstituted (5- to 30-membered)heteroarylene.

Specifically, the examples of the second host material are as follows, but are not limited thereto.

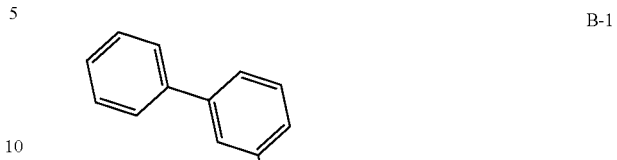

B-1

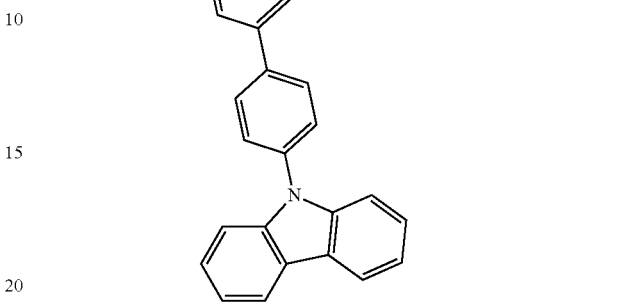

B-2

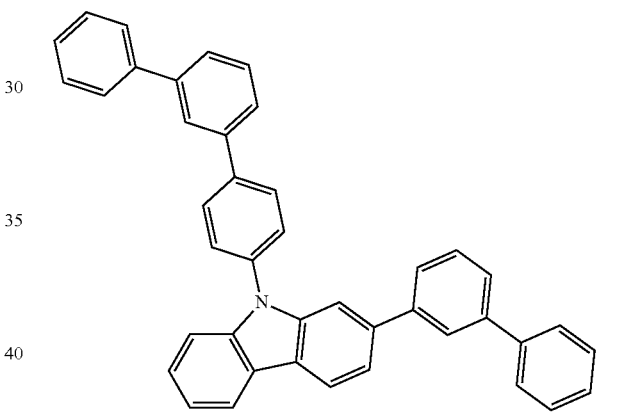

B-3

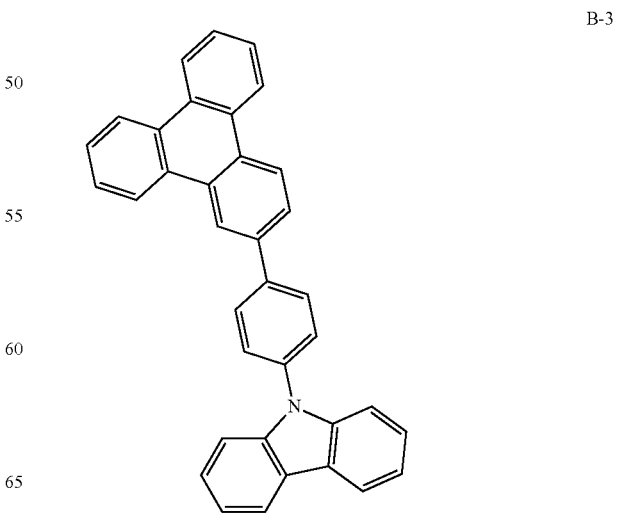

-continued
B-4
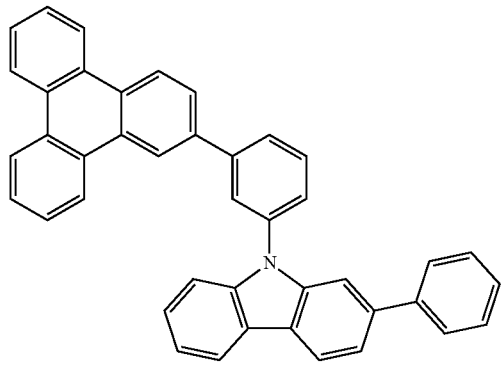
B-5
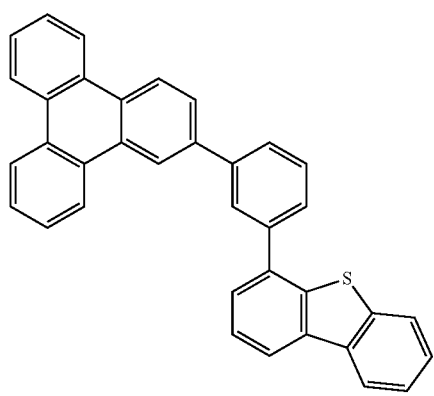
B-6
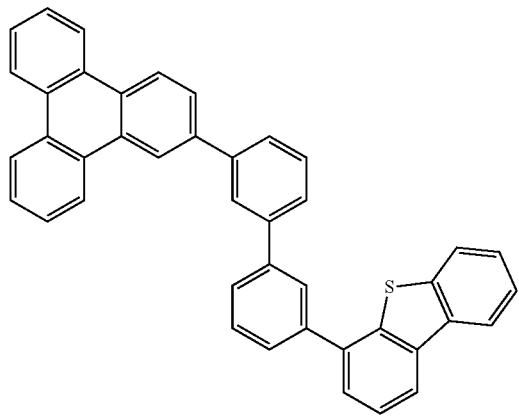
B-7
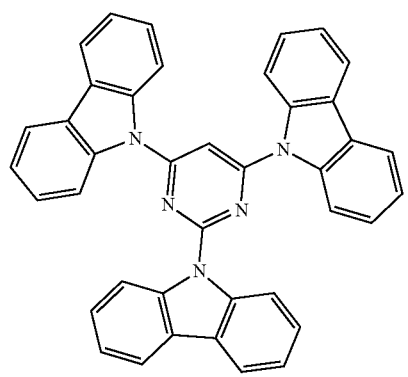
B-8
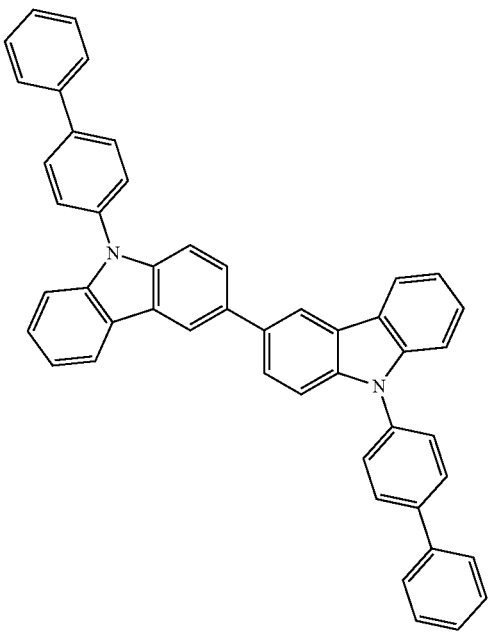
B-9
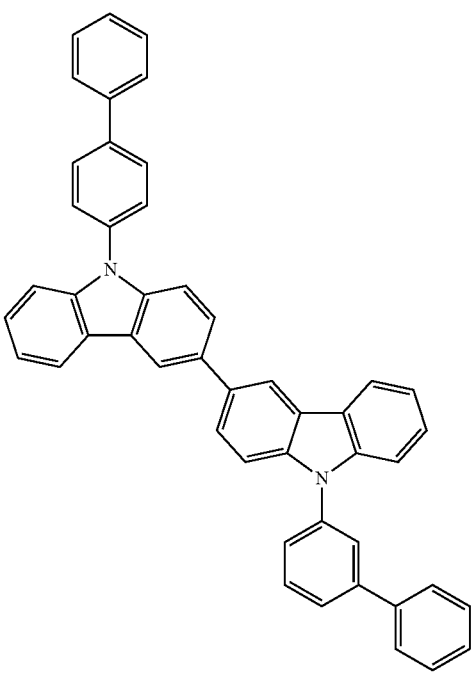

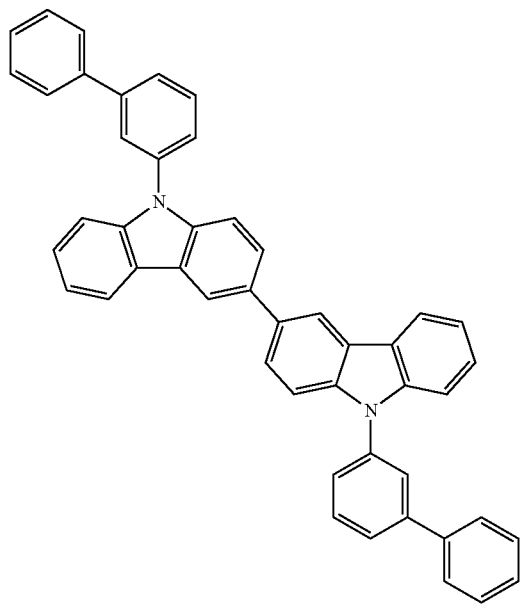
B-10
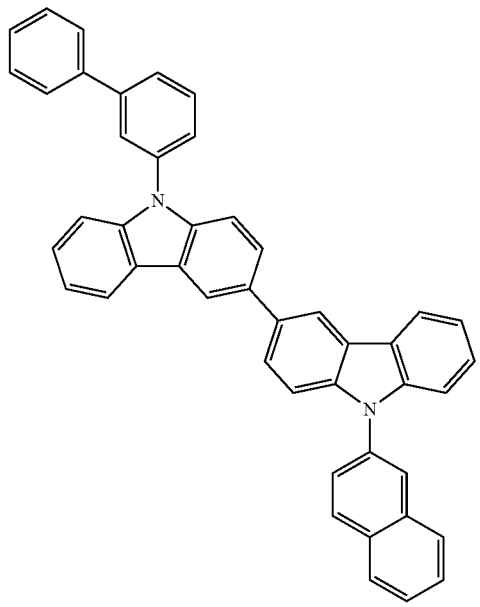
B-12
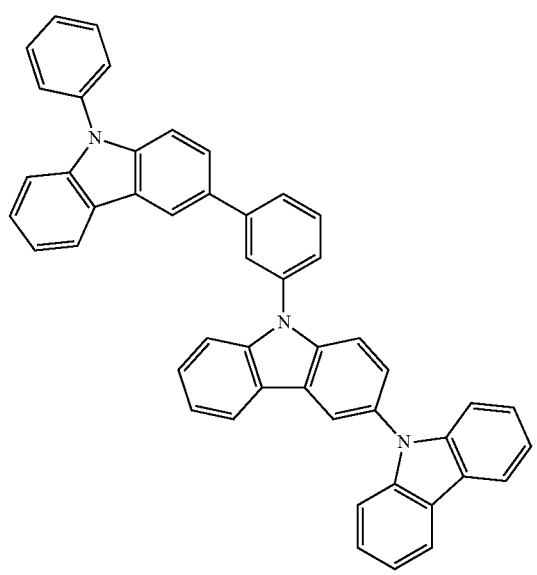
B-13
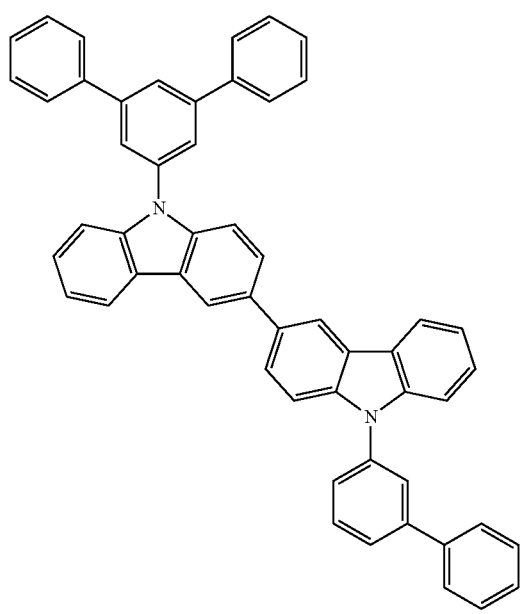
B-11
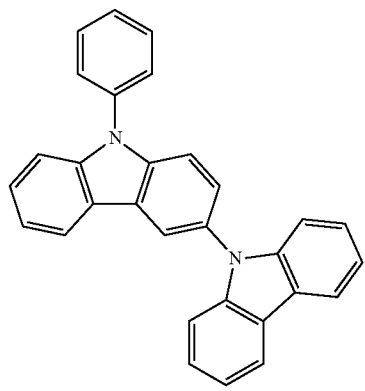
B-14

B-15
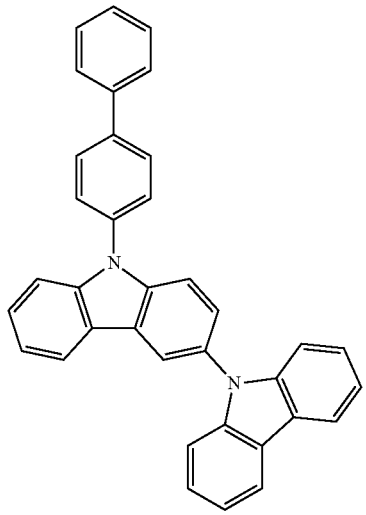
B-16
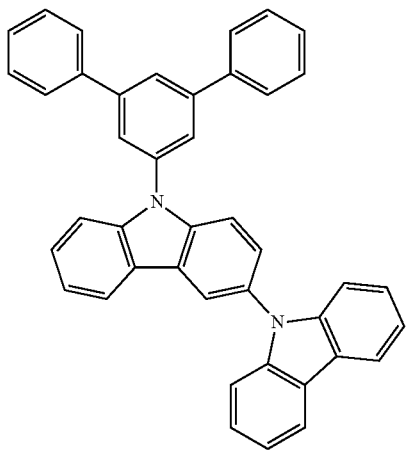
B-17
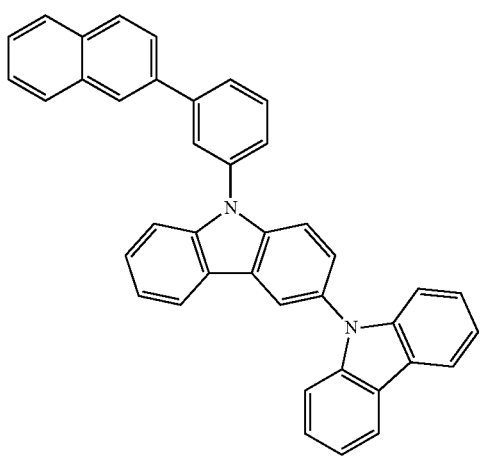
B-18
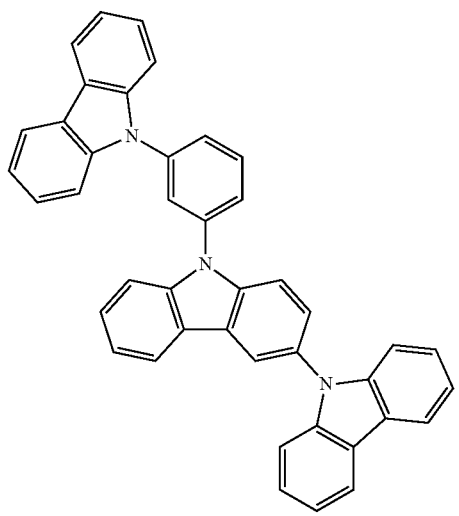
B-19
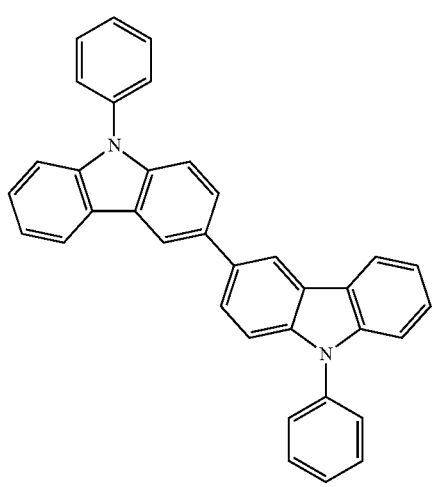
B-20
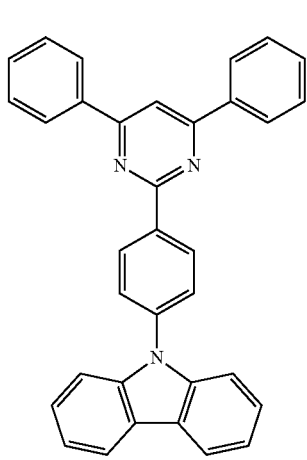

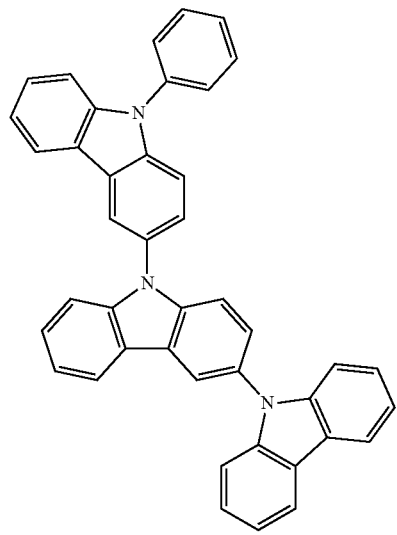
B-21
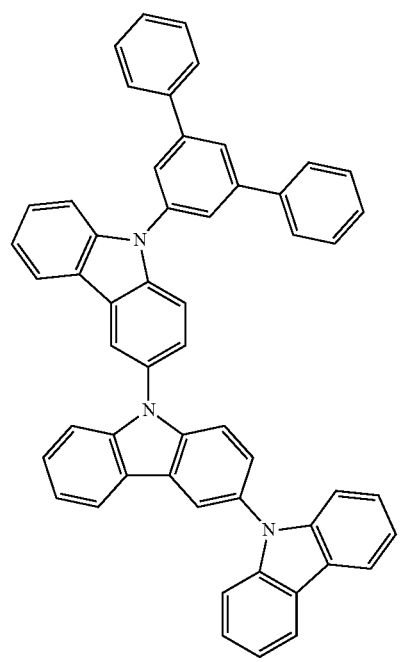
B-23
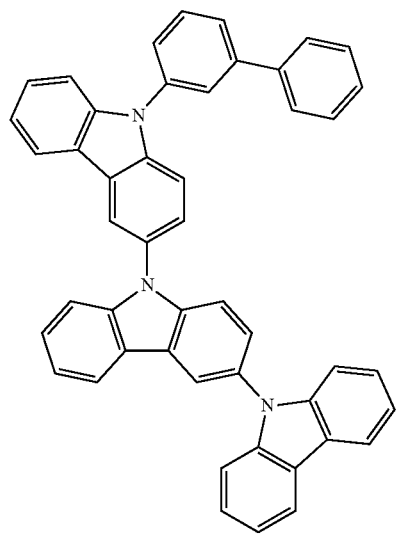
B-22
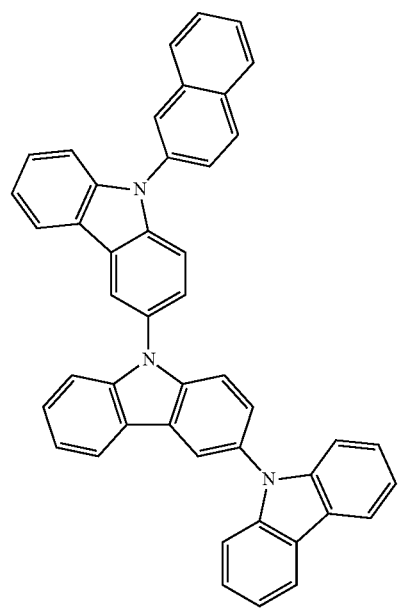
B-24

B-25
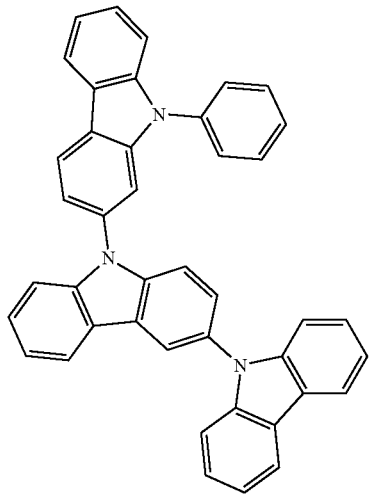
B-26
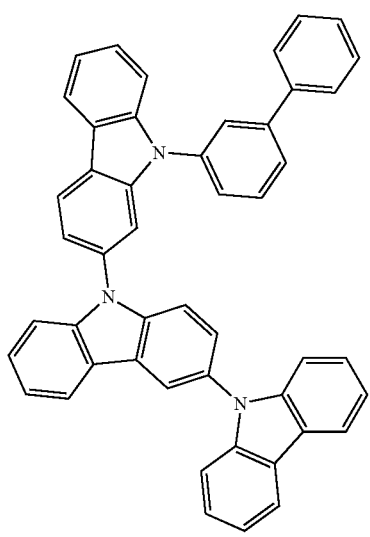
B-27
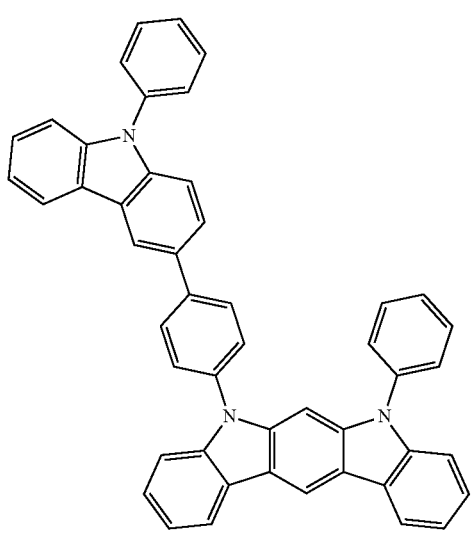
B-28
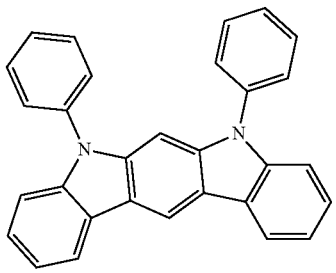
B-29
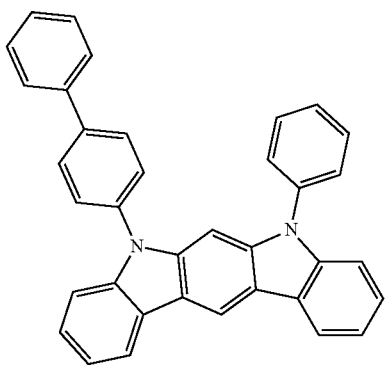
B-30
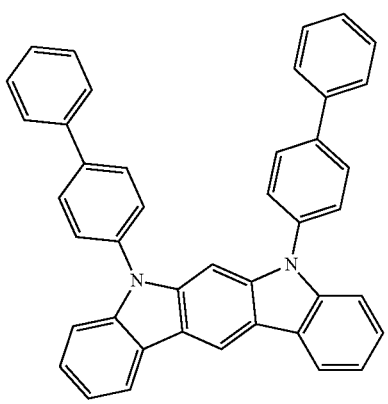
B-31
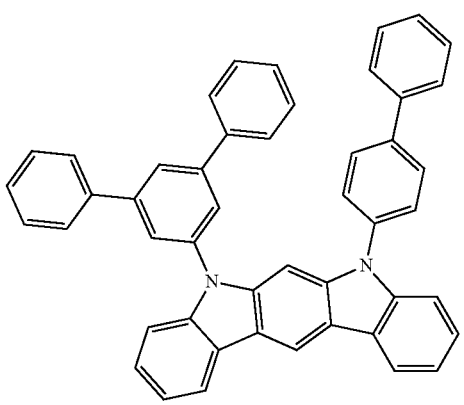

B-32
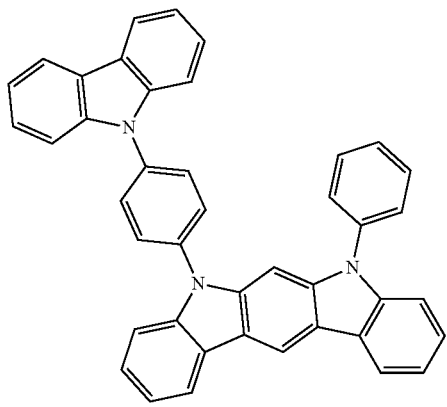
B-33
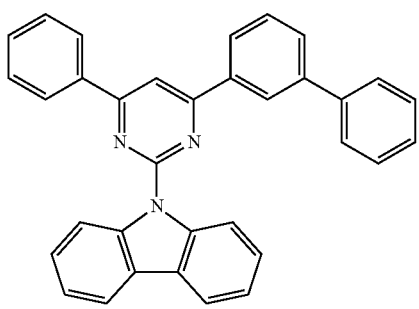
B-34
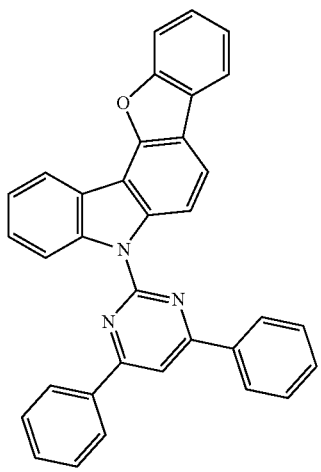
B-35
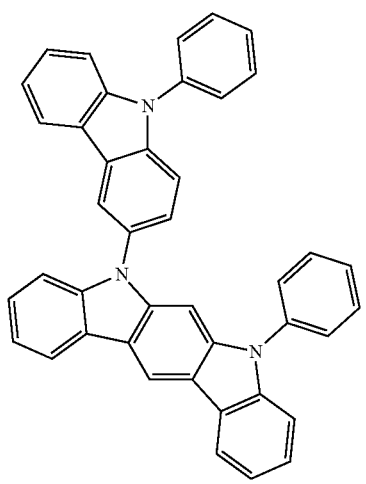
B-36
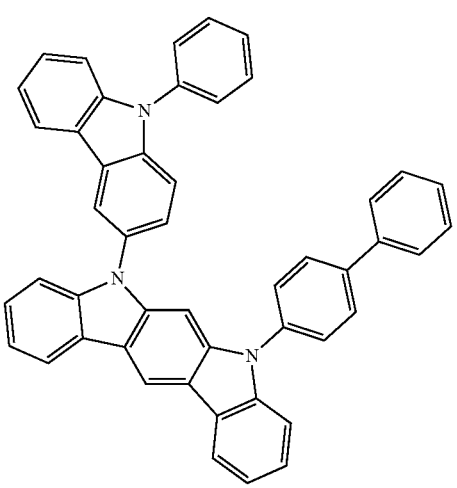
B-37
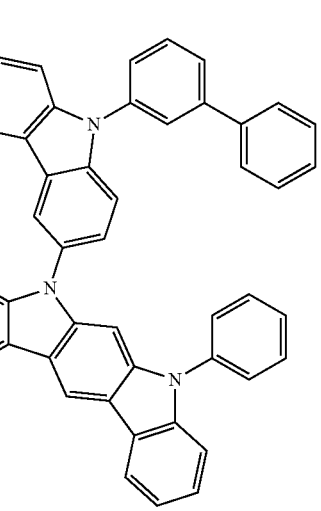
B-38
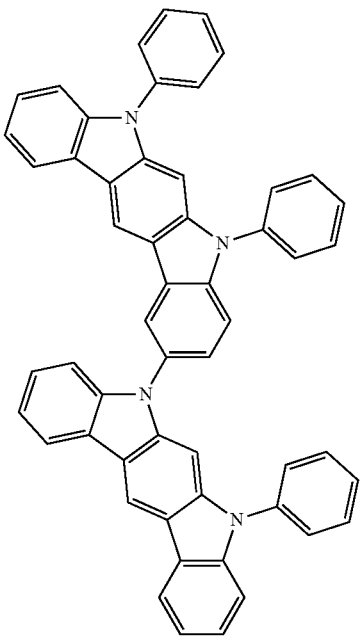

B-39 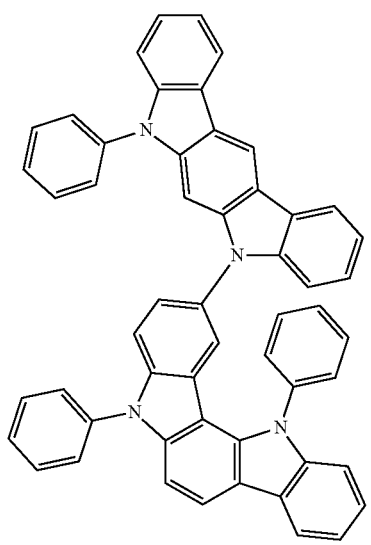
B-40 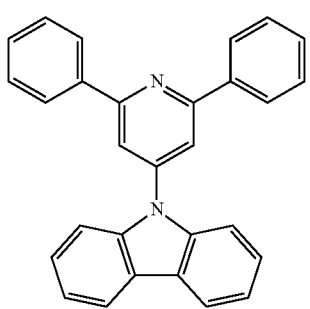
B-41 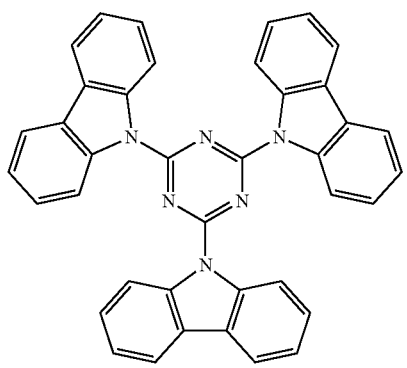
B-42 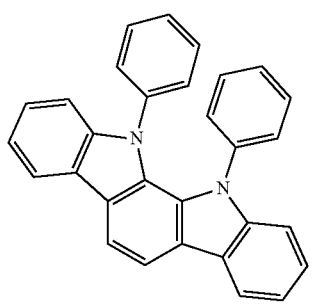
B-43 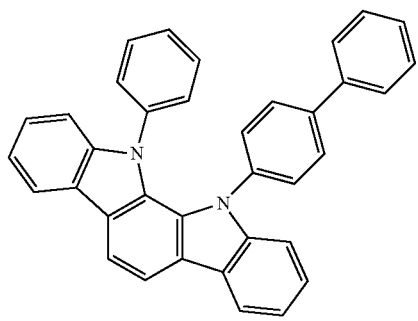
B-44 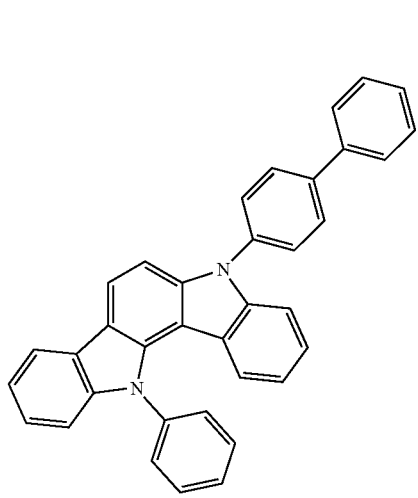
B-45 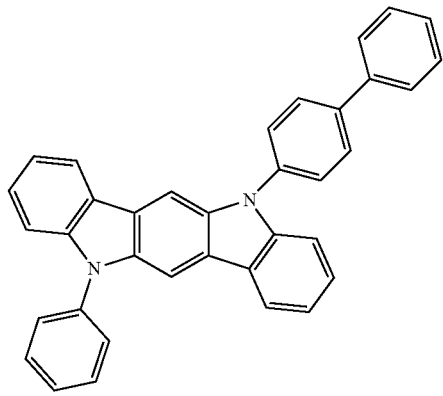
B-46 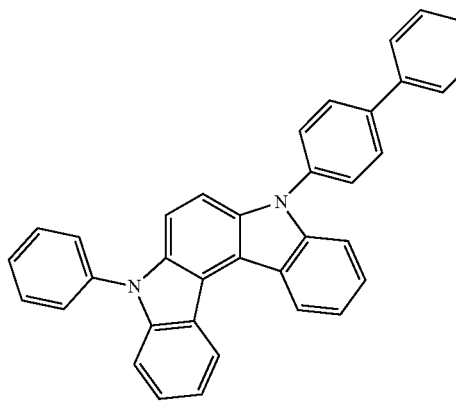

B-47
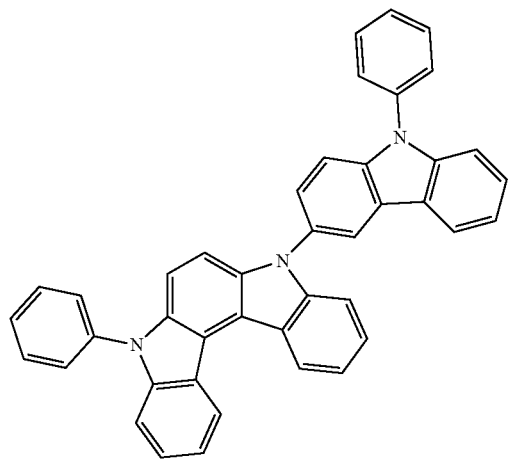
B-48
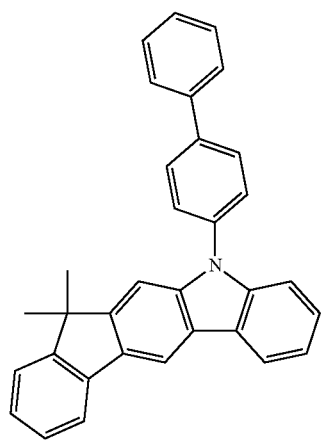
B-49
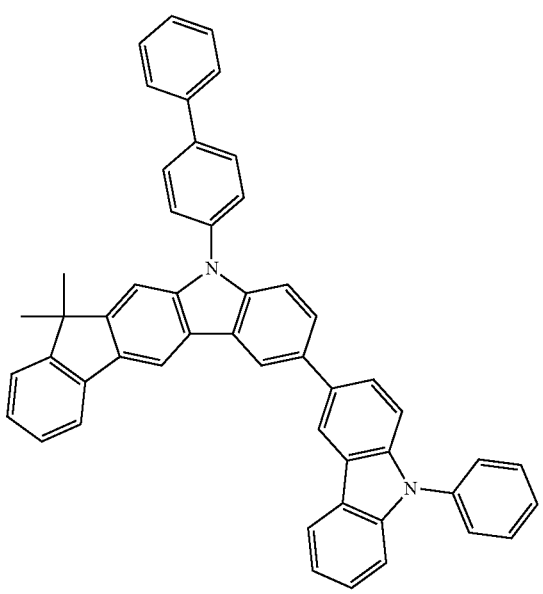
B-50
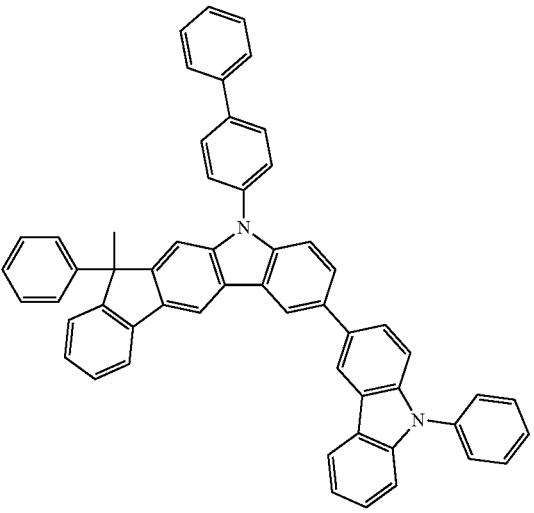
B-51
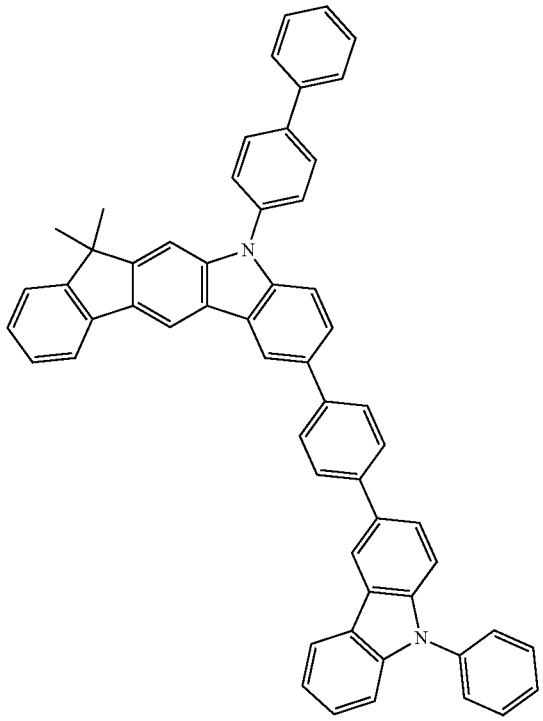

B-52
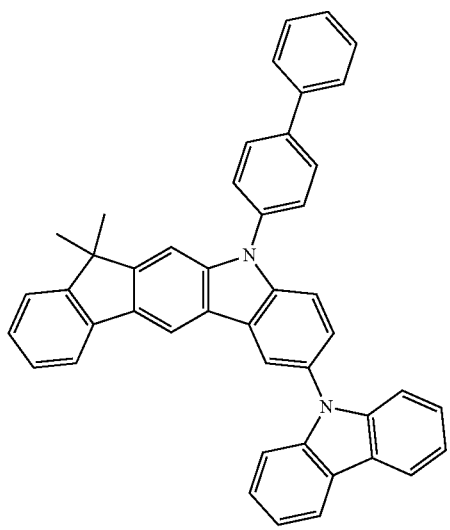
B-53
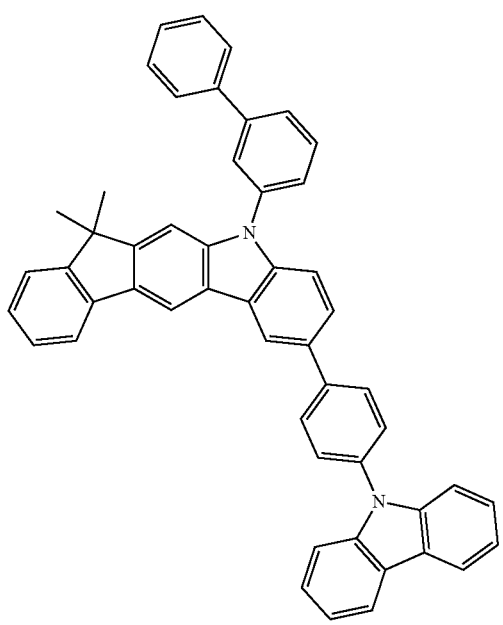
B-55
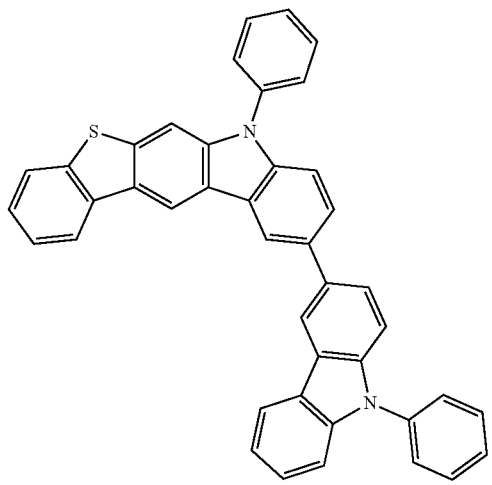
B-56
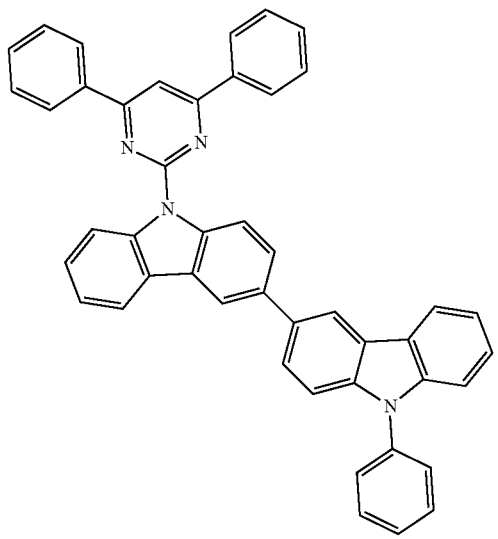
B-54

B-57
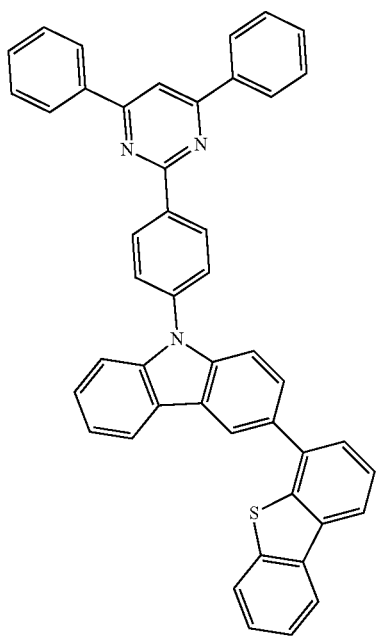
B-58
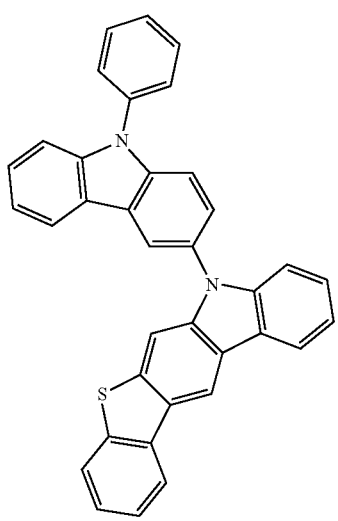
B-59
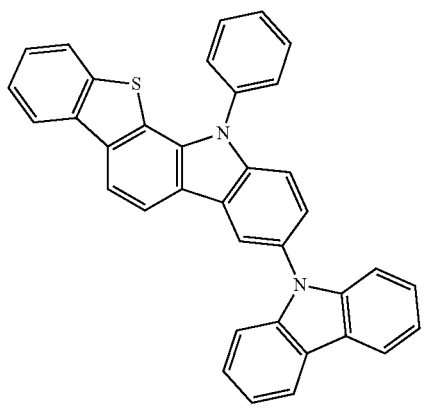
B-60
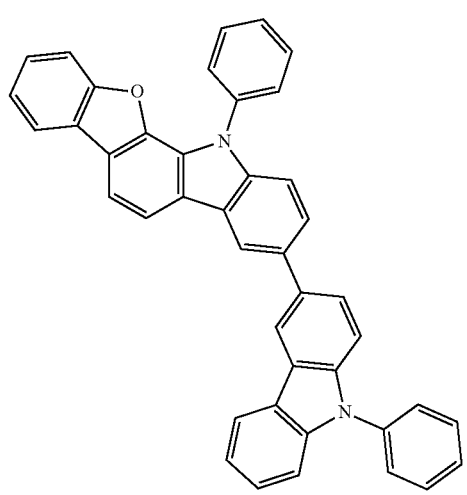
B-61
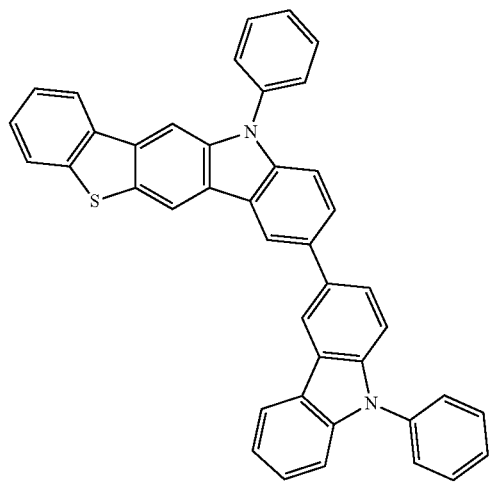
B-62
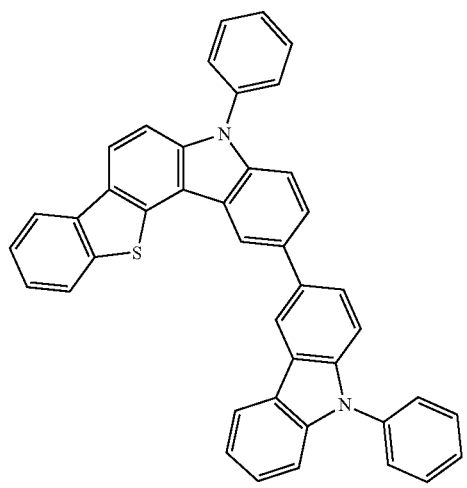

B-63
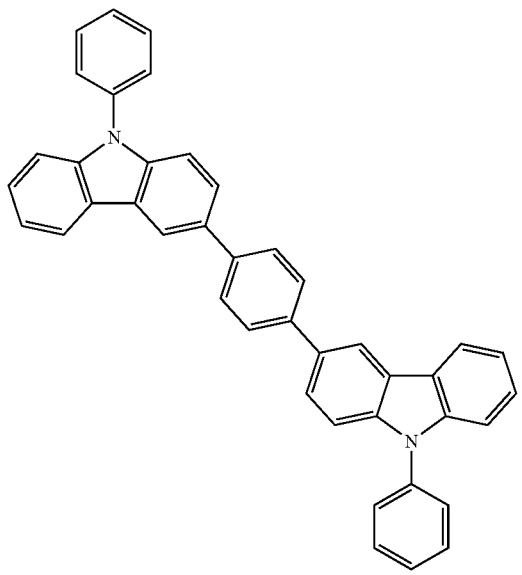
B-64
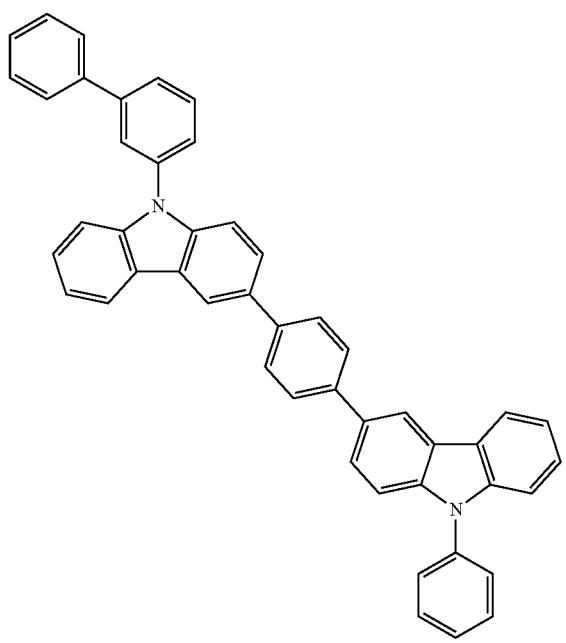
B-65
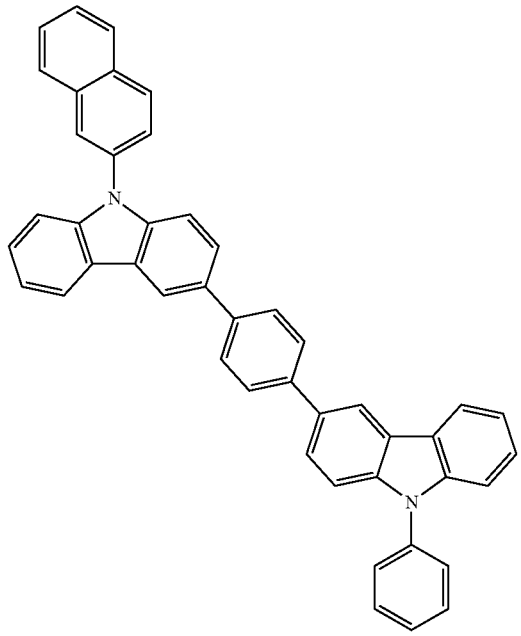
B-66
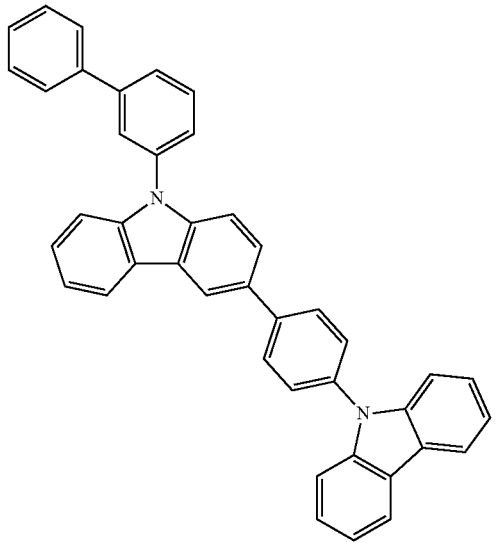

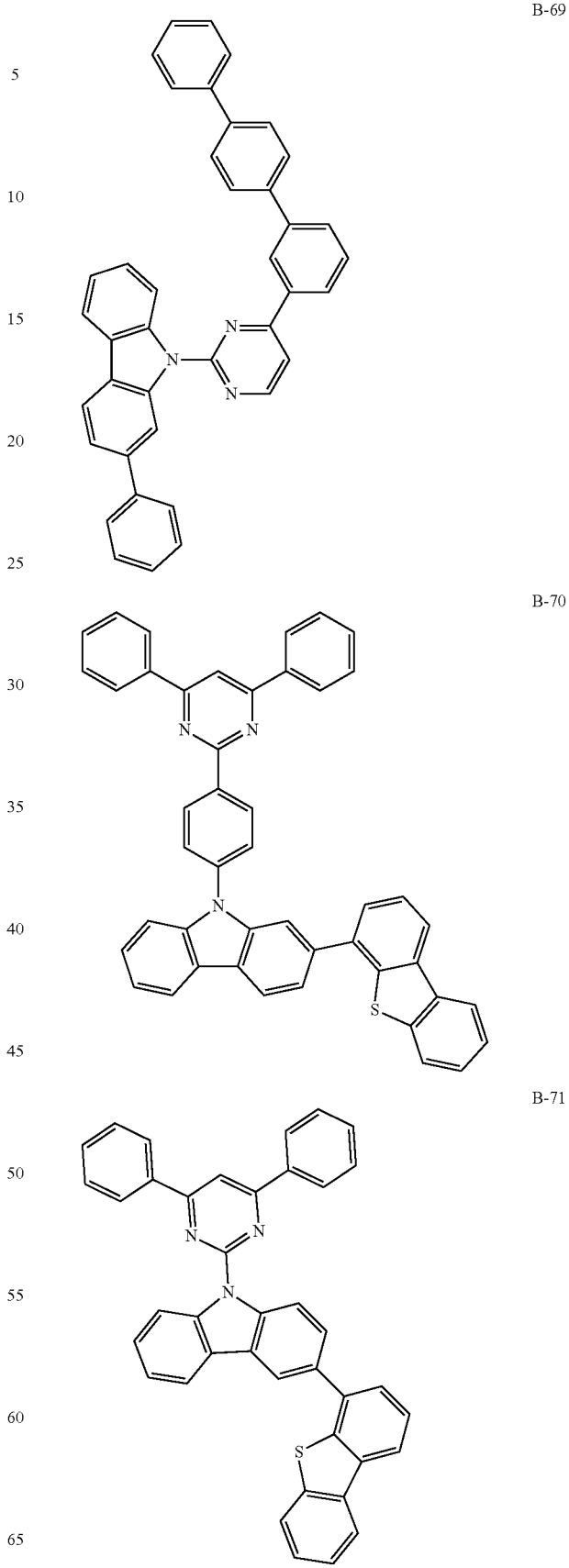

B-72
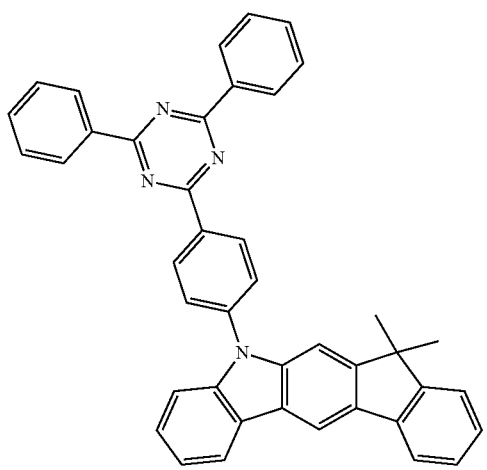
B-73
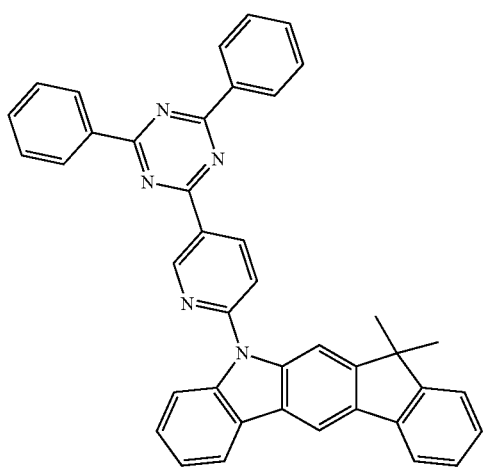
B-74
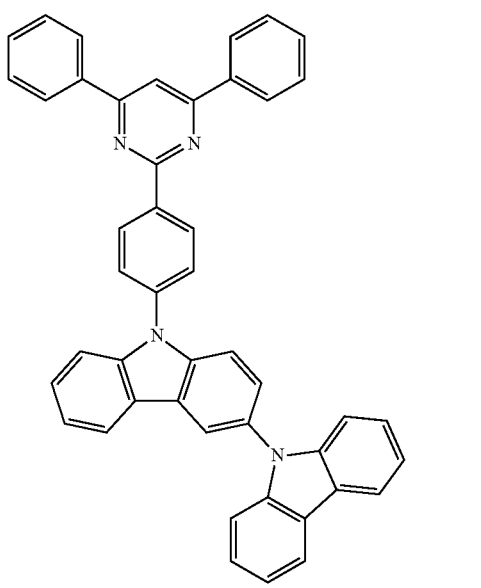
B-75
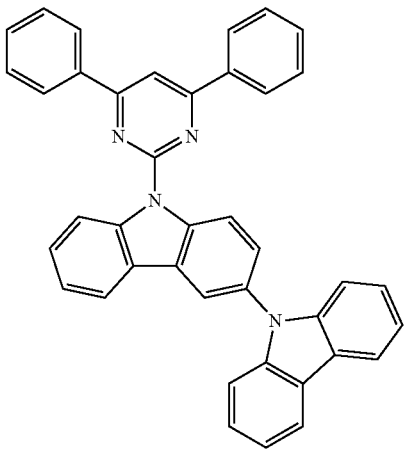
B-76
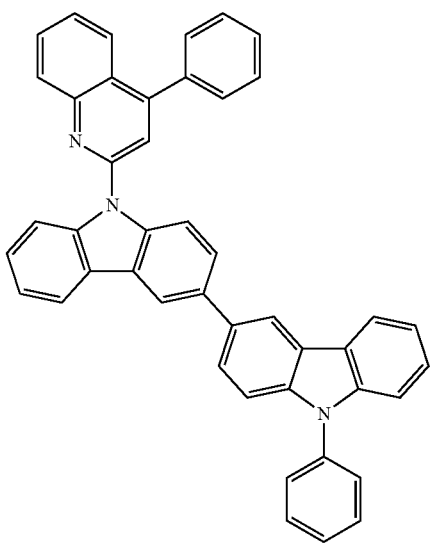
B-77
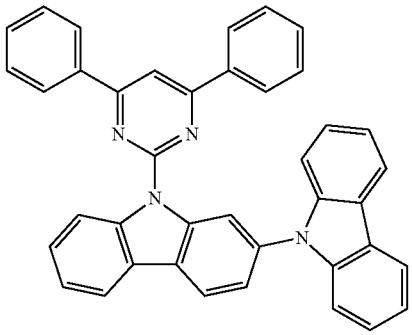

-continued
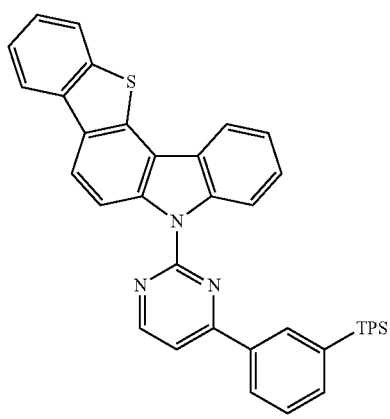
B-78
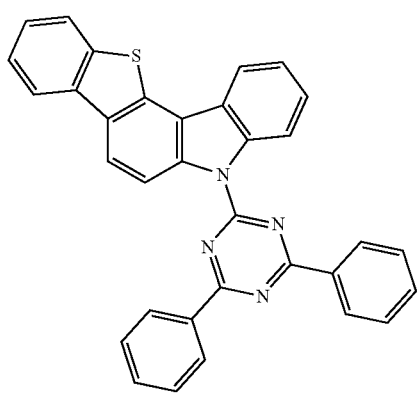
B-79
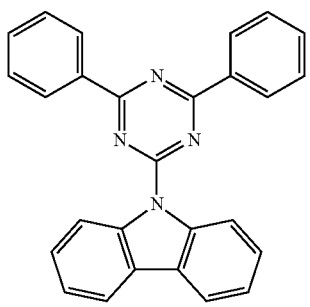
B-80
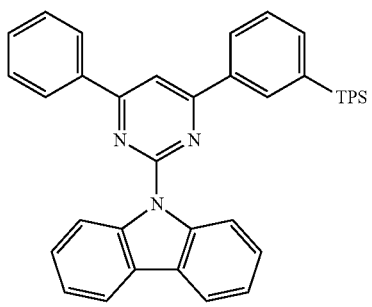
B-81
-continued
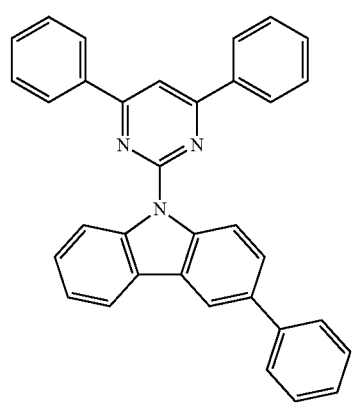
B-82
B-83
B-84
B-85

B-86
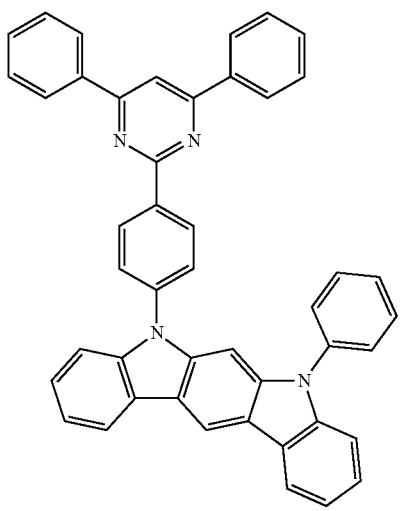
B-89
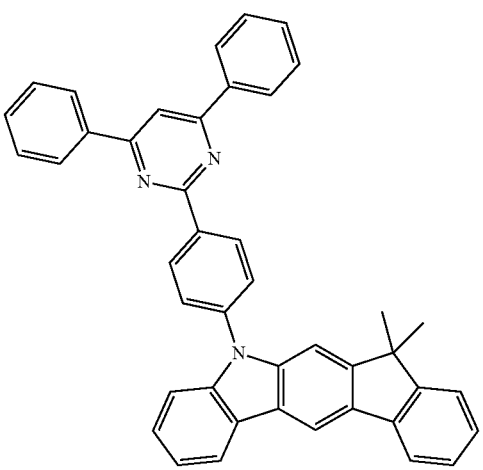
B-87
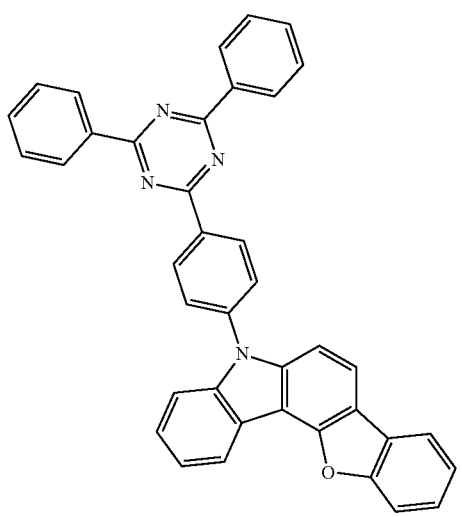
B-90
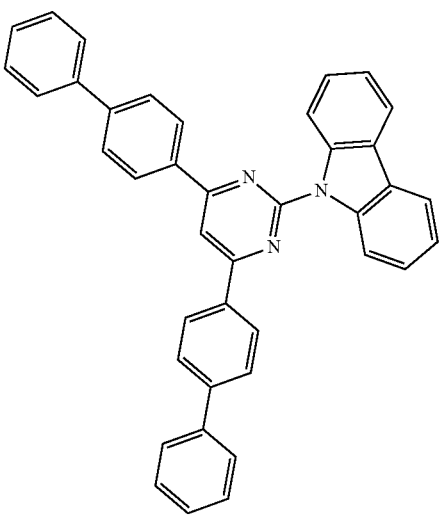
B-88
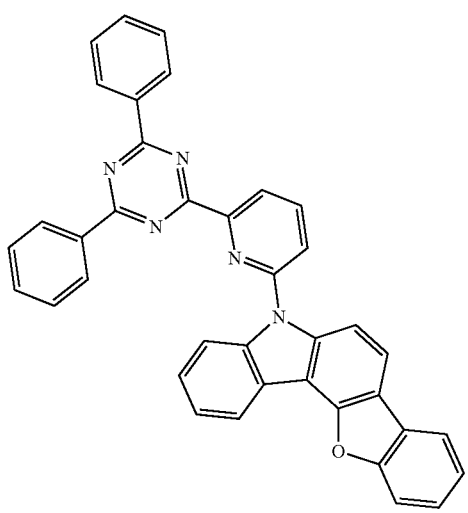
B-91
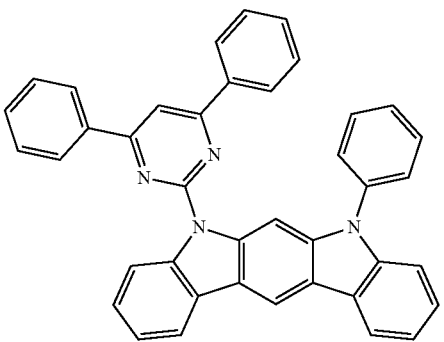

B-92
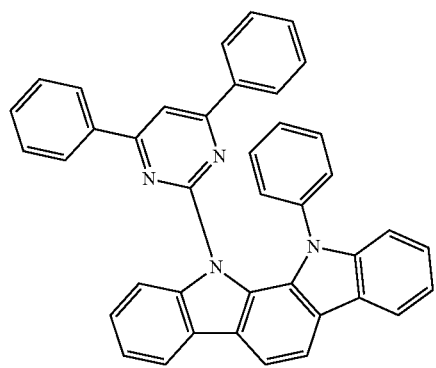
B-95
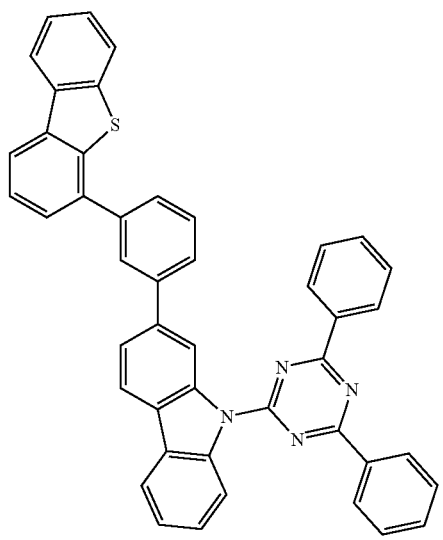
B-93
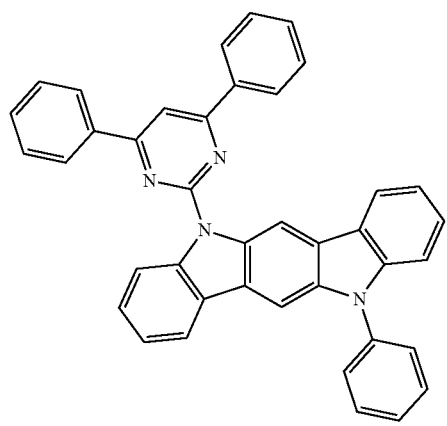
B-96
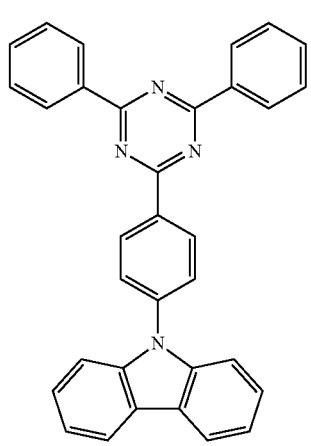
B-94
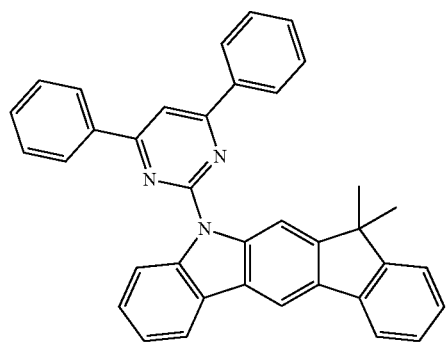
B-97
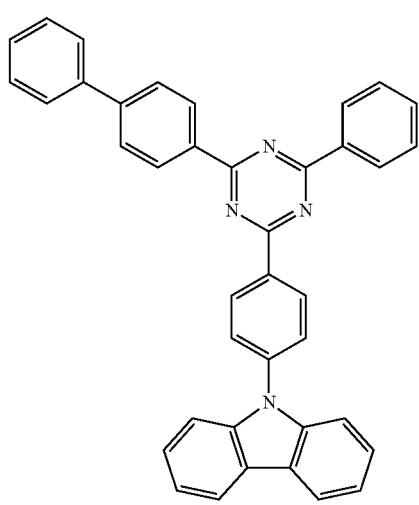

B-98
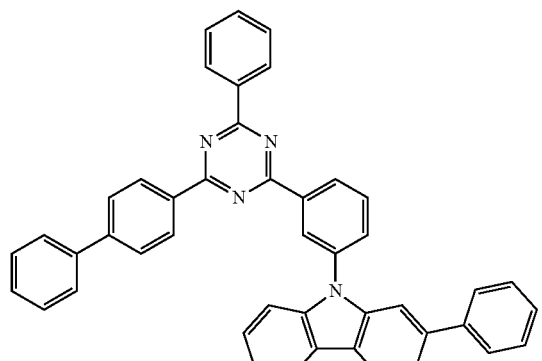
B-99
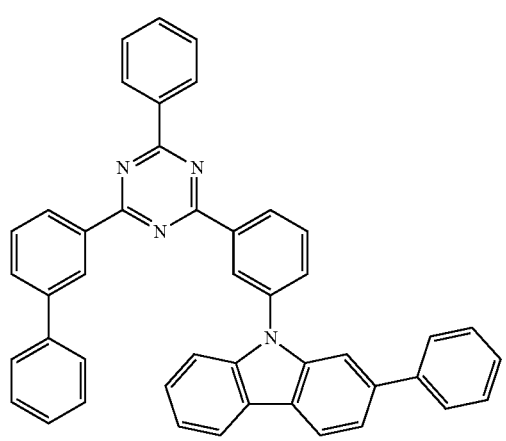
B-100
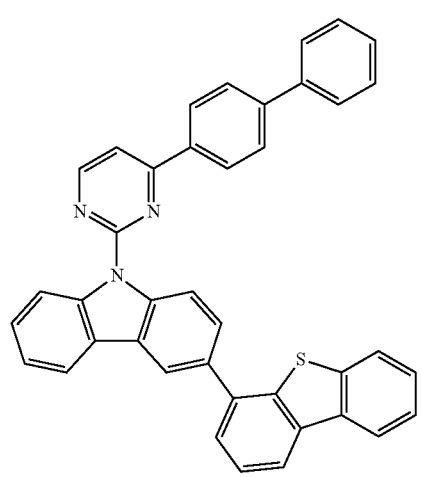
B-101
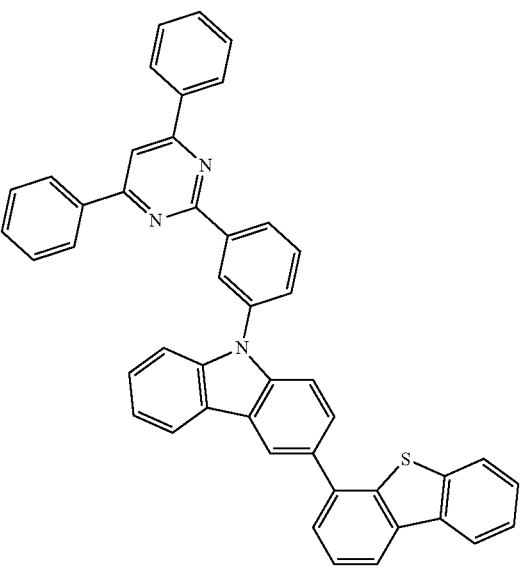
B-102
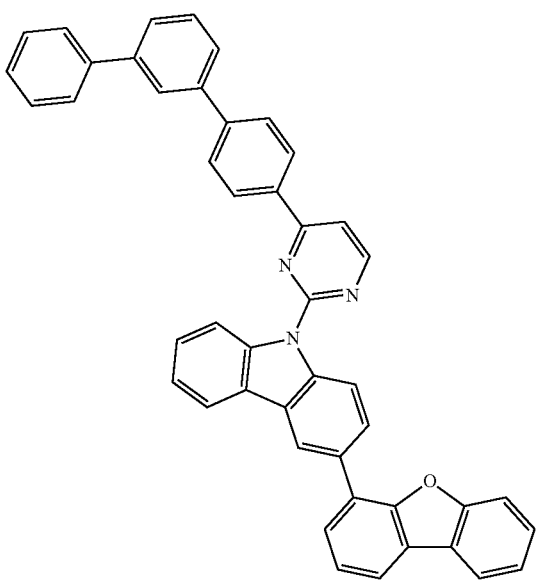

B-103
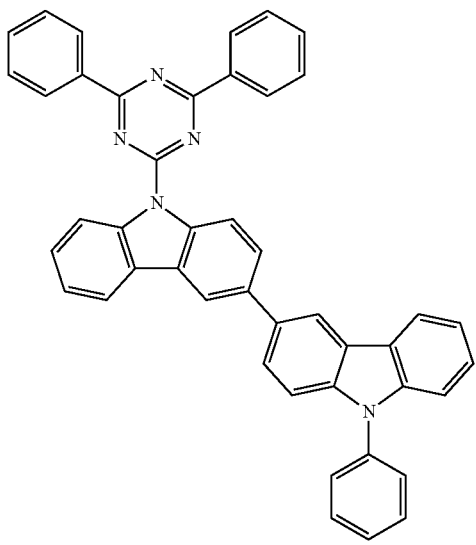
B-104
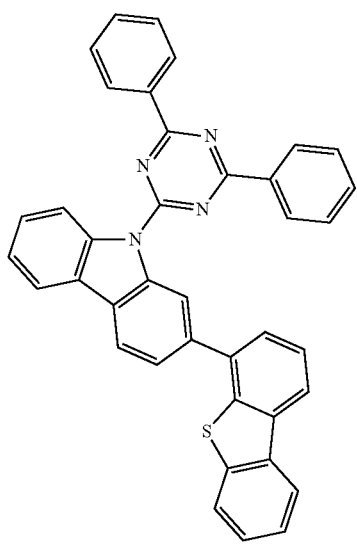
B-105
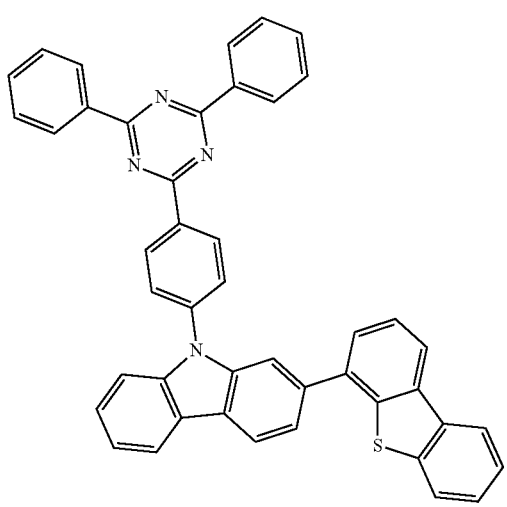
B-106
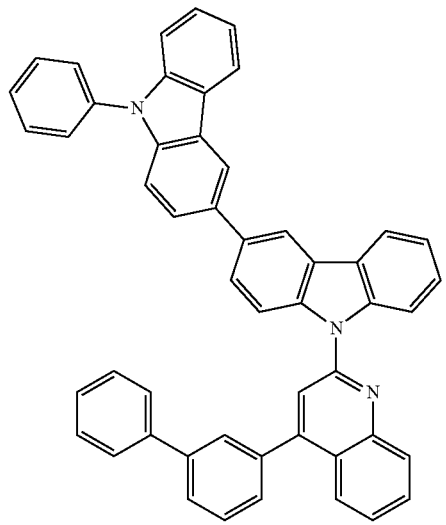
B-107
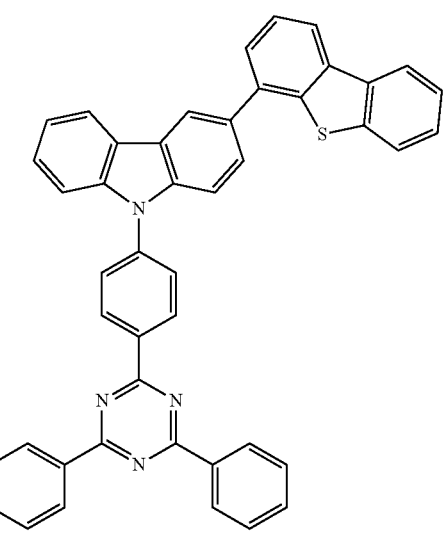
B-108
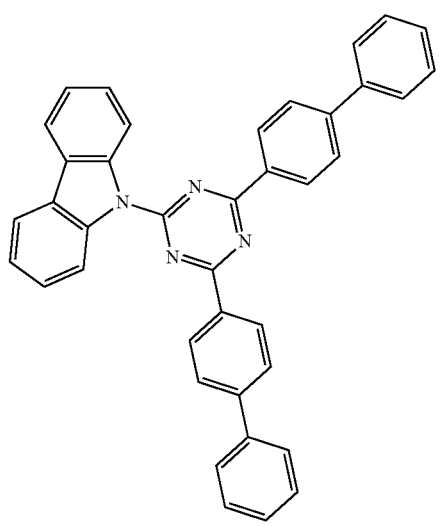

B-109
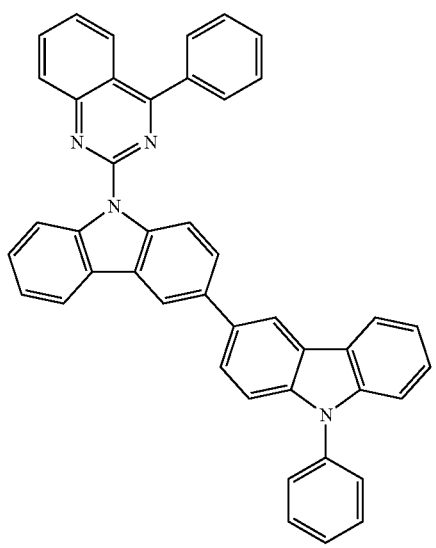
B-110
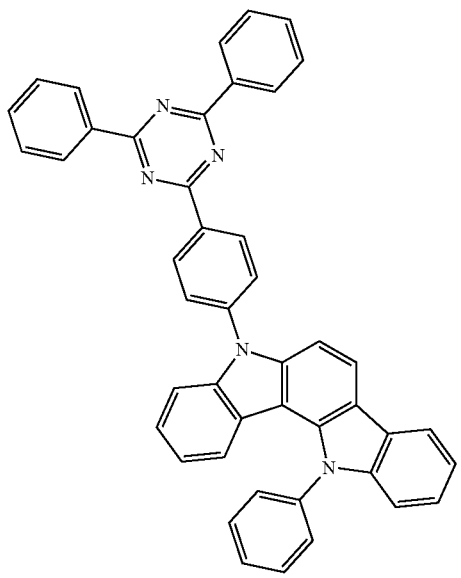
B-111
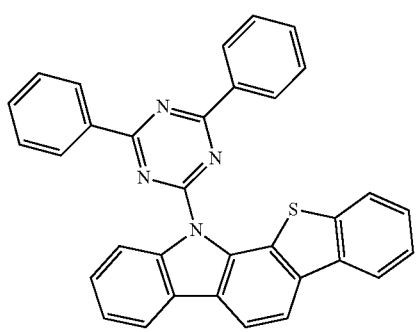
B-112
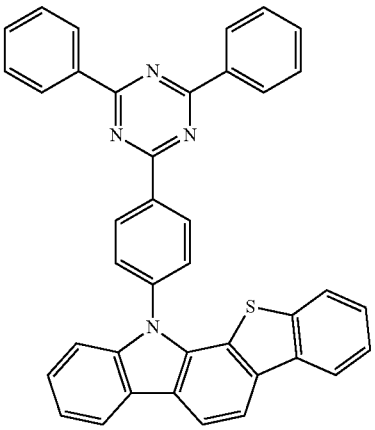
B-113
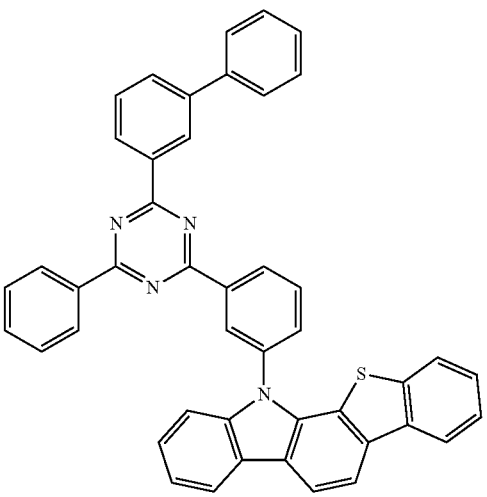
B-114
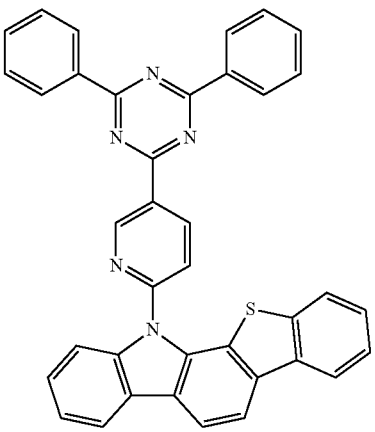

B-115
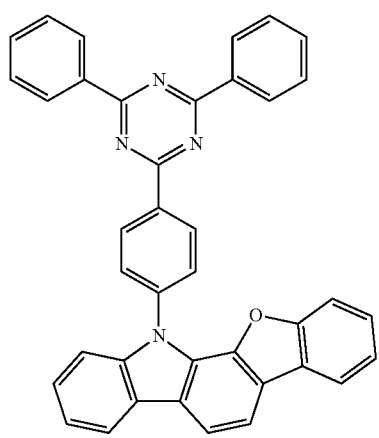
B-116
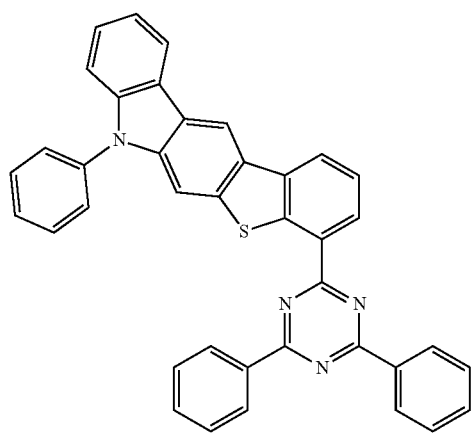
B-117
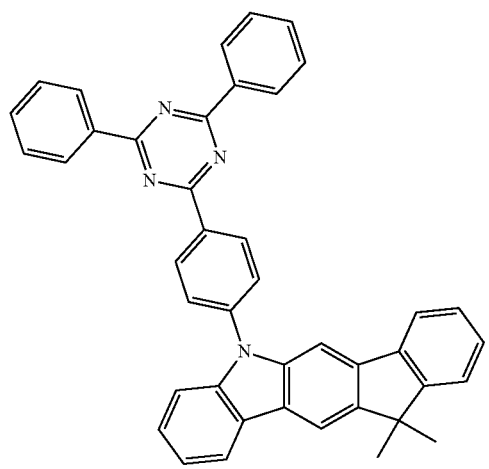
B-118
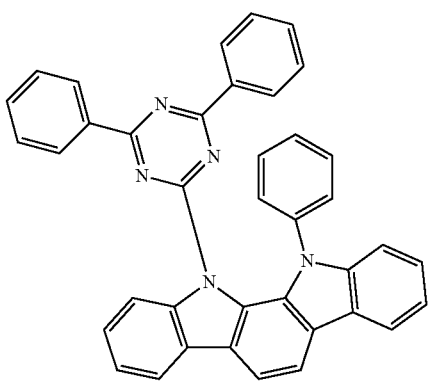
B-119
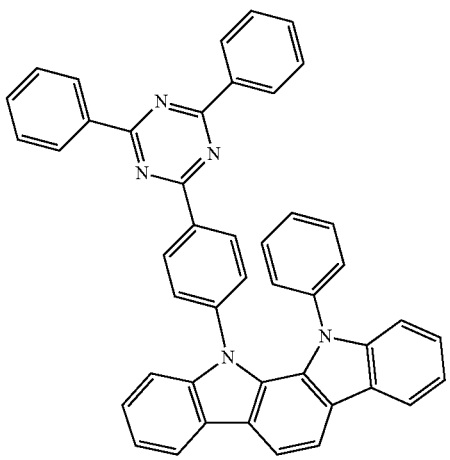
B-120
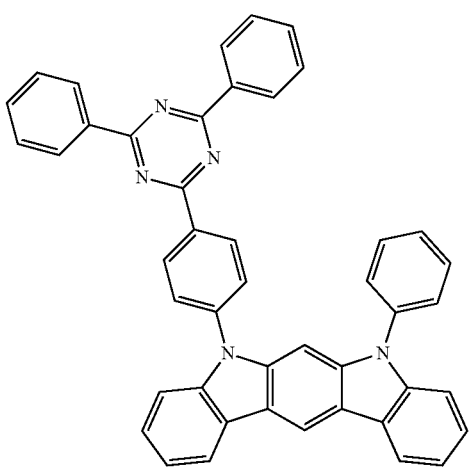

B-121
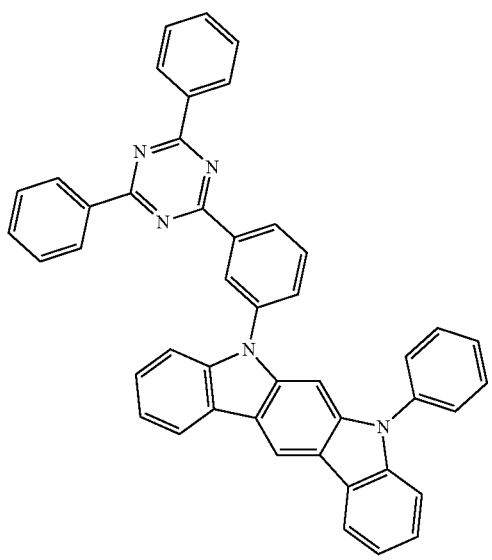
B-122
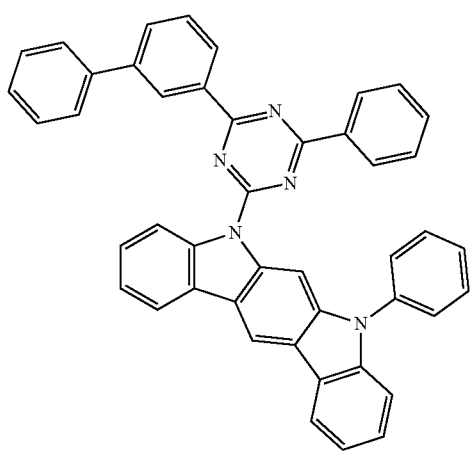
B-123
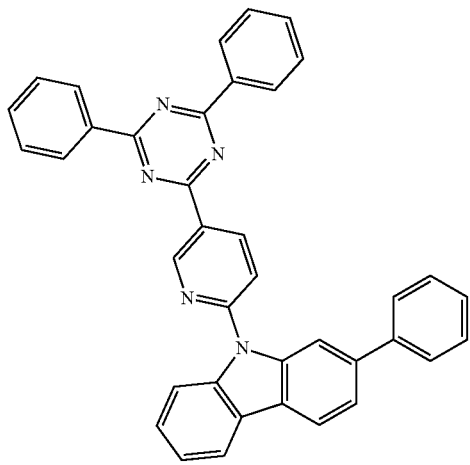
B-124
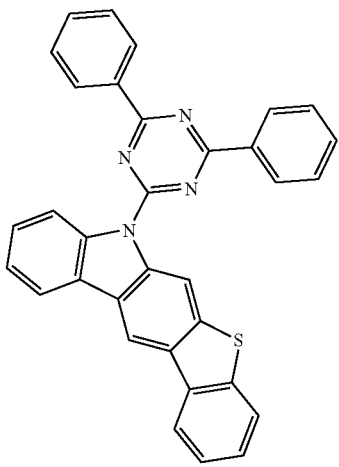
B-125
B-126
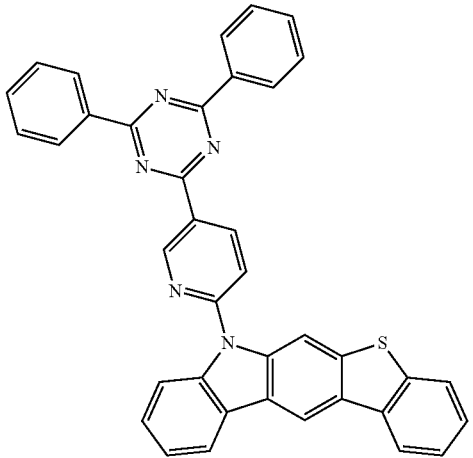

B-127
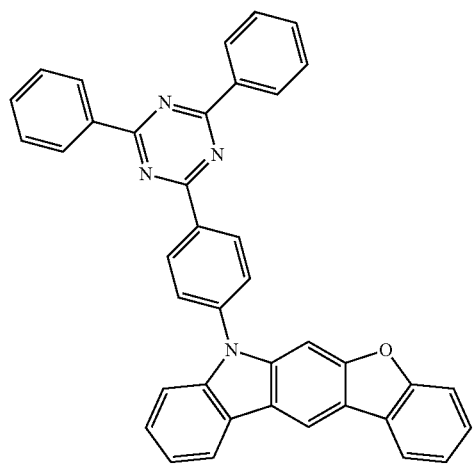
B-128
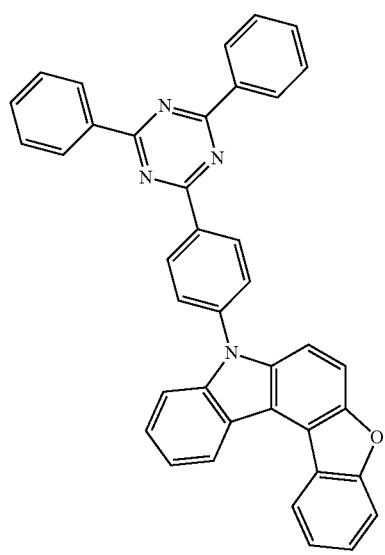
B-129
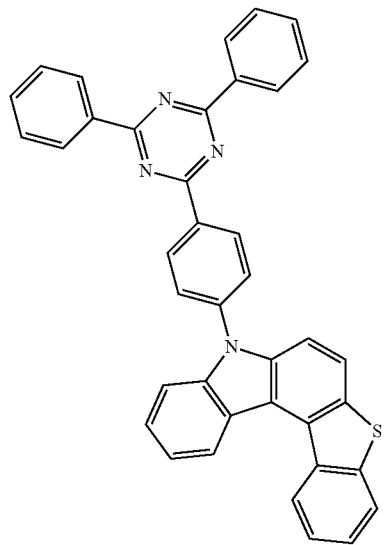
B-130
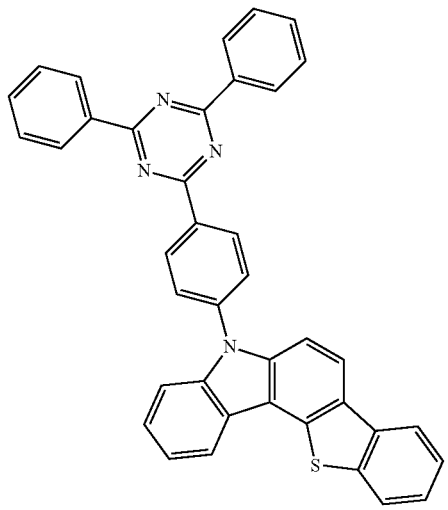
B-131
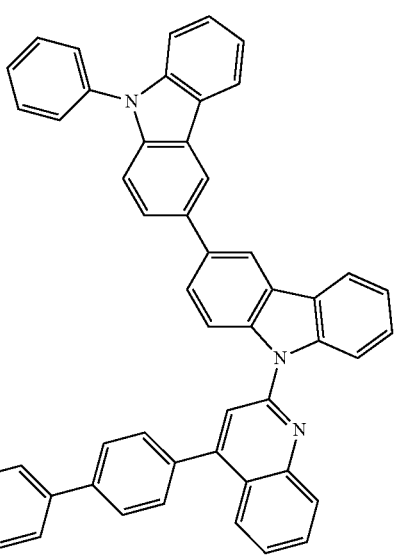
B-132
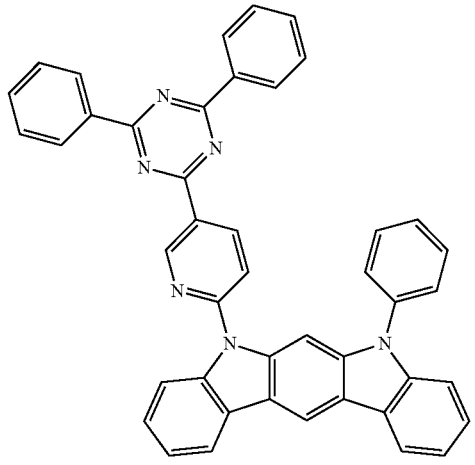

B-133
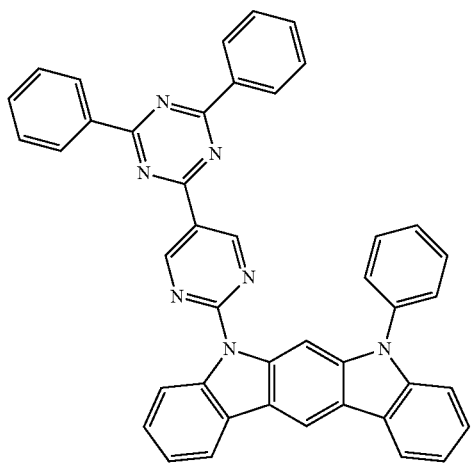
B-134
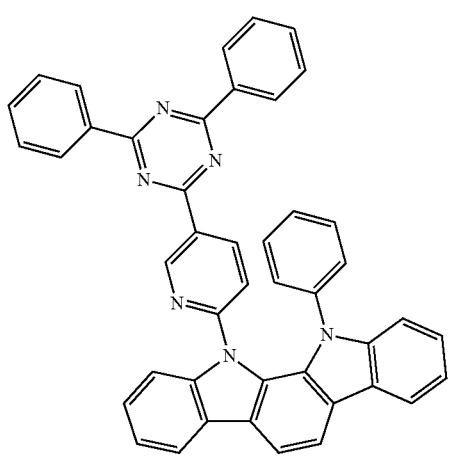
B-135
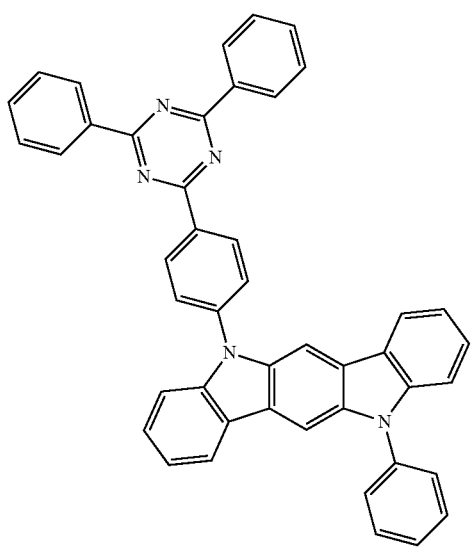
B-136
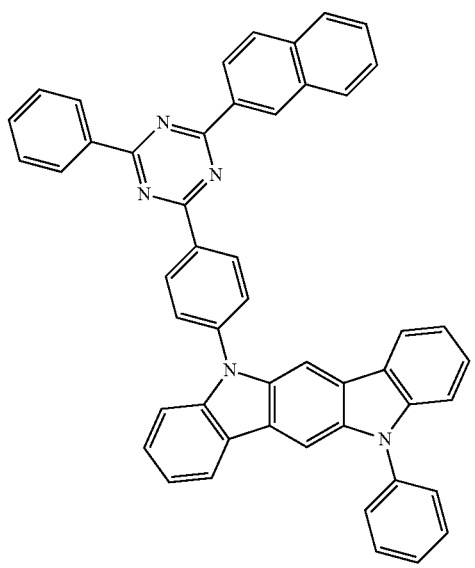
B-137
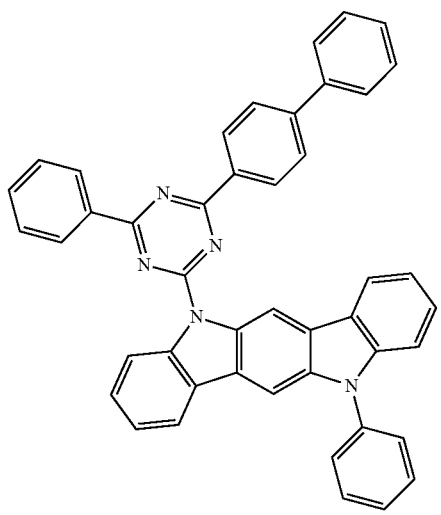
B-138
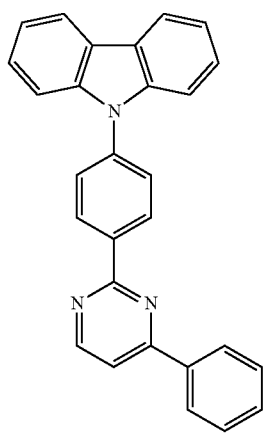

B-139
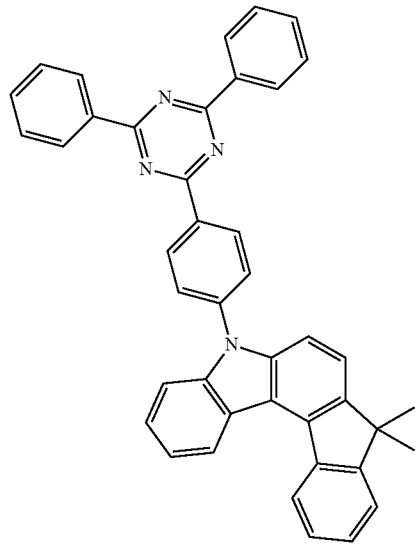
B-140
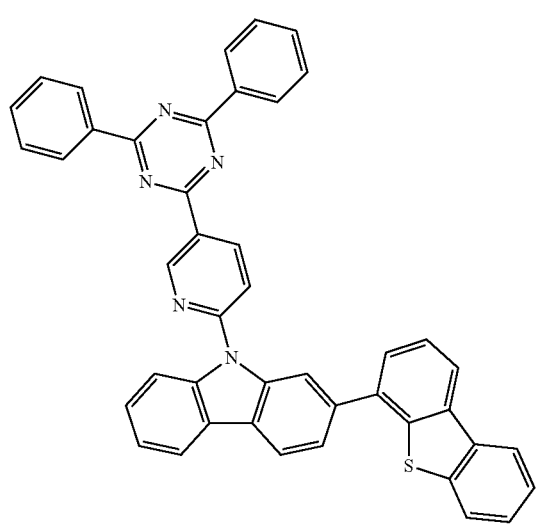
B-141
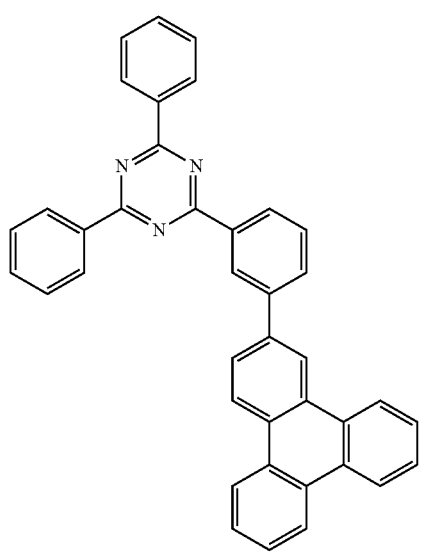
B-142
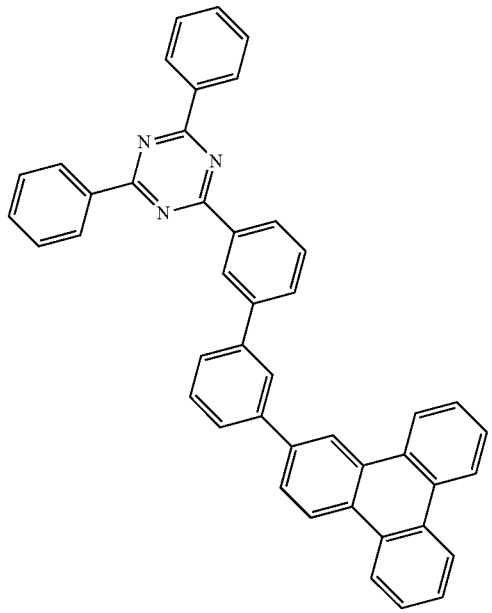
B-143
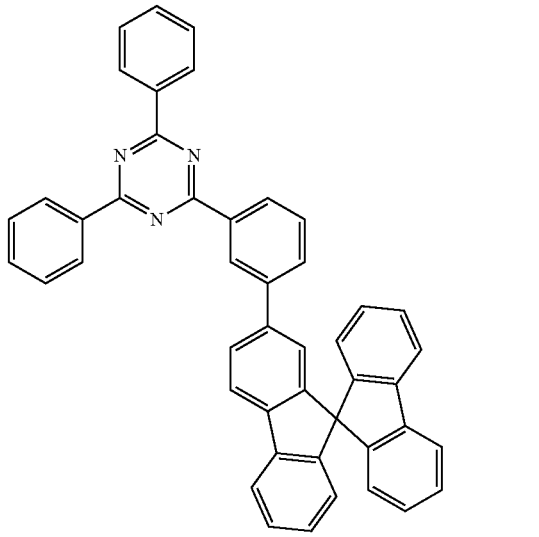
B-144
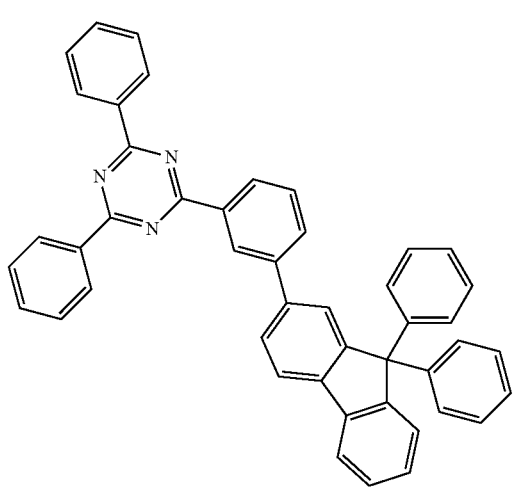

B-145
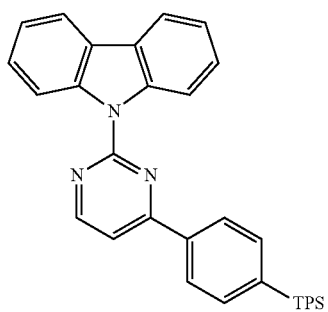
B-146
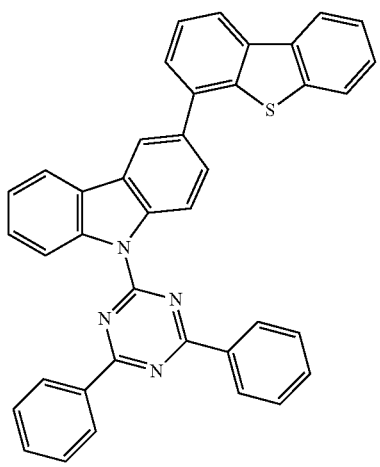
B-147
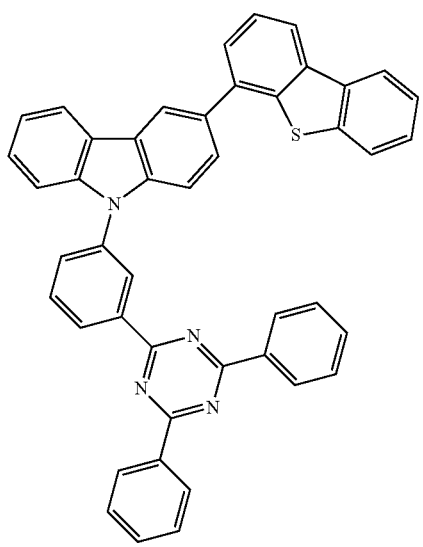
B-148
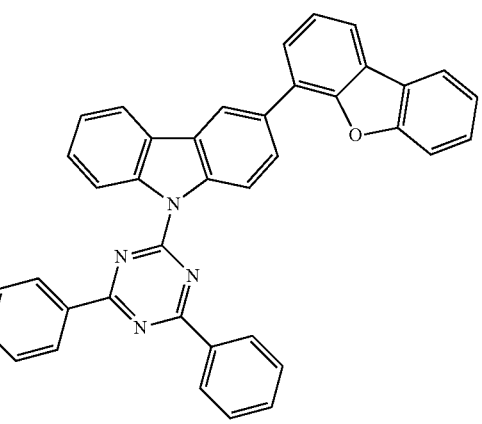
B-149
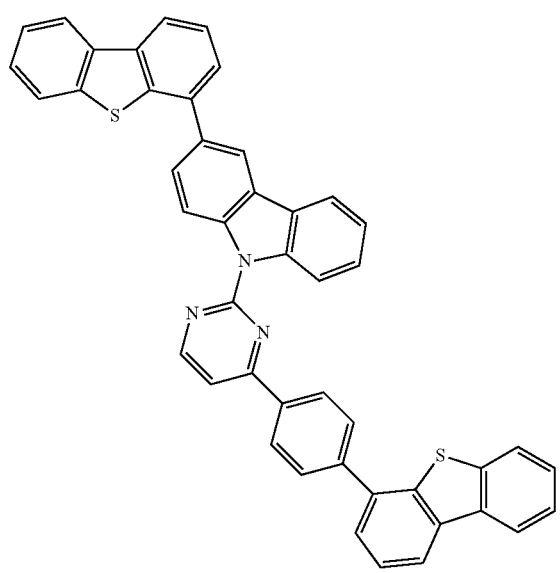
B-150
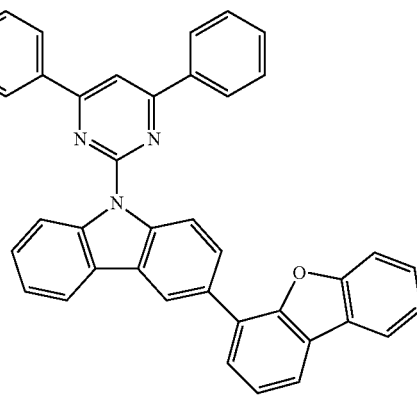

-continued
B-151
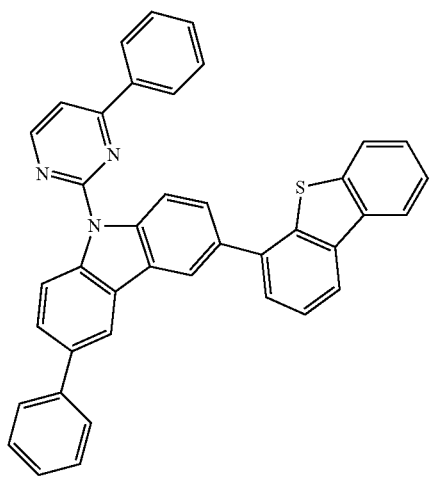
B-152
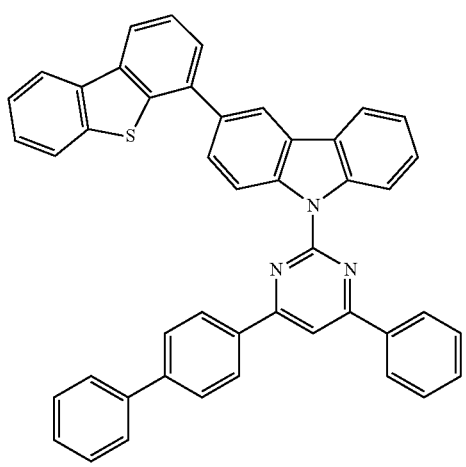
B-153
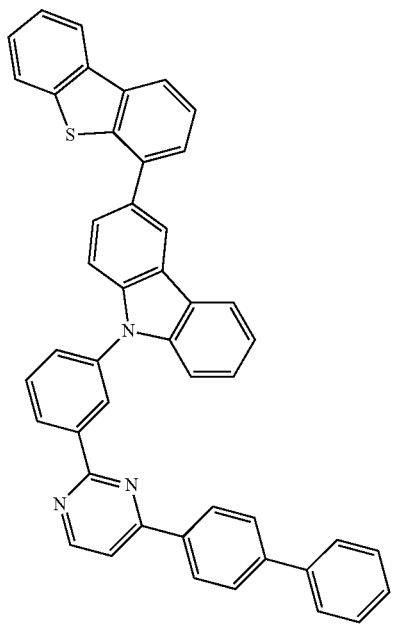
-continued
B-154
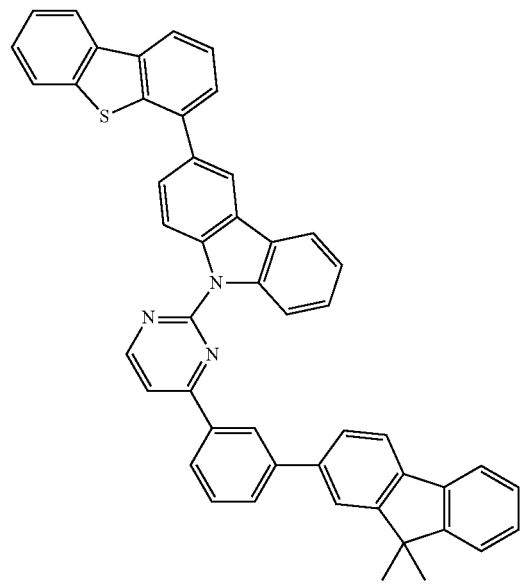
B-155
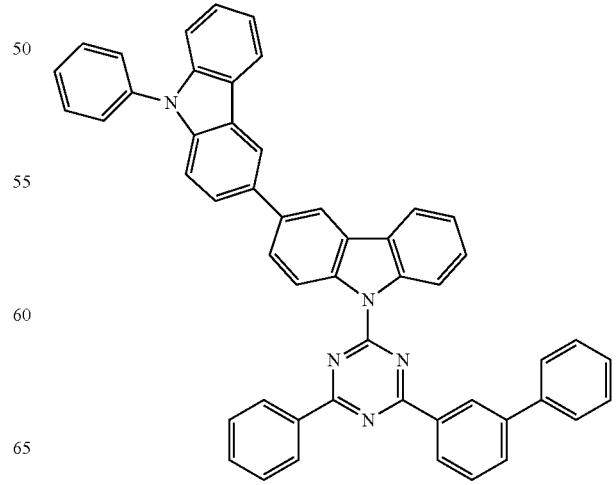

B-156
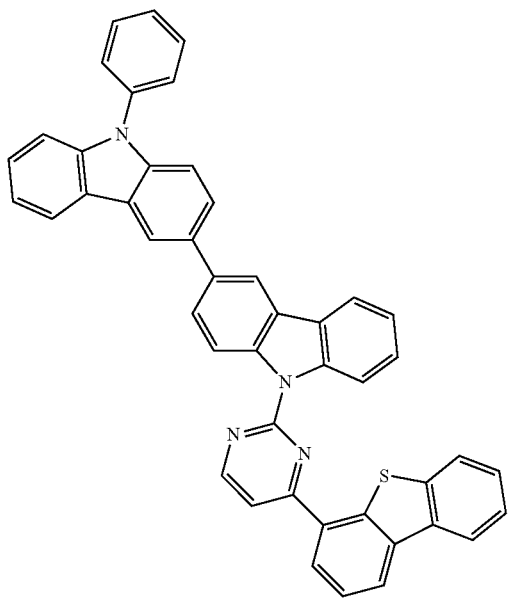
B-158
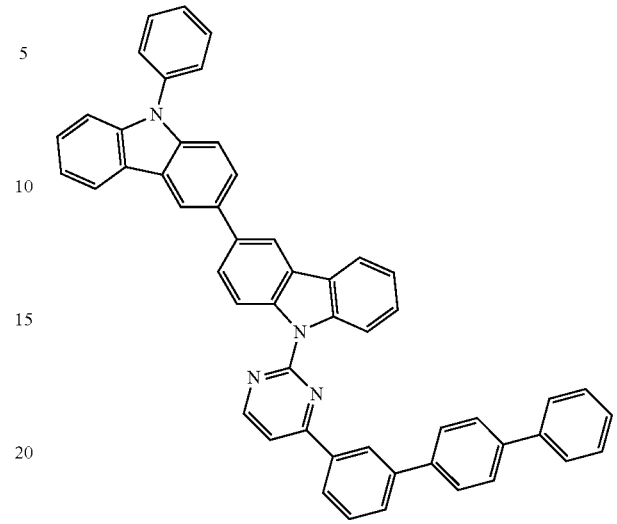
B-157
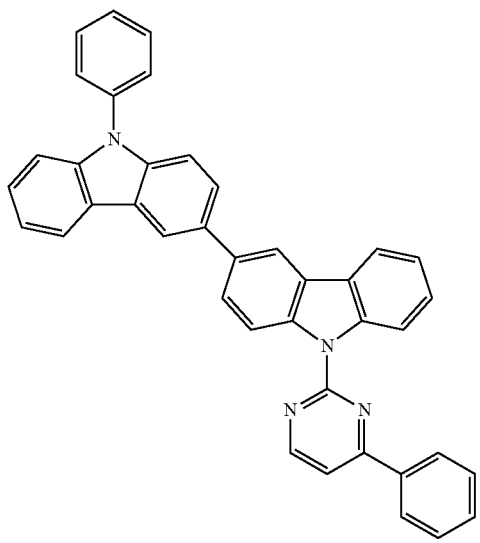
B-159
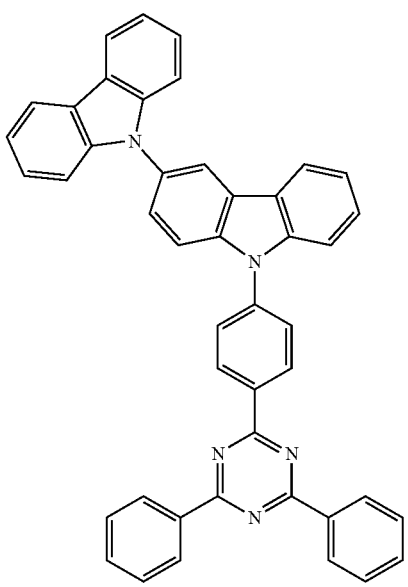

-continued
B-160
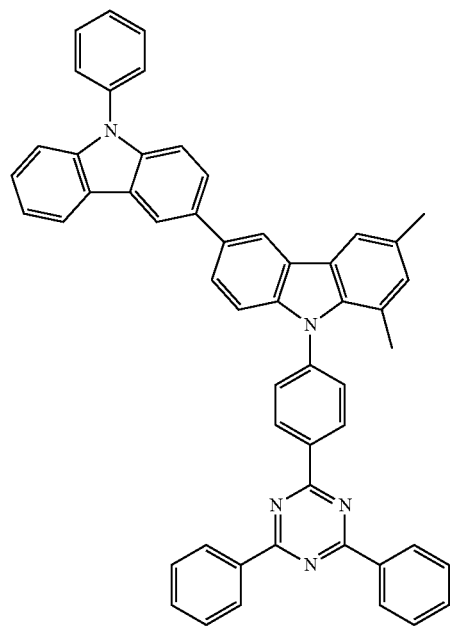
B-161
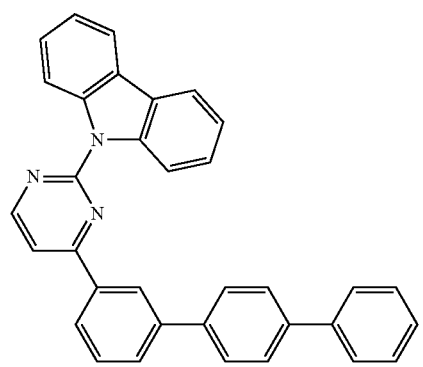
B-162
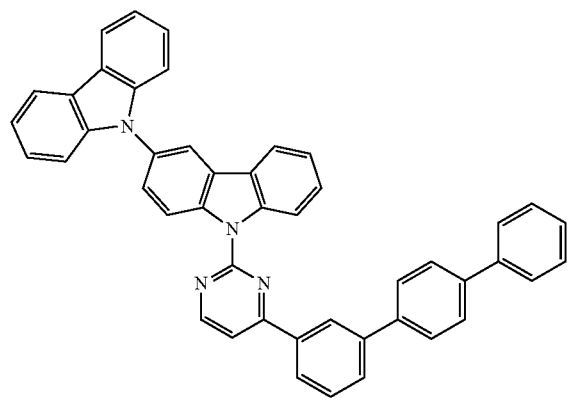
-continued
B-163
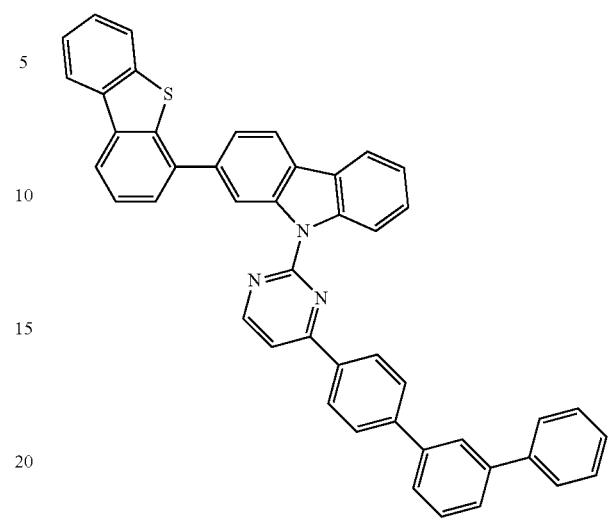
B-164
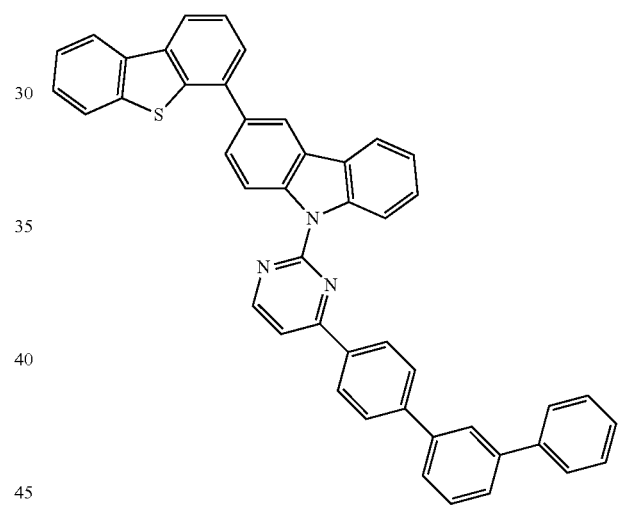
B-165
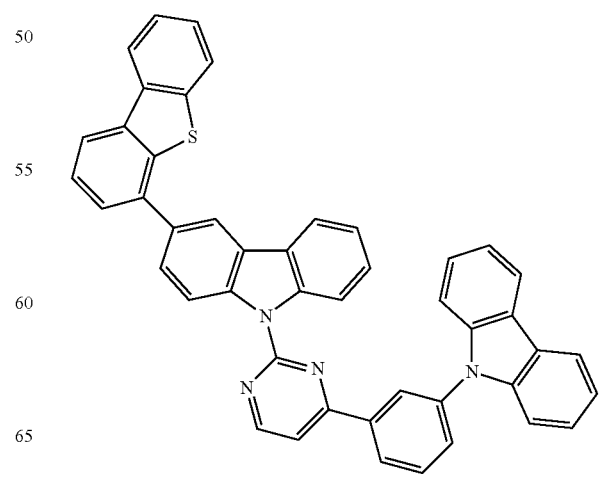

B-166
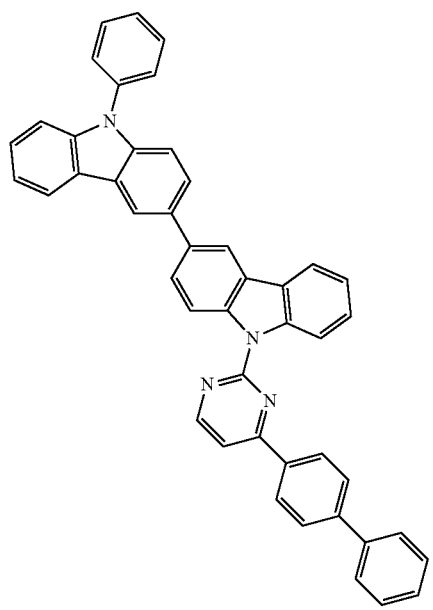
B-167
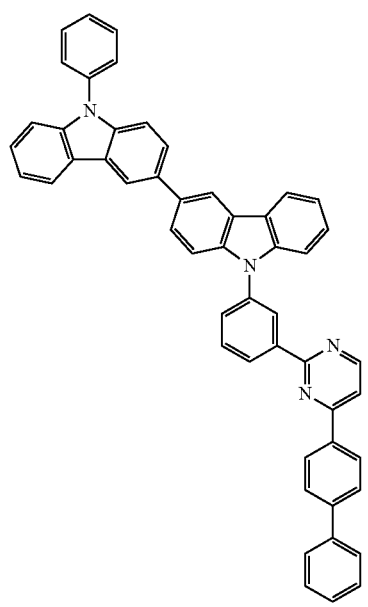
B-168
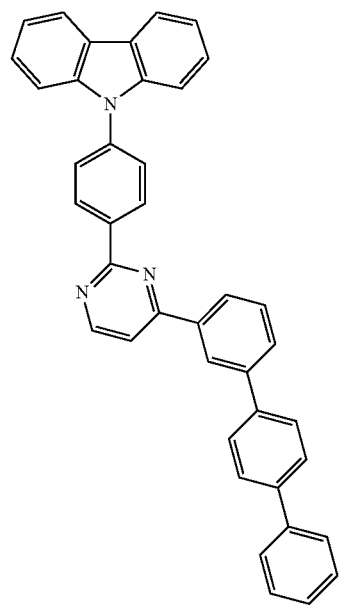
B-169
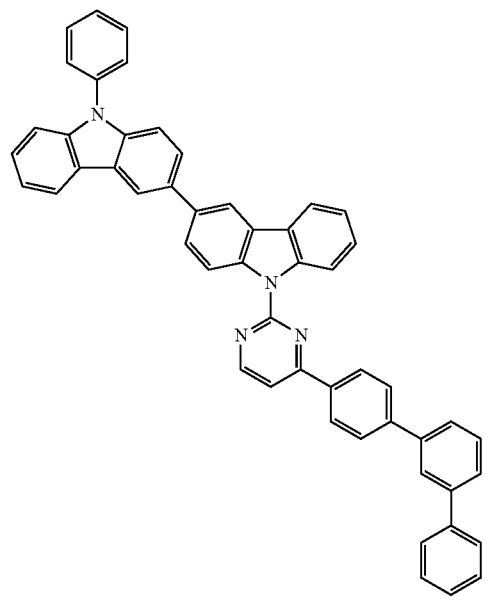

B-170
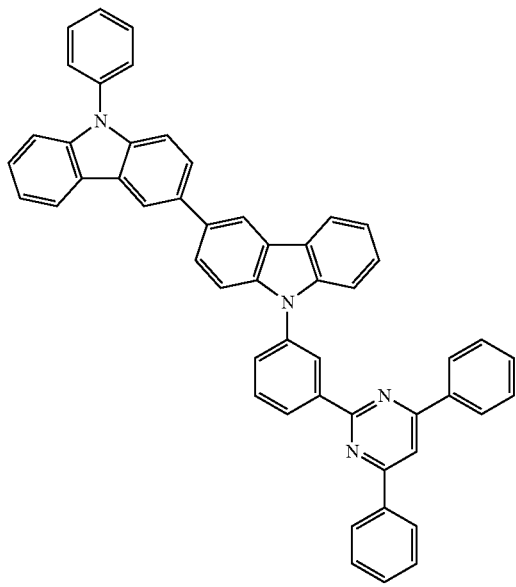
B-172
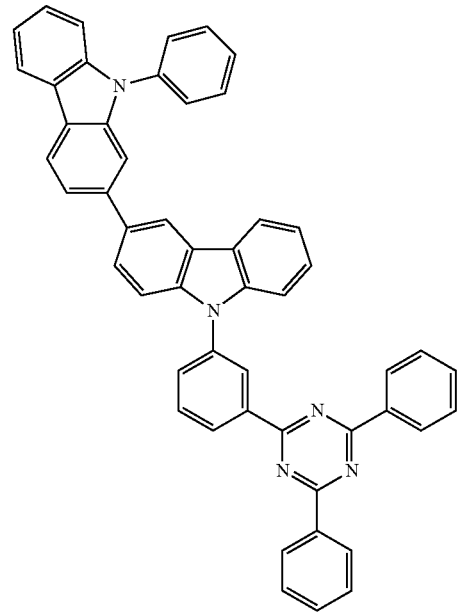
B-171
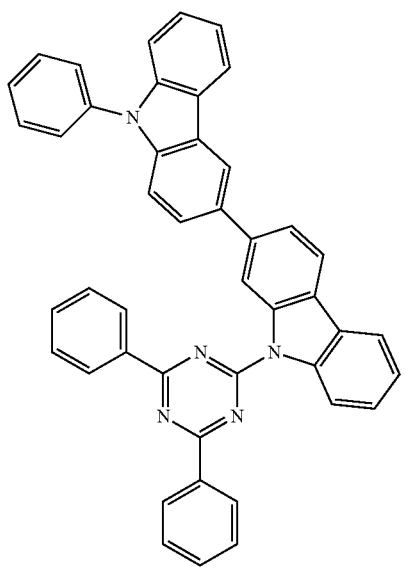
B-173
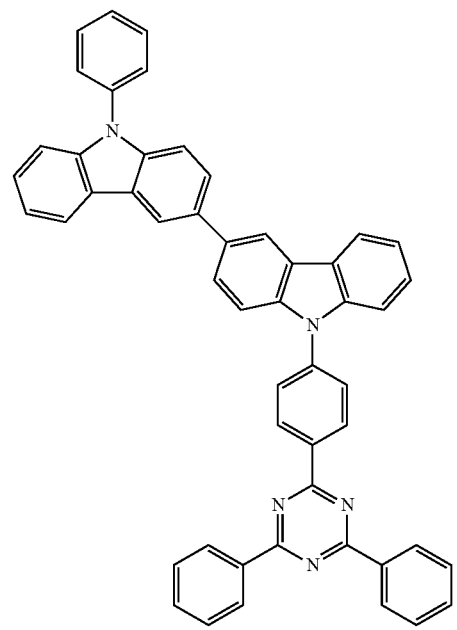

B-174
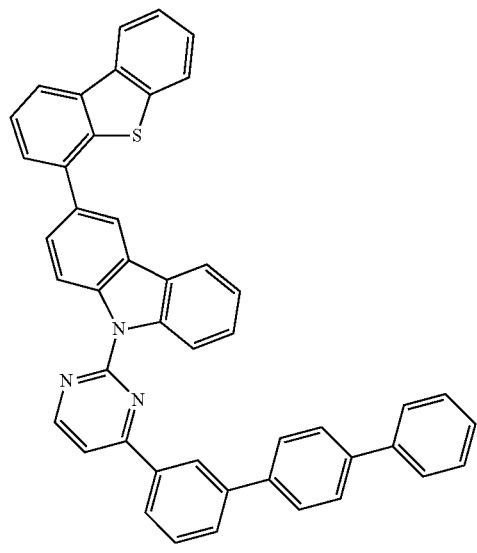
B-175
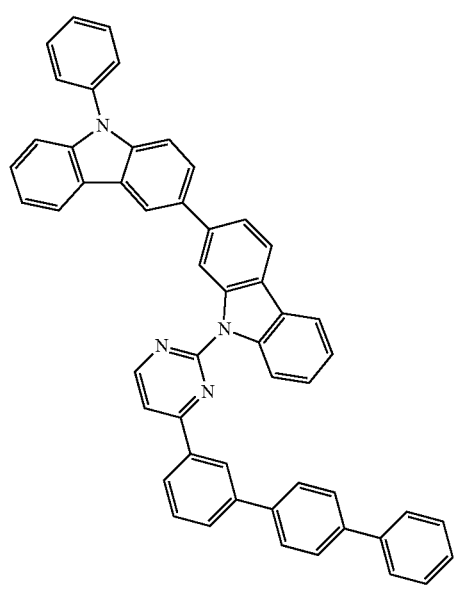
B-176
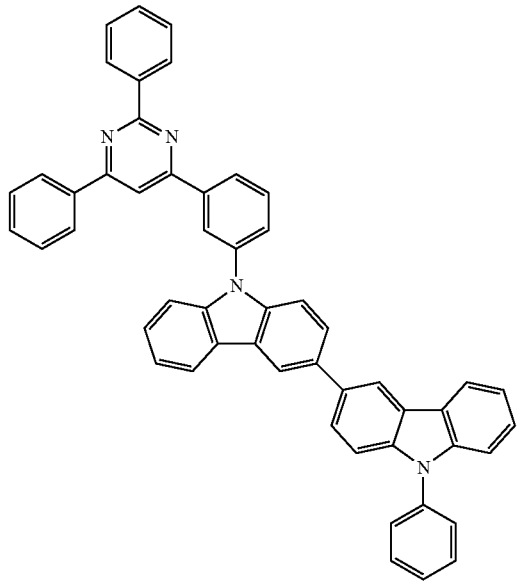
B-177
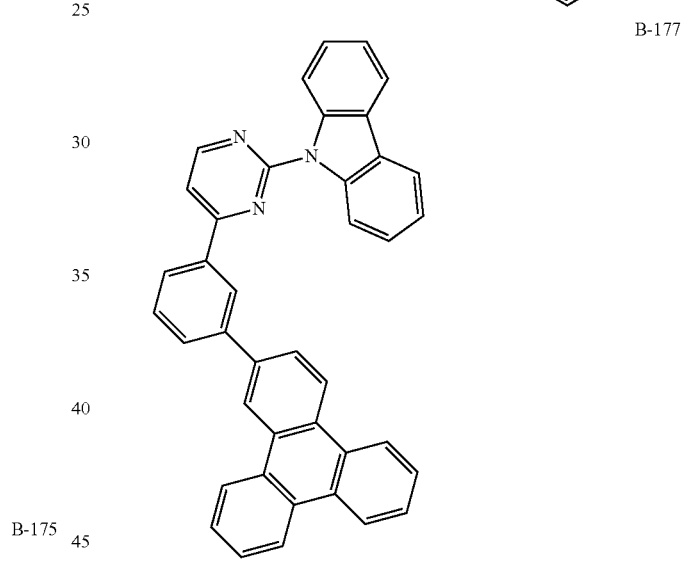
B-178
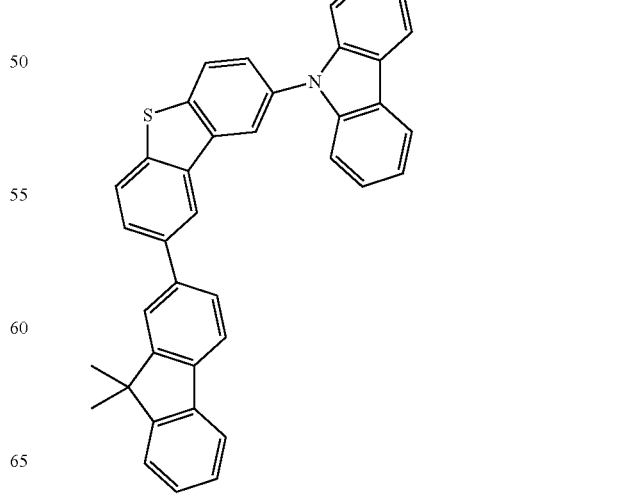

B-179
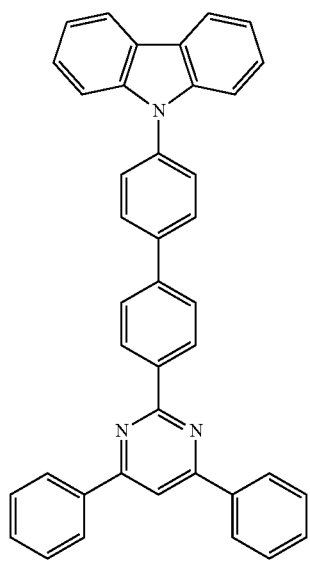
B-180
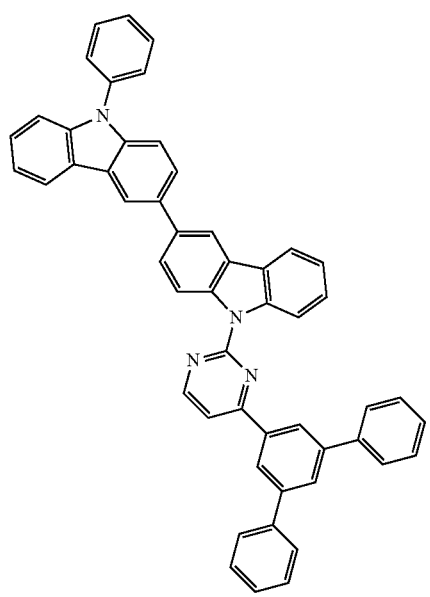
B-181
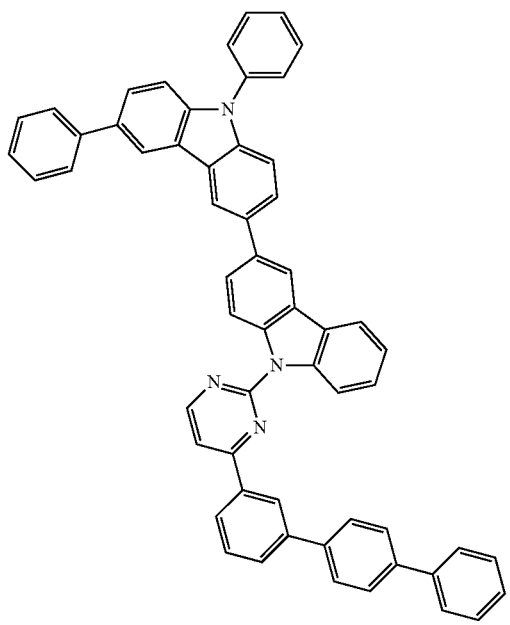
B-182
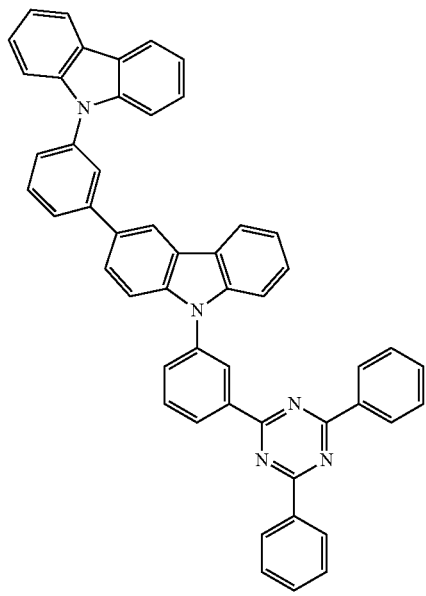

B-183
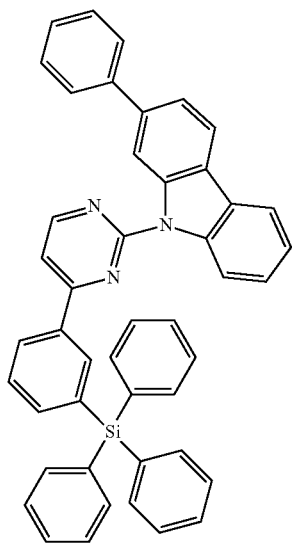
B-184
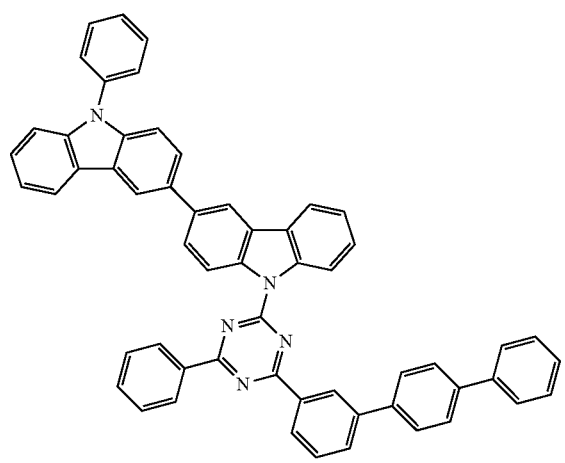
B-185
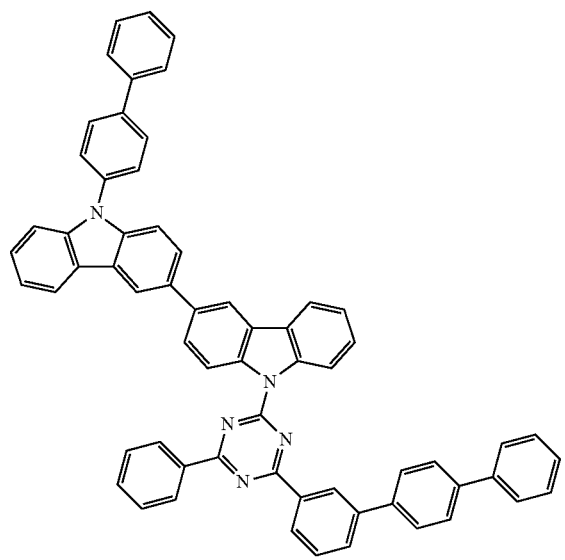
B-186
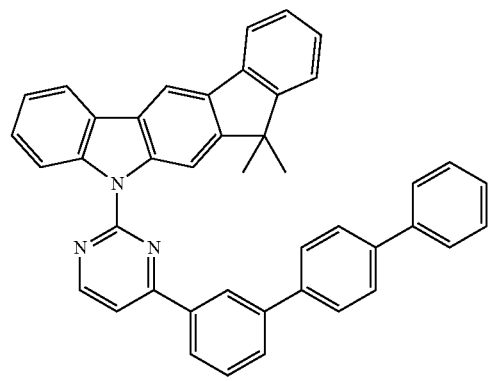
B-187
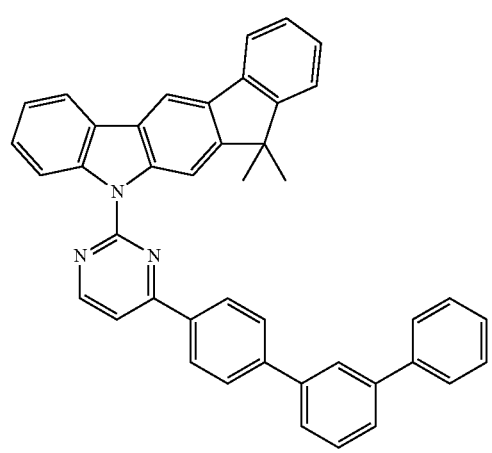
B-188
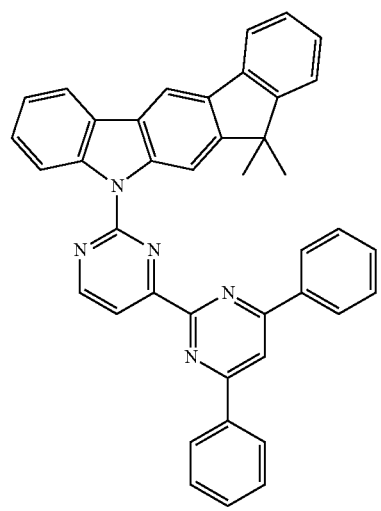

B-189
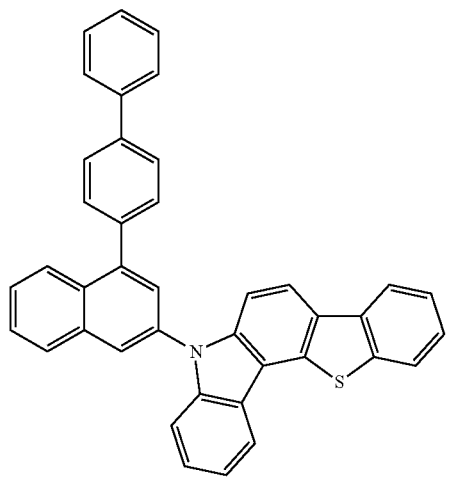
B-192
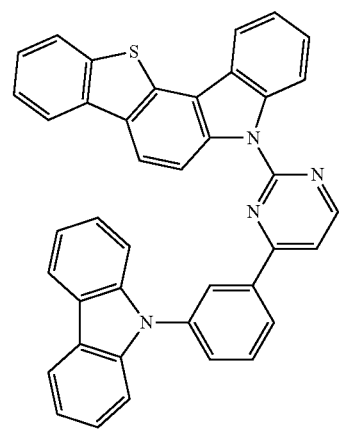
B-190
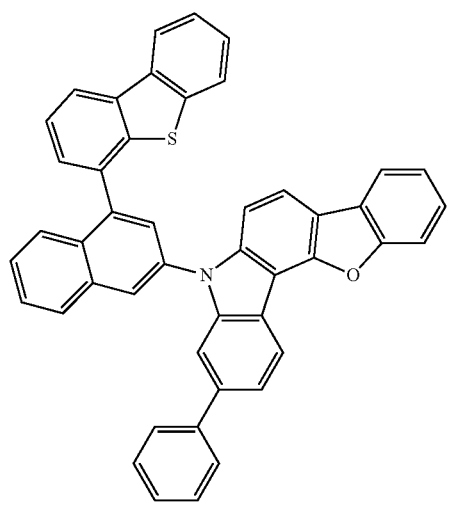
B-193
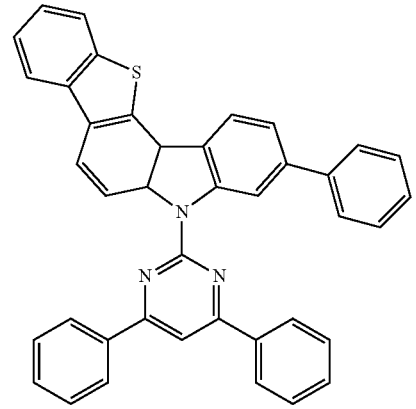
B-191
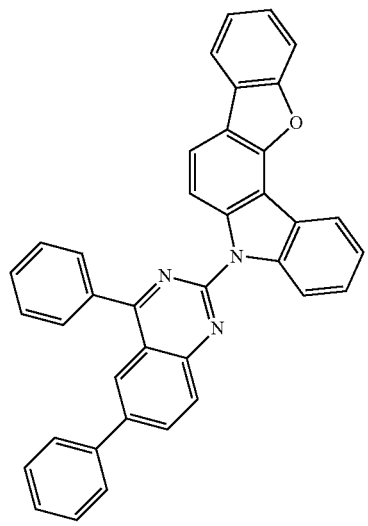
B-194
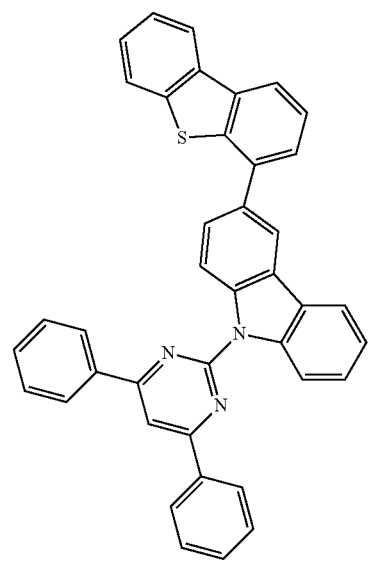

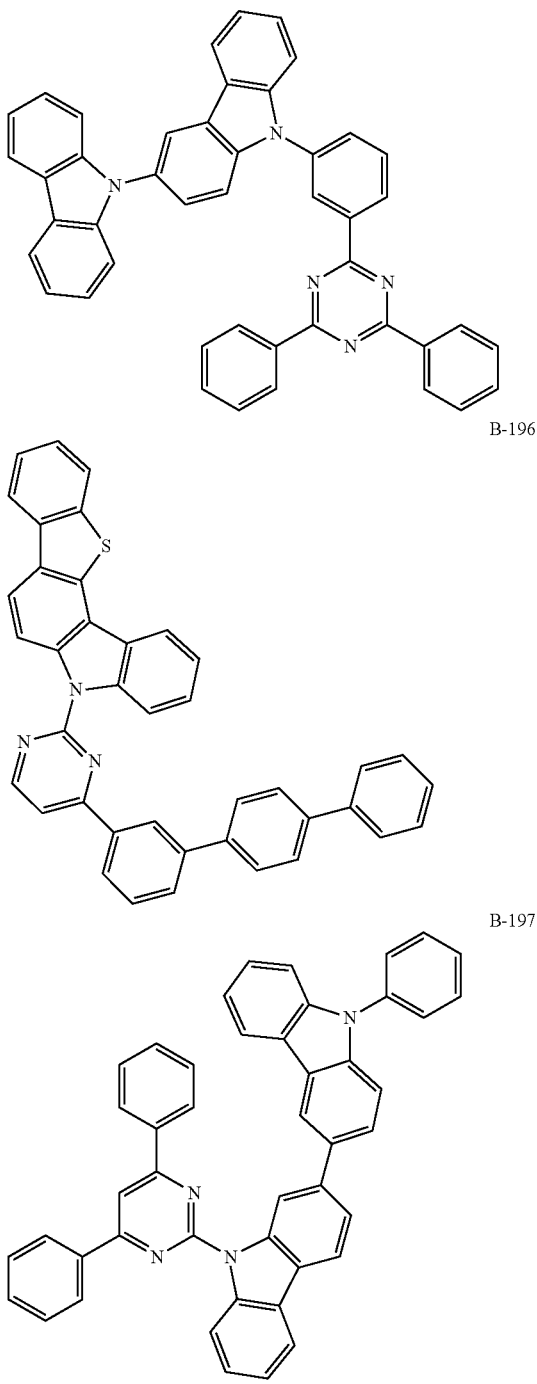

[wherein TPS represents a triphenylsilyl group]

As for the dopant comprised in the organic electroluminescent device according to the present disclosure, at least one phosphorescent or fluorescent dopant may be used, and at least one phosphorescent dopant may be preferable. The phosphorescent dopant materials applied to the organic electroluminescent device according to the present disclosure are not particularly limited, but may be selected from metallated complex compounds of iridium (Ir), osmium (Os), copper (Cu), and platinum (Pt), may be preferably selected from ortho-metallated complex compounds of iridium (Ir), osmium (Os), copper (Cu), and platinum (Pt), and may be more preferably an ortho-metallated iridium complex compound.

The dopant comprised in the organic electroluminescent device of the present disclosure may be selected from the group consisting of the compounds represented by formulas 101 to 104 below, but is not limited thereto.

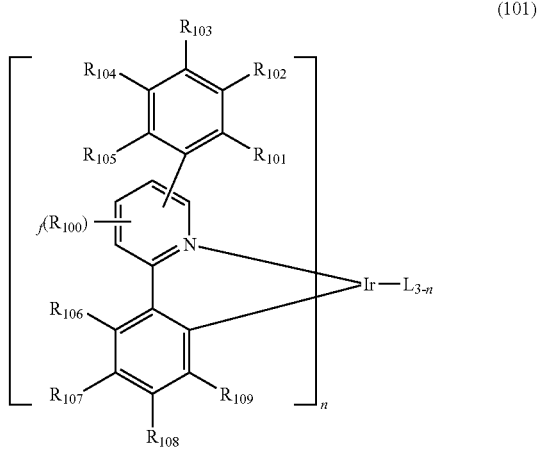

(101)

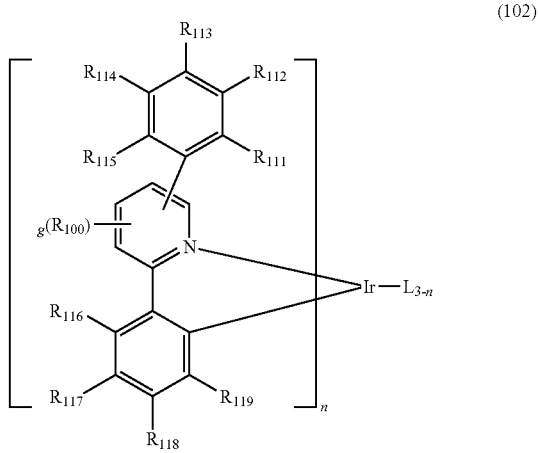

(102)

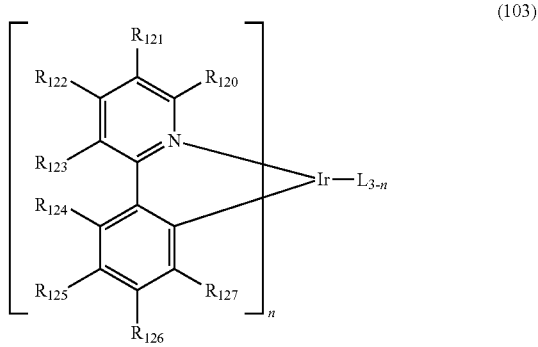

(103)

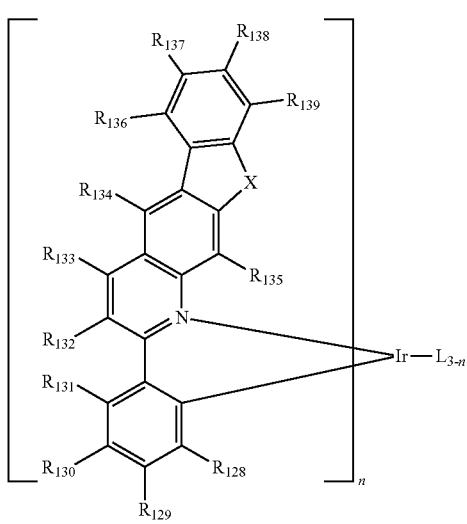

(104)

wherein L is selected from the following structures:

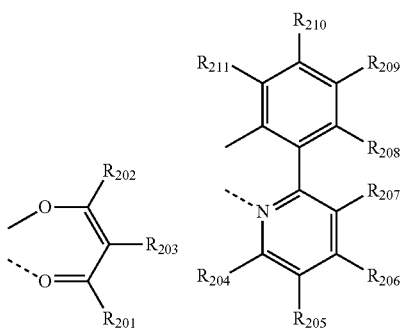

$R_{100}$, $R_{134}$, and $R_{135}$, each independently, represent hydrogen, deuterium, a substituted or unsubstituted (C1-C30)alkyl, or a substituted or unsubstituted (C3-C30)cycloalkyl;

$R_{101}$ to $R_{109}$ and $R_{111}$ to $R_{123}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a cyano, or a substituted or unsubstituted (C1-C30)alkoxy; adjacent substituents of $R_{106}$ to $R_{109}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl; and adjacent substituents of $R_{120}$ to $R_{123}$ may be linked to each other to form a substituted or unsubstituted fused ring, e.g., a quinoline unsubstituted or substituted with at least one of an alkyl, an aryl, an aralkyl, and an alkylaryl;

$R_{124}$ to $R_{133}$ and $R_{136}$ to $R_{139}$, each independently, represent hydrogen, deuterium, a halogen, a substituted or unsubstituted (C1-C30)alkyl, or a substituted or unsubstituted (C6-C30)aryl; and adjacent substituents of $R_{124}$ to $R_{127}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

X represents $CR_{51}R_{52}$, O, or S;

$R_{51}$ and $R_{52}$, each independently, represent a substituted or unsubstituted (C1-C10)alkyl, or a substituted or unsubstituted (C6-C30)aryl;

$R_{201}$ to $R_{211}$, each independently, represent hydrogen, deuterium, a halogen, a (C1-C30)alkyl unsubstituted or substituted with deuterium or a halogen, a substituted or unsubstituted (C3-C30)cycloalkyl, or a (C6-C30)aryl unsubstituted or substituted with an alkyl or deuterium; and adjacent substituents of $R_{208}$ to $R_{211}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

f and g, each independently, represent an integer of 1 to 3; where f or g is an integer of 2 or more, each $R_{100}$ may be the same or different; and n represents an integer of 1 to 3.

Specifically, the examples of the dopant compound are as follows, but not limited thereto.

D-1

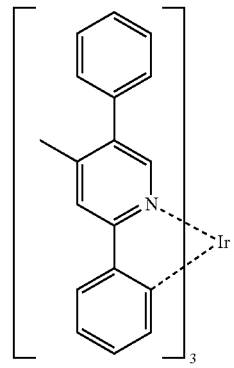

D-2

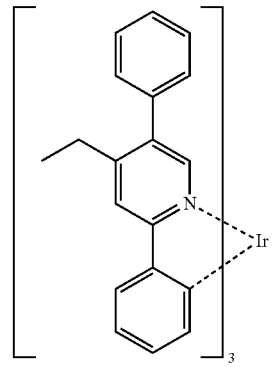

D-3

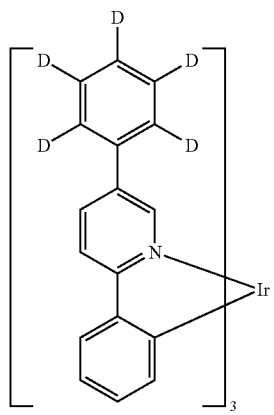
D-4
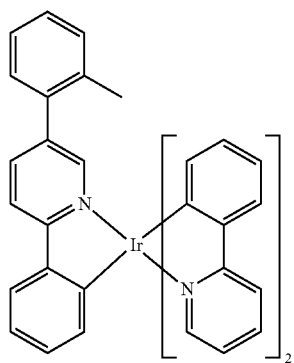
D-5
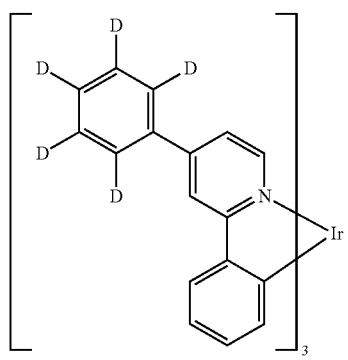
D-6
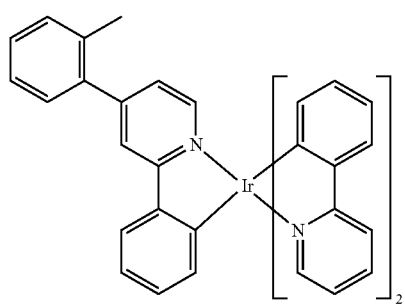
D-7
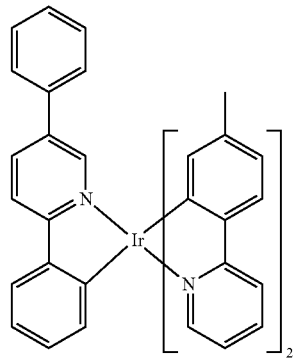
D-8
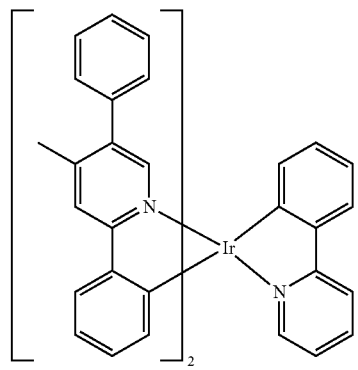
D-9
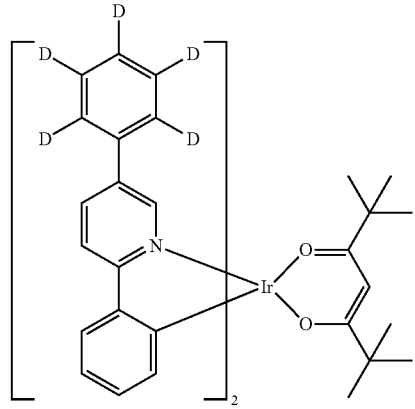
D-10
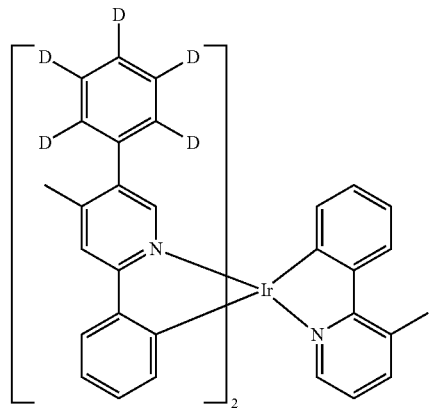
D-11

-continued
D-12
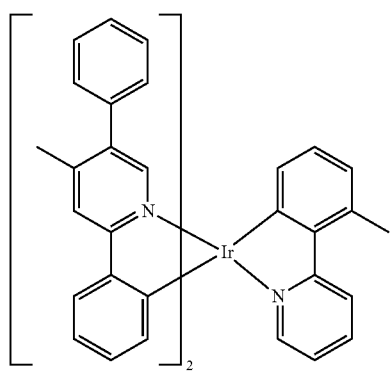
D-13
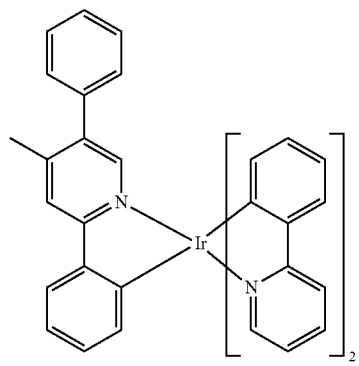
D-14
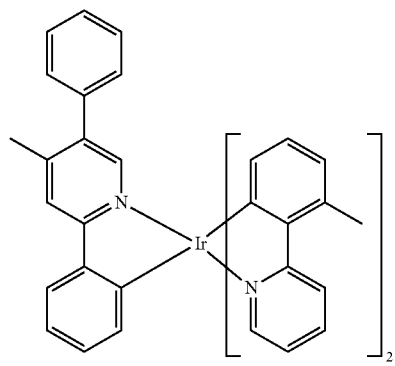
D-15
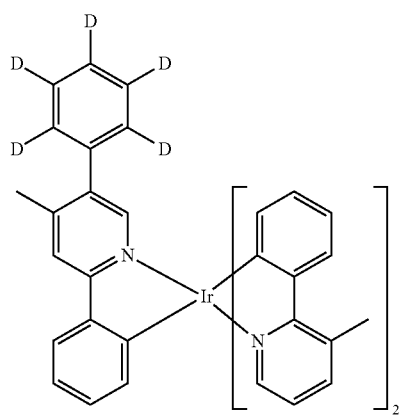
-continued
D-16
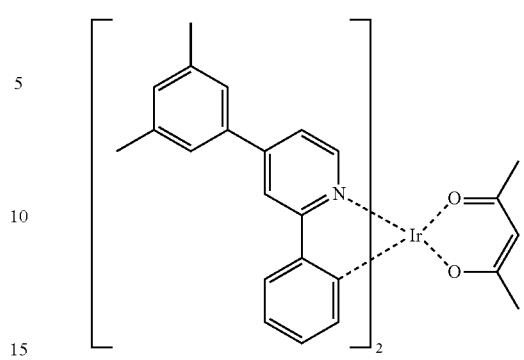
D-17
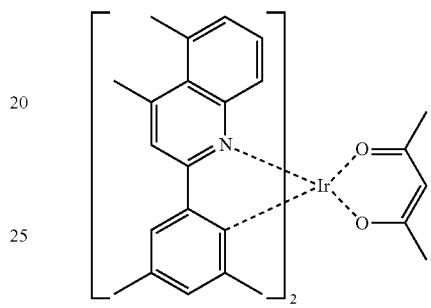
D-18
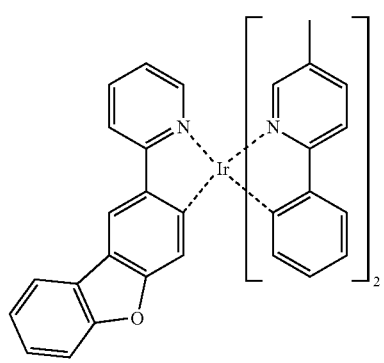
D-19
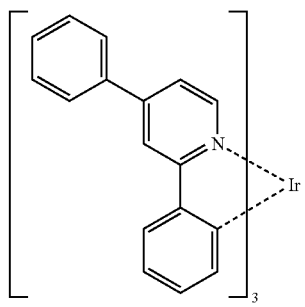
D-20
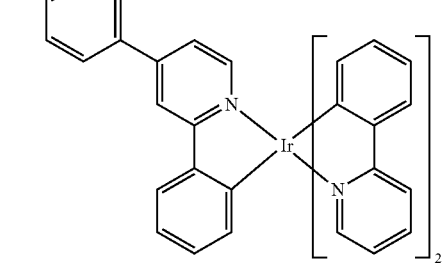

-continued
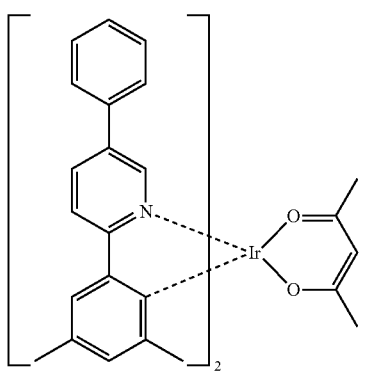
D-21
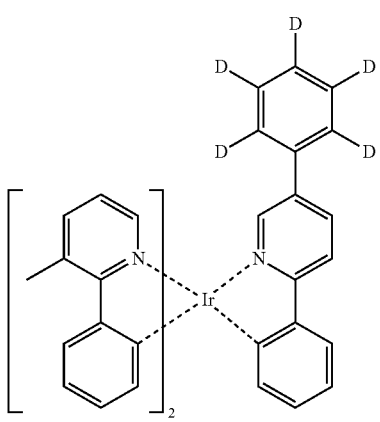
D-22
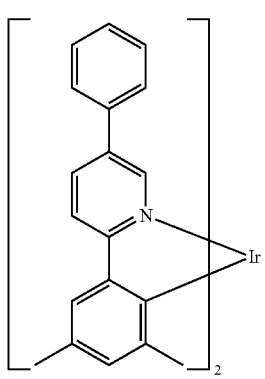
D-23
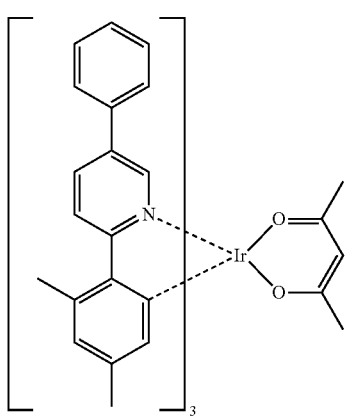
D-24
-continued
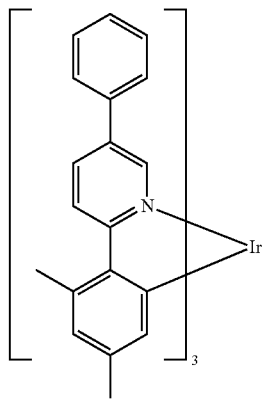
D-25
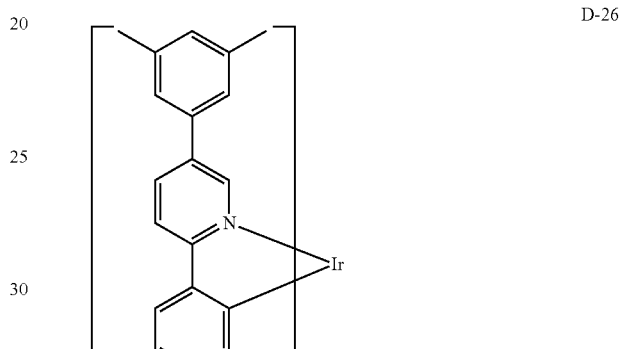
D-26
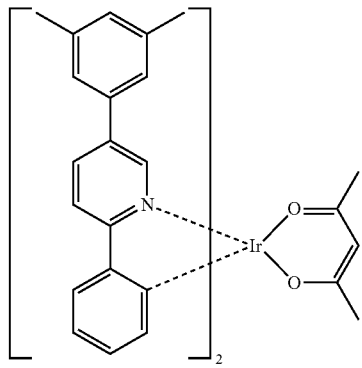
D-27
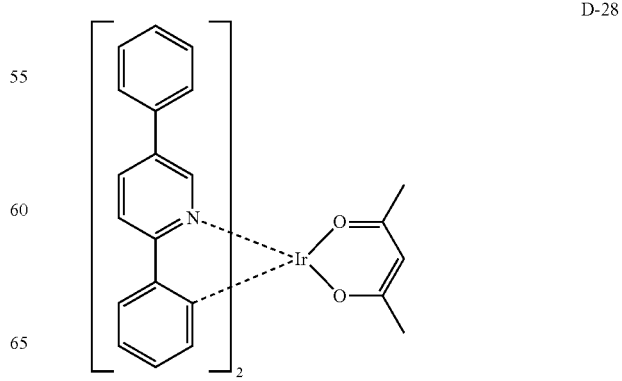
D-28

-continued
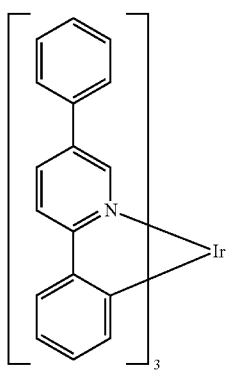
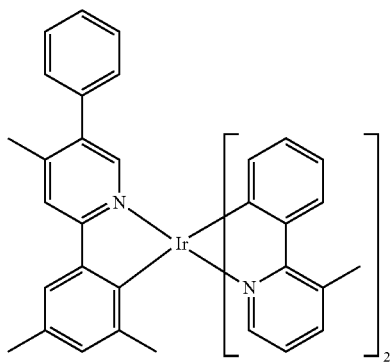
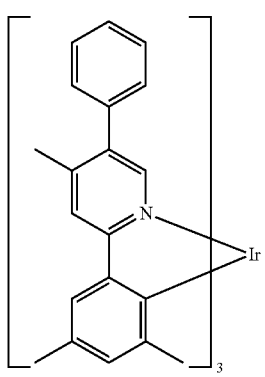
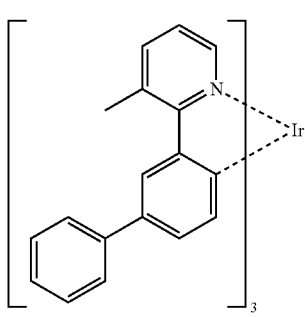
-continued
D-33
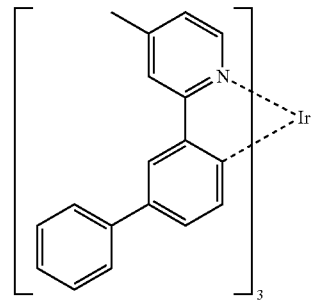
D-34
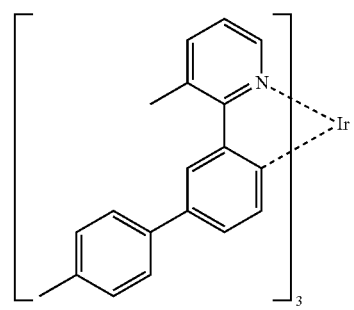
D-35
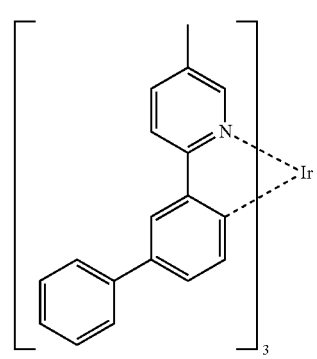
D-36
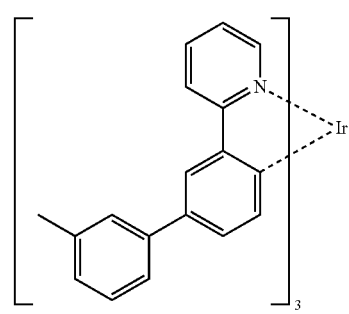
D-37
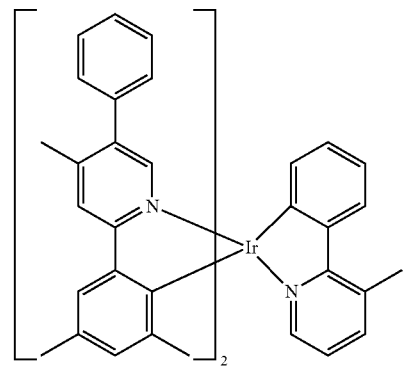

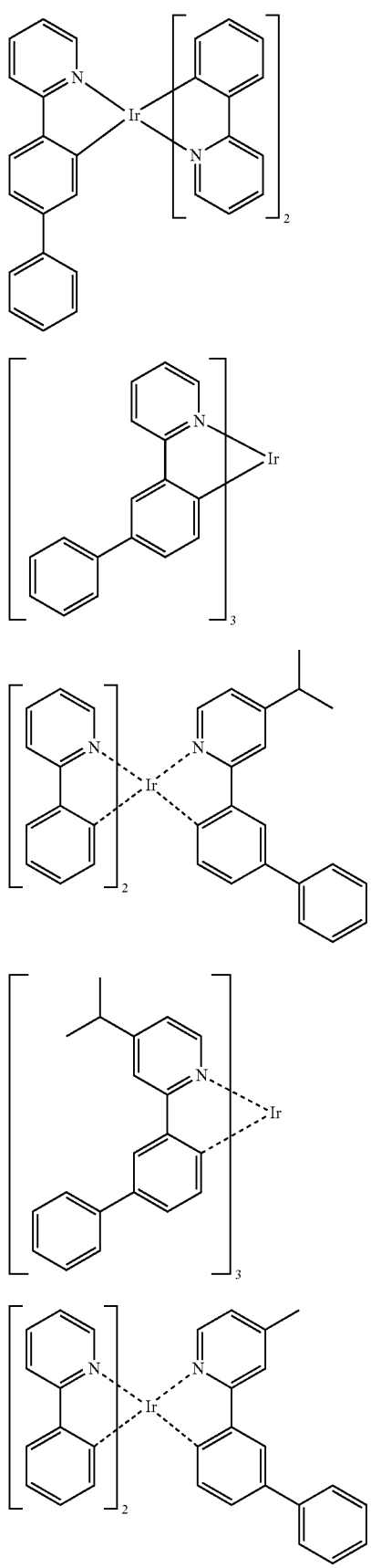
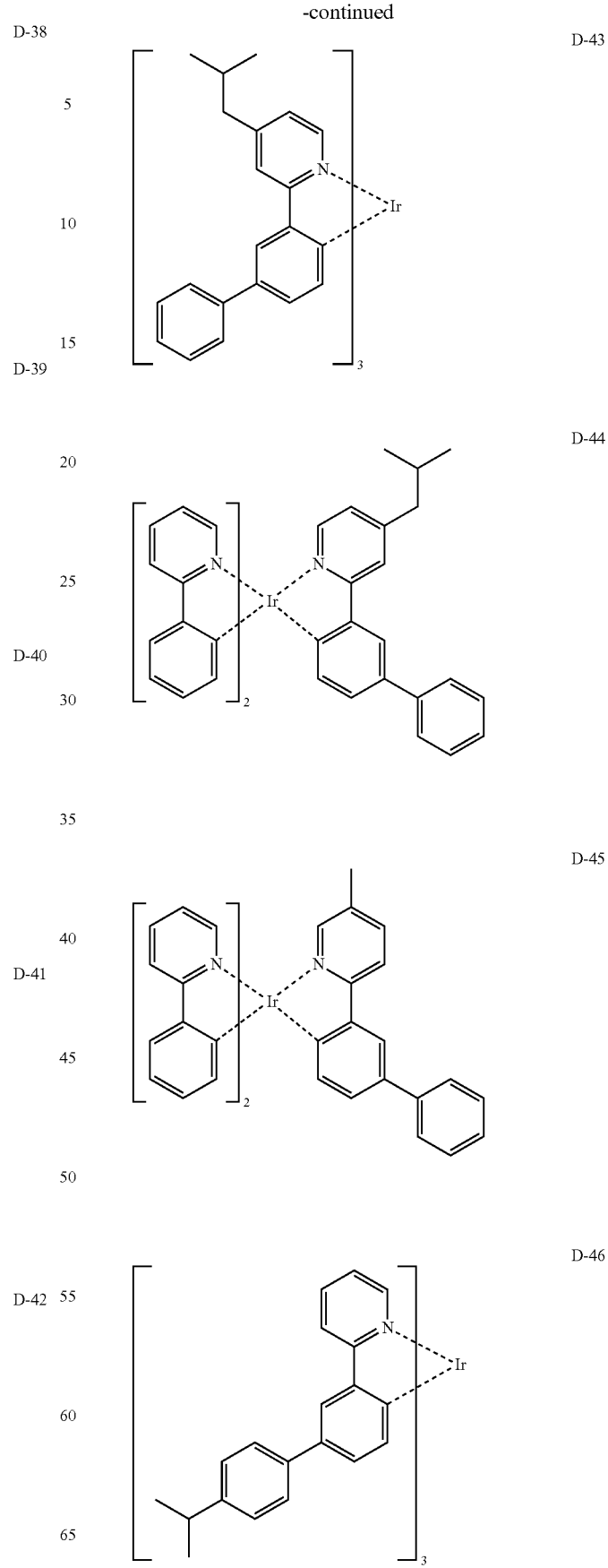
D-38
D-39
D-40
D-41
D-42
D-43
D-44
D-45
D-46

-continued
D-47
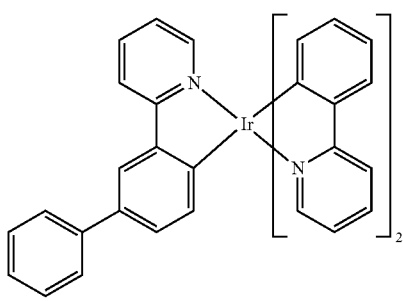
D-48
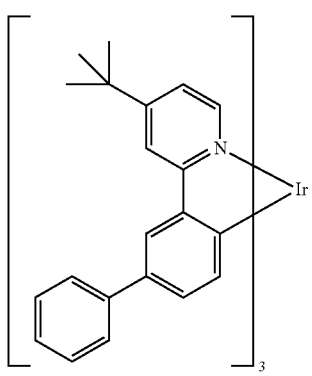
D-49
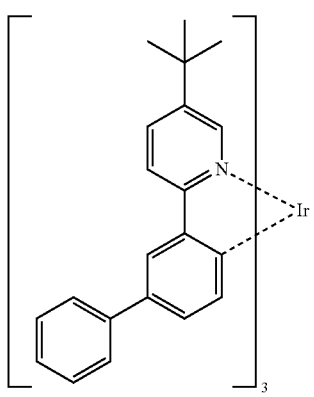
D-50
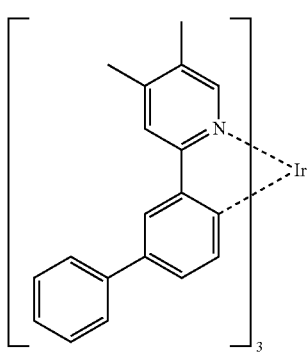
-continued
D-51
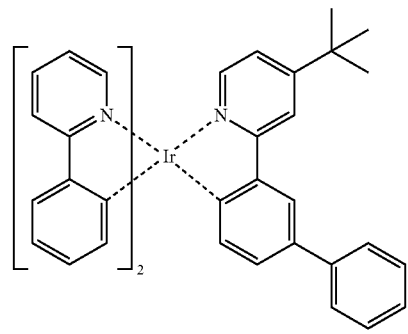
D-52
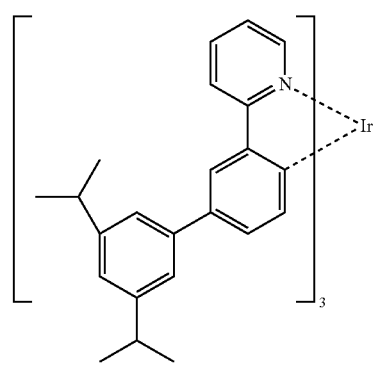
D-53
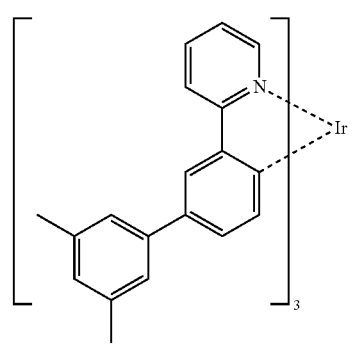
D-54
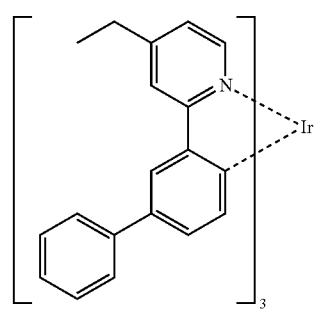

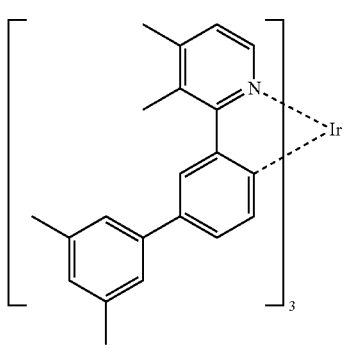
D-55
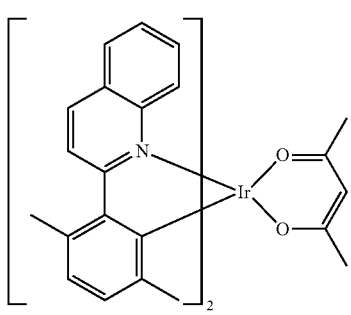
D-56
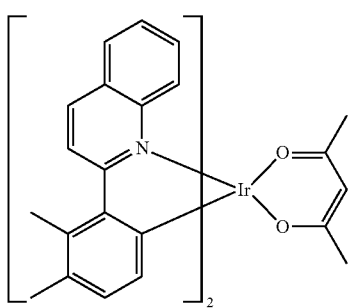
D-57
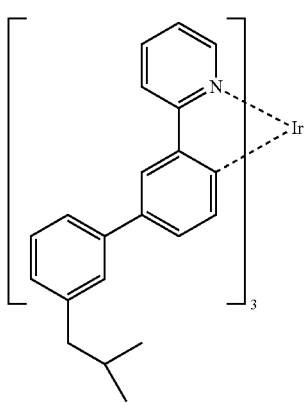
D-58
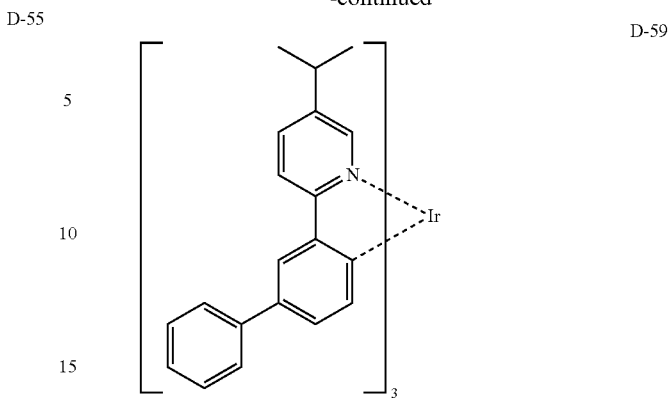
D-59
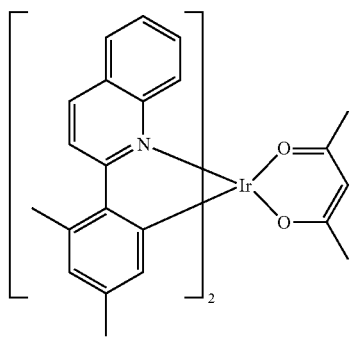
D-60
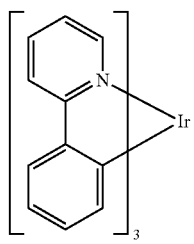
D-61
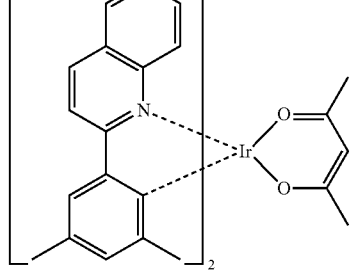
D-62

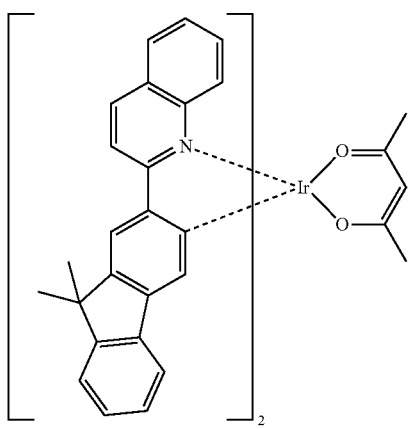
D-63
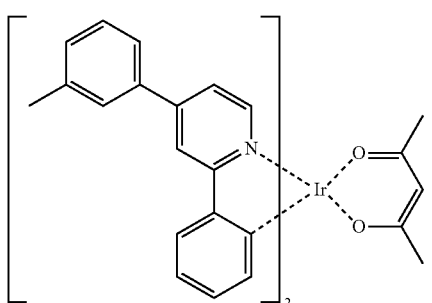
D-64
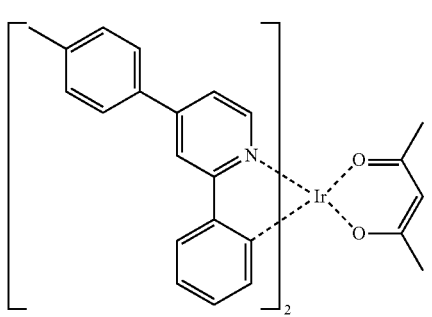
D-65
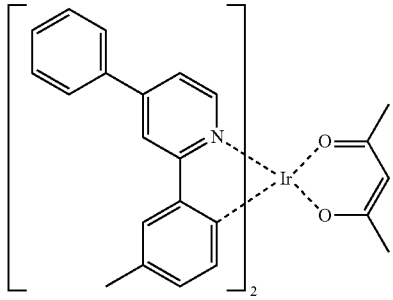
D-66
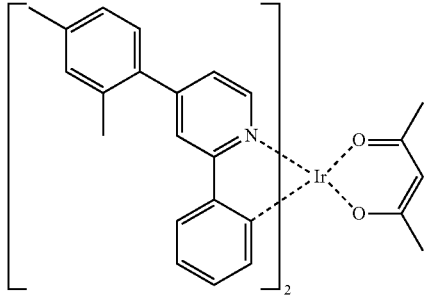
D-67
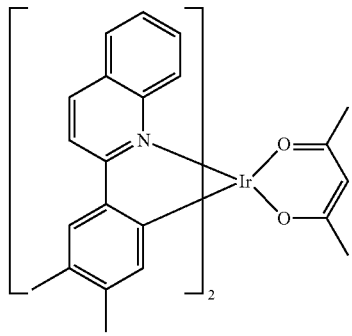
D-68
D-69
D-70
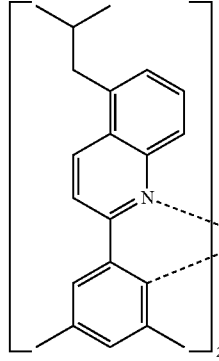
D-71

D-72
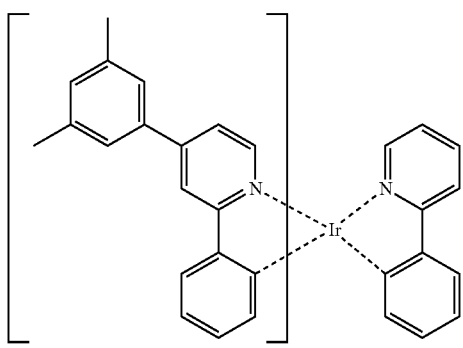
D-73
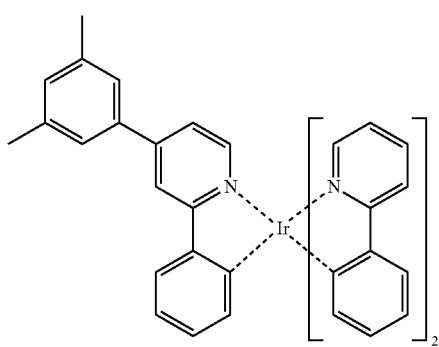
D-74
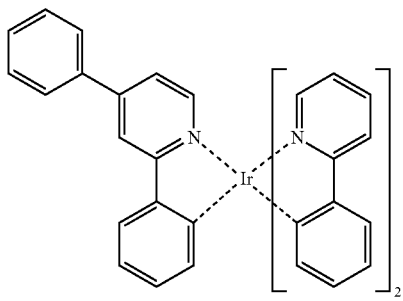
D-75
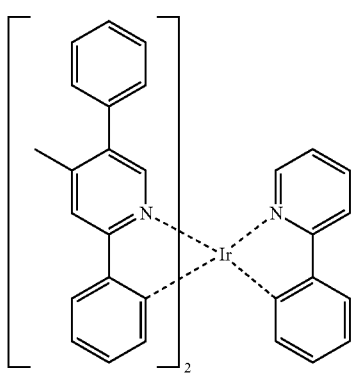
D-76
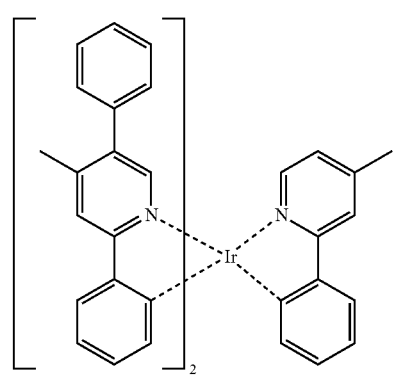
D-77
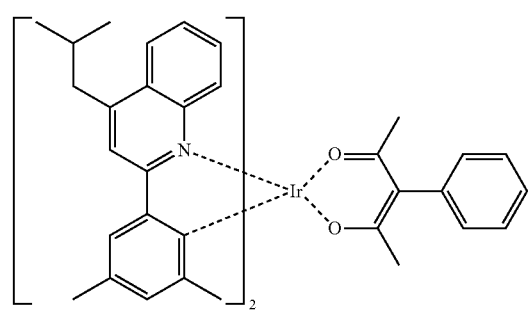
D-78
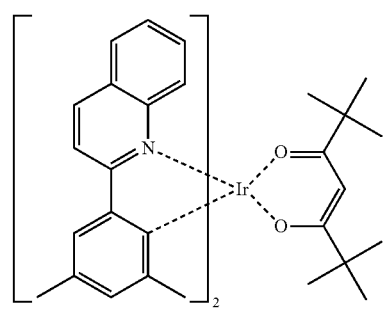
D-79
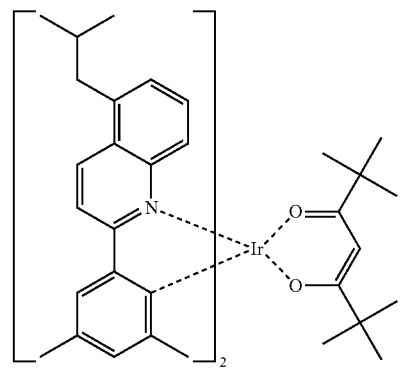

D-80 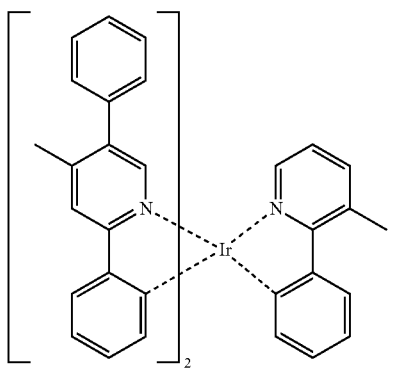
D-81 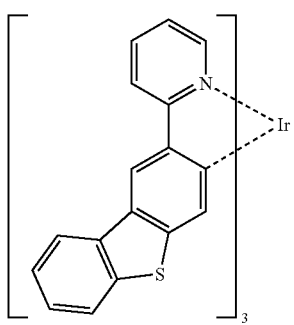
D-82 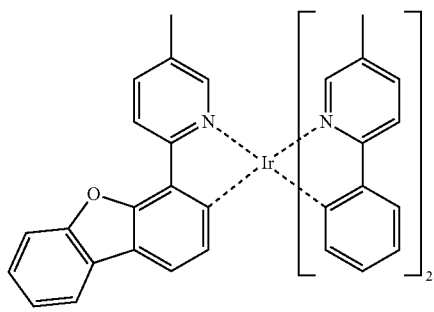
D-83 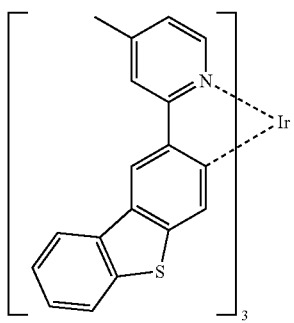
D-84 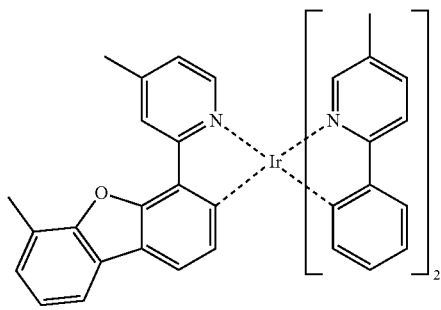
D-85 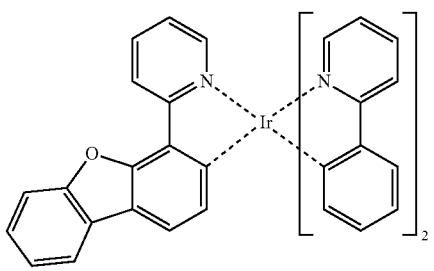
D-86 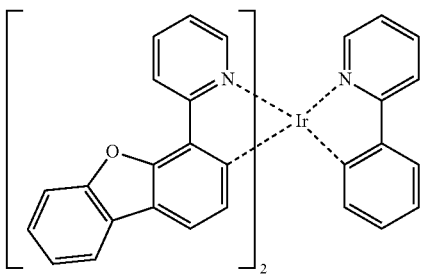
D-87 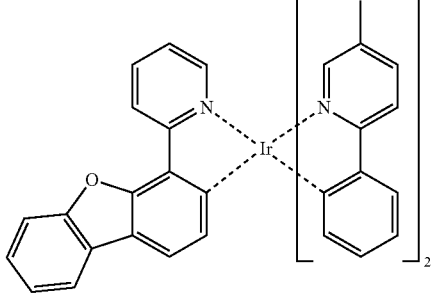
D-88 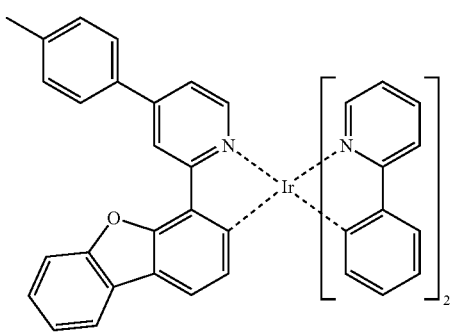
D-89 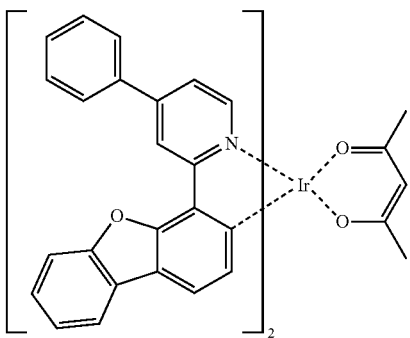

D-90
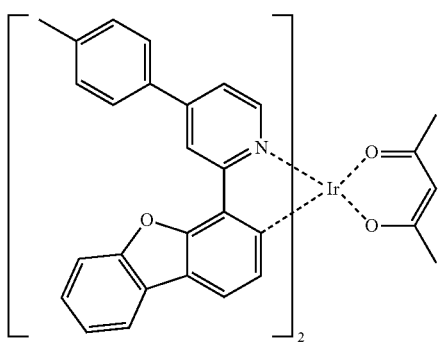
D-91
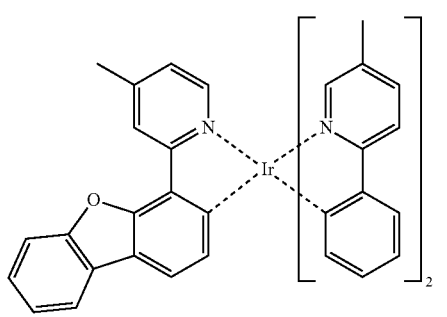
D-92
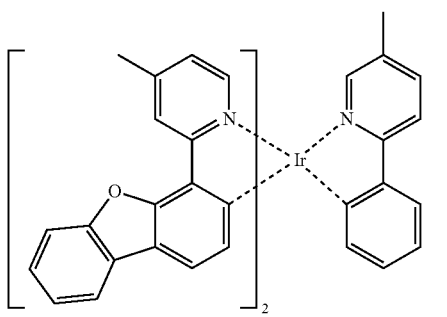
D-93
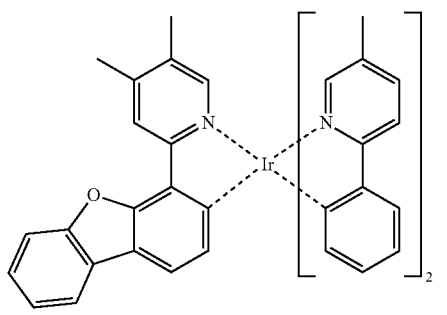
D-94
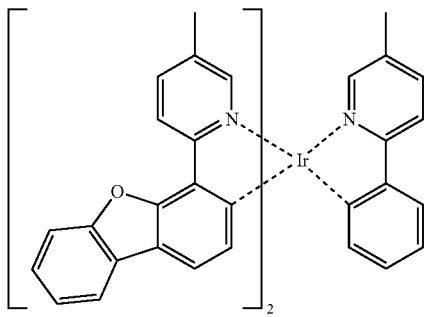
D-95
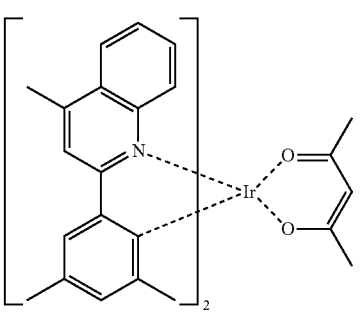
D-96
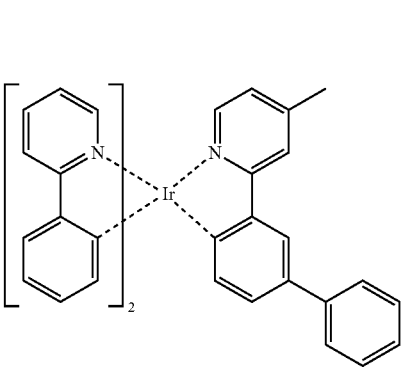
D-97
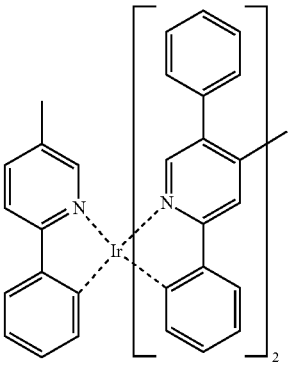
D-98
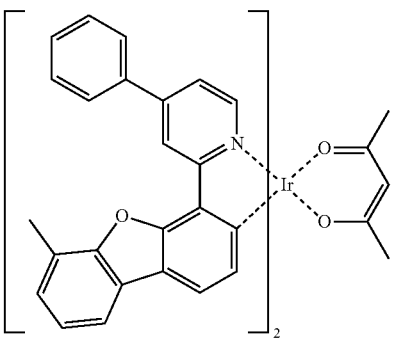

D-99
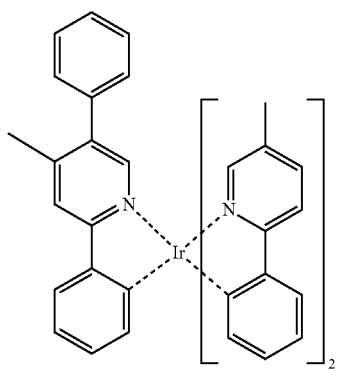
D-100
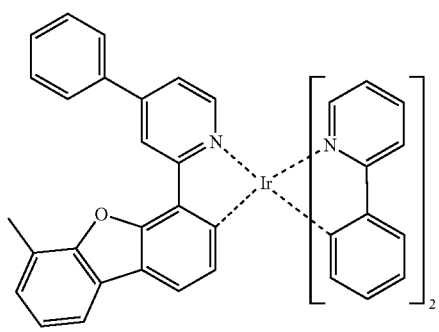
D-101
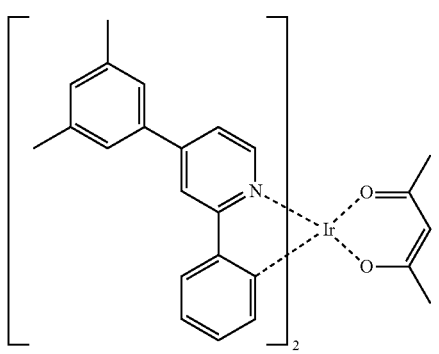
D-102
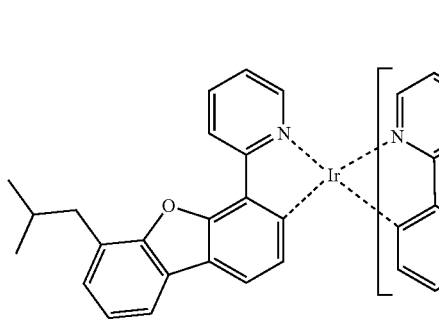
D-103
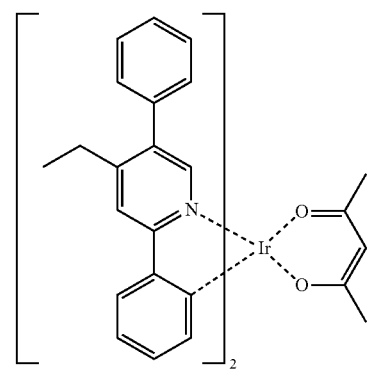
D-104
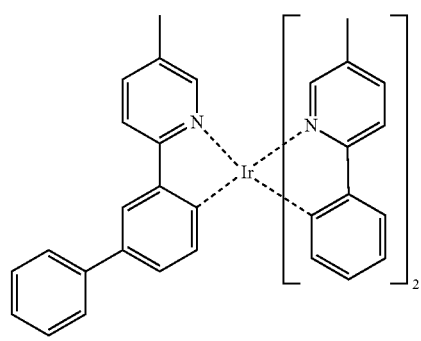
D-105
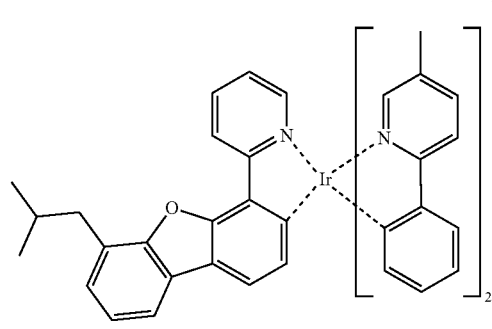
D-106
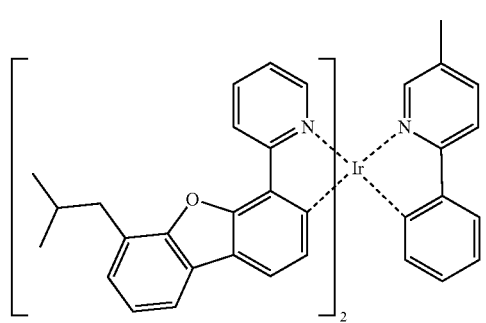

-continued
D-107
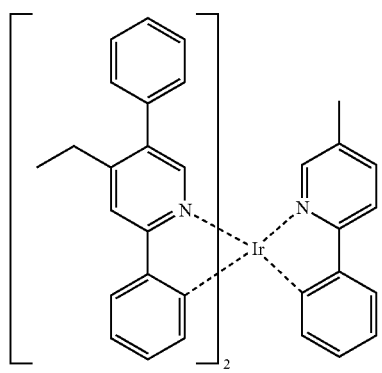
D-108
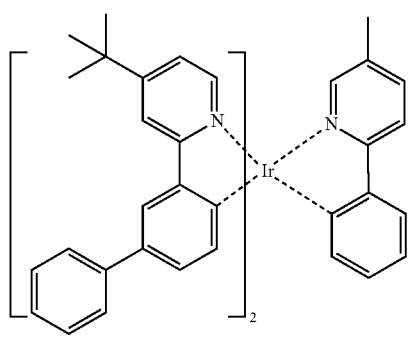
D-109
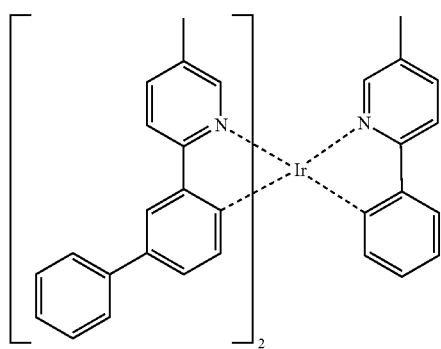
D-110
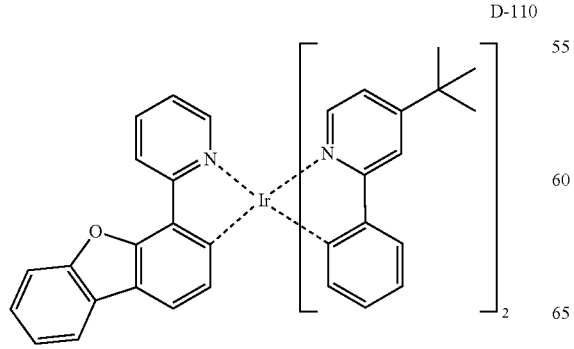
-continued
D-111
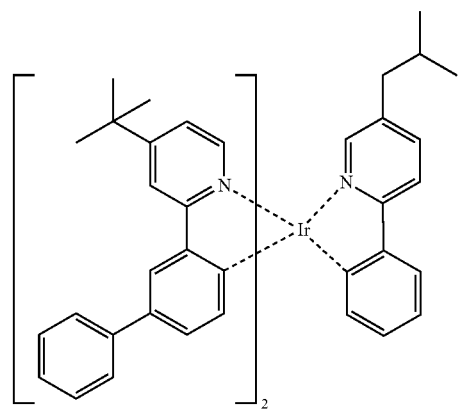
D-112
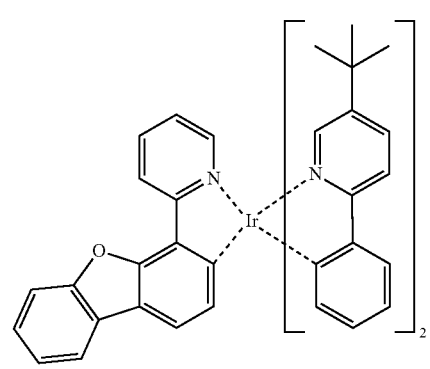
D-113
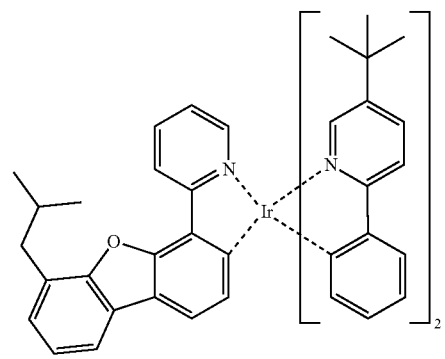
D-114
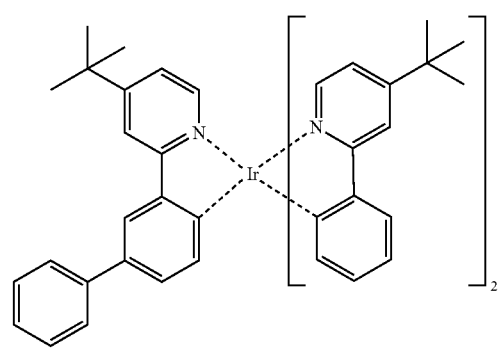

-continued
D-115
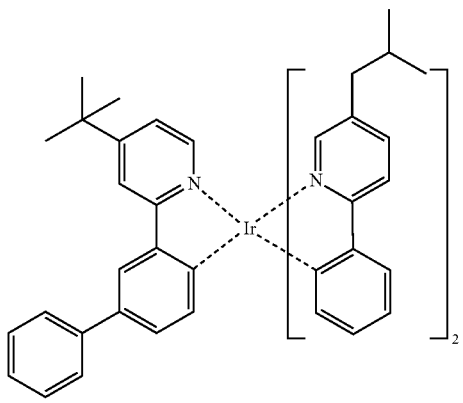
D-116
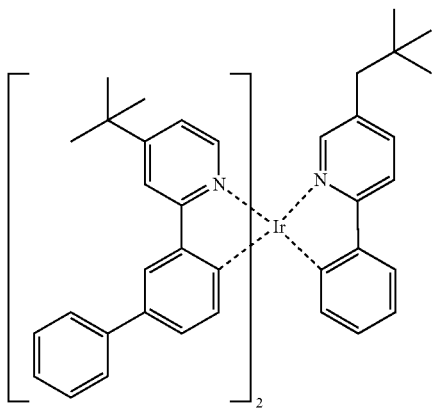
D-117
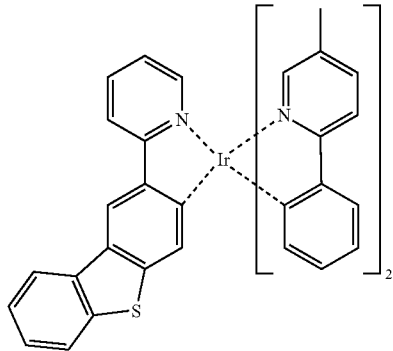
D-118
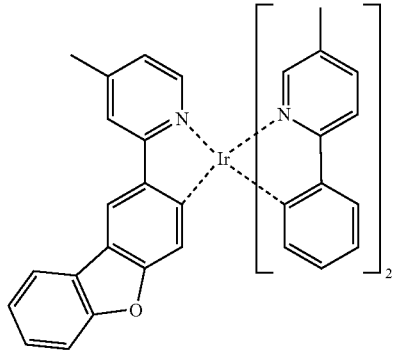
-continued
D-119
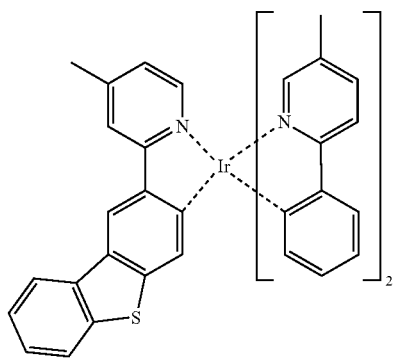
D-120
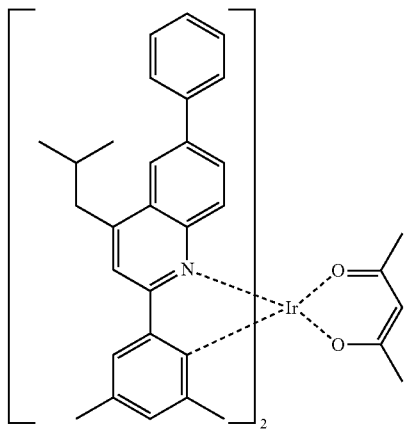
D-121
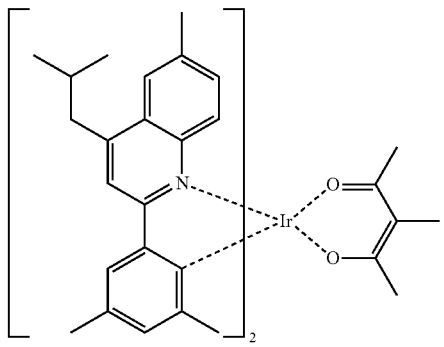
D-122
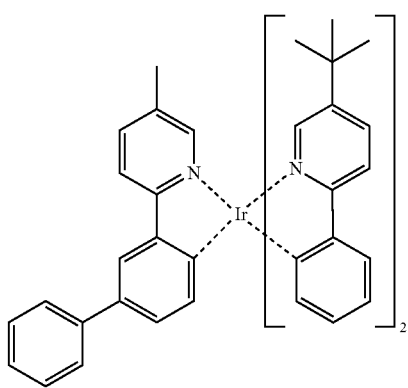

-continued
D-123
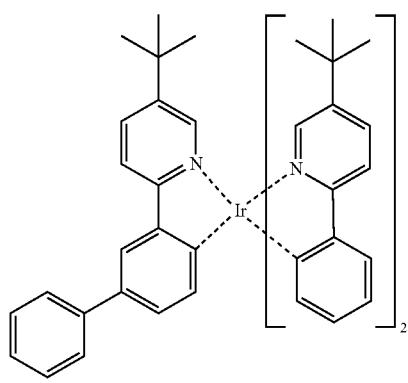
D-124
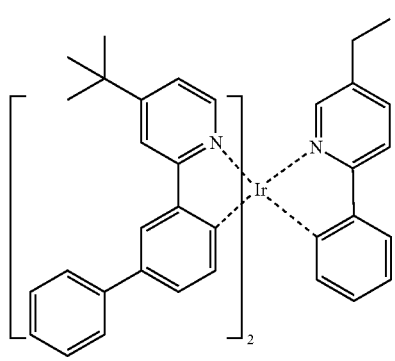
D-125
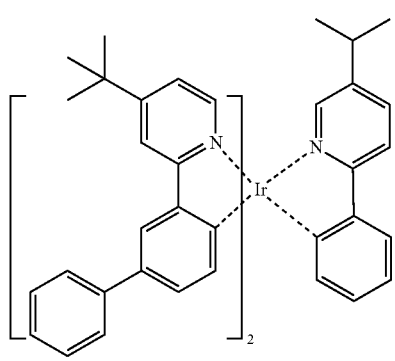
D-126
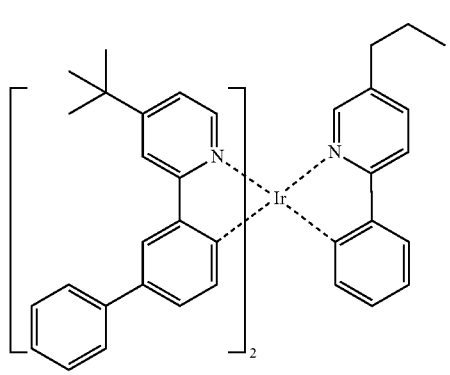
-continued
D-127
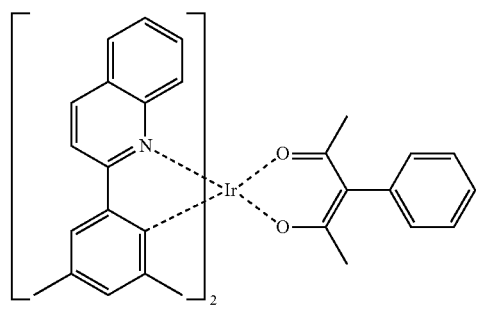
D-128
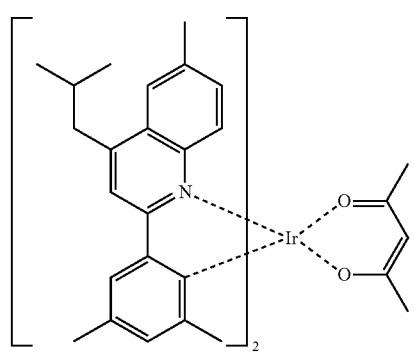
D-129
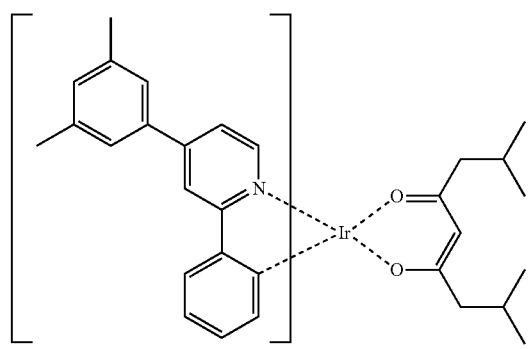
D-130
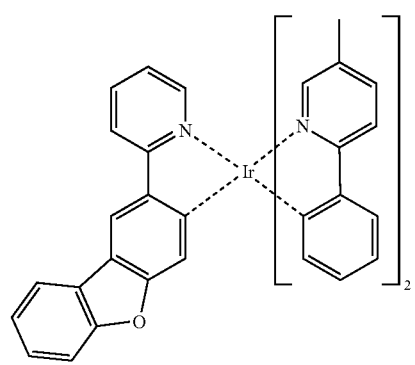

D-131
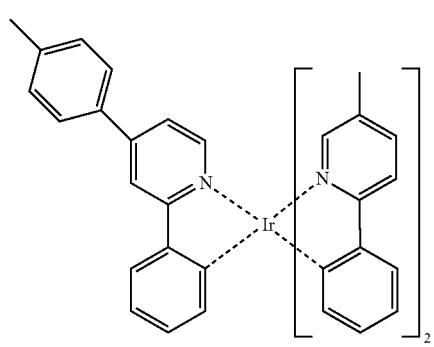
D-132
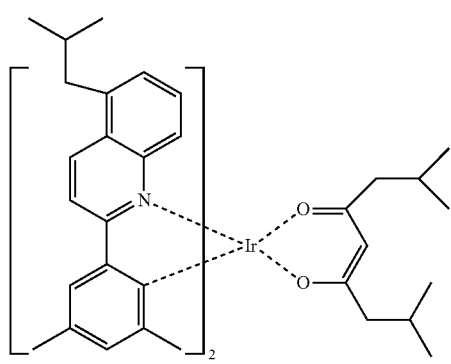
D-133
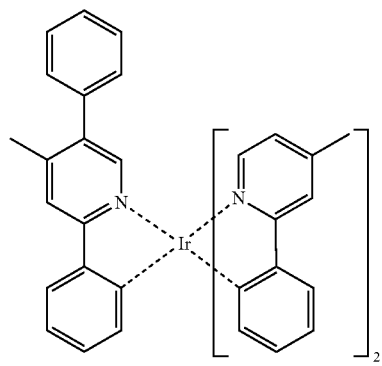
D-134
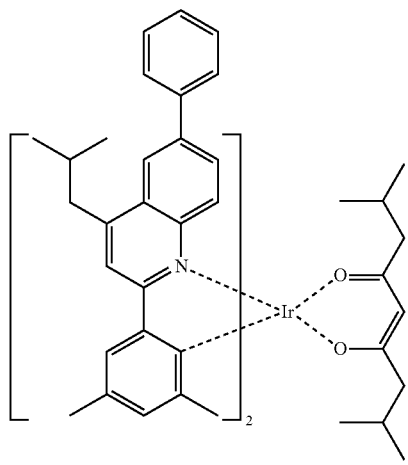
D-135
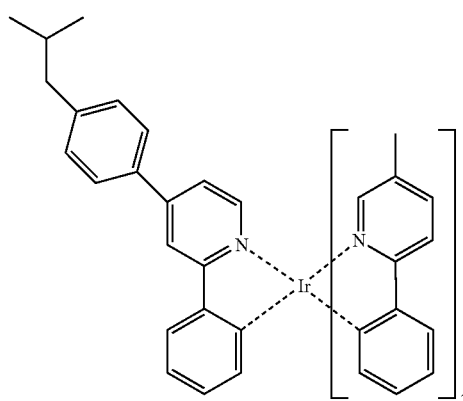
D-136
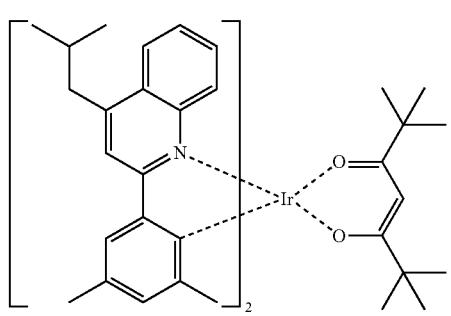
D-137
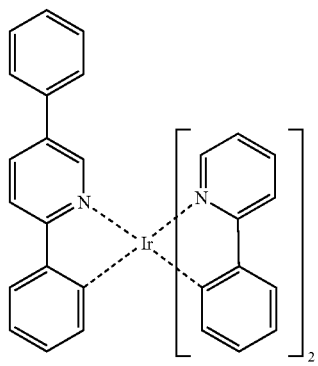
D-138
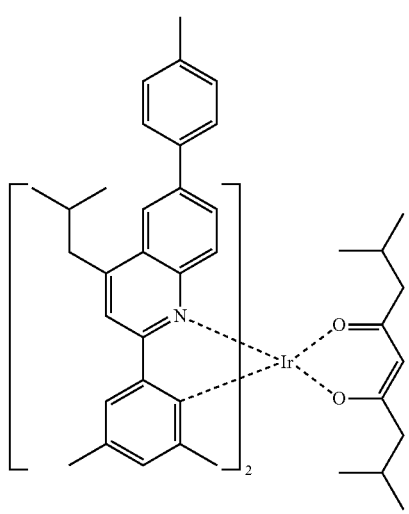

D-139
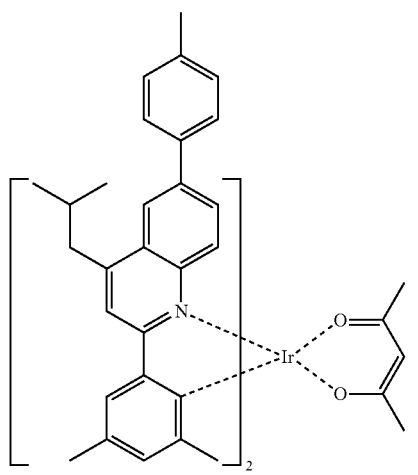
D-140
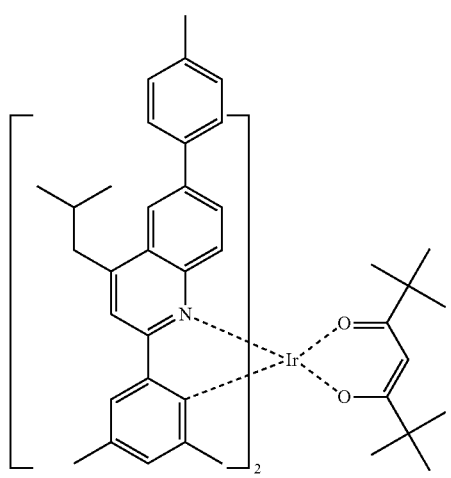
D-141
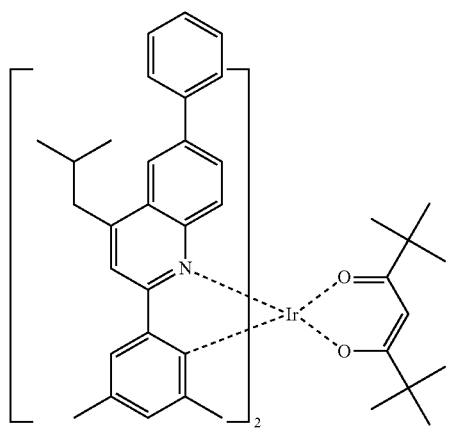
D-142
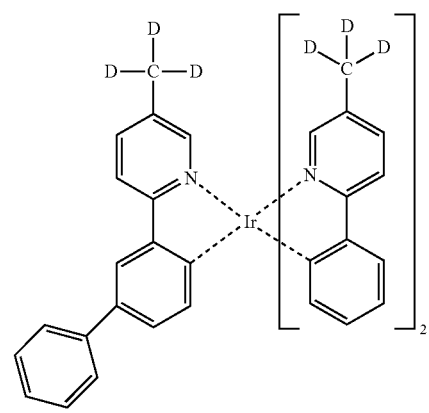
D-143
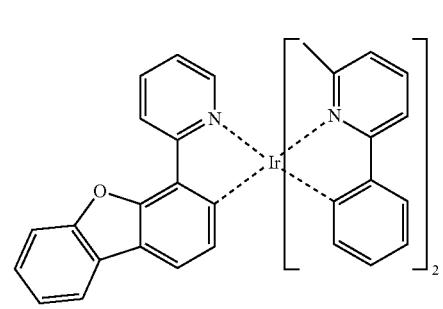
D-144
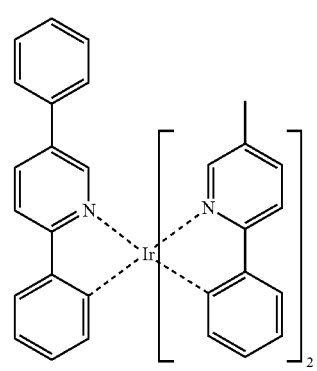
D-145
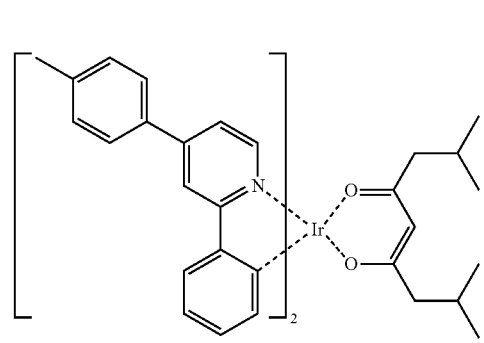

D-146
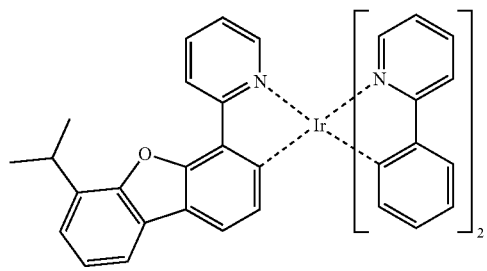
D-147
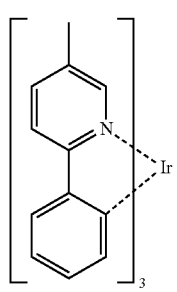
D-148
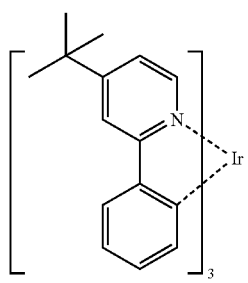
D-149
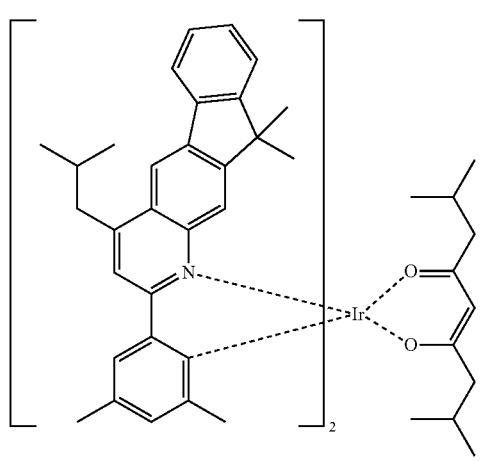
D-150
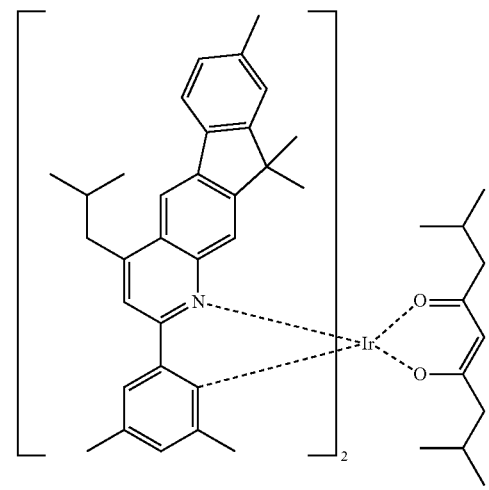
D-151
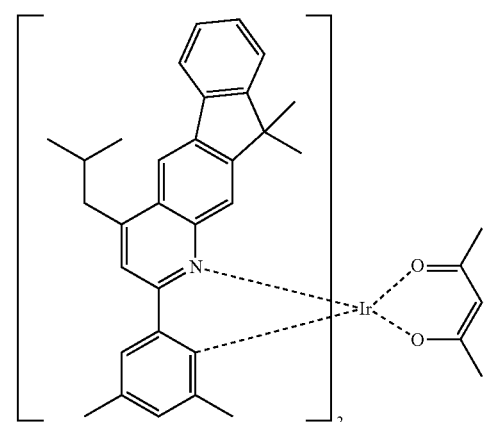
D-152
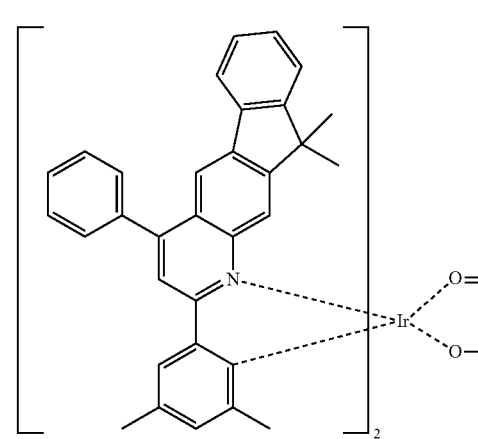

D-153

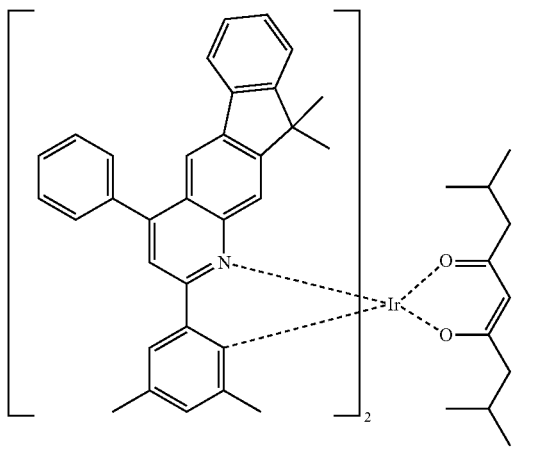

D-154

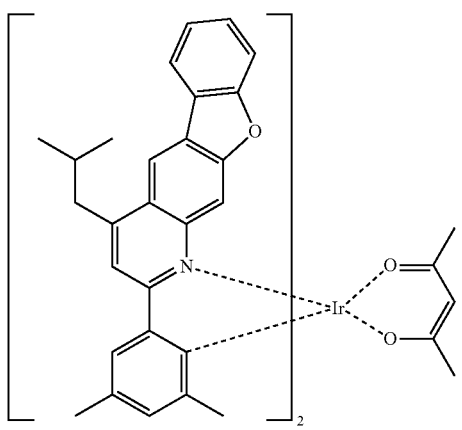

D-155

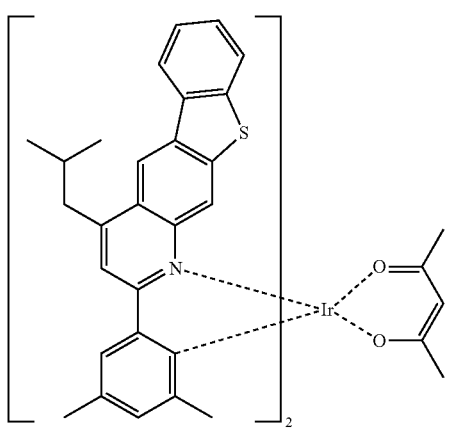

D-156

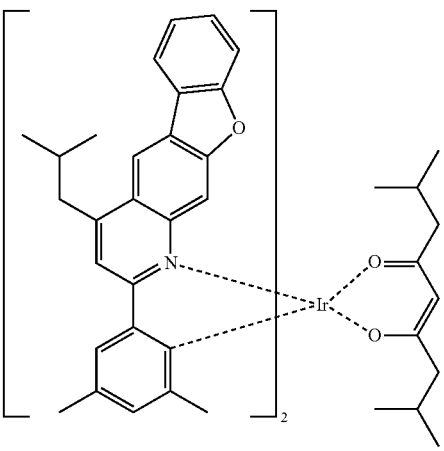

D-157

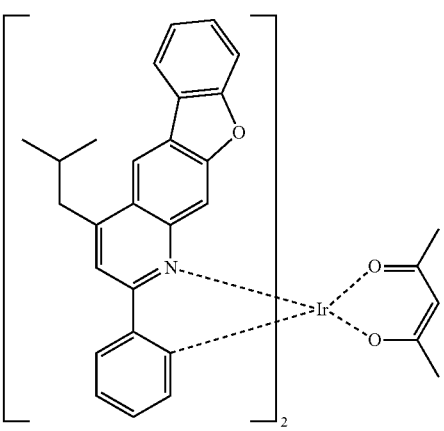

The organic electroluminescent device according to the present disclosure comprises a first electrode; a second electrode; and at least one organic layer between the first and second electrodes.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The organic layer may further comprise at least one compound selected from the group consisting of arylamine-based compounds and styrylarylamine-based compounds.

In addition, in the organic electroluminescent device according to the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

In addition, the organic electroluminescent device according to the present disclosure may emit white light by further comprising at least one light-emitting layer which comprises a blue electroluminescent compound, a red electroluminescent compound or a green electroluminescent compound known in the field, besides the compound according to the present disclosure. Also, if necessary, a yellow or orange light-emitting layer can be further comprised in the device.

In the organic electroluminescent device according to the present disclosure, at least one layer (hereinafter, "a surface layer") is preferably placed on an inner surface(s) of one or both electrode(s); selected from a chalcogenide layer, a metal halide layer, and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_x$ (1≤X≤2), $AlO_x$ (1≤X≤1.5), SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic EL device having two or more light-emitting layers which emits white light.

In order to form each layer constituting the organic electroluminescent device of the present disclosure, dry film-forming methods such as vacuum deposition, sputtering, plasma, ion plating methods, etc., or wet film-forming methods such as spin coating, dip coating, flow coating methods, etc., can be used. When forming the film of the first and second host compounds of the present disclosure, a co-evaporation or a mixed evaporation method is used.

When using a wet film-forming method, a thin film is formed by dissolving or dispersing the material constituting each layer in suitable solvents, such as ethanol, chloroform, tetrahydrofuran, dioxane, etc. The solvents are not particularly limited as long as the material constituting each layer is soluble or dispersible in the solvents, which do not cause any problems in forming a film.

By using the organic electroluminescent device of the present disclosure, a display device, for example, for smartphones, tablets, notebooks, PCs, TVs, or vehicles, or a lighting device, for example, an indoor or outdoor lighting device, can be produced.

Hereinafter, the preparation method of the compounds of the present disclosure, the physical properties of the compounds, and the luminous properties of the organic electroluminescent device comprising the compounds will be explained in detail with reference to the representative compounds of the present disclosure. However, the present disclosure is not limited to the Examples below.

Example 1: Preparation of Compound C-81

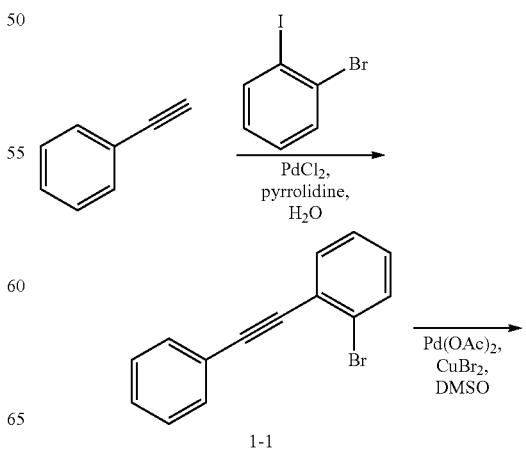

-continued

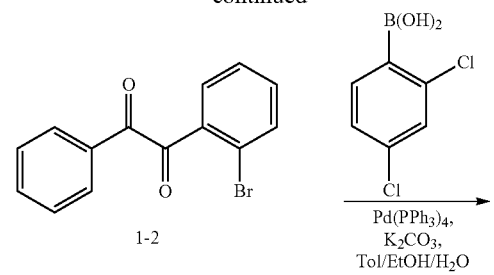

1-2

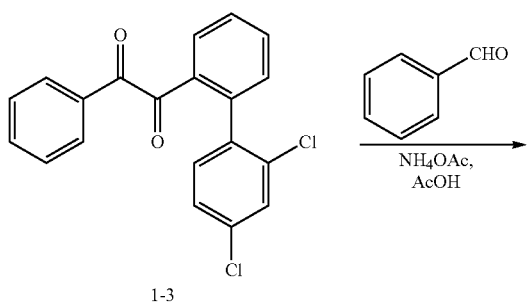

1-3

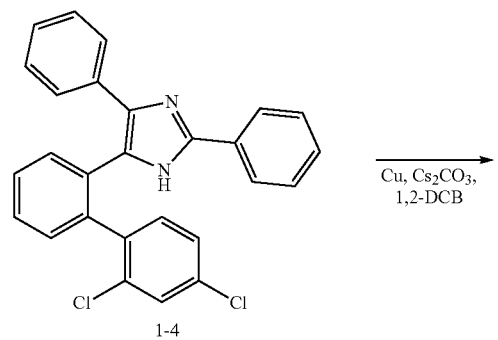

1-4

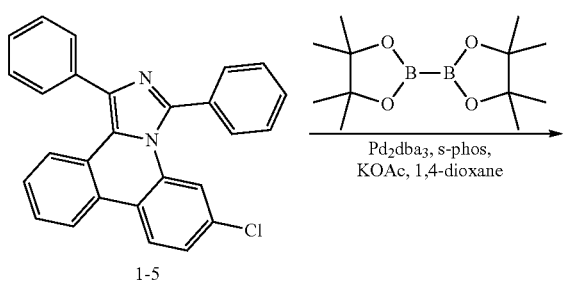

1-5

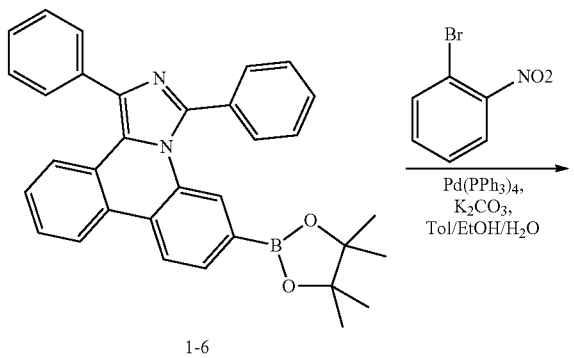

1-6

-continued

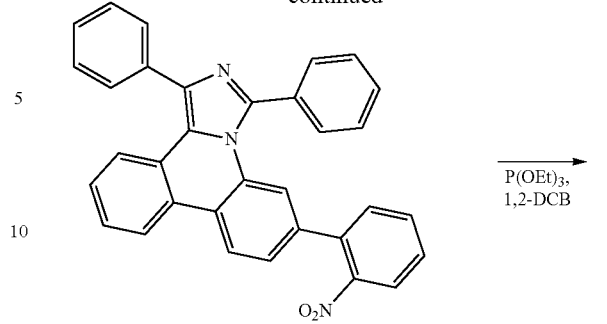

1-7

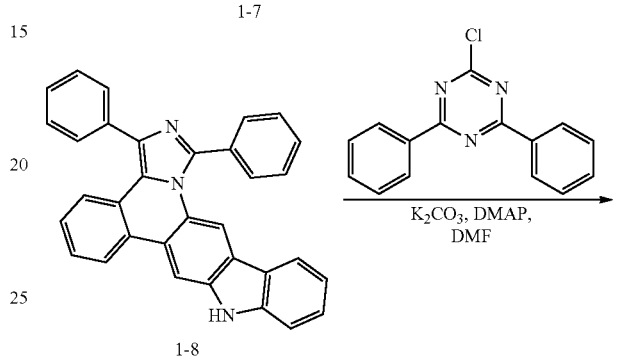

1-8

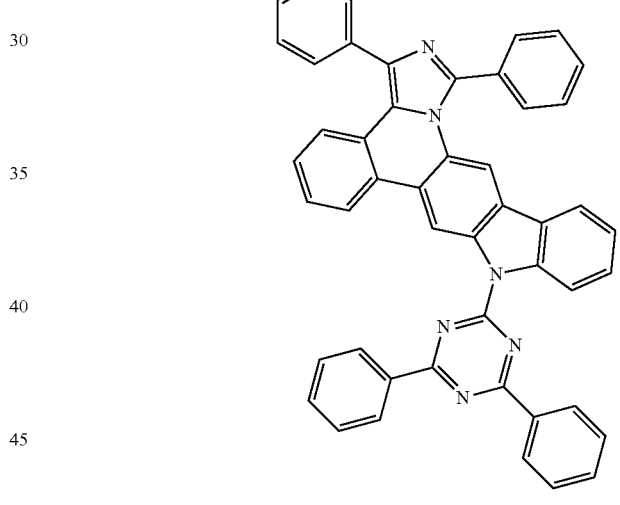

C-81

1) Synthesis of Compound 1-1

17.3 g of phenylacetylene (170 mmol), 40 g of 1-bromo-2-iodobenzene (141 mmol), 0.2 g of palladium(II) chloride (1 mmol), 50 g of pyrrolidine (707 mmol), and 180 mL of water were introduced into a flask and dissolved, and the mixture was stirred for 24 hours at 50° C. After completion of the reaction, an organic layer was extracted with ethyl acetate, and the remaining moisture was removed using magnesium sulfate. Thereafter, the resulting product was dried and separated by column chromatography to obtain 29 g of compound 1-1 (yield: 80%).

2) Synthesis of Compound 1-2

28 g of compound 1-1 (109 mmol), 2.4 g of palladium(II) acetate (11 mmol), 2.4 g of cupric bromide (11 mmol), and 440 mL of DMSO were introduced into a flask and dissolved, and the mixture was refluxed for 20 hours. After completion of the reaction, an organic layer was extracted with ethyl acetate, and the remaining moisture was removed using magnesium sulfate. Thereafter, the resulting product was dried and separated by column chromatography to obtain 16.3 g of compound 1-2 (yield: 52%).

3) Synthesis of Compound 1-3

18.2 g of compound 1-2 (63 mmol), 14.4 g of 2,4-dichlorophenyl boronic acid (76 mmol), 3.6 g of tetrakis(triphenylphosphine)palladium(0) (3 mmol), 21.7 g of 2 M potassium carbonate (80 mmol), 320 mL of toluene, and 80 mL of ethanol were introduced into a flask and dissolved, and the mixture was refluxed for 5 hours. After completion of the reaction, an organic layer was extracted with ethyl acetate, and the remaining moisture was removed using magnesium sulfate. Thereafter, the resulting product was dried and separated by column chromatography to obtain 20.6 g of compound 1-3 (yield: 92%).

4) Synthesis of Compound 1-4

20.6 g of compound 1-3 (58 mmol), 6.1 g of benzaldehyde (58 mmol), 26.8 g of ammonium acetate (348 mmol), and 290 mL of acetic acid were introduced into a flask and dissolved, and the mixture was refluxed for 24 hours. After completion of the reaction, an organic layer was extracted with ethyl acetate, and the remaining moisture was removed using magnesium sulfate. Thereafter, the resulting product was dried and separated by column chromatography to obtain 23.5 g of compound 1-4 (yield: 91.8%).

5) Synthesis of Compound 1-5

23.5 g of compound 1-4 (53 mmol), 3.38 g of copper powder (53 mmol), 69 g of cesium carbonate (213 mmol), and 350 mL of 1,2-dichlorobenzene were introduced into a flask and dissolved, and the mixture was refluxed for 17 hours. After completion of the reaction, an organic layer was extracted with ethyl acetate, and the remaining moisture was removed using magnesium sulfate. Thereafter, the resulting product was dried and separated by column chromatography to obtain 18.3 g of compound 1-5 (yield: 85%).

6) Synthesis of Compound 1-6

18.3 g of compound 1-5 (45 mmol), 13.7 g of bis(pinacolato)diboron (54 mmol), 2.0 g of tris(dibenzylideneacetone)dipalladium (2 mmol), 1.85 g of 2-dichlorohexylphosphine-2',6'-dimethoxybiphenyl (s-phos) (5 mmol), 11 g of potassium acetate (113 mmol), and 230 mL of 1,4-dioxane were introduced into a flask and dissolved, and the mixture was stirred under reflux for 4 hours. After completion of the reaction, an organic layer was extracted with ethyl acetate, and the remaining moisture was removed using magnesium sulfate. Thereafter, the resulting product was dried and separated by column chromatography to obtain 13.7 g of compound 1-6 (yield: 61%).

7) Synthesis of Compound 1-7

13.2 g of compound 1-6 (27 mmol), 4.45 g of 2-bromonitrobenzene (22 mmol), 1.26 g of tetrakis(triphenylphosphine)palladium(0) (1 mmol), 7.64 g of 2 M potassium carbonate (55 mmol), 120 mL of toluene, and 30 mL of ethanol were introduced into a flask and dissolved, and the mixture was refluxed for 6 hours. After completion of the reaction, an organic layer was extracted with ethyl acetate, and the remaining moisture was removed using magnesium sulfate. Thereafter, the resulting product was dried and separated by column chromatography to obtain 7.2 g of compound 1-7 (yield: 55%).

8) Synthesis of Compound 1-8

6.2 g of compound 1-7 (13 mmol), 42 mL of triethyl phosphite, and 42 mL of 1,2-dichlorobenzene were introduced into a flask and dissolved, and the mixture was refluxed for 17 hours. After completion of the reaction, an organic layer was extracted with ethyl acetate after distillation under reduced pressure, and the remaining moisture was removed using magnesium sulfate. Thereafter, the resulting product was dried and separated by column chromatography to obtain 1.5 g of compound 1-8 (yield: 25%).

9) Synthesis of Compound C-81

1.5 g of compound 1-8 (3 mmol), 1.05 g of 2-chloro-4,6-diphenyl-1,3,5-triazine (4 mmol), 0.9 g of potassium carbonate (7 mmol), 0.04 g of 4-dimethylaminopyridine (0.3 mmol), 32 mL of dimethylformamide were introduced into a flask and dissolved, and the mixture was refluxed for 4 hours. After completion of the reaction, the produced solid was filtered and the filtrate was separated by column chromatography to obtain 1.7 g of compound C-81 (yield: 75%).

| Compound | MW | UV | PL | M.P. |
| --- | --- | --- | --- | --- |
| C-81 | 690.81 | 342 nm | 463 nm | 389° C. |

Device Example 1: Production of an OLED Device Using the Organic Electroluminescent Compound According to the Present Disclosure as a Host An OLED device was produced comprising the organic electroluminescent compound of the present disclosure. A transparent electrode indium tin oxide (ITO) thin film (10 Ω/sq) on a glass substrate for an OLED device (Geomatec, Japan) was subjected to an ultrasonic washing with acetone, ethanol, and distilled water, sequentially, and was then stored in isopropanol. Next, the ITO substrate was mounted on a substrate holder of a vacuum vapor depositing apparatus. Compound HIL-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Compound HIL-2 was then introduced into another cell of said vacuum vapor depositing apparatus, and was evaporated by applying an electric current to the cell, thereby forming a second hole injection layer having a thickness of 5 nm on the first hole injection layer. Compound HTL-1 was introduced into another cell of said vacuum vapor depositing apparatus, and was evaporated by applying an electric current to the cell, thereby forming a first hole transport layer having a thickness of 10 nm on the second hole injection layer. Compound HTL-2 was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. Compound C-81 was introduced into one cell of the vacuum vapor depositing apparatus as a host, and compound D-71 was introduced into another cell as a dopant. The two materials were evaporated at different rates and were deposited in a doping amount of 3 wt % based on the total amount of the host and dopant to form a light-emitting layer having a thickness of 40 nm on the second hole transport layer. Compound ETL-1 and Liq were then introduced into two other cells, simultaneously evaporated at the rate of 1:1, and deposited to form an electron transport layer having a thickness of 30 nm on the light-emitting layer. Next, after depositing Liq as an electron injection layer having a thickness of 2 nm on the electron transport layer, an Al cathode having a thickness of 80 nm was deposited by another vacuum vapor deposition apparatus on the electron injection layer. Thus, an OLED device was produced.

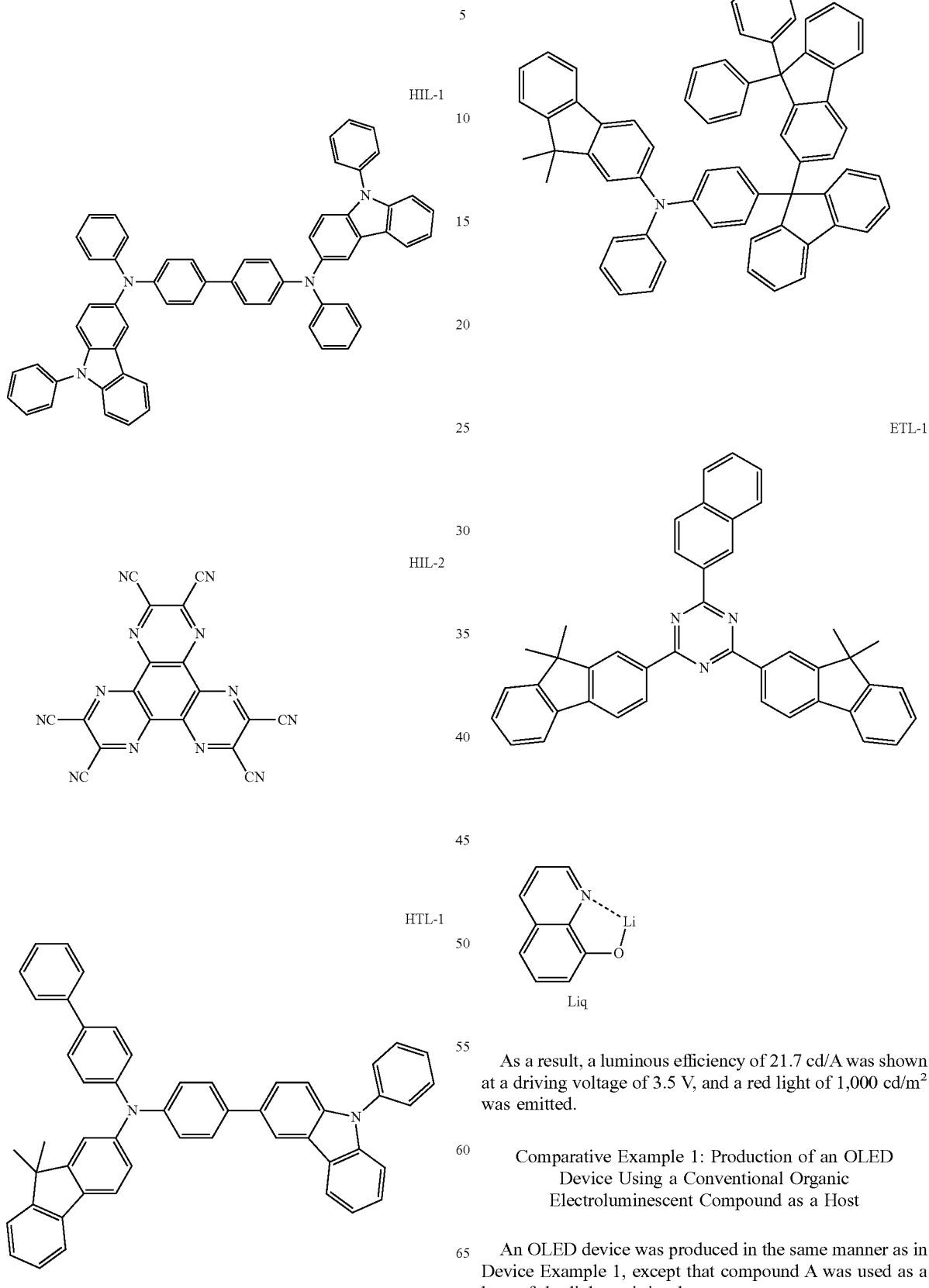

As a result, a luminous efficiency of 21.7 cd/A was shown at a driving voltage of 3.5 V, and a red light of 1,000 cd/m² was emitted.

Comparative Example 1: Production of an OLED Device Using a Conventional Organic Electroluminescent Compound as a Host An OLED device was produced in the same manner as in Device Example 1, except that compound A was used as a host of the light-emitting layer.

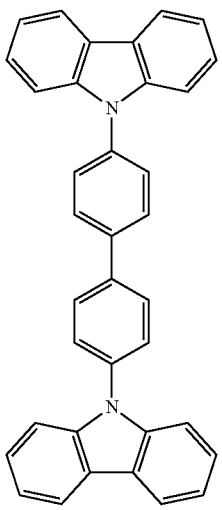

As a result, a luminous efficiency of 14.3 cd/A was shown at a driving voltage of 10.0 V, and a red light of 1,000 cd/m² was emitted.

It was verified that the driving voltage and luminous efficiency characteristics of the organic electroluminescent device using the organic electroluminescent compound of the present disclosure as a host are much superior to the organic electroluminescent device using a conventional organic electroluminescent compound.

The invention claimed is:

1. An organic electroluminescent compound represented by the following formula 1:

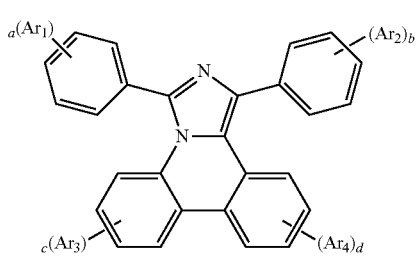

(1)

wherein

Ar$_1$ and Ar$_2$ each independently represent hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered) heterocycloalkyl, or a substituted or unsubstituted (C3-C30)cycloalkyl;

Ar$_3$ and Ar$_4$ each independently represent hydrogen, deuterium, a halogen, a cyano, —NR$_{11}$R$_{12}$, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; and at least one of two Ar$_3$'s and two Ar$_4$'s are linked to each other to form a fused ring of

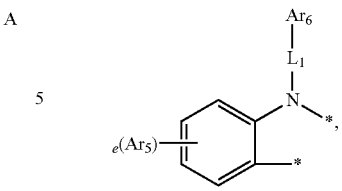

in which * represents a bonding site of Ar$_3$ or Ar$_4$;

R$_{11}$ and R$_{12}$ each independently represent hydrogen, deuterium, a halogen, a substituted or unsubstituted (C1-C30)alkyl, a substituted or unsubstituted (C6-C30)aryl, a substituted or unsubstituted (5- to 30-membered) heteroaryl, a substituted or unsubstituted (3- to 7-membered) heterocycloalkyl, or a substituted or unsubstituted (C3-C30)cycloalkyl;

L$_1$ represents a single bond, or a substituted or unsubstituted (C6-C30)arylene;

Ar$_5$ represents hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl;

Ar$_6$ represents a substituted or unsubstituted (C6-C30) aryl, or a substituted or unsubstituted (5- to 30-membered)heteroaryl;

the heteroaryl contains at least one heteroatom selected from B, N, O, S, Si, and P;

a and b each independently represent an integer of 1 to 5, and c to e each independently represent an integer of 1 to 4;

where a to e is an integer of 2 or more, each Ar$_1$, each Ar$_2$, each Ar$_3$, each Ar$_4$, and each Ar$_5$ may be the same or different.

2. The organic electroluminescent compound according to claim 1, wherein the substituents of the substituted (C1-C30)alkyl, the substituted (C6-C30)aryl(ene), the substituted (5- to 30-membered)heteroaryl, the substituted (3- to 7-membered)heterocycloalkyl, and the substituted (C3-C30) cycloalkyl in Ar$_1$ to Ar$_6$, and L$_1$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl(s); a (C6-C30)aryl unsubstituted or substituted with a (5- to 30-membered) heteroaryl(s); a tri(C1-C30)alkylsilyl, a tri(C6-C30)arylsilyl; a di(C1-C30)alkyl(C6-C30)arylsilyl; a (C1-C30)alkyldi(C6-C30)arylsilyl; an amino; a mono- or di-(C1-C30) alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30) alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

3. The organic electroluminescent compound according to claim 1, wherein formula 1 is represented by any one of the following formulas 2 and 3:

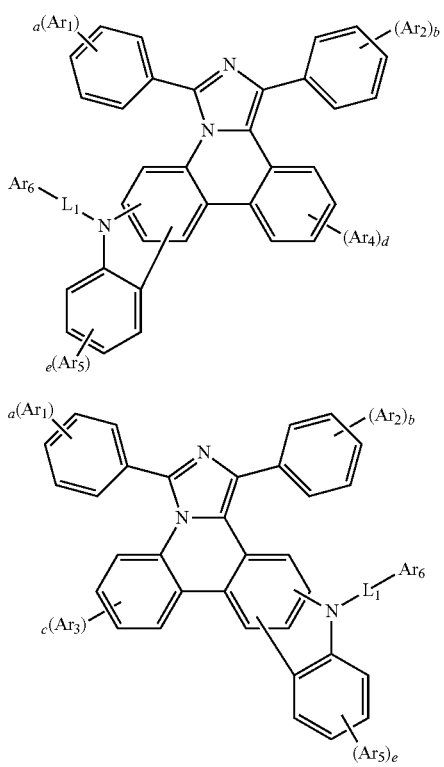

(2)

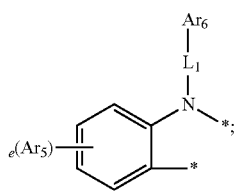

(3)

wherein

Ar₁ to Ar₆, L₁, and a to e are as defined in claim 1.

4. The organic electroluminescent compound according to claim 1, wherein Ar₁ and Ar₂ each independently represent hydrogen, a substituted or unsubstituted (C6-C20)aryl, or a substituted or unsubstituted (5- to 20-membered)heteroaryl;

Ar₃ and Ar₄ each independently represent hydrogen, a halogen, —NR₁₁R₁₂, a substituted or unsubstituted (C6-C20)aryl, or a substituted or unsubstituted (5- to 20-membered)heteroaryl; and at least one of two Ar₃'s and two Ar₄'s are linked to each other to form a fused ring of

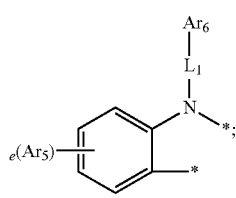

L₁ represents a single bond;

R₁₁ and R₁₂ each independently represent hydrogen, a substituted or unsubstituted (C6-C20)aryl, or a substituted or unsubstituted (5- to 20-membered)heteroaryl;

Ar₅ represents hydrogen, or a substituted or unsubstituted (C6-C20)aryl; and

Ar₆ represents a substituted or unsubstituted (C6-C20) aryl, or a substituted or unsubstituted (5- to 20-membered)heteroaryl.

5. The organic electroluminescent compound according to claim 1, wherein Ar₁ and Ar₂ each independently represent hydrogen, an unsubstituted (C6-C20)aryl, or a (5- to 20-membered) heteroaryl substituted with a (C6-C12)aryl(s);

Ar₃ and Ar₄ each independently represent hydrogen, a (C6-C20)aryl unsubstituted or substituted with a nitro(s), or a (5- to 20-membered)heteroaryl unsubstituted or substituted with a (C6-C12)aryl(s); and at least one of two Ar₃'s and two Ar₄'s are linked to each other to form a fused ring of

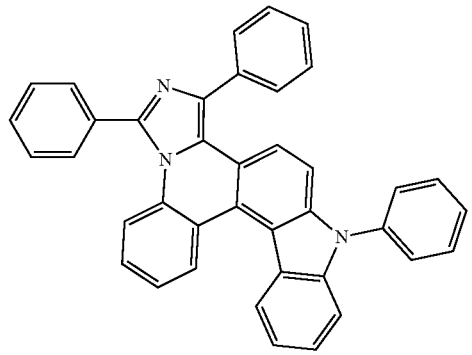

L₁ represents a single bond;

Ar₅ represents hydrogen, or an unsubstituted (C6-C20) aryl; and

Ar₆ represents an unsubstituted (C6-C20)aryl, or a (5- to 20-membered)heteroaryl unsubstituted or substituted with a (C6-C12)aryl(s).

6. The organic electroluminescent compound according to claim 1, wherein the compound represented by formula 1 is at least one selected from the group consisting of:

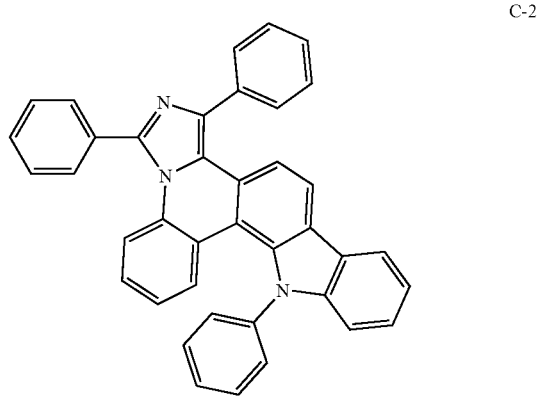

C-3
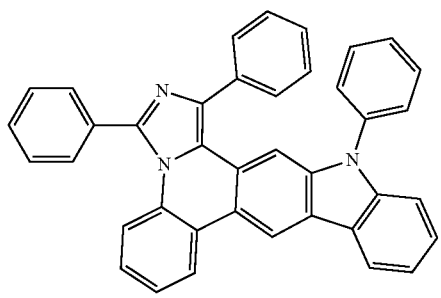
C-4
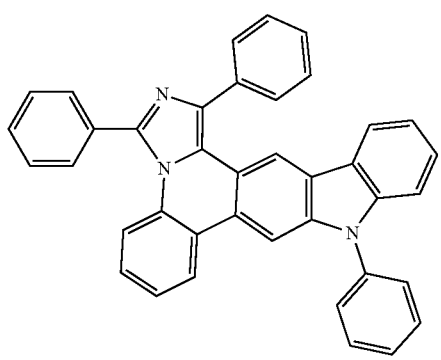
C-5
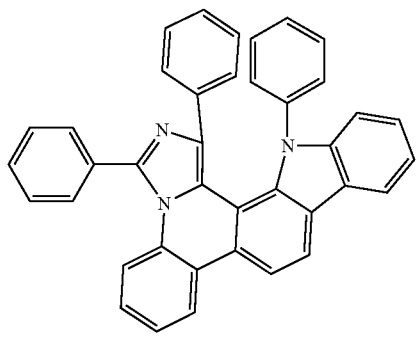
C-6
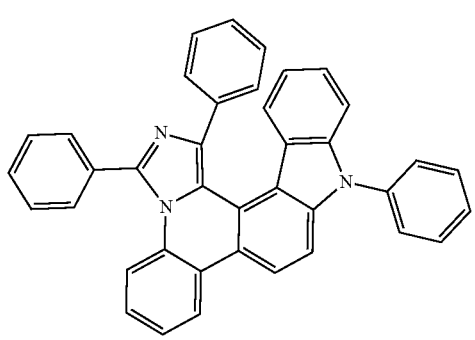
C-7
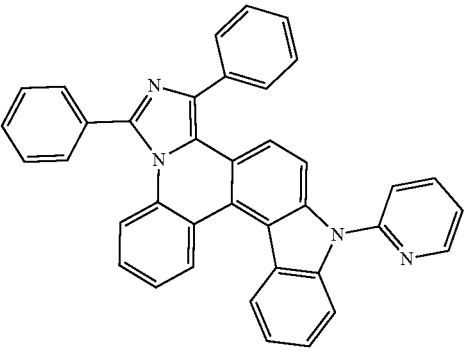
C-8
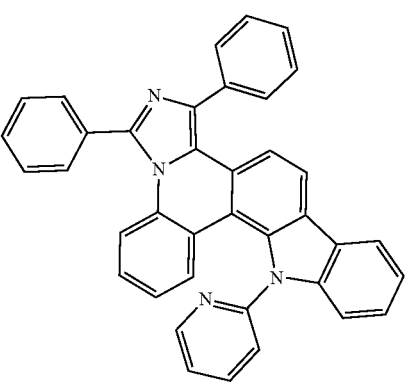
C-9
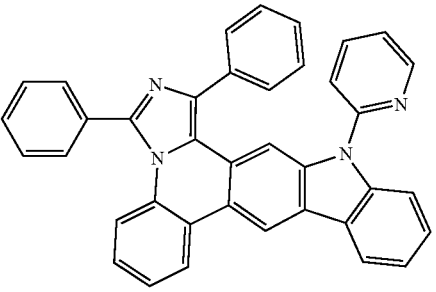
C-10
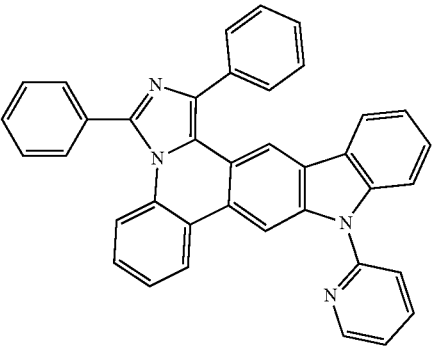

C-11
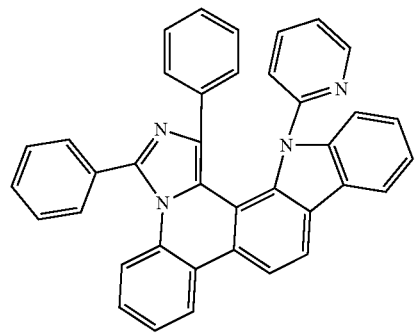
C-12
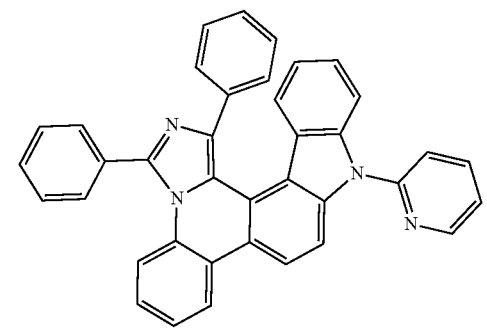
C-13
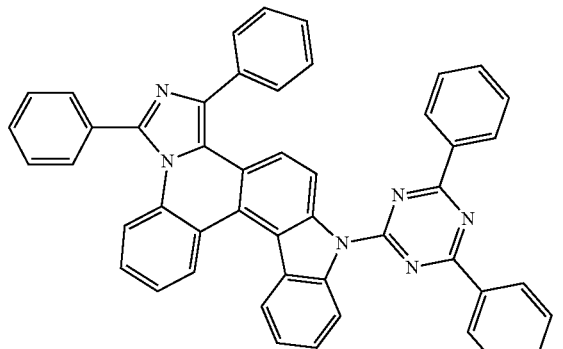
C-14
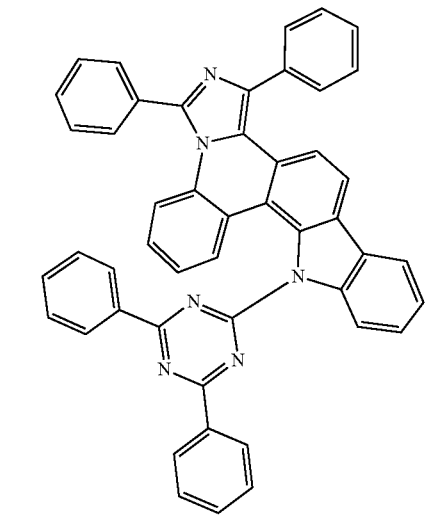
C-15
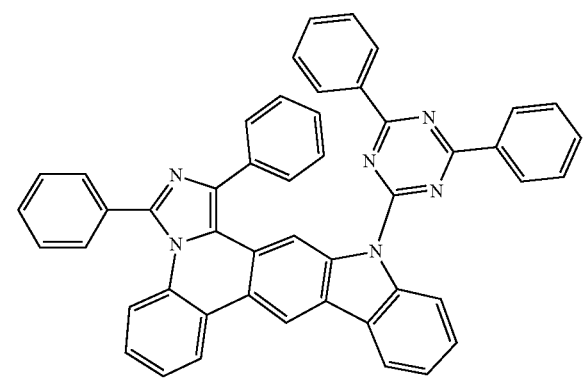
C-16
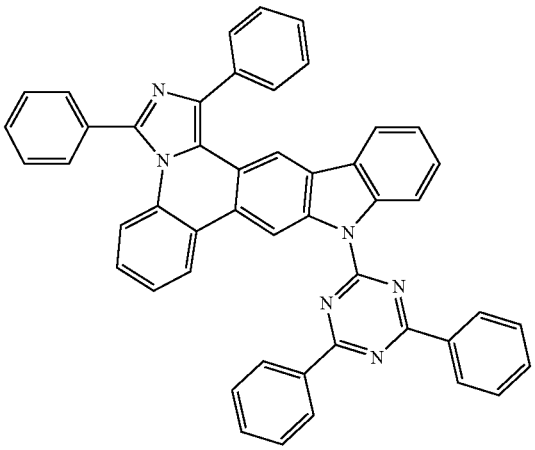
C-17
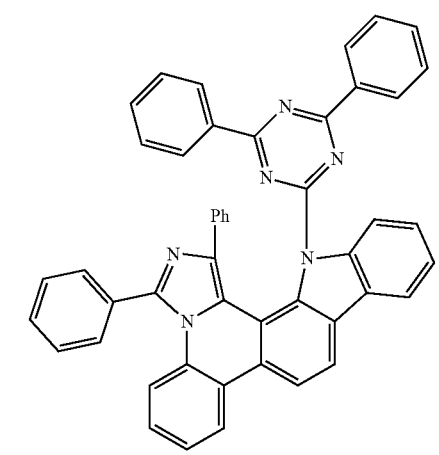

-continued
C-18
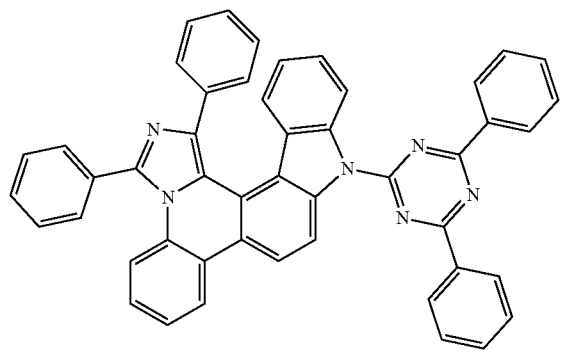
C-19
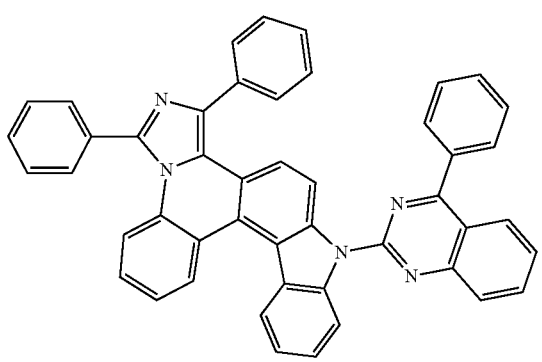
C-20
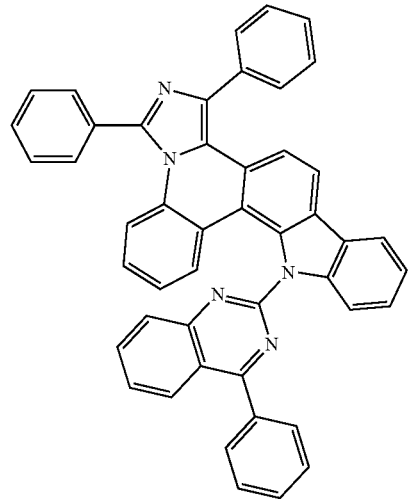
C-21
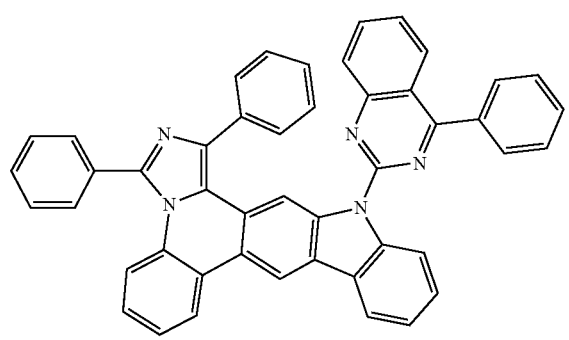
-continued
C-22
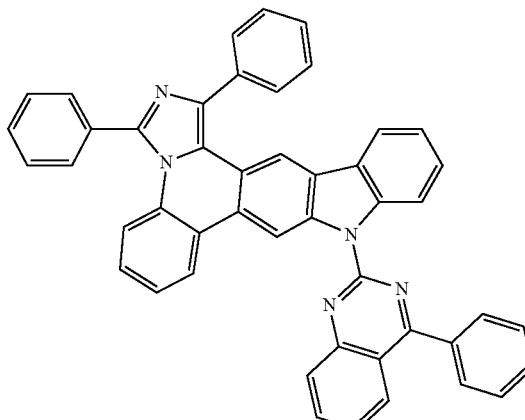
C-23
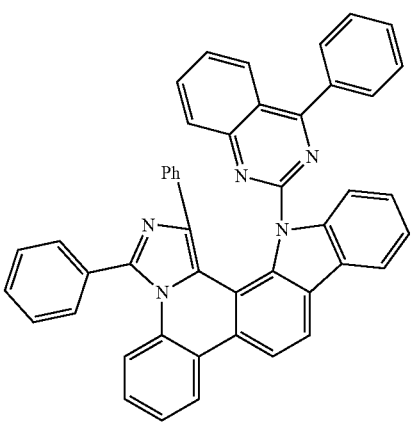
C-24
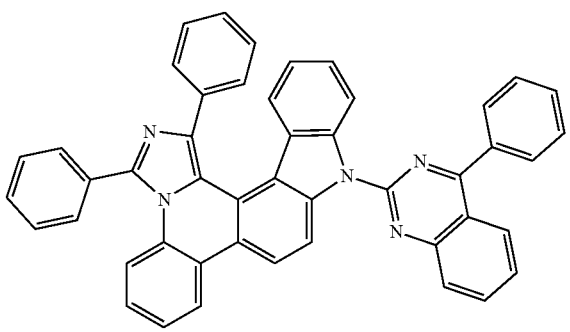
C-25
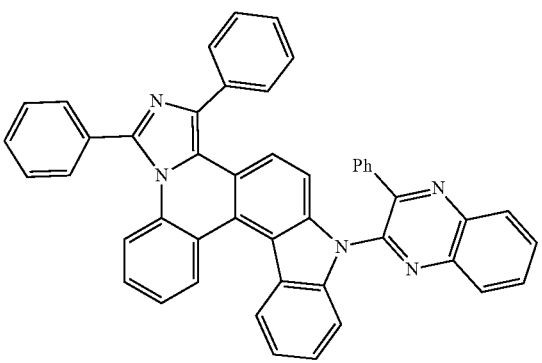

C-26
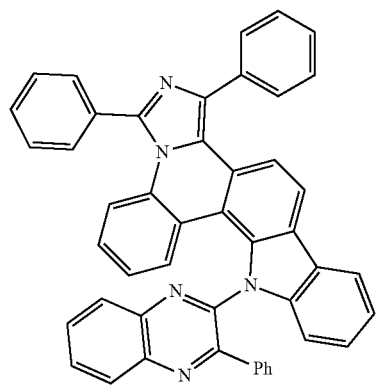
C-27
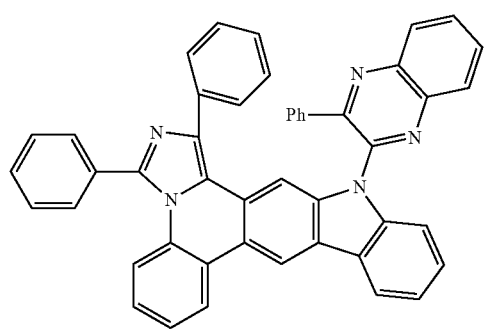
C-28
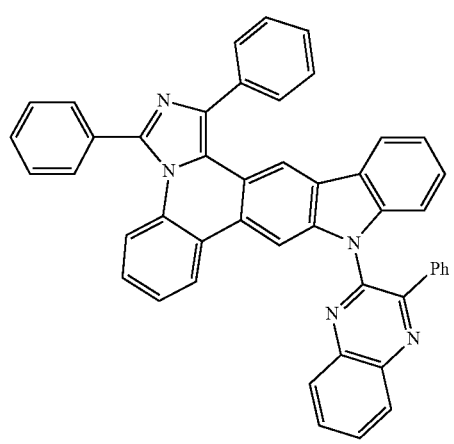
C-29
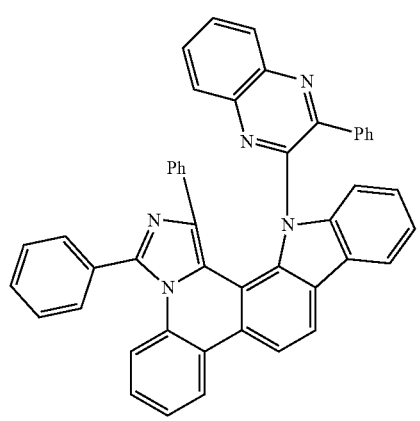
C-30
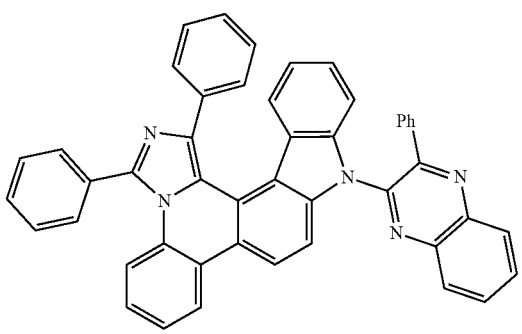
C-31
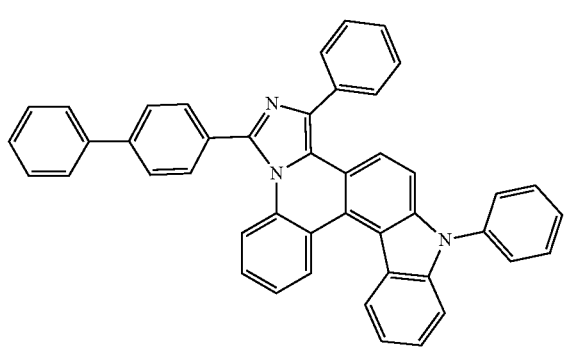
C-32
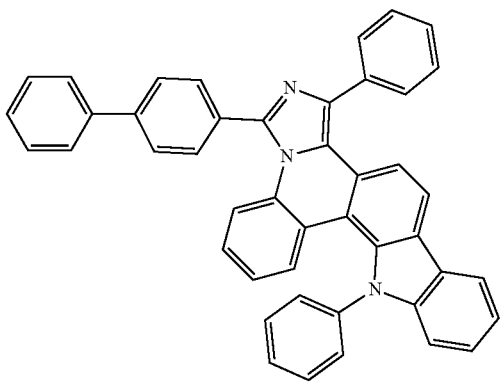
C-33
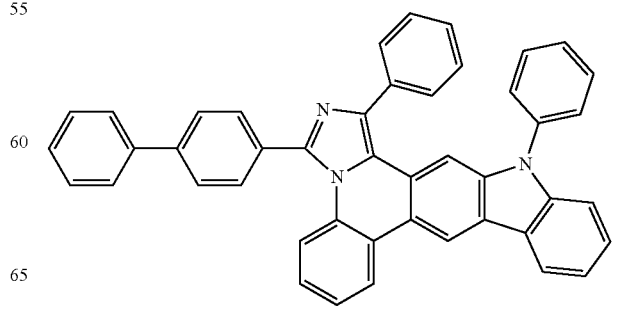

C-34
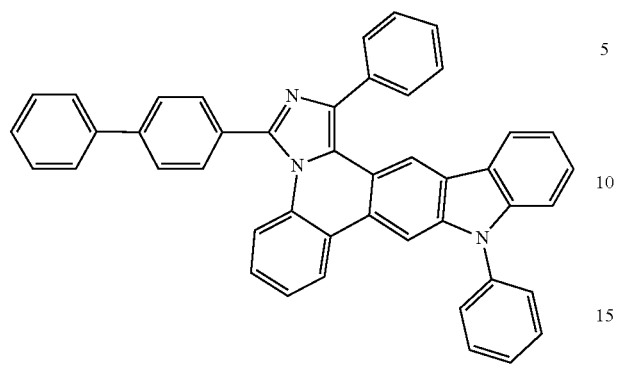
C-38
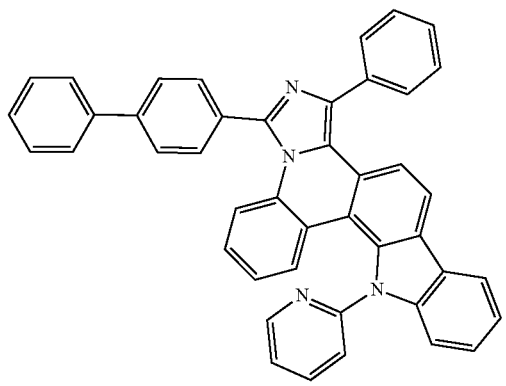
C-35
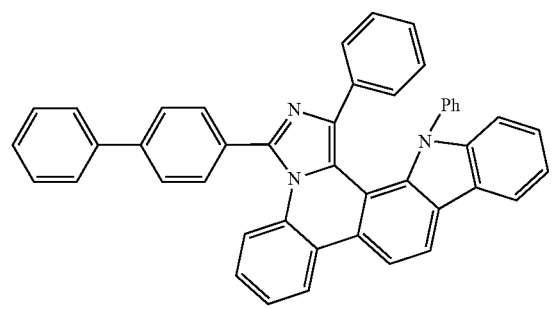
C-39
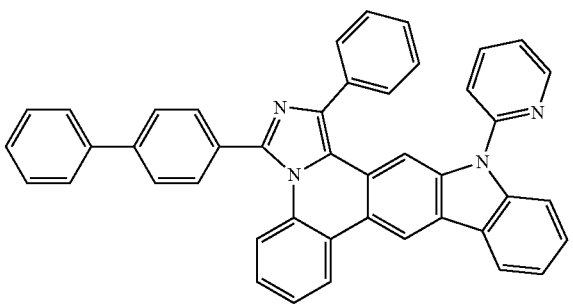
C-36
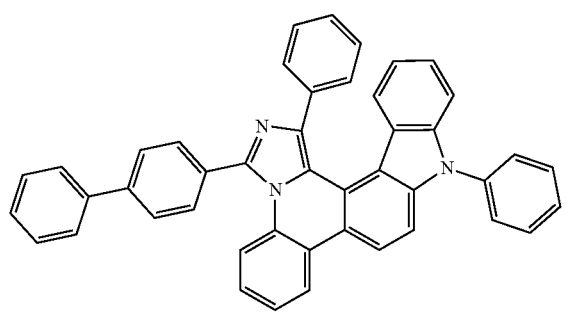
C-40
C-37
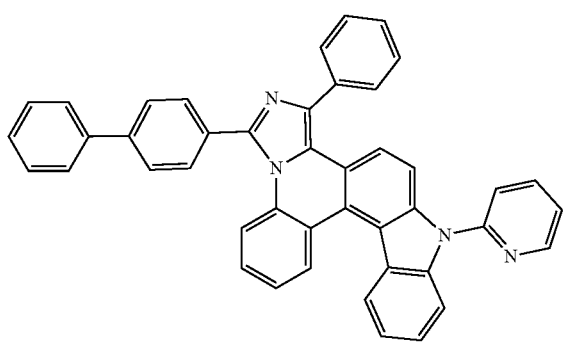
C-41
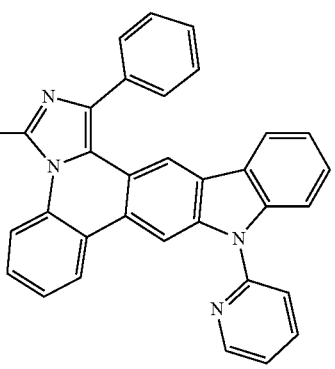
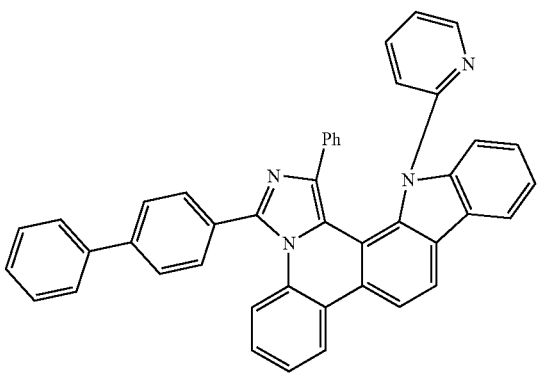

-continued
C-42
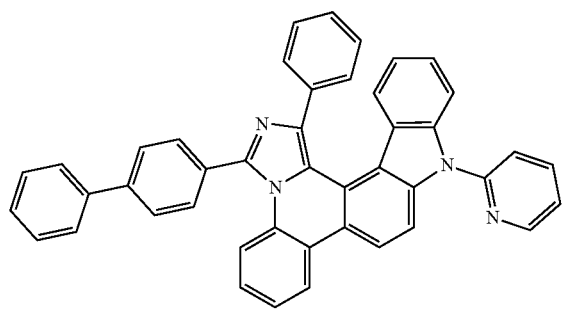
C-43
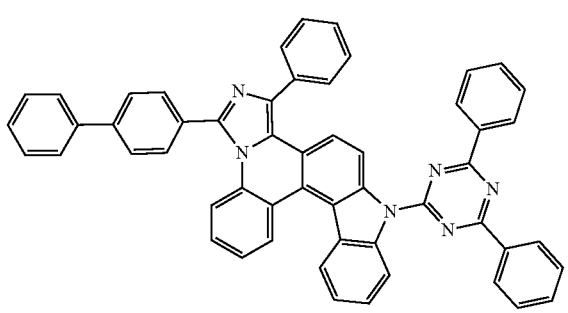
C-44
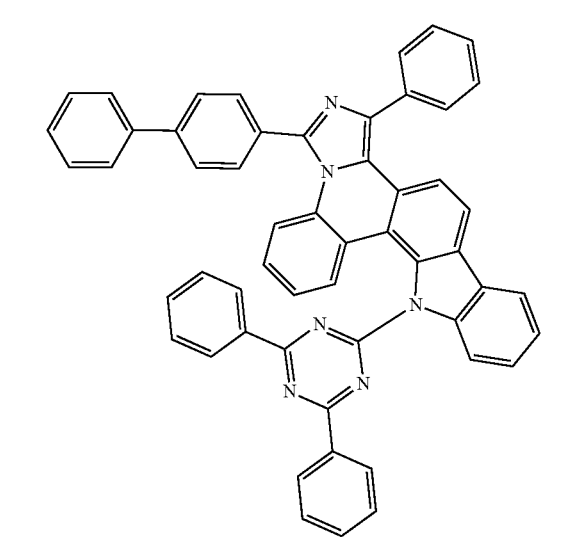
C-45
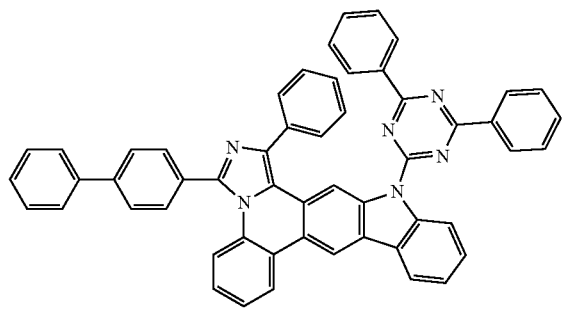
-continued
C-46
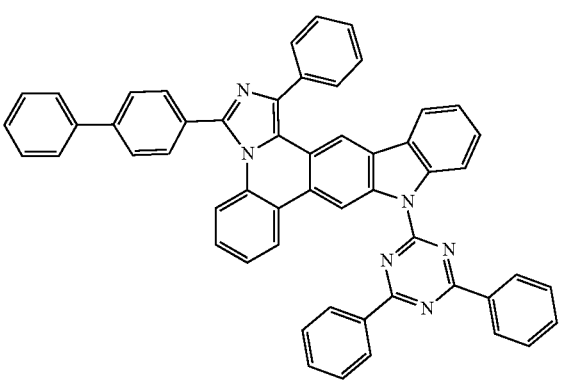
C-47
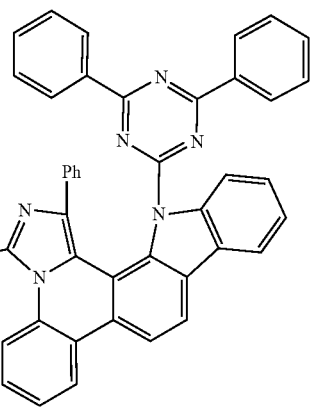
C-48
C-49

C-50
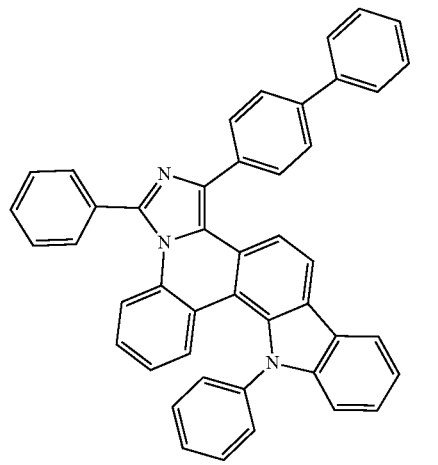
C-51
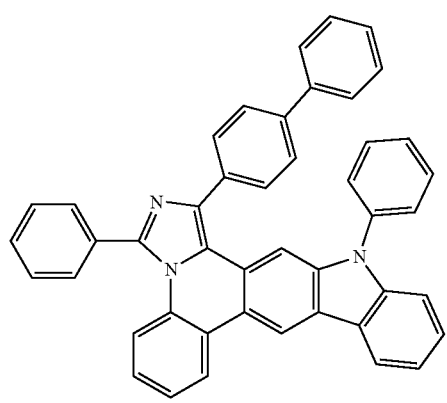
C-52
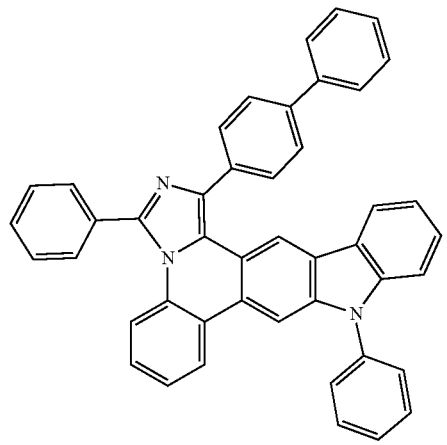
C-53
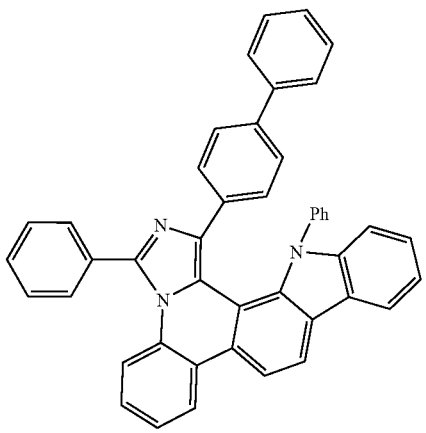
C-54
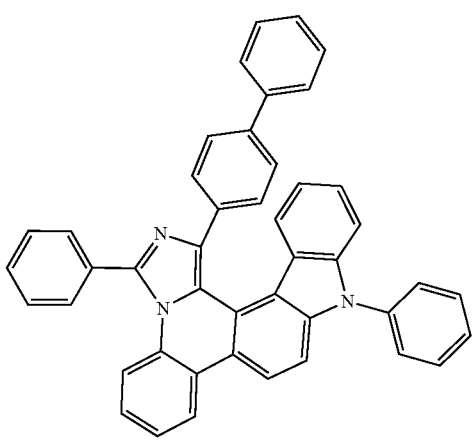
C-55
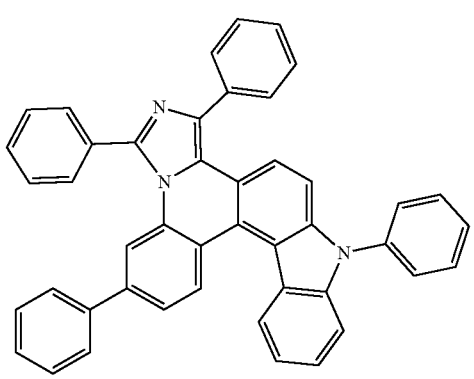
C-56
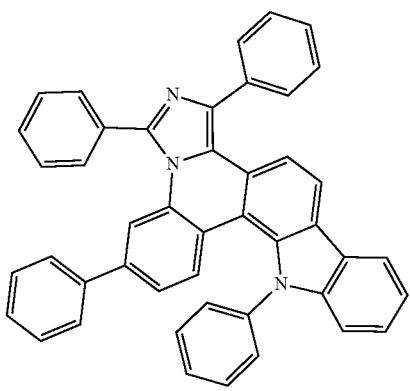

C-57
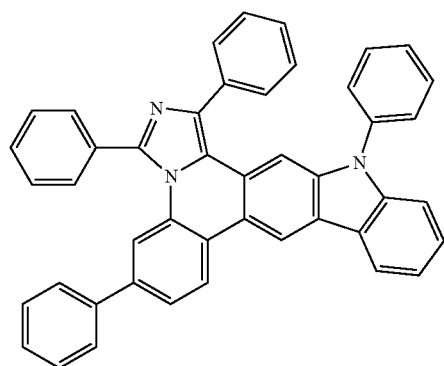
C-61
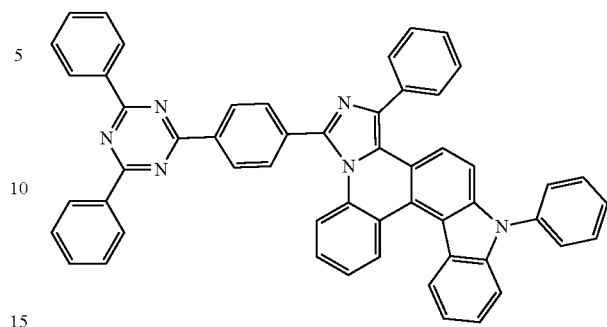
C-58
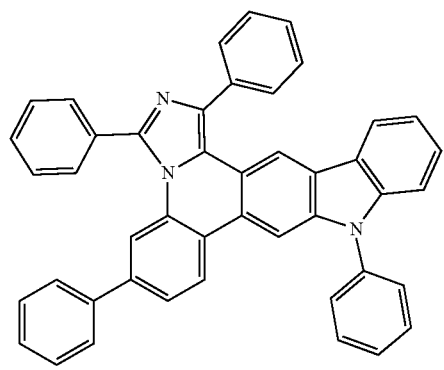
C-62
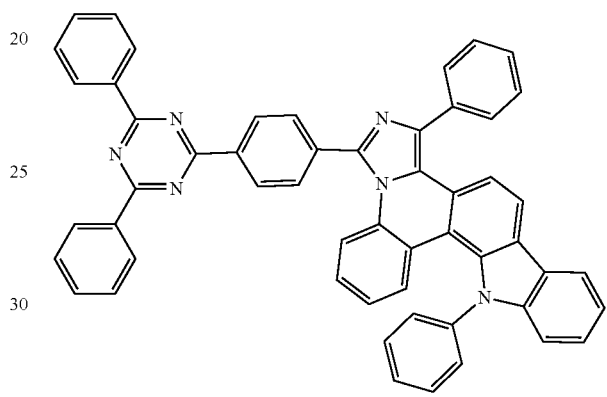
C-59
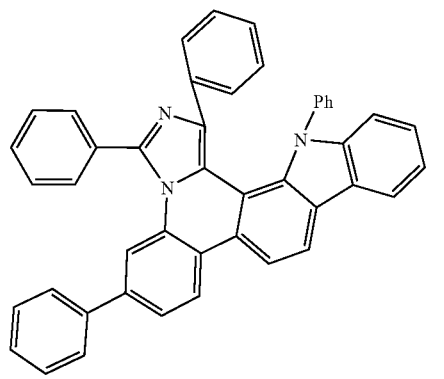
C-63
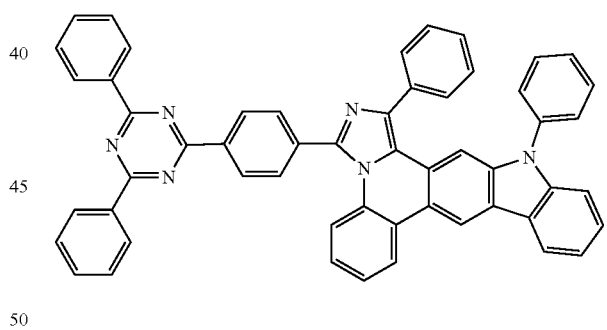
C-60
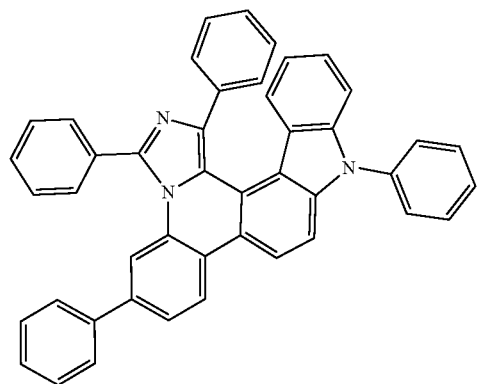
C-64
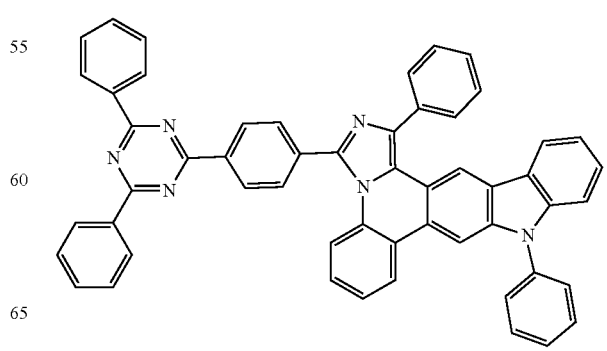

C-65
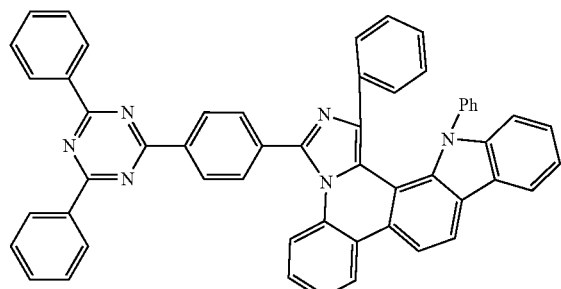
C-66
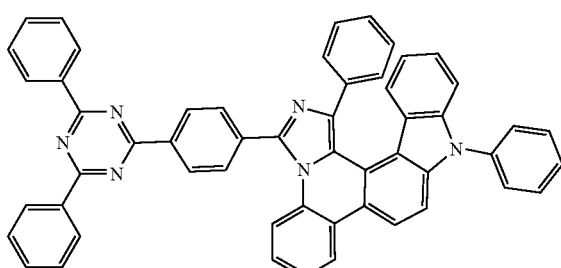
C-67
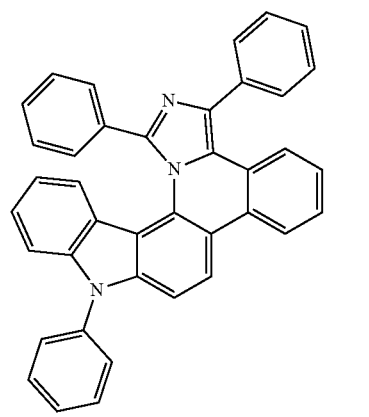
C-68
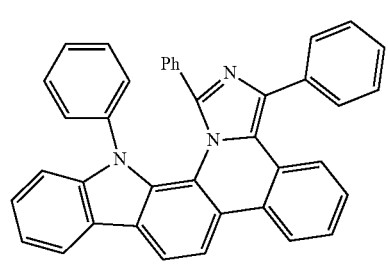
C-69
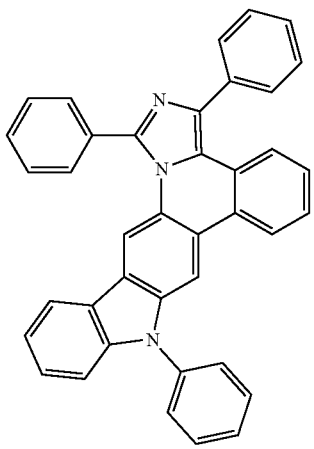
C-70
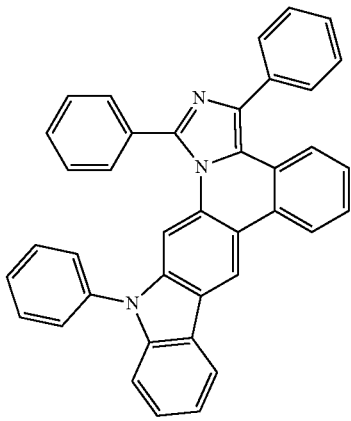
C-71
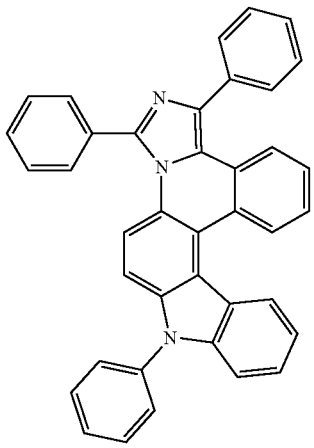

-continued
C-72
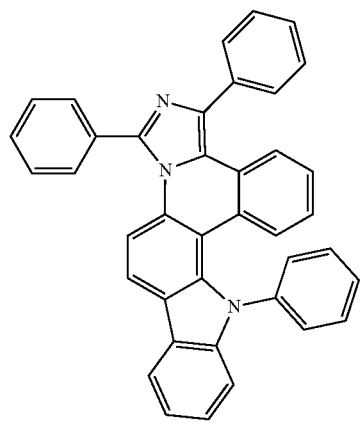
C-73
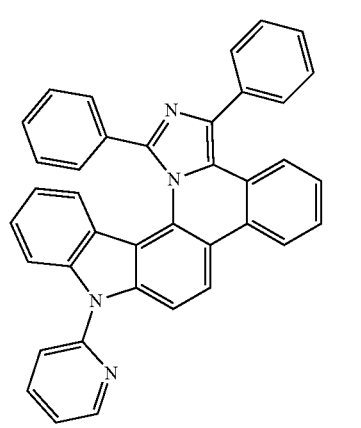
C-74
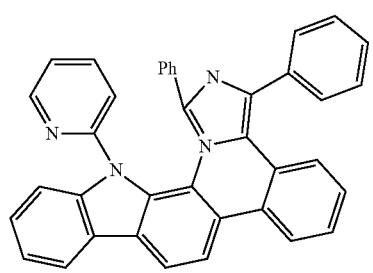
C-75
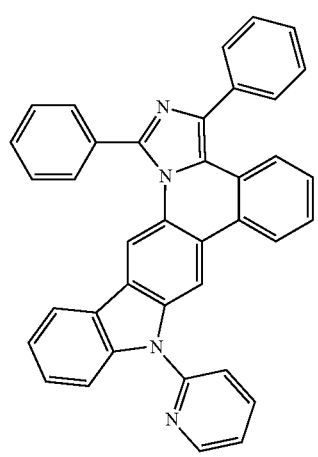
-continued
C-76
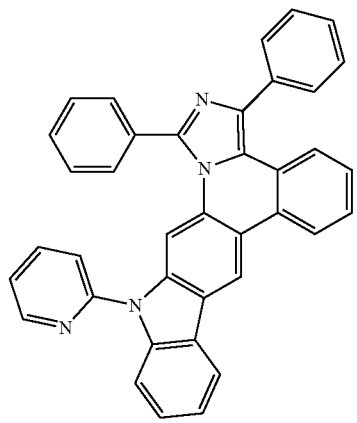
C-77
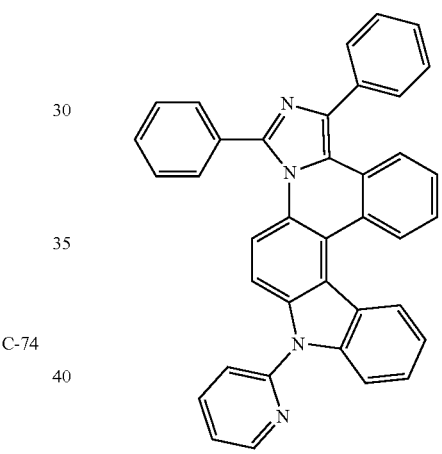
C-78
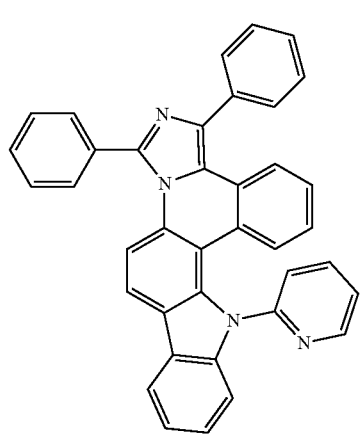

C-79
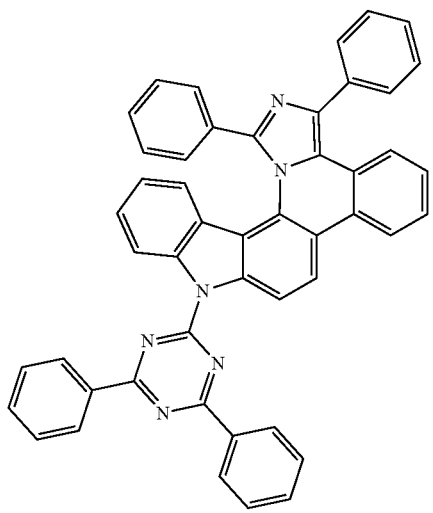
C-80
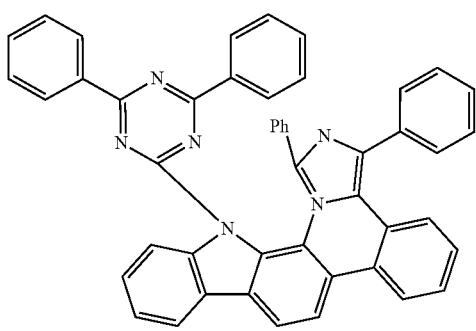
C-81
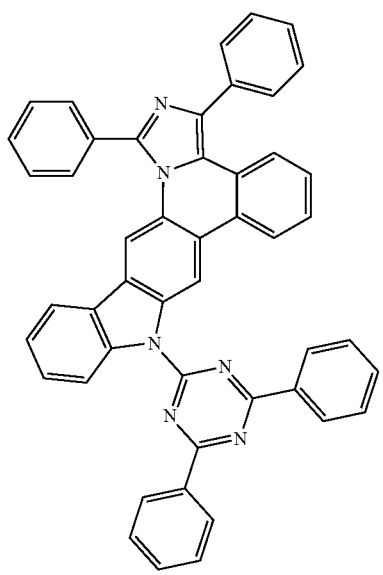
C-82
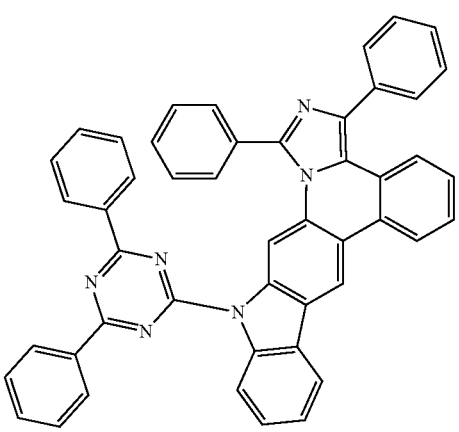
C-83
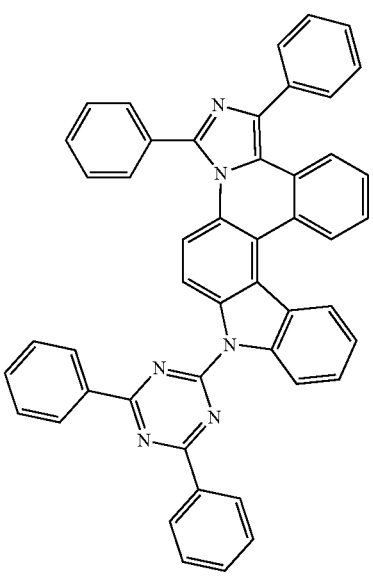
C-84
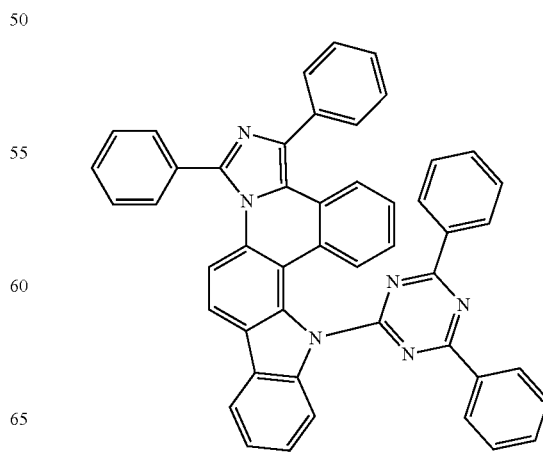

C-85
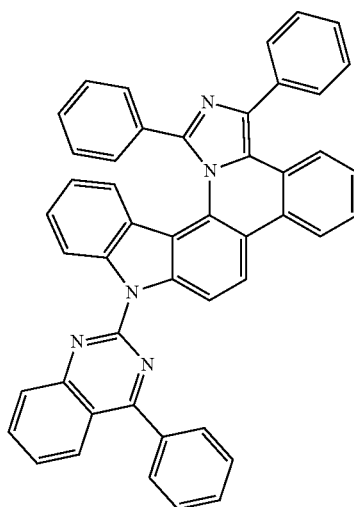
C-86
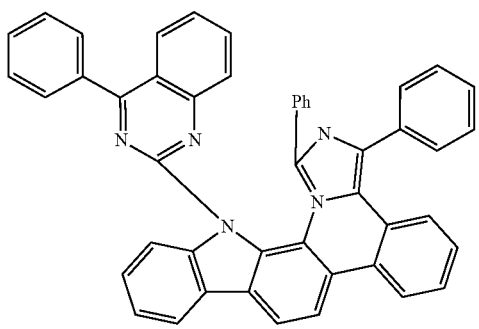
C-87
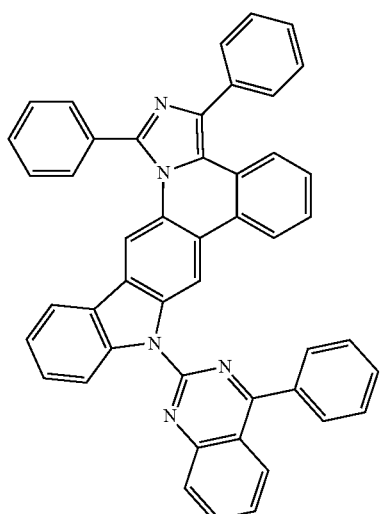
C-88
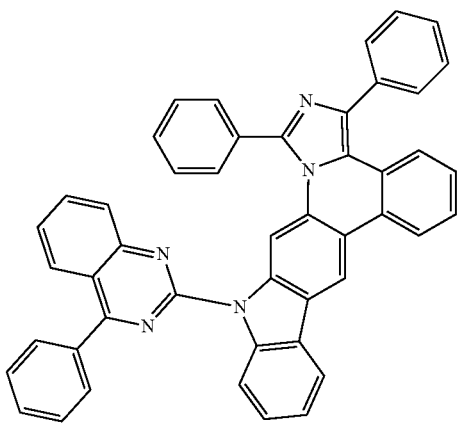
C-89
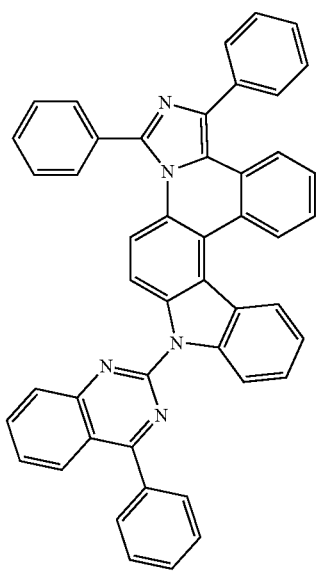
C-90
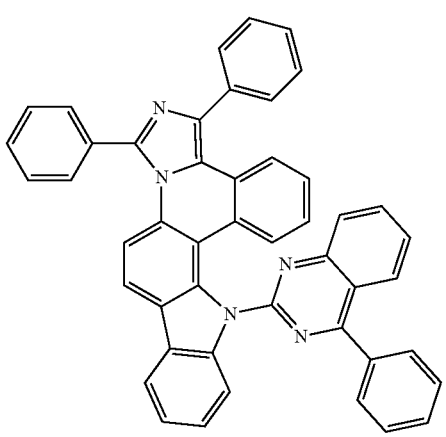

-continued
C-91
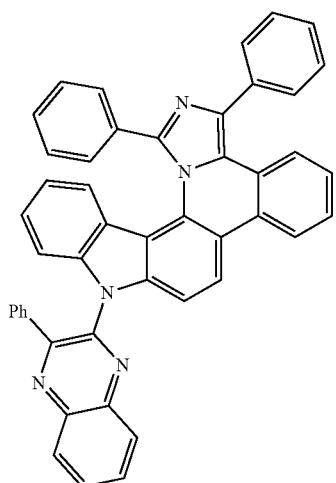
C-92
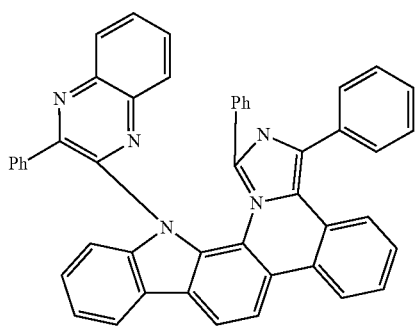
C-93
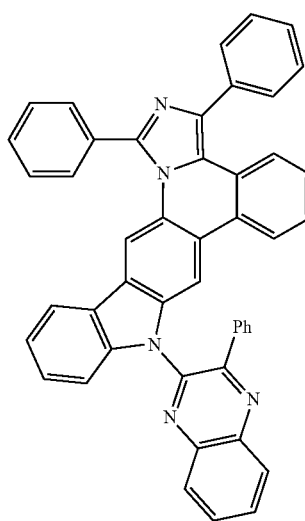
-continued
C-94
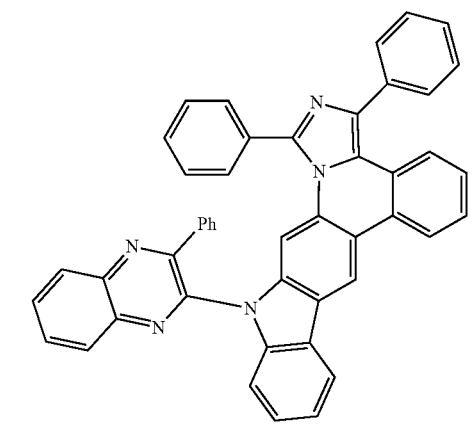
C-95
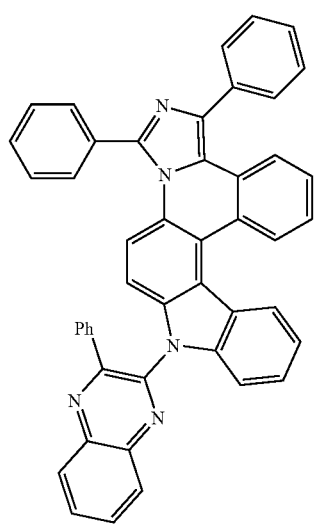
C-96
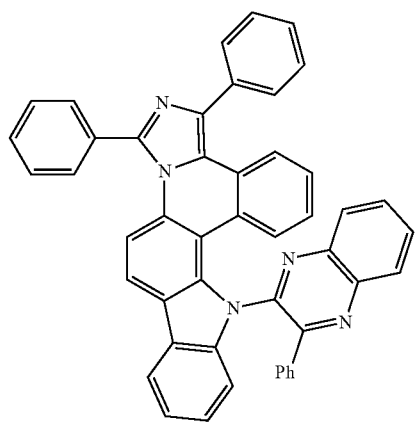

C-97
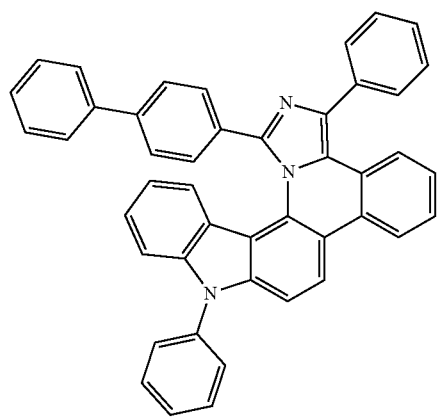
C-98
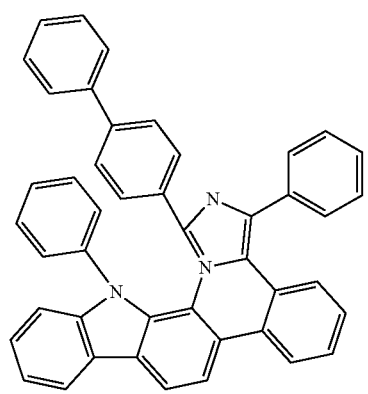
C-99
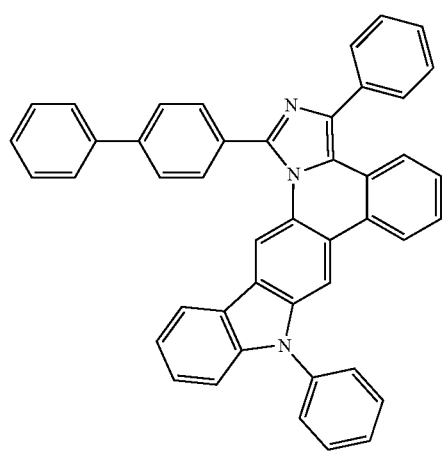
C-100
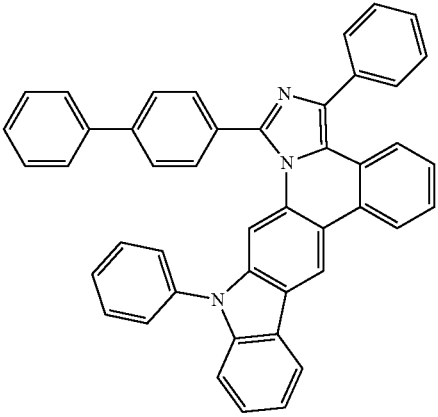
C-101
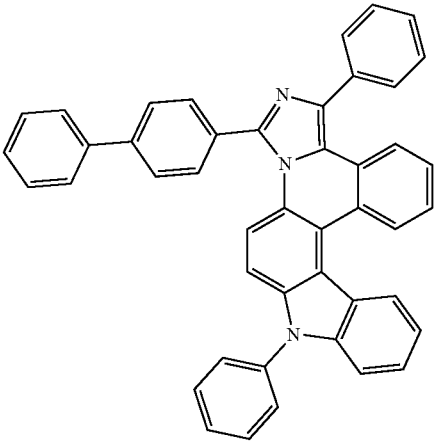
C-102
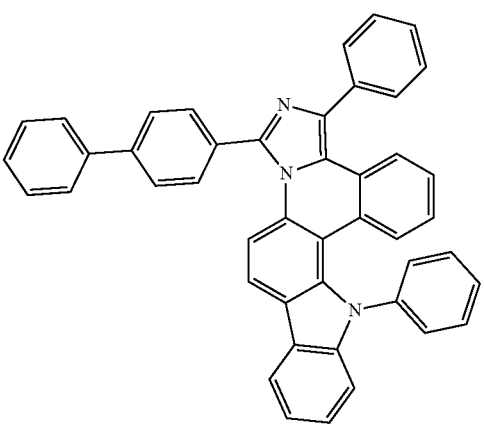

C-103
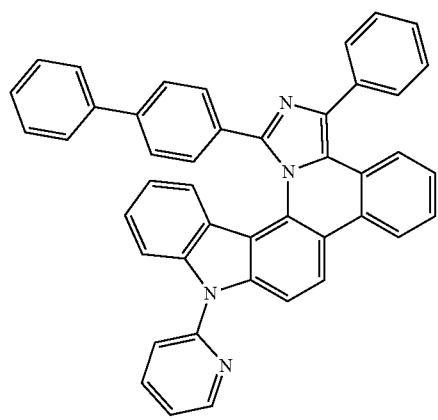
C-106
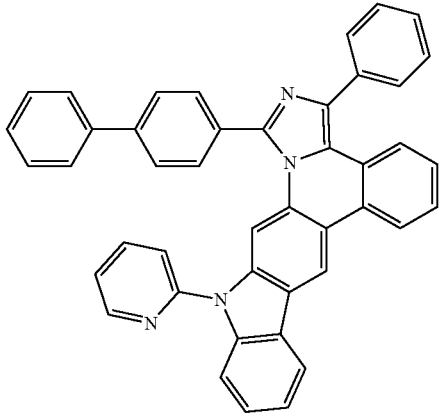
C-104
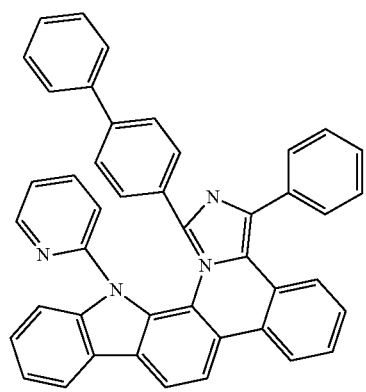
C-107
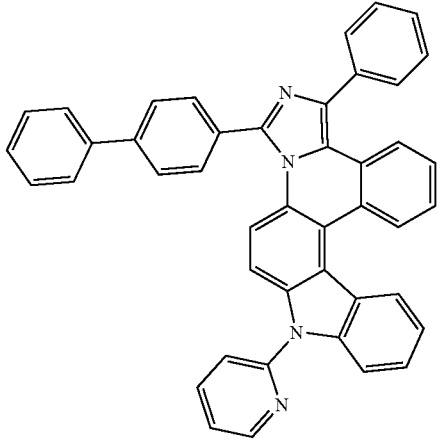
C-105
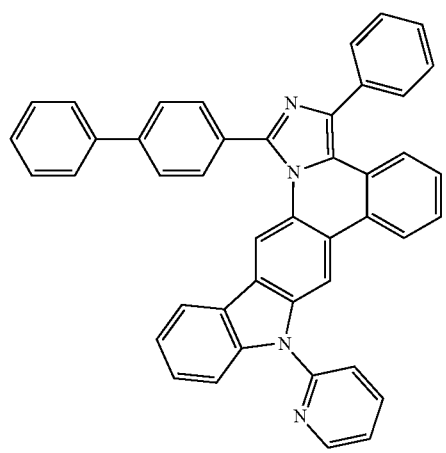
C-108
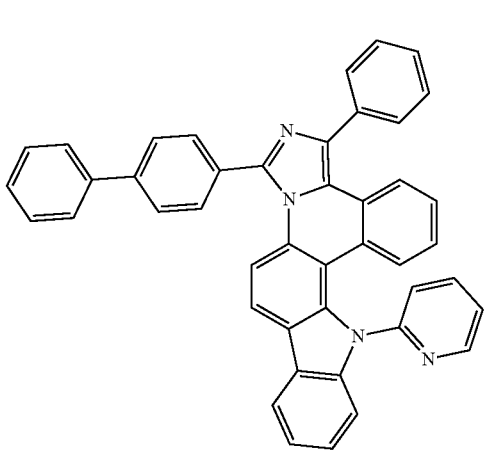

C-109
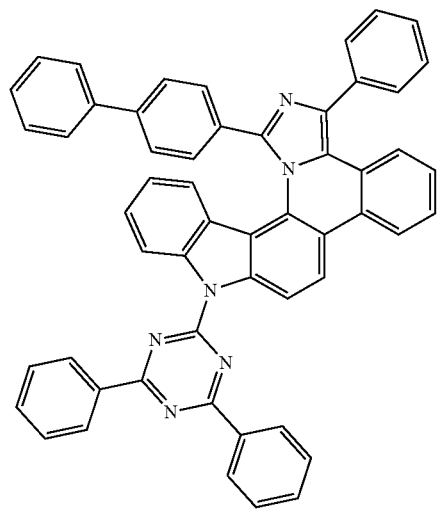
C-110
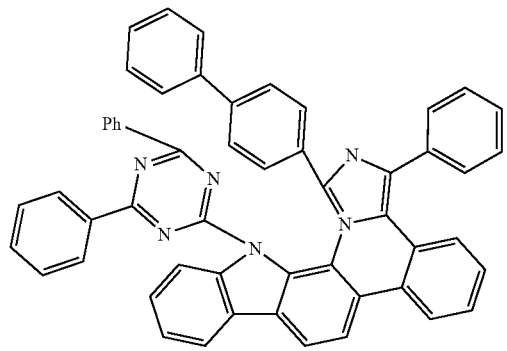
C-111
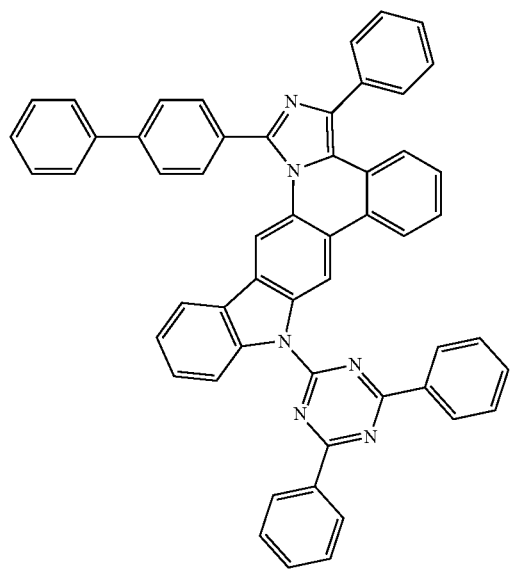
C-112
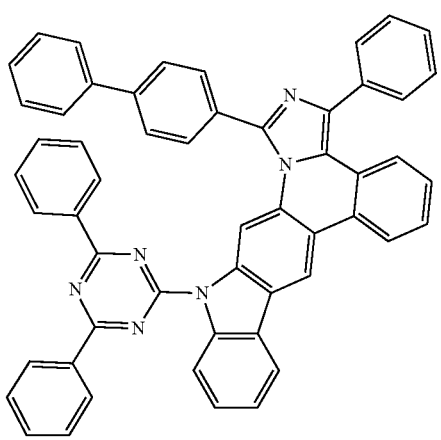
C-113
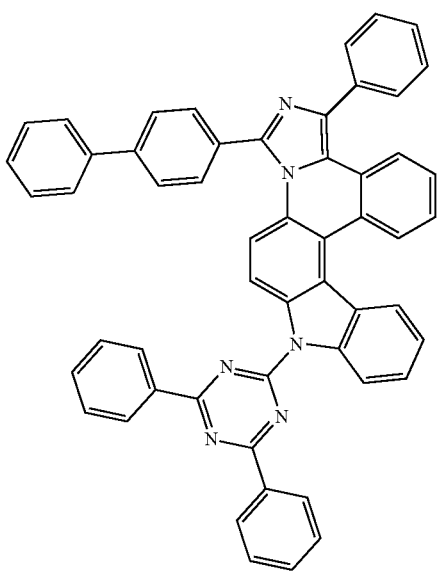
C-114
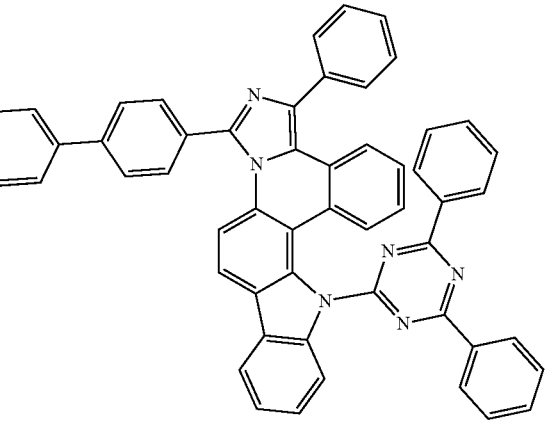

C-115
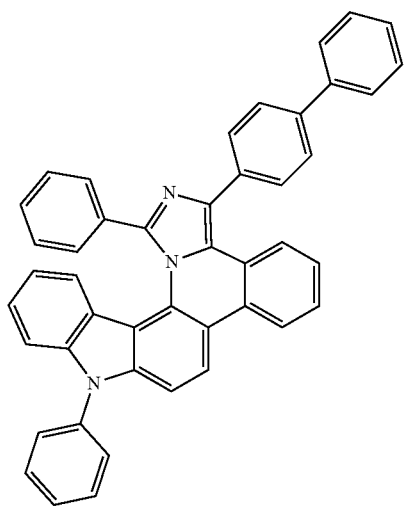
C-116
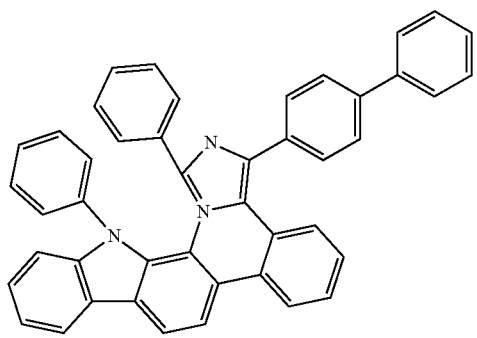
C-117
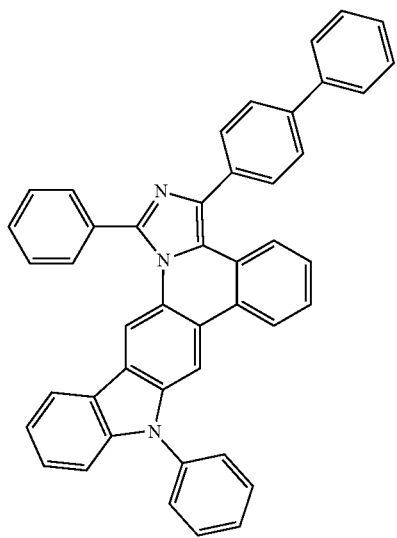
C-118
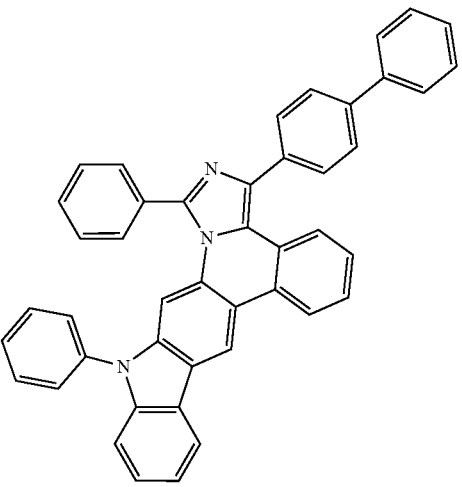
C-119
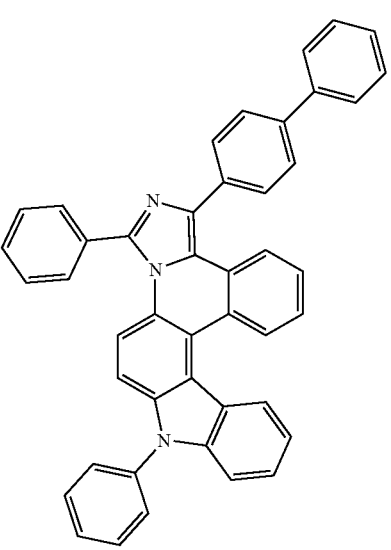
C-120
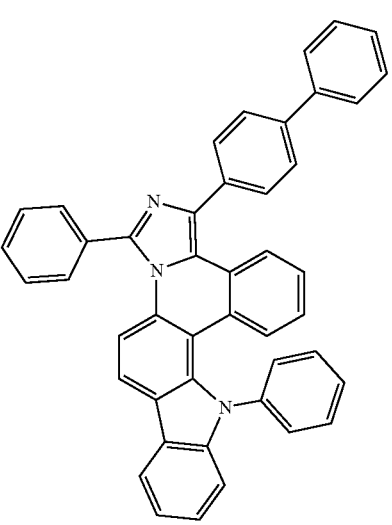

C-121
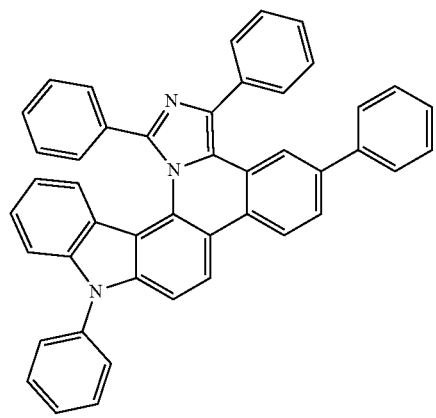
C-122
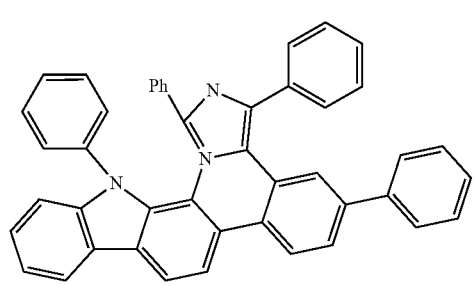
C-123
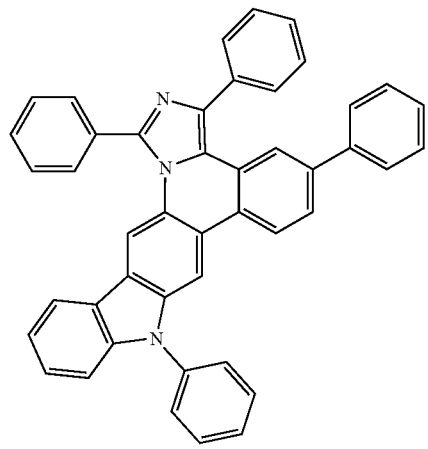
C-124
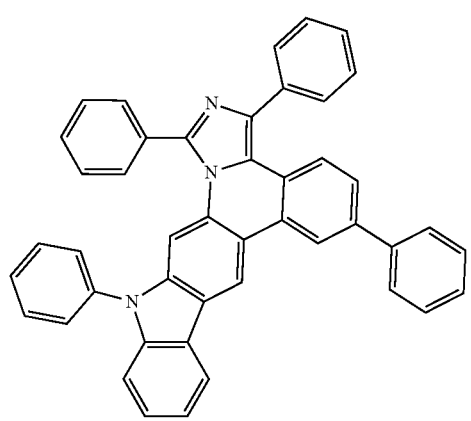
C-125
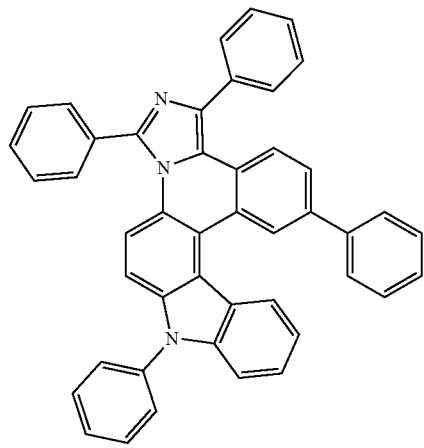
C-126
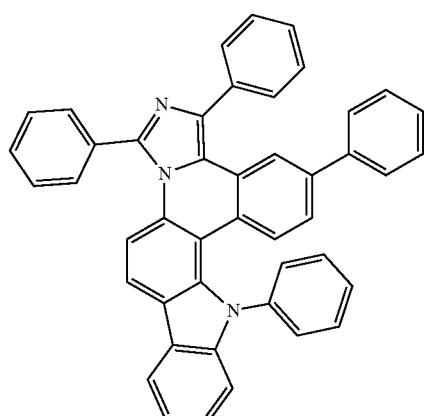
C-127
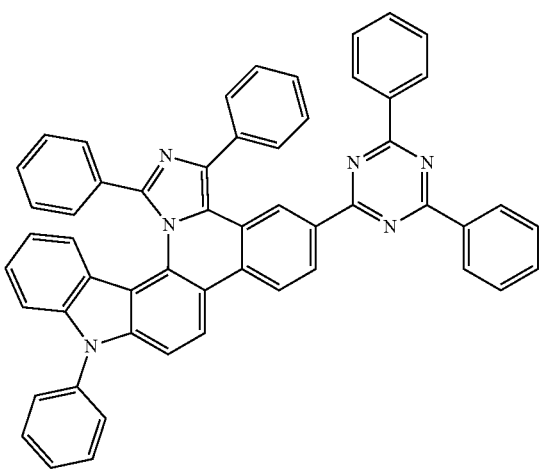

-continued
C-128
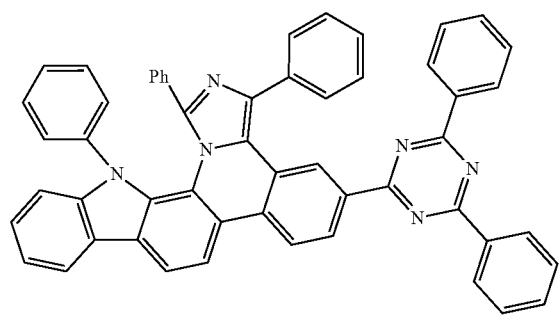
C-129
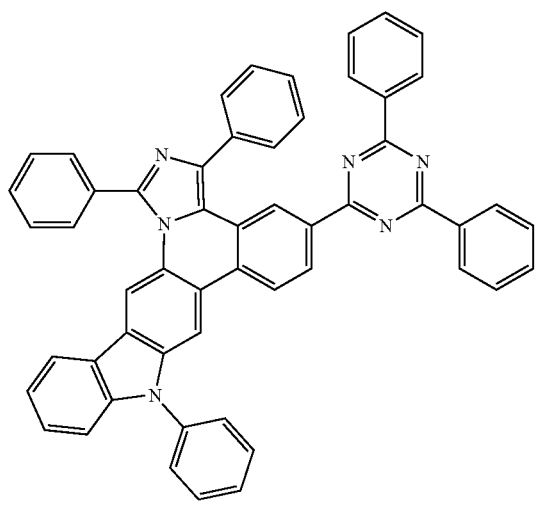
C-130
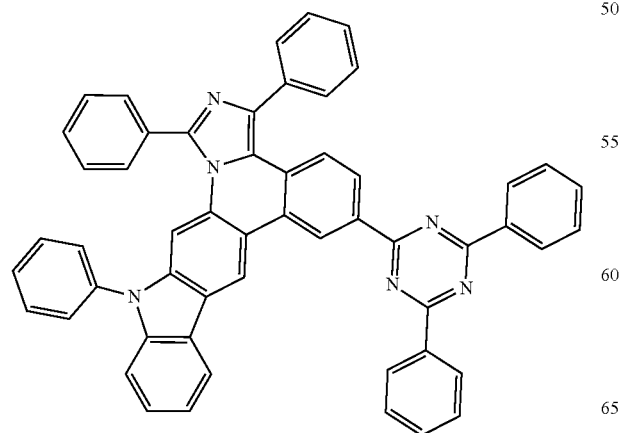
-continued
C-131
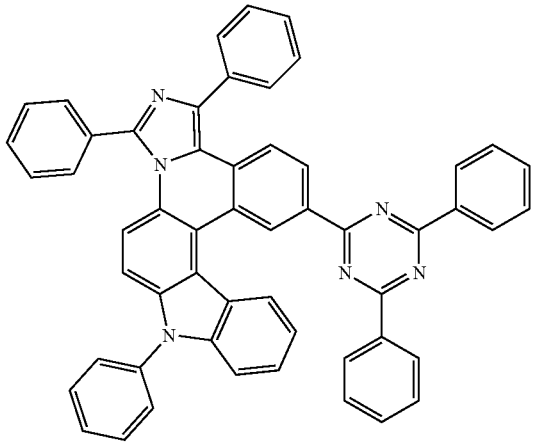
C-132
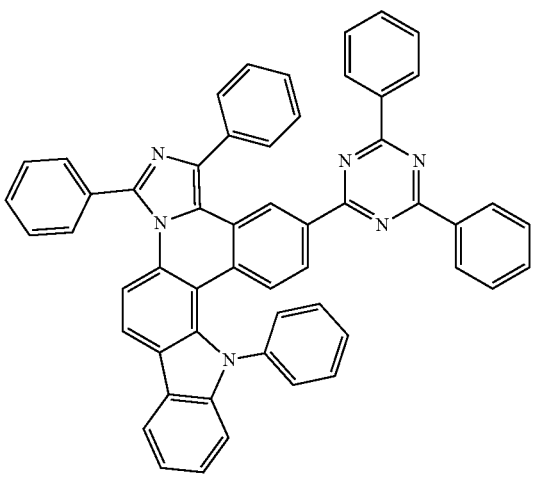
C-133
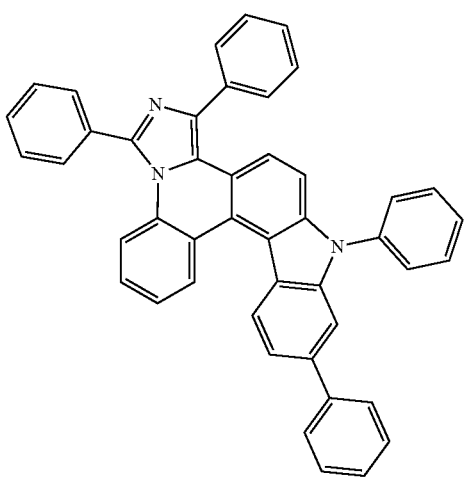

C-134
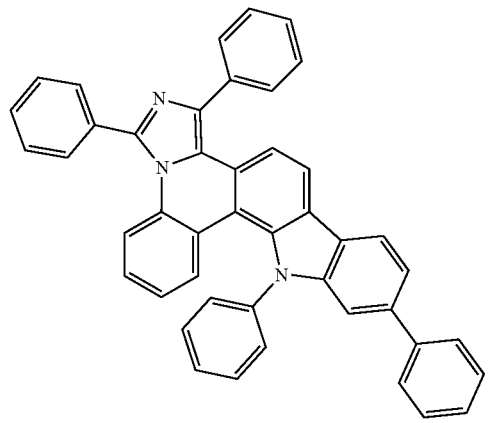
C-135
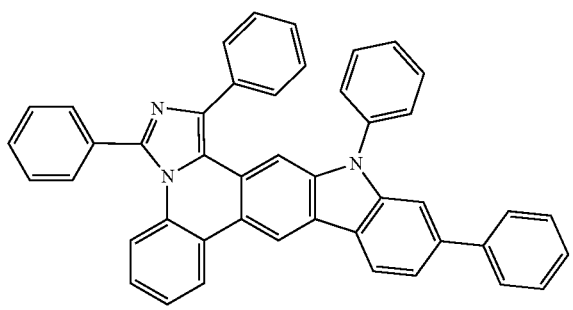
C-136
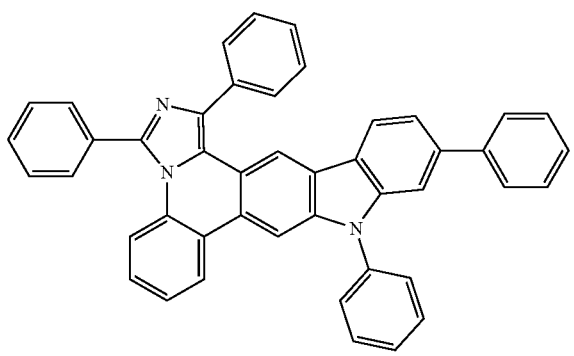
C-137
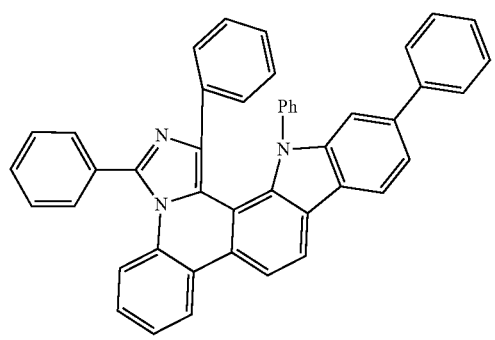
C-138
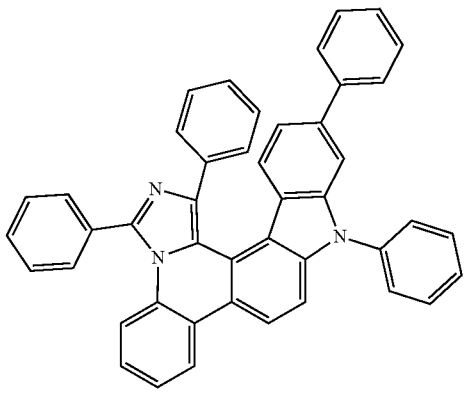
C-139
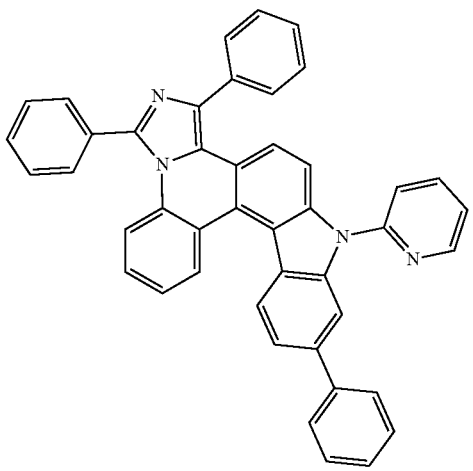
C-140
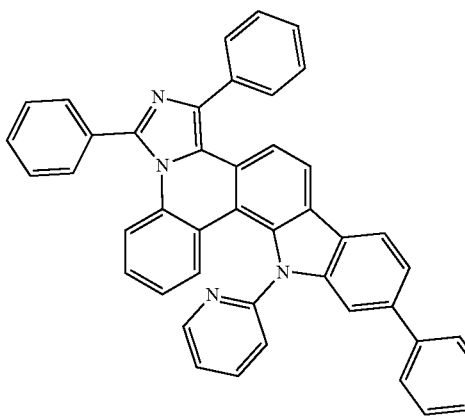
C-141
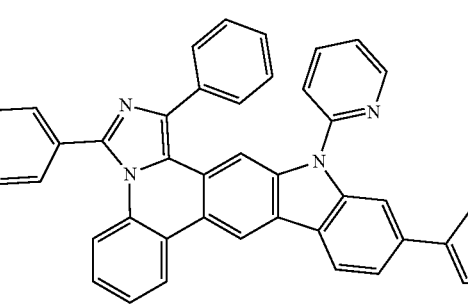

C-142
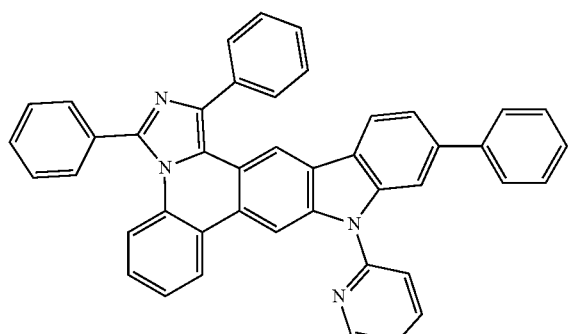
C-143
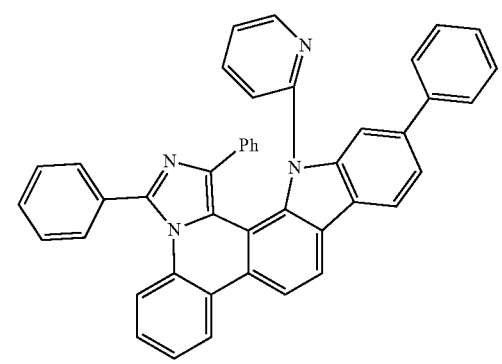
C-144
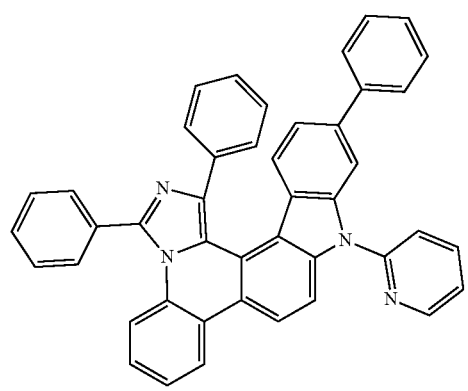
C-145
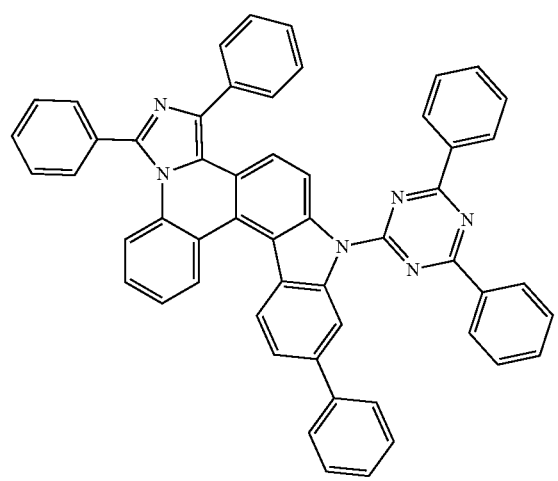
C-146
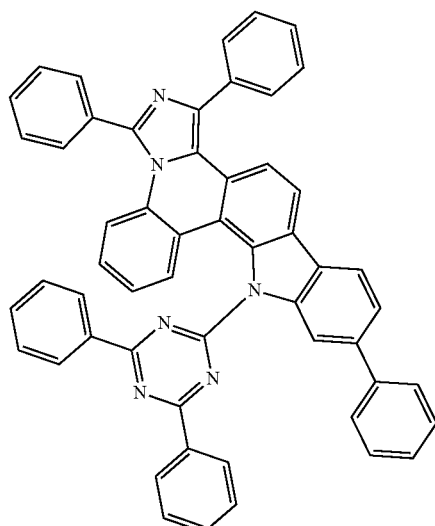
C-147
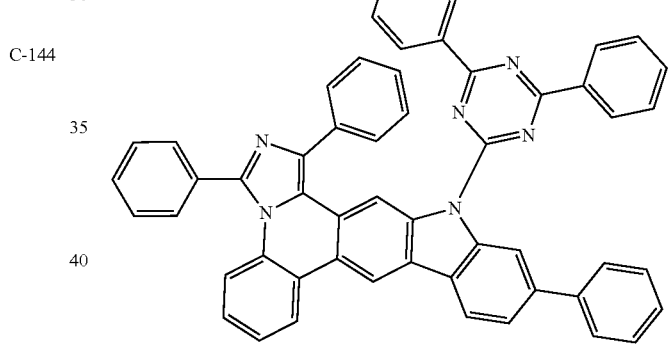
C-148
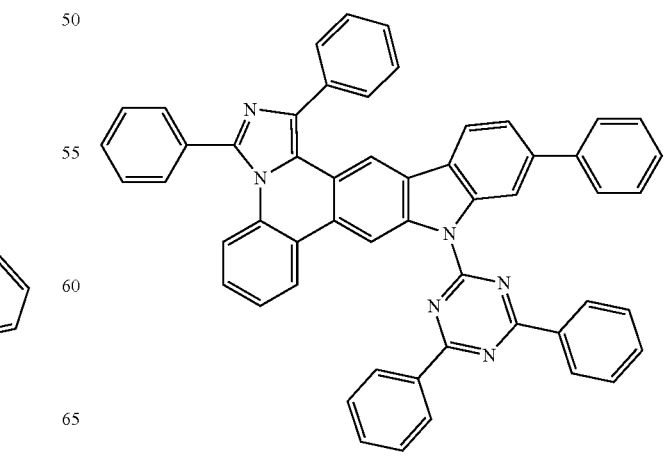

C-149
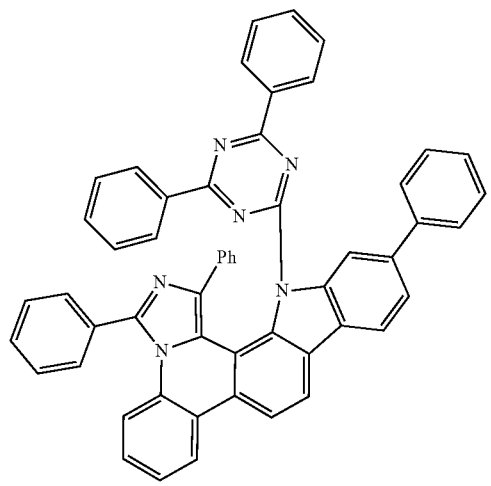
C-150
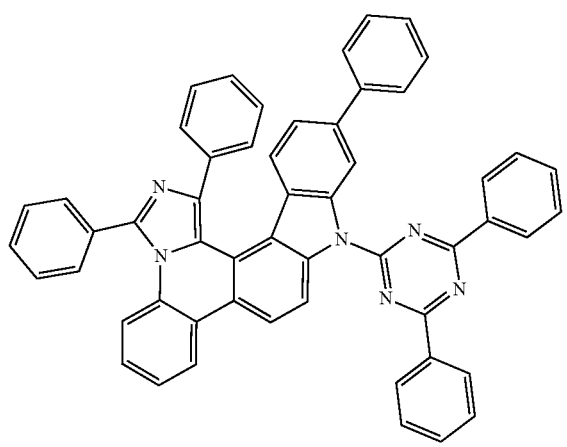
C-151
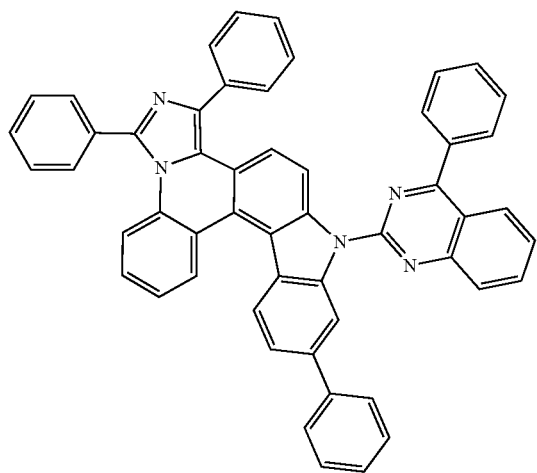
C-152
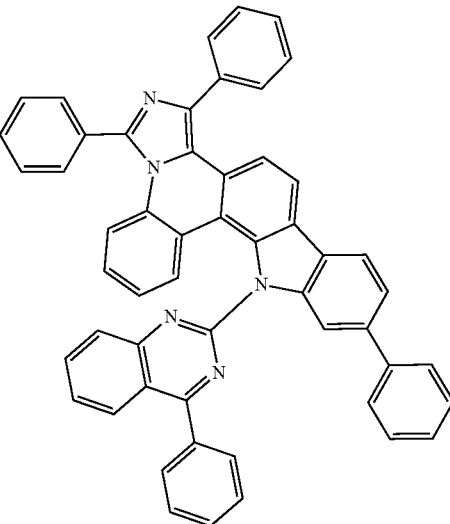
C-153
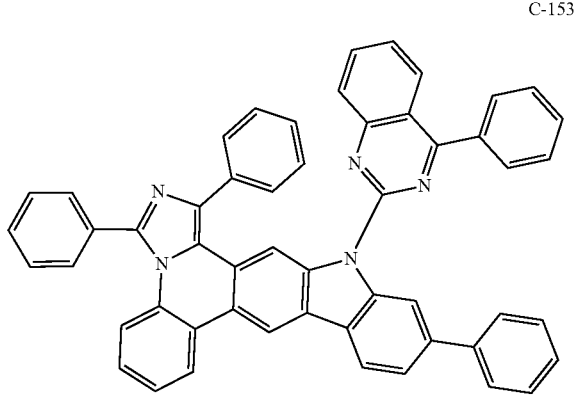
C-154
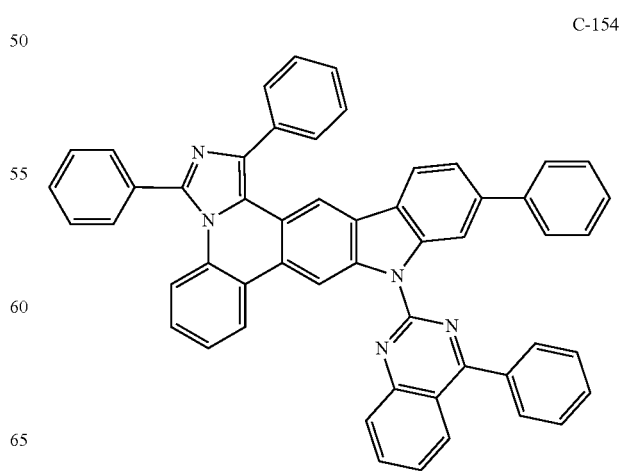

C-155
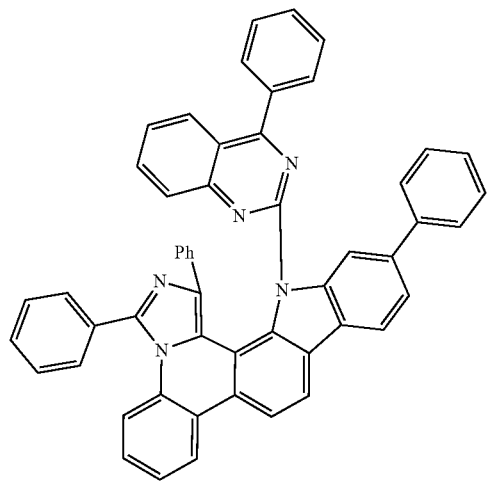
C-158
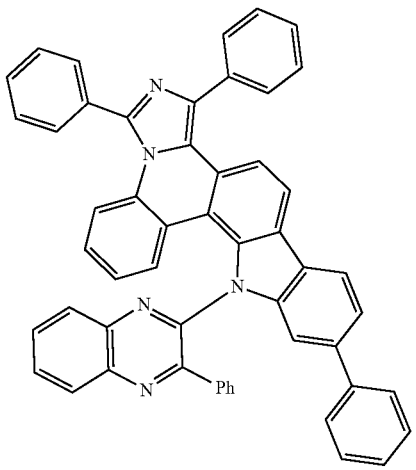
C-156
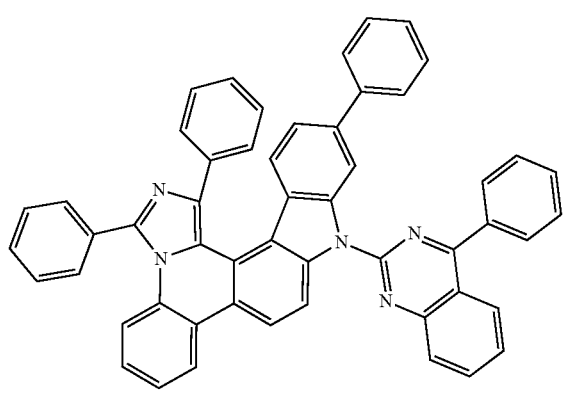
C-157
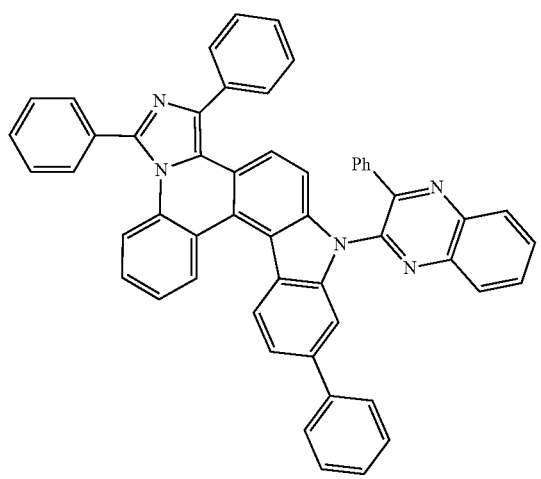
C-159
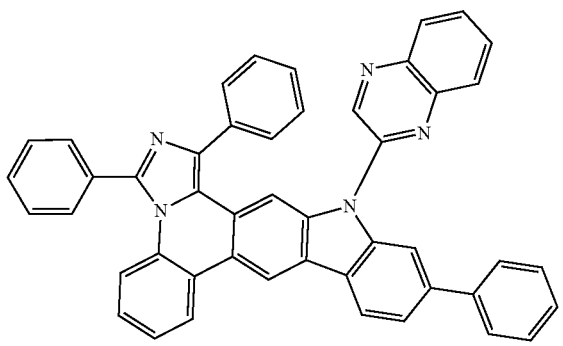

C-160
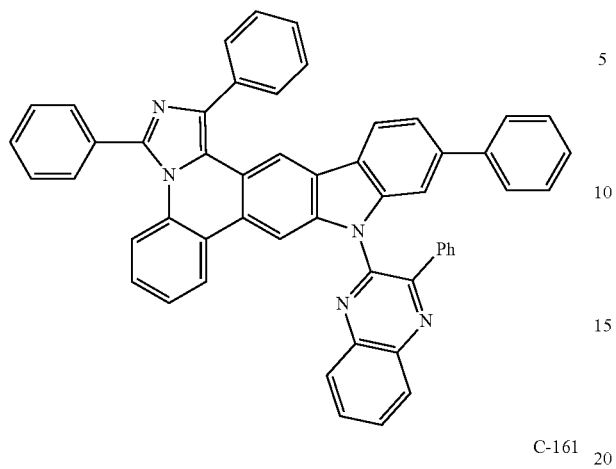
C-161
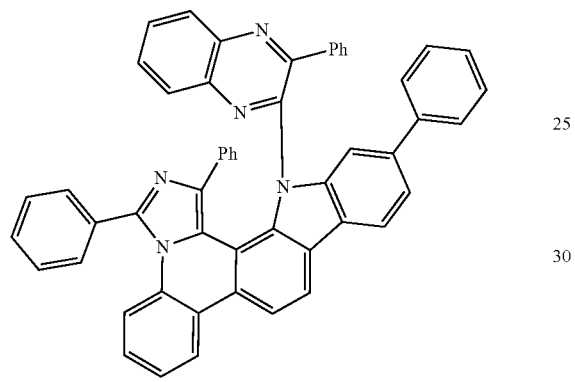
C-162
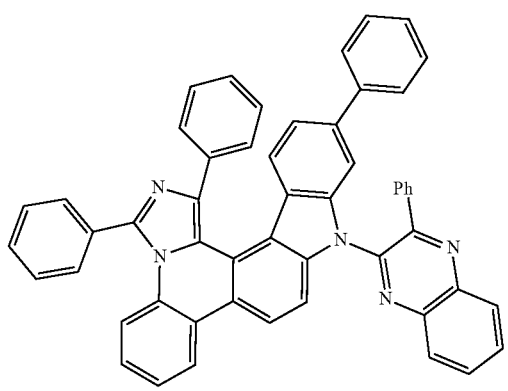
7. An organic electroluminescent material comprising the organic electroluminescent compound according to claim 1.
8. An organic electroluminescent device comprising the organic electroluminescent compound according to claim 1.
9. A display device comprising the organic electroluminescent compound according to claim 1.
* * * * *

UNITED STATES PATENT AND TRADEMARK OFFICE
CERTIFICATE OF CORRECTION

PATENT NO. : 11,289,662 B2
APPLICATION NO. : 16/479616
DATED : March 29, 2022
INVENTOR(S) : Jeong-Eun Yang It is certified that error appears in the above-identified patent and that said Letters Patent is hereby corrected as shown below:

In the Claims

In Claim 1, the description of formula 1 at Column 179, Line 59:
"$Ar_\alpha$" should be "$Ar_4$"

Signed and Sealed this
Seventeenth Day of May, 2022

Katherine Kelly Vidal
*Director of the United States Patent and Trademark Office*